(12) United States Patent
Heo et al.

(10) Patent No.: US 12,202,838 B2
(45) Date of Patent: Jan. 21, 2025

(54) HETEROCYCLIC COMPOUND AND ORGANIC LIGHT EMITTING DEVICE COMPRISING SAME

(71) Applicant: LG CHEM, LTD., Seoul (KR)

(72) Inventors: Dong Uk Heo, Daejeon (KR); Sung Kil Hong, Daejeon (KR); Jungoh Huh, Daejeon (KR); Yongbum Cha, Daejeon (KR); Miyeon Han, Daejeon (KR); Jae Tak Lee, Daejeon (KR); Junghoon Yang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 986 days.

(21) Appl. No.: 17/275,985

(22) PCT Filed: Nov. 8, 2019

(86) PCT No.: PCT/KR2019/015197
§ 371 (c)(1),
(2) Date: Mar. 12, 2021

(87) PCT Pub. No.: WO2020/105920
PCT Pub. Date: May 28, 2020

(65) Prior Publication Data
US 2023/0042871 A1 Feb. 9, 2023

(30) Foreign Application Priority Data

Nov. 19, 2018 (KR) .................. 10-2018-0142880
Nov. 5, 2019 (KR) .................. 10-2019-0140359

(51) Int. Cl.
*C07D 493/10* (2006.01)
*C07D 495/10* (2006.01)
(Continued)

(52) U.S. Cl.
CPC ......... *C07D 493/10* (2013.01); *C07D 495/10* (2013.01); *C07D 498/10* (2013.01);
(Continued)

(58) Field of Classification Search
CPC .. C07D 493/10; C07D 495/10; C07D 498/10; C07D 493/04; C07D 495/04;
(Continued)

(56) References Cited

U.S. PATENT DOCUMENTS

2004/0251816 A1 12/2004 Leo et al.
2014/0346483 A1 11/2014 Yu et al.
(Continued)

FOREIGN PATENT DOCUMENTS

CN 108047244 A 5/2018
KR 10-2013-0073537 A 7/2013
(Continued)

*Primary Examiner* — Taylor V Oh
(74) *Attorney, Agent, or Firm* — Bryan Cave Leighton Paisner LLP

(57) ABSTRACT

A heterocyclic compound represented by Chemical Formula 1 and an organic light emitting device including the same, and the heterocyclic compound which is used as a material of an organic material layer of the organic light emitting device and provides improved efficiency, low driving voltage and improved lifetime characteristics of the organic light emitting device.

(Continued)

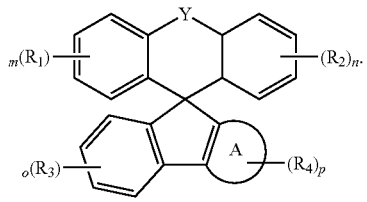

[Chemical Formula 1]

8 Claims, 1 Drawing Sheet

(51) Int. Cl.
  *C07D 498/10* (2006.01)
  *H10K 85/60* (2023.01)
  *H10K 50/11* (2023.01)
  *H10K 101/10* (2023.01)
  *H10K 101/30* (2023.01)
  *H10K 101/40* (2023.01)

(52) U.S. Cl.
  CPC ....... *H10K 85/654* (2023.02); *H10K 85/6574* (2023.02); *H10K 85/6576* (2023.02); *H10K 50/11* (2023.02); *H10K 2101/10* (2023.02); *H10K 2101/30* (2023.02); *H10K 2101/40* (2023.02)

(58) Field of Classification Search
  CPC ............. H10K 85/654; H10K 85/6574; H10K 85/6576; H10K 50/11; H10K 2101/10; H10K 2101/30; H10K 2101/40; H10K 50/16; H10K 50/17; H10K 50/171
  USPC ......................................................... 549/390
  See application file for complete search history.

(56) References Cited

U.S. PATENT DOCUMENTS

| | | |
|---|---|---|
| 2017/0141327 A1 | 5/2017 | Parham et al. |
| 2017/0217992 A1 | 8/2017 | Jun et al. |
| 2018/0287073 A1 | 10/2018 | Ha et al. |
| 2018/0351112 A1 | 12/2018 | Cha et al. |
| 2021/0198567 A1* | 7/2021 | Jun ................... H10K 85/6576 |

FOREIGN PATENT DOCUMENTS

| | | |
|---|---|---|
| KR | 10-2015-0113642 A | 10/2015 |
| KR | 10-2016-0018406 A | 2/2016 |
| KR | 10-2017-0016507 A | 2/2017 |
| KR | 10-2017-0041645 A | 4/2017 |
| KR | 10-2017-0055743 A | 5/2017 |
| KR | 10-2017-0059910 A | 5/2017 |
| KR | 10-2018-0022190 A | 3/2018 |
| KR | 10-2018-0069423 A | 6/2018 |
| KR | 10-2018-0075914 A | 7/2018 |
| WO | 2003-012890 A2 | 8/2003 |
| WO | 2016-021989 A1 | 2/2016 |
| WO | 2017-023021 A1 | 2/2017 |
| WO | 2017-082556 A | 5/2017 |
| WO | 2018-038401 A1 | 3/2018 |

\* cited by examiner

【FIG. 1】
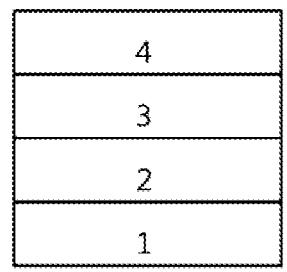
【FIG. 2】
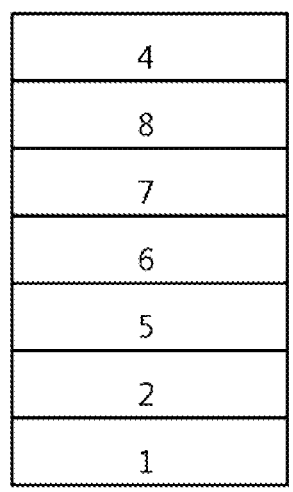

HETEROCYCLIC COMPOUND AND ORGANIC LIGHT EMITTING DEVICE COMPRISING SAME

CROSS-REFERENCE TO RELATED APPLICATION(S)

This application is a National Stage Application of International Application No. PCT/KR2019/015197 filed on Nov. 8, 2019, which claims priority to or the benefit of Korean Patent Application No. 10-2018-0142880 filed on Nov. 19, 2018 and Korean Patent Application No. 10-2019-0140359 filed on Nov. 5, 2019, the disclosures of which are incorporated herein by reference in their entirety.

TECHNICAL FIELD

The present disclosure relates to a novel compound and to an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

Related Arts (Patent Literature 0001) Korean Patent Application Publication No. 10-2013-073537

DETAILED DESCRIPTION

Technical Problem

It is an object of the present disclosure to provide a novel compound and an organic light emitting device including the same.

Technical Solution

In one aspect of the disclosure, there is provided a compound represented by the following Chemical Formula 1.

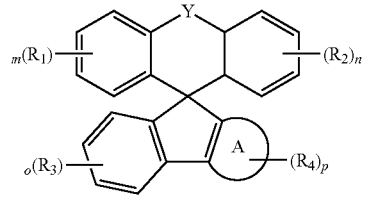

[Chemical Formula 1]

wherein, in Chemical Formula 1,

Y is O or S,

A is a benzofuran ring, a benzothiophene ring, dibenzofuran ring or dibenzothiophene ring, $R_1$, $R_2$, $R_3$ and $R_4$ are each independently a substituent represented by the following Chemical Formula 2, and m, n, o and p are each independently 0 or 1, and at least one thereof is 1,

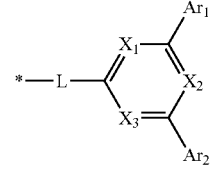

[Chemical Formula 2]

wherein, in Chemical Formula 2,

L is a single bond or a substituted or unsubstituted $C_{6-30}$ arylene, $X_1$, $X_2$ and $X_3$ are each independently N or CR', and at least two thereof are N, each R' is independently hydrogen, deuterium, a substituted or unsubstituted $C_{1-10}$ alkyl, a substituted or unsubstituted $C_{6-30}$ aryl, or a substituted or unsubstituted $C_{5-60}$ heteroaryl containing one or more heteroatoms selected from the group consisting of N, O and S, and $Ar_1$ and $Ar_2$ are each independently hydrogen, deuterium, a substituted or unsubstituted $C_{1-10}$ alkyl, a substituted or unsubstituted $C_{6-30}$ aryl, or a substituted or unsubstituted $C_{5-60}$ heteroaryl containing one or more heteroatoms selected from the group consisting of N, O and S.

In another aspect of the prevent disclosure, there is provided an organic light emitting device including a first electrode; a second electrode that is disposed to face the first electrode; and one or more organic material layers that are disposed between the first electrode and the second electrode, wherein one or more layers of the organic material layers include the polymer according to the present disclosure.

Advantageous Effects

The compound represented by Chemical Formula 1 described above can be used as a material of an organic material layer of an organic light emitting device, and may improve the efficiency, achieve low driving voltage and/or improve lifetime characteristics in the organic light emitting device. In particular, the compound represented by Chemical Formula 1 described above can be used as a material for hole injection, hole transport, hole injection and transport, light emitting, electron transport, or electron injection.

DESCRIPTION OF THE DRAWINGS

FIG. 1 depicts an example of an organic light emitting device comprising a substrate 1, an anode 2, a light emitting layer 3, and a cathode 4.

FIG. 2 depicts an example of an organic light emitting device comprising a substrate 1, an anode 2, a hole injection layer 5, a hole transport layer 6, a light emitting layer 7, an electron transport layer 8 and a cathode 4.

DETAILED DESCRIPTION

Hereinafter, embodiments of the present disclosure are described in more detail to facilitate understanding of the disclosure.

As used herein, the notation , means a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group and may be interpreted as a substituent to which two phenyl groups are linked.

In the present specification, the number of carbon atoms of a carbonyl group is not particularly limited, but is preferably 1 to 40. Specifically, the carbonyl group may be a compound having the following structural formulas, but is not limited thereto.

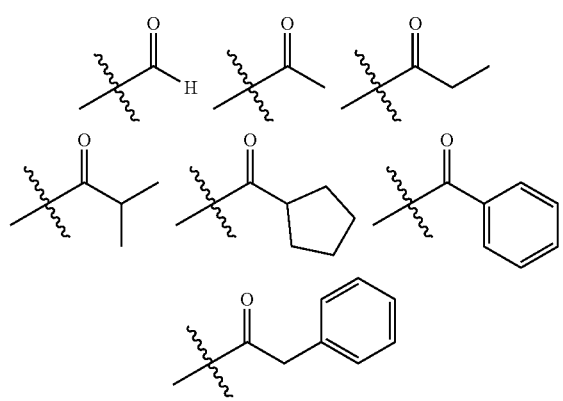

In the present specification, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas, but is not limited thereto.

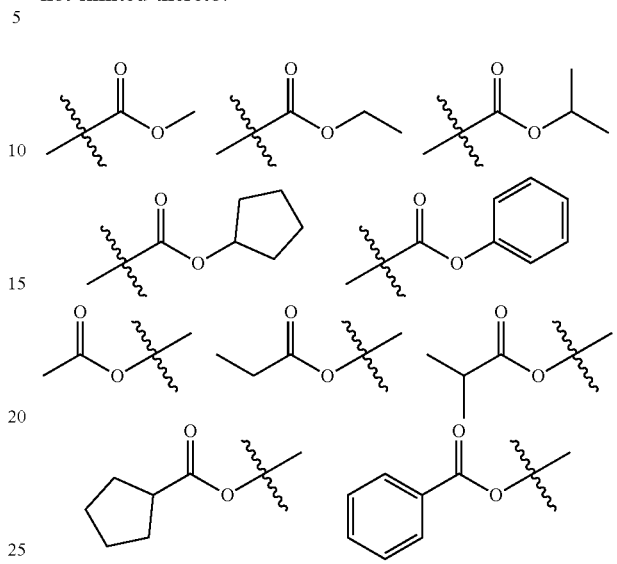

In the present specification, the number of carbon atoms of an imide group is not particularly limited, but is preferably 1 to 25. Specifically, the imide group may be a compound having the following structural formulas, but is not limited thereto.

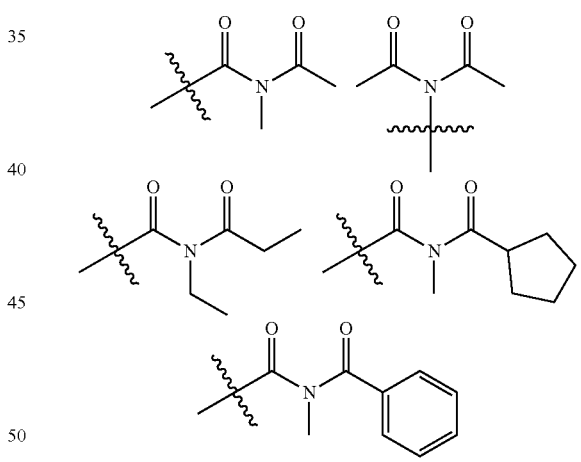

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group may be straight-chain or branched-chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

In the present specification, the alkenyl group may be straight-chain or branched-chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and it may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group or the like, but is not limited thereto.

In the present specification, a fluorenyl group may be substituted, and two substituent groups may be bonded to each other to form a spiro structure. In the case where the fluorenyl group is substituted,

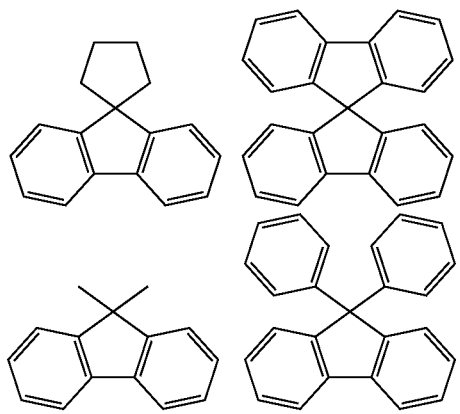

the like can be formed. However, the structure is not limited thereto.

In the present specification, a heterocyclic group is a heterocyclic group including one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocylic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocyclic group is not a monovalent group but formed by combining two substituent groups.

Preferably, the compound represented by Chemical Formula 1 may be any one selected from compounds represented by the following Chemical Formulas 3 to 18:
[Chemical Formula 3]
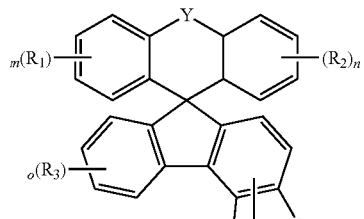
[Chemical Formula 4]
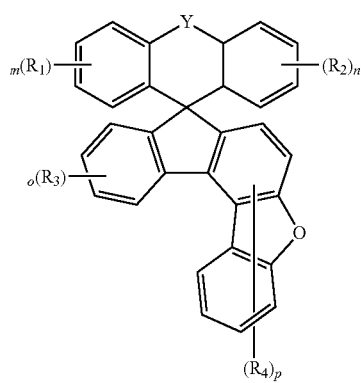
[Chemical Formula 5]
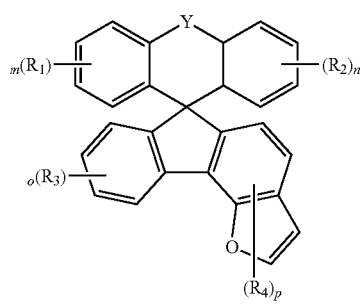
[Chemical Formula 6]
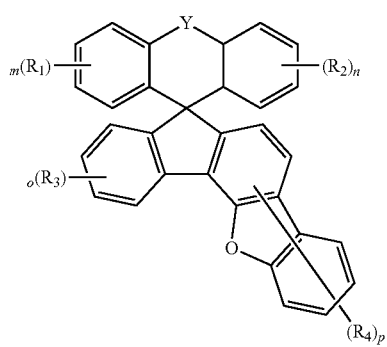
[Chemical Formula 7]
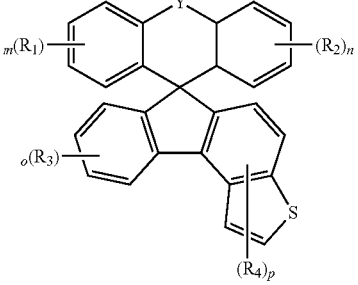
[Chemical Formula 8]
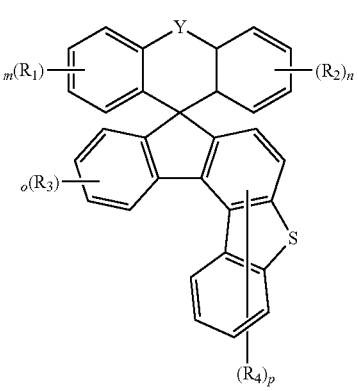
[Chemical Formula 9]
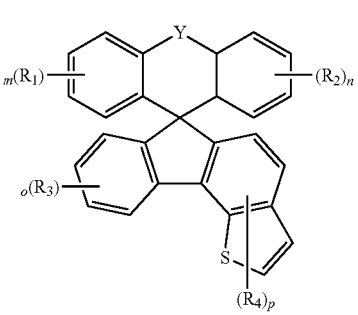
[Chemical Formula 10]
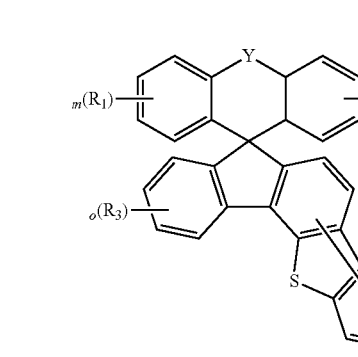
[Chemical Formula 11]
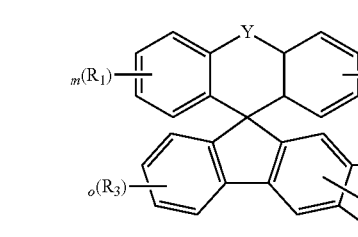

[Chemical Formula 12]

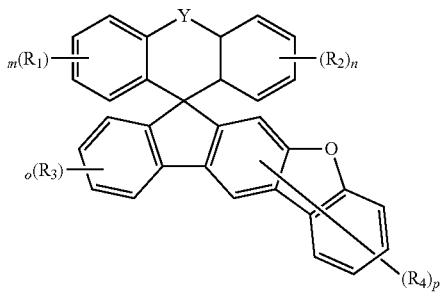

[Chemical Formula 13]

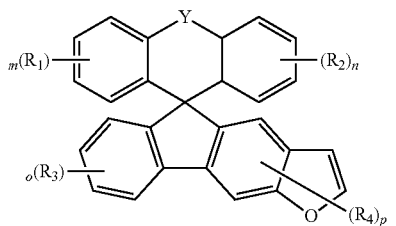

[Chemical Formula 14]

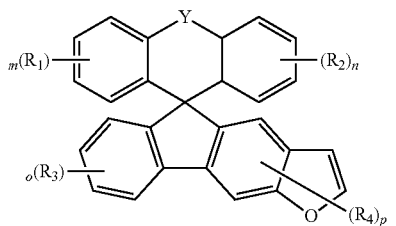

[Chemical Formula 15]

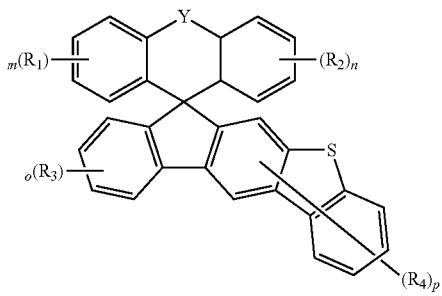

[Chemical Formula 16]

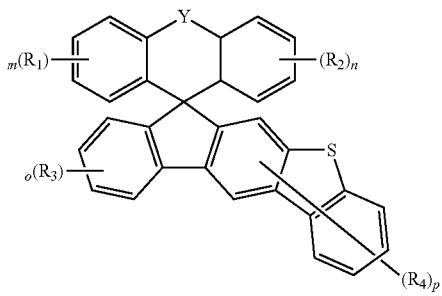

[Chemical Formula 17]

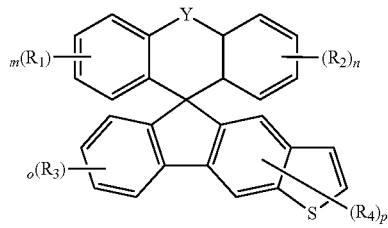

[Chemical Formula 18]

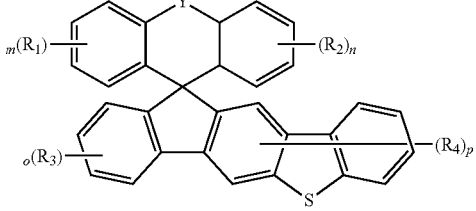

wherein, in Chemical Formulas 3 to 18,

Y, $R_1$, $R_2$, $R_3$, $R_4$, m, n, o and p are the same as defined above.

Preferably, L may be a single bond, phenylene or biphenylylene.

Preferably, $Ar_1$ and $Ar_2$ are each independently phenyl, biphenylyl, naphthyl, terphenylyl, dimethylfluorenyl, diphenylfluorenyl or pyridyl. They may be each independently unsubstituted or substituted with cyano, $C_{1-10}$ alkyl or $C_{1-10}$ alkoxy.

Preferably, $Ar_1$ and $Ar_2$ are each independently phenyl, biphenylyl, naphthyl or pyridyl. They may be each independently unsubstituted or substituted with cyano, $C_{1-10}$ alkyl or $C_{1-10}$ alkoxy.

Preferably, R' may be hydrogen.

Preferably, the compound represented by Chemical Formula 1 may be any one selected from the group consisting of the following:

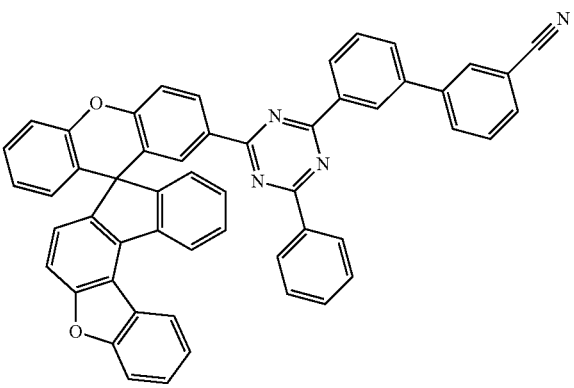

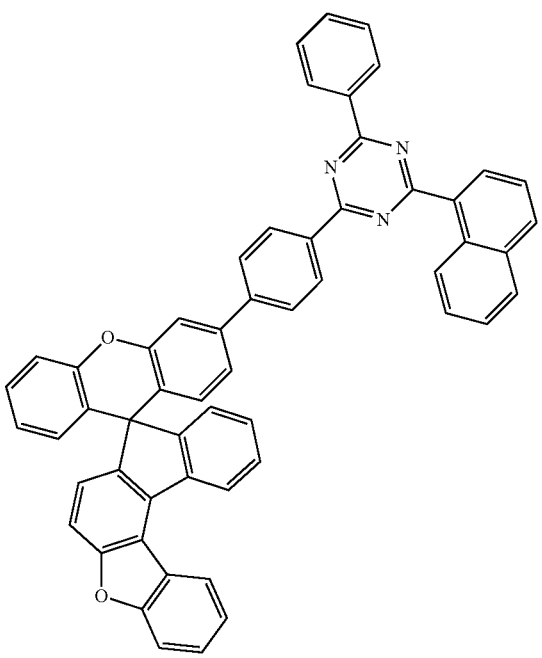
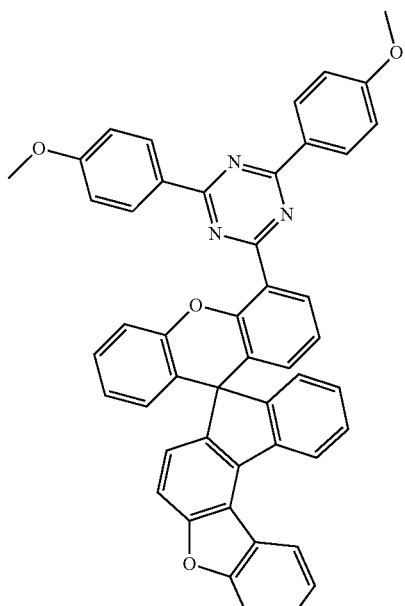
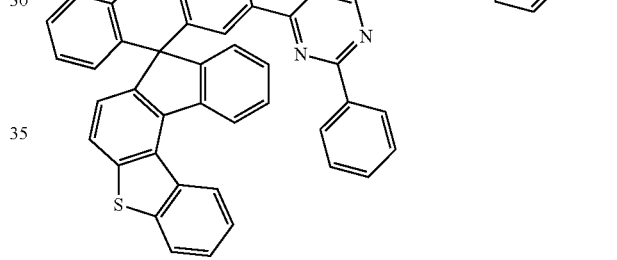
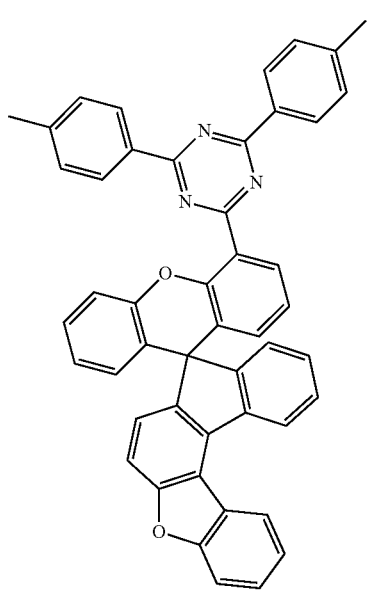
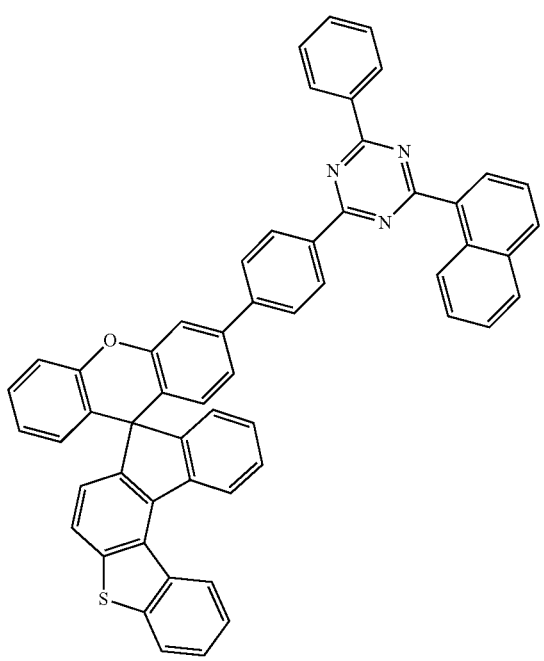

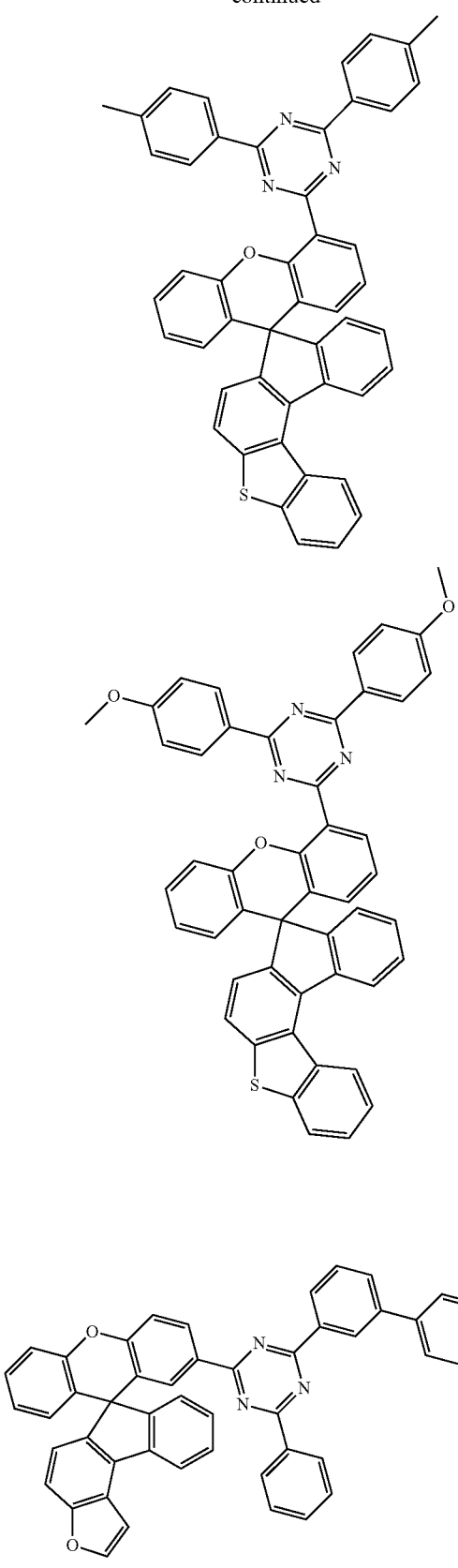
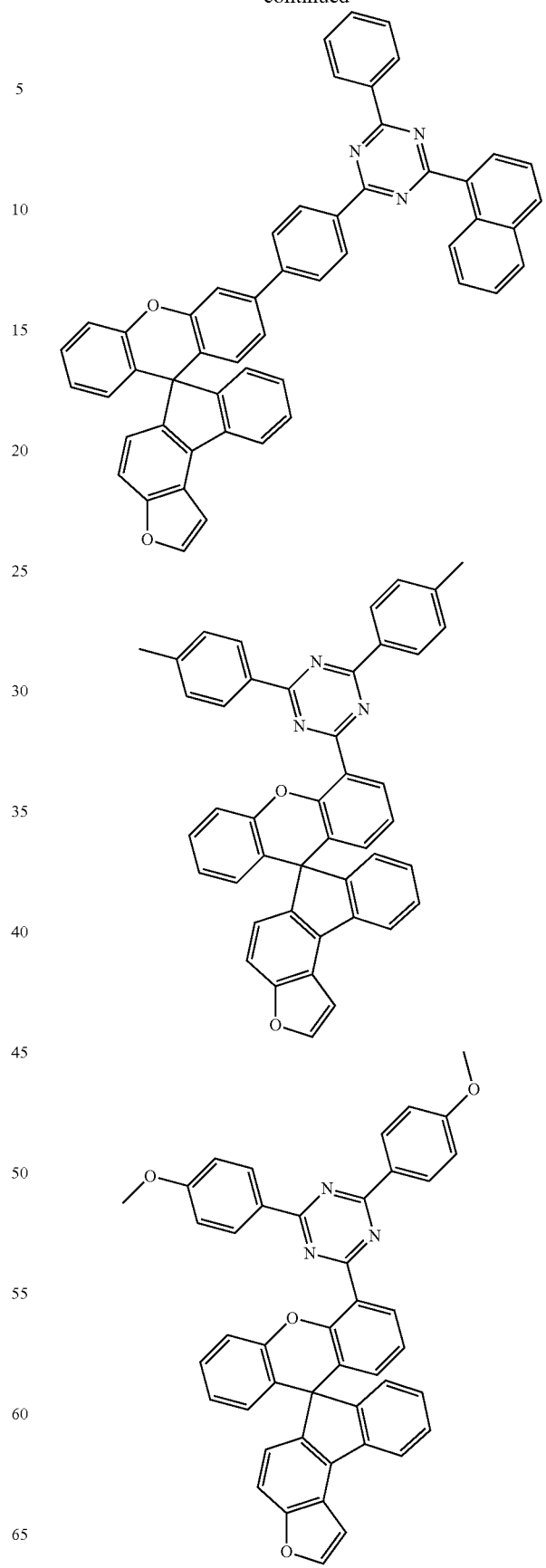

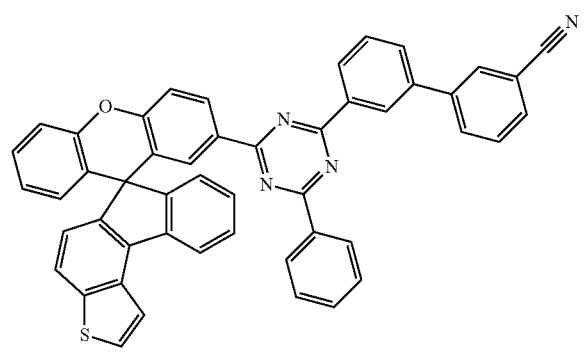
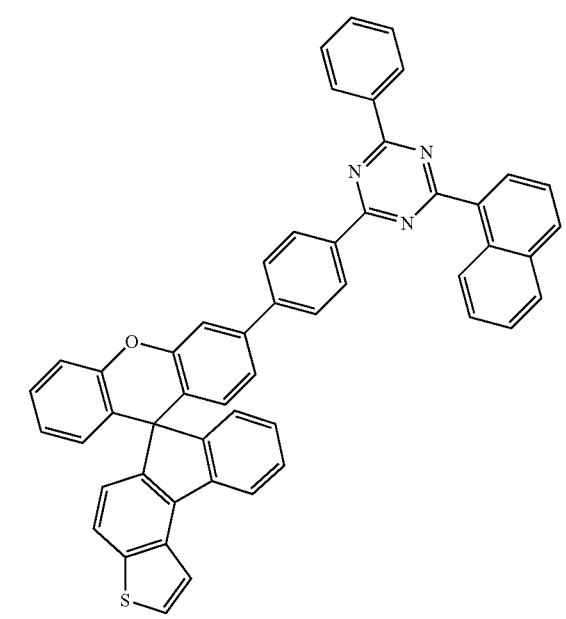
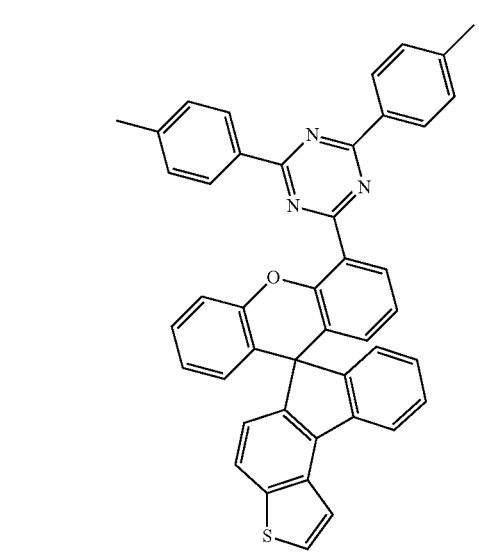
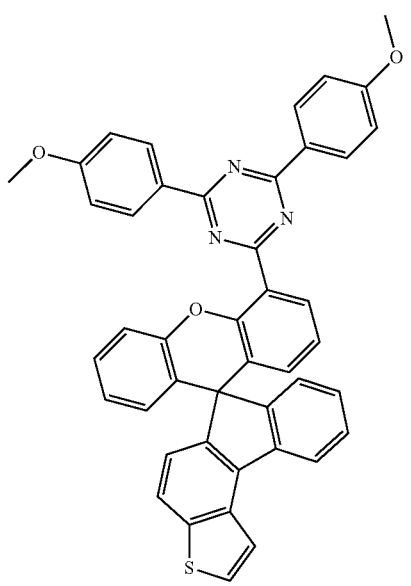 [SMILES: COc1ccc(-c2nc(-c3ccc(OC)cc3)nc(-c3cccc4c3Oc3ccccc3C43c4ccccc4-c4c3ccc3sccc43)n2)cc1]
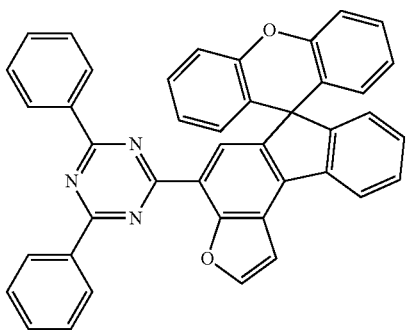
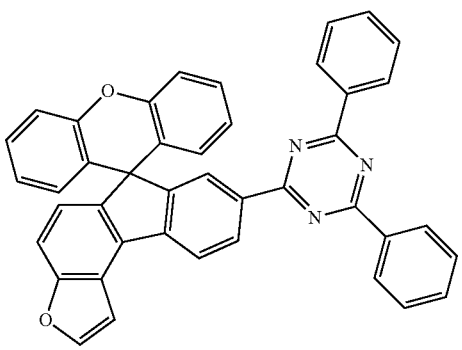
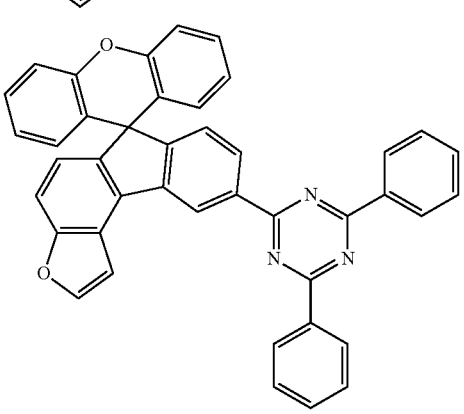

-continued
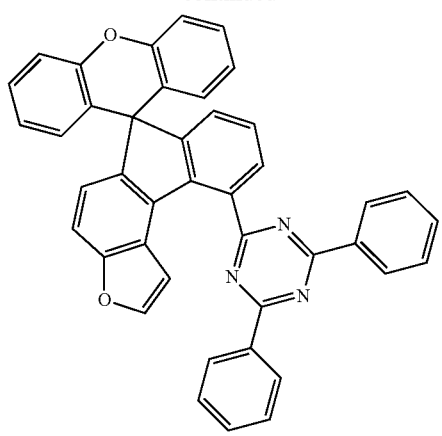
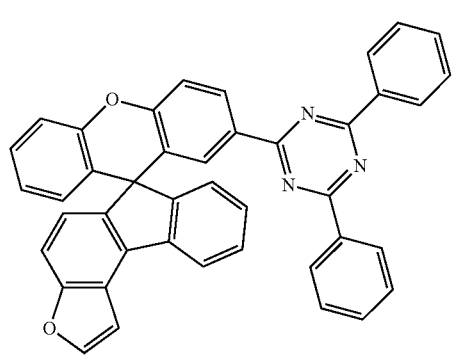
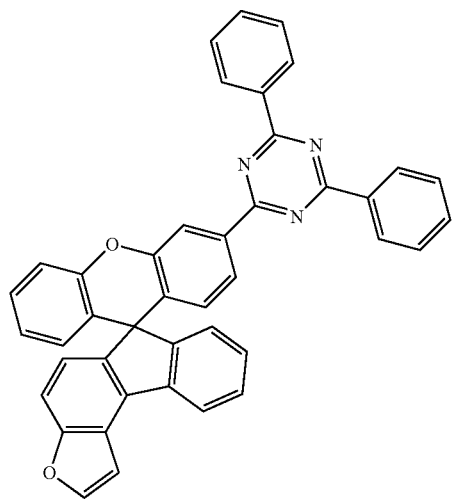
-continued
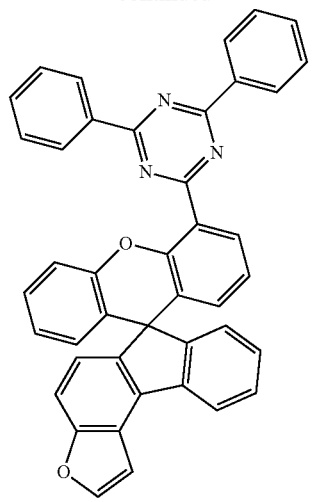
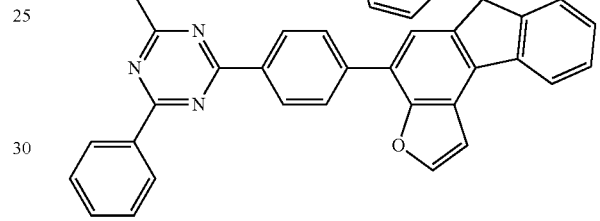
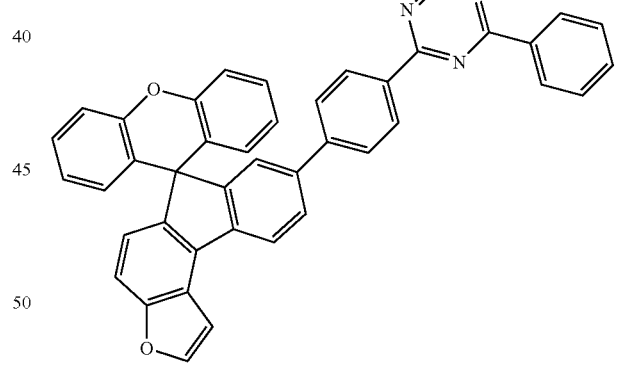
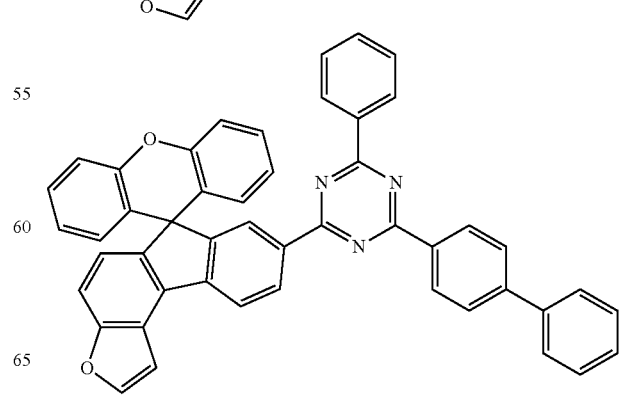

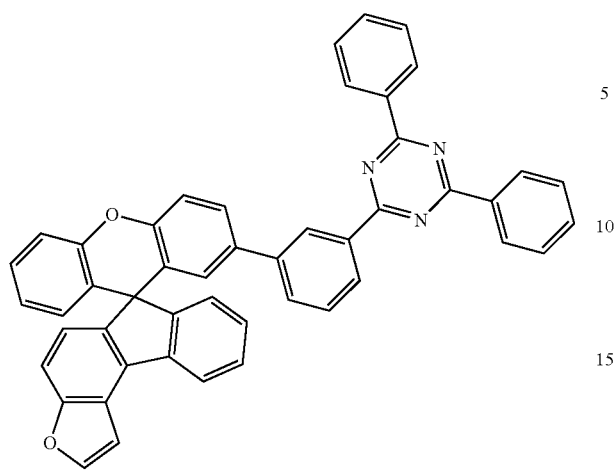
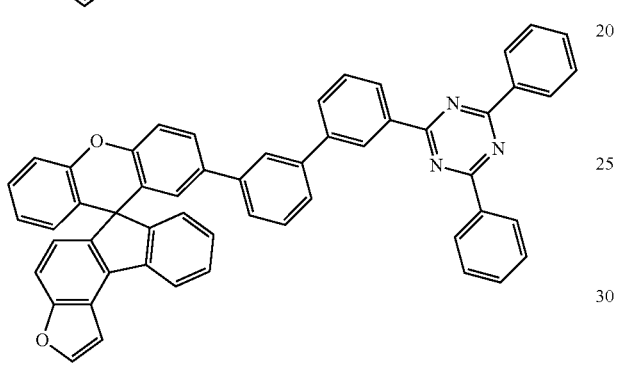
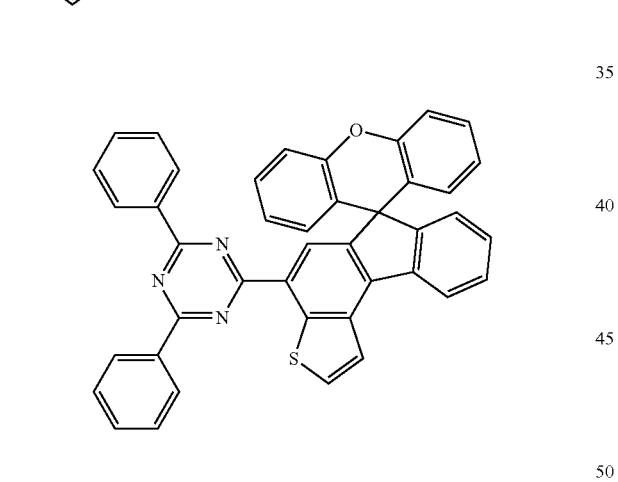
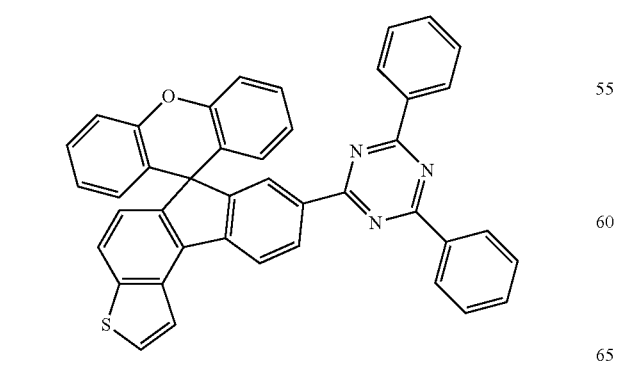
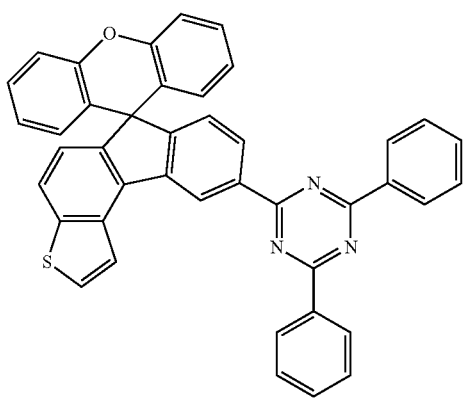
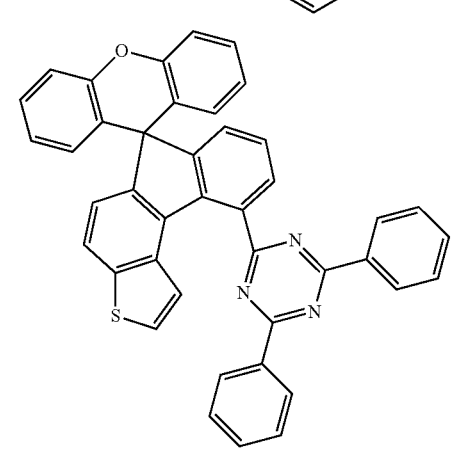
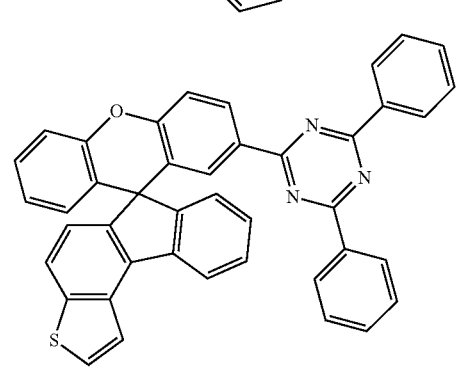
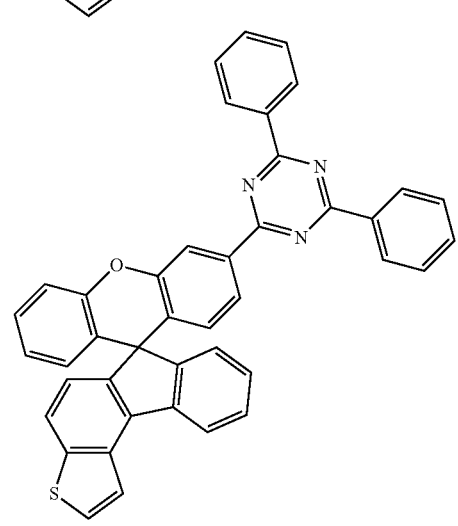

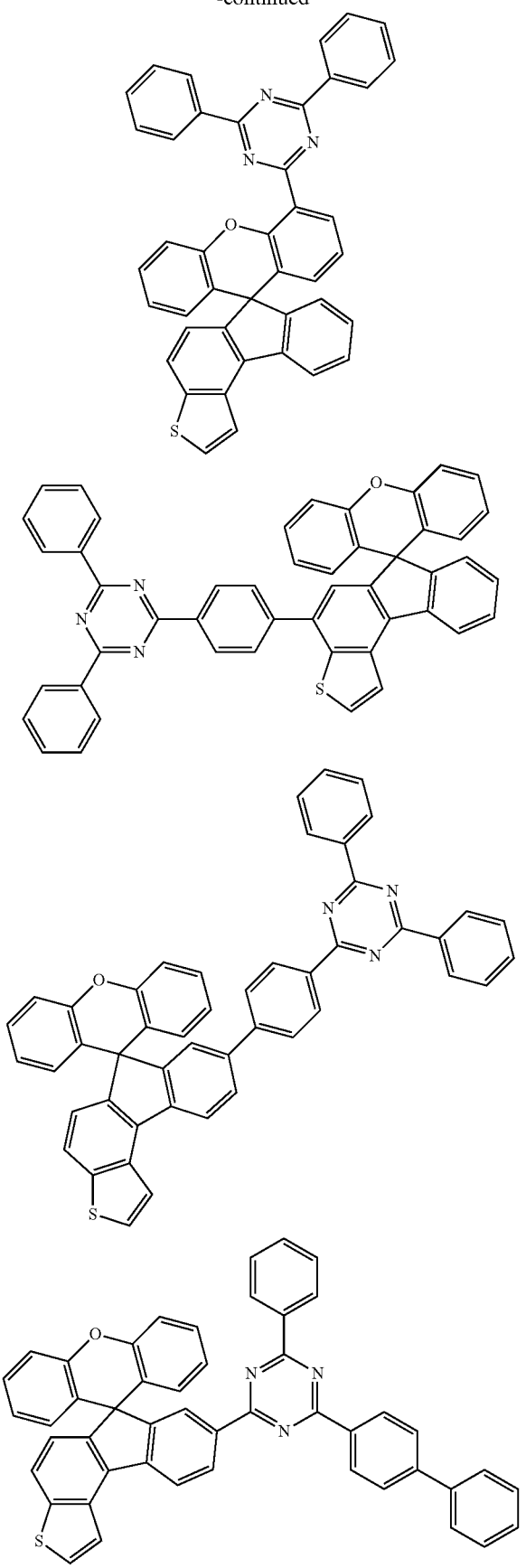
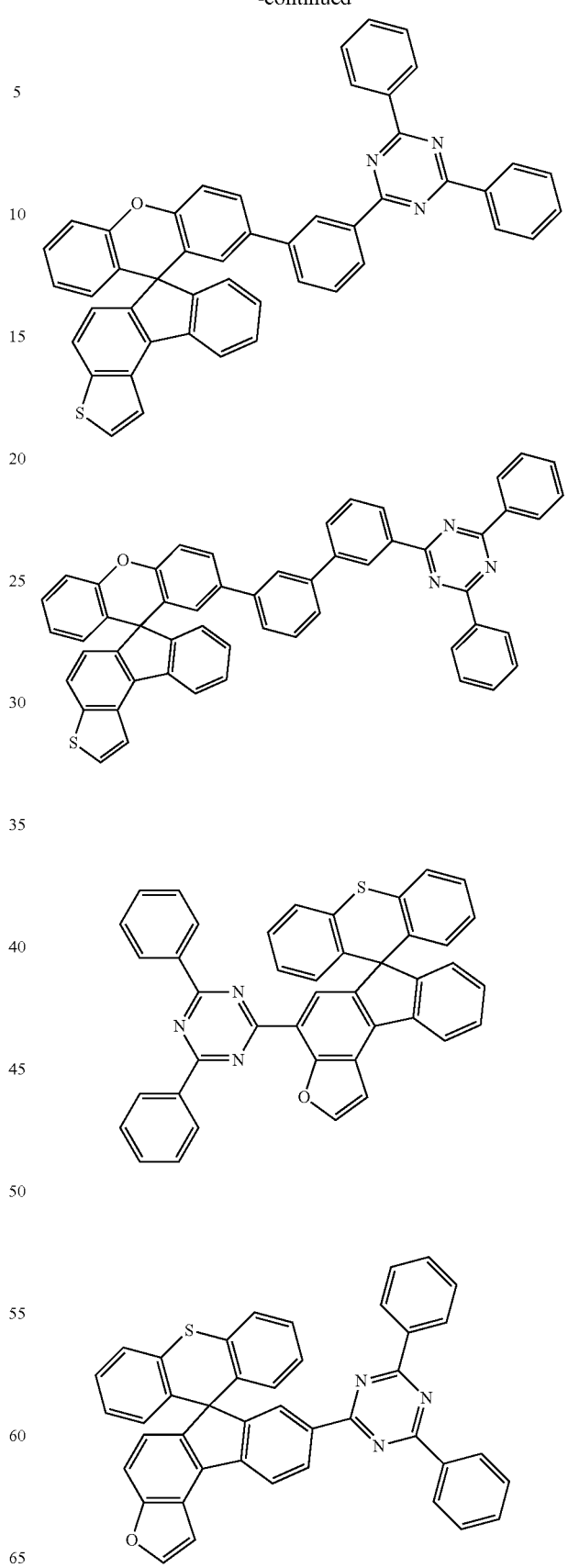

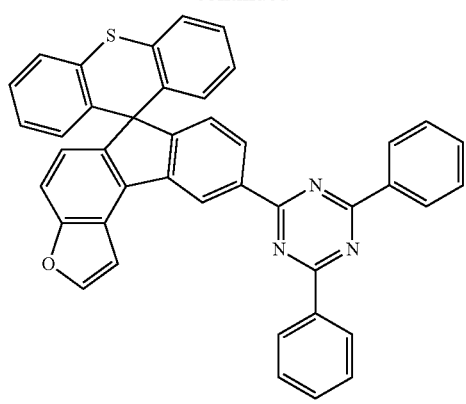
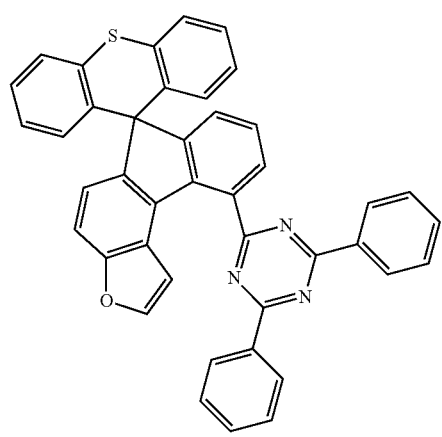
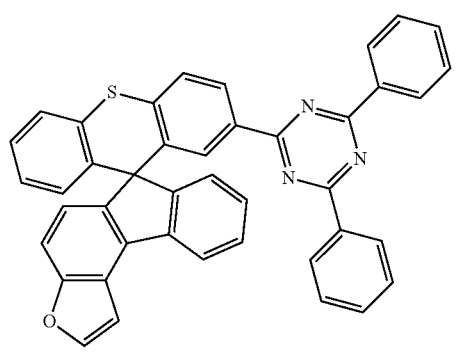
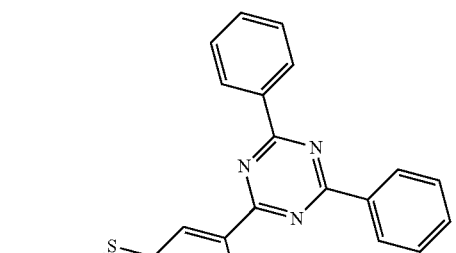
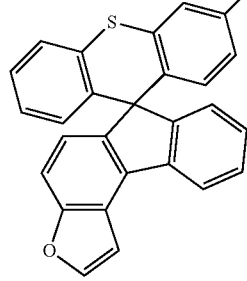
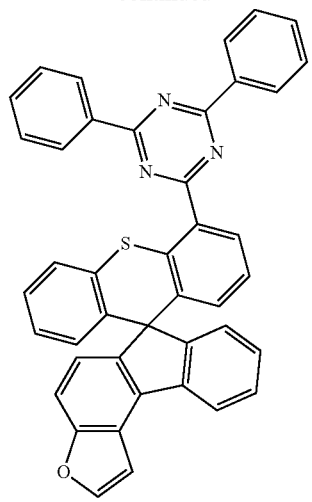
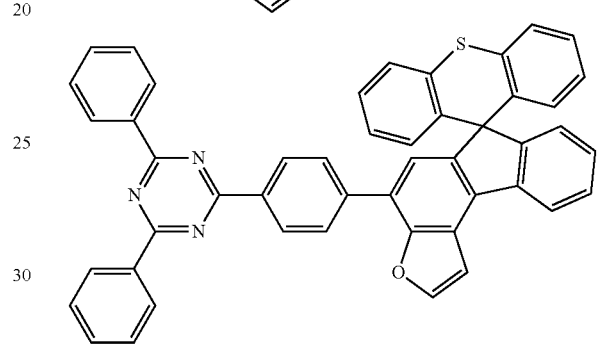
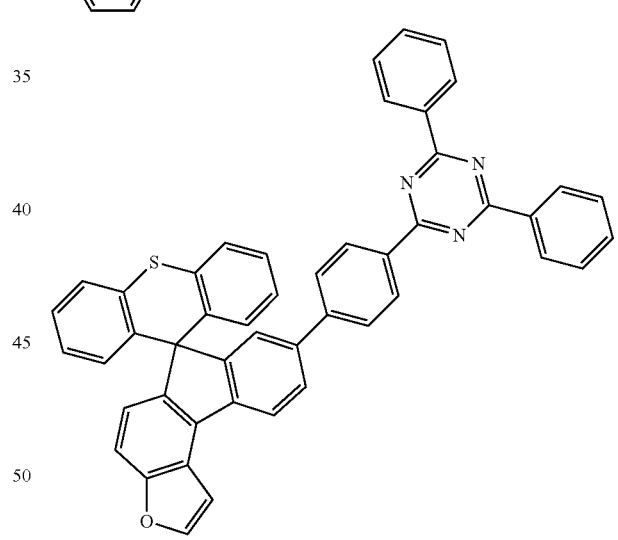
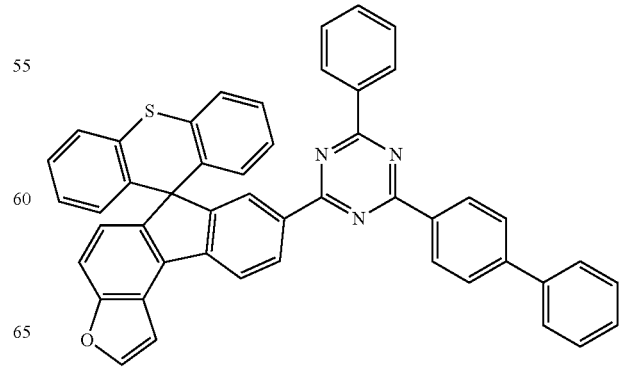

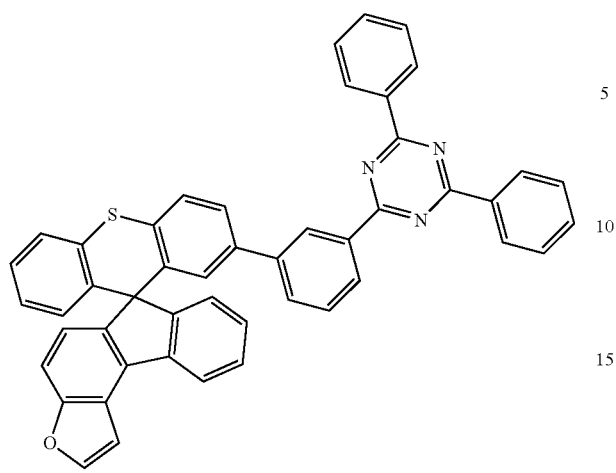
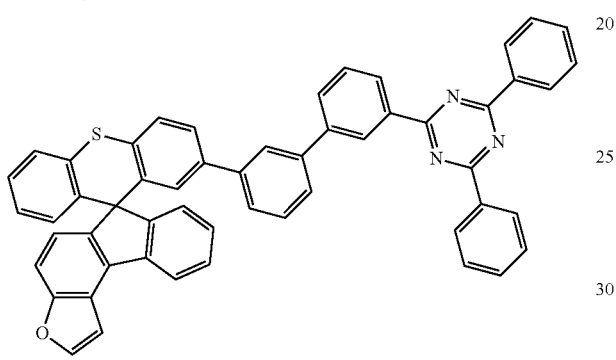
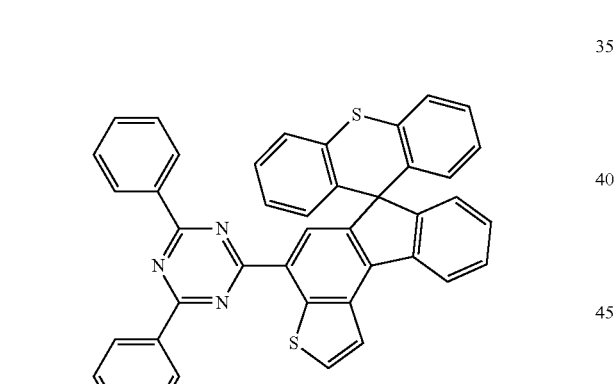
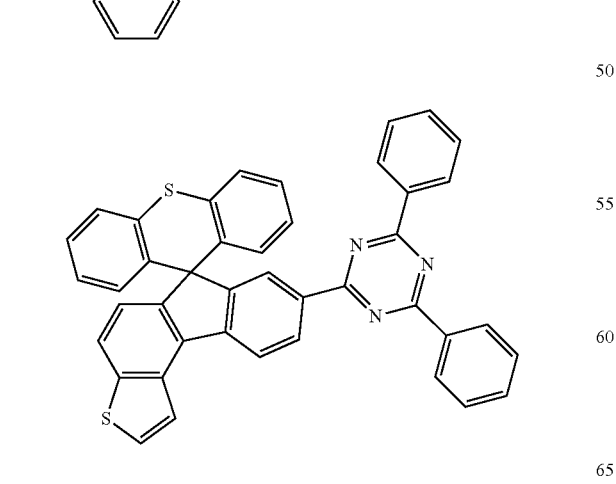
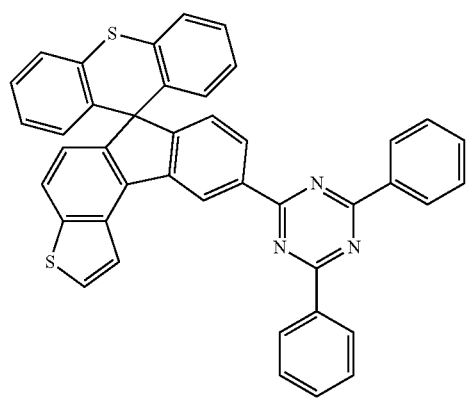
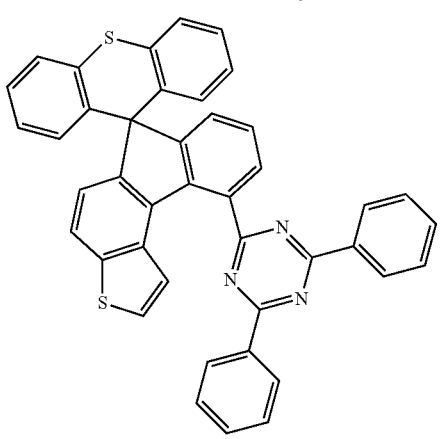
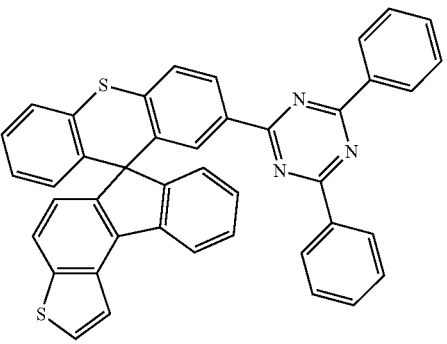
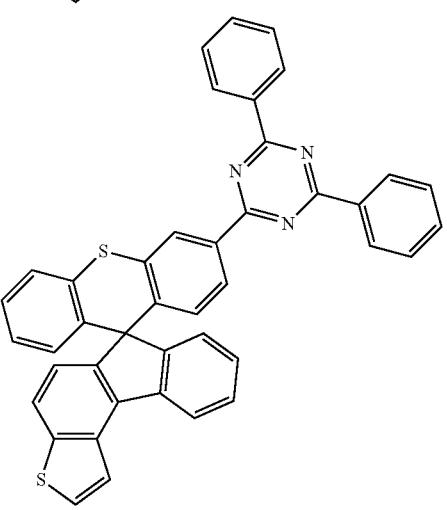

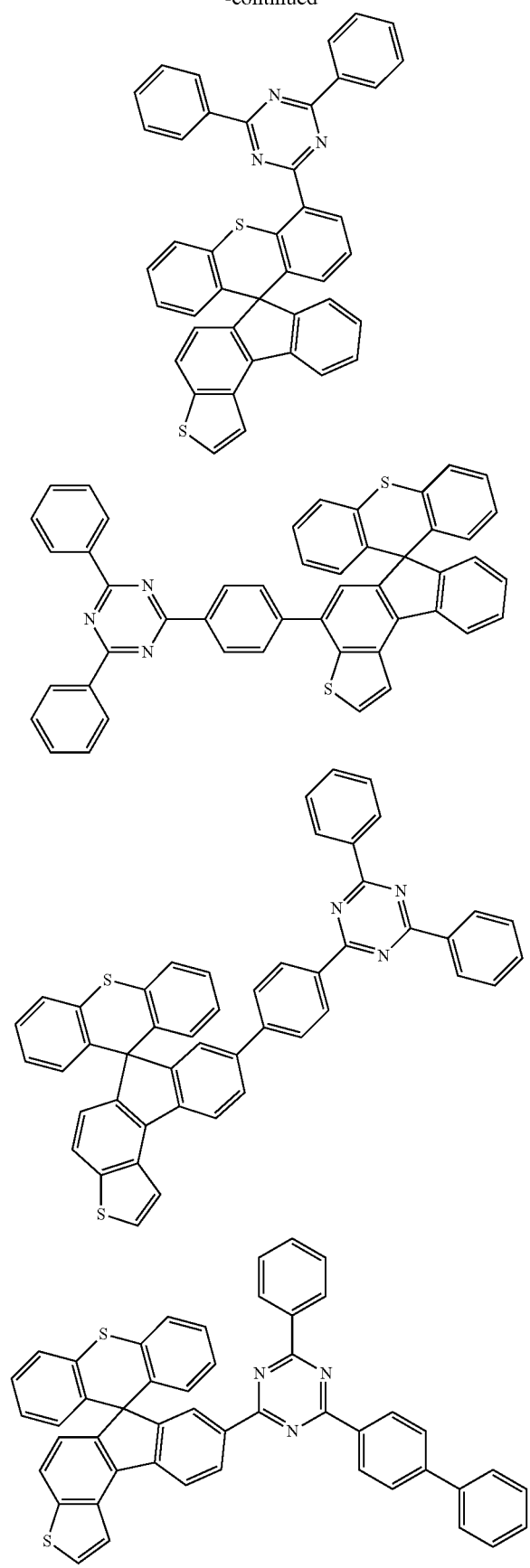
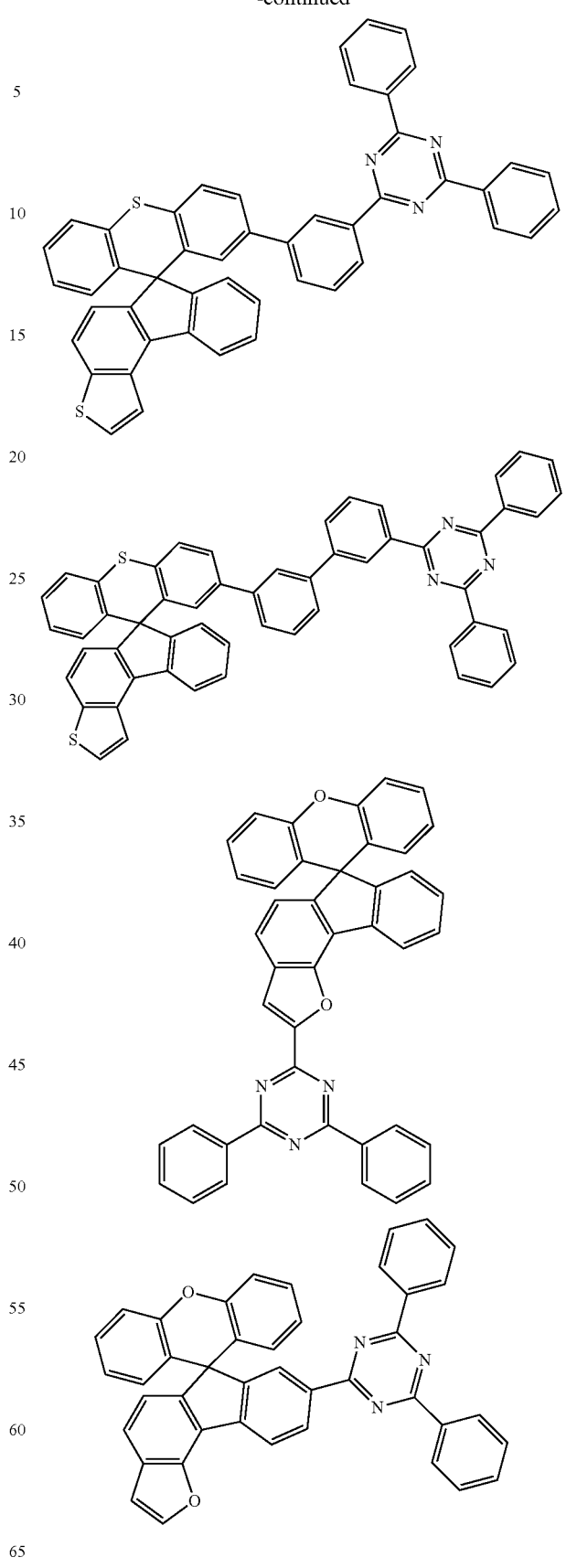

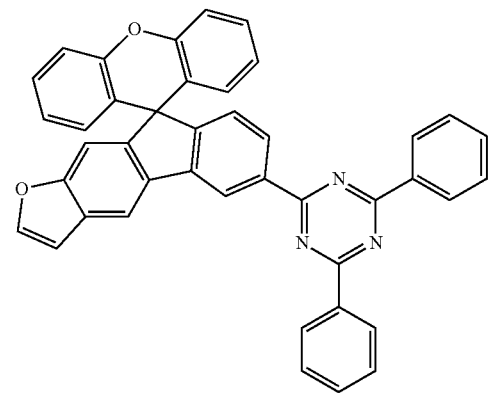
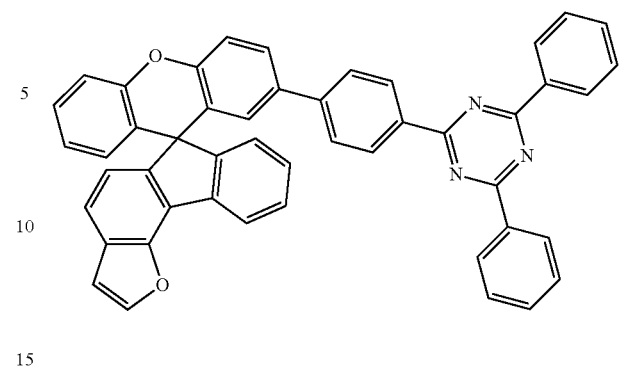
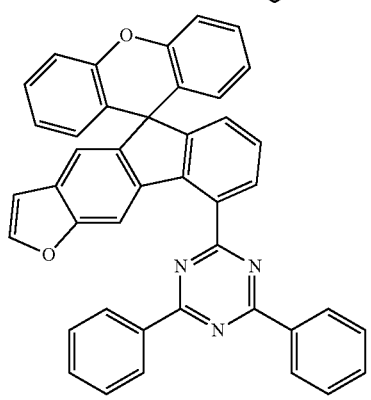
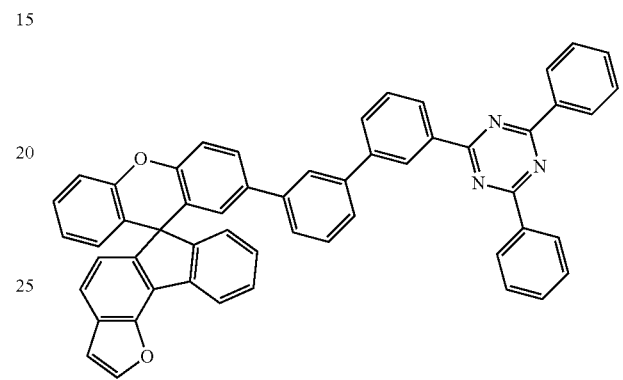
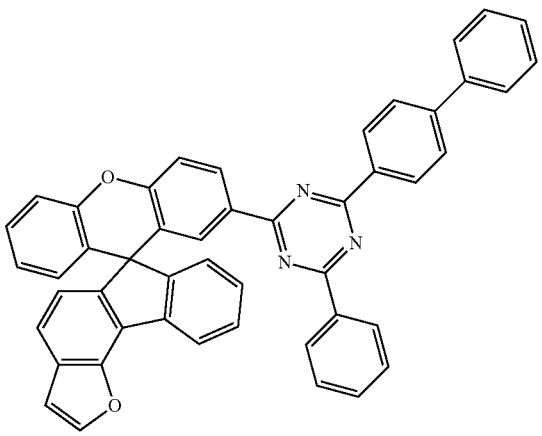
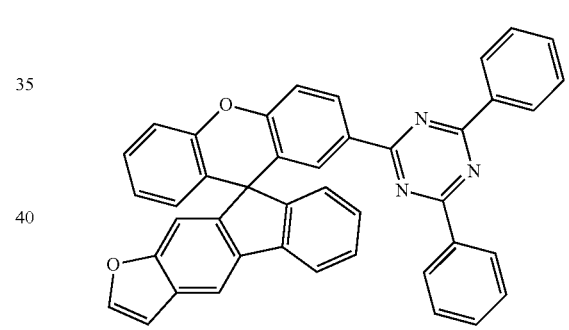
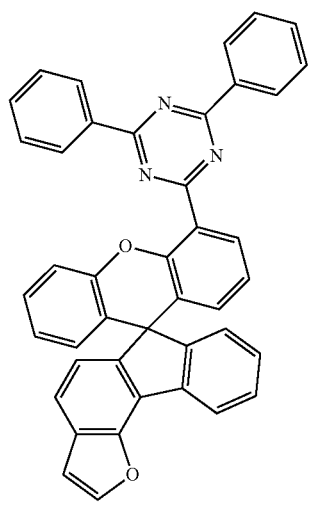
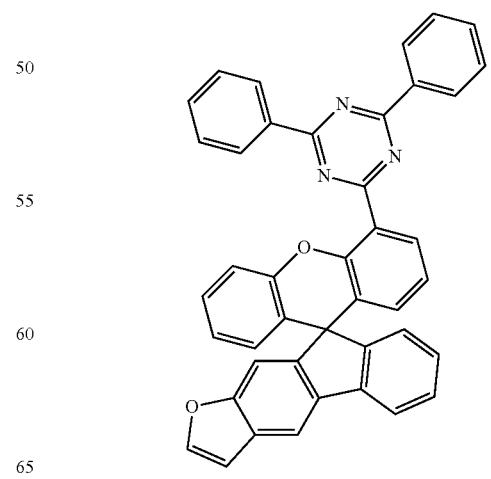

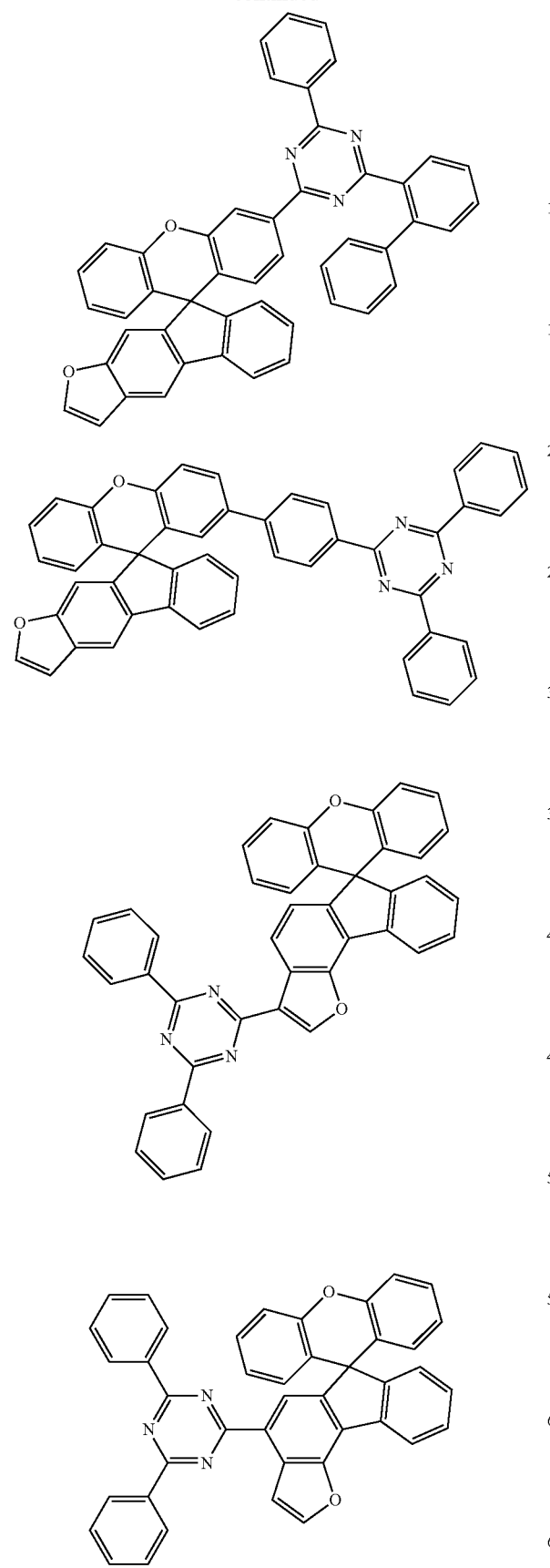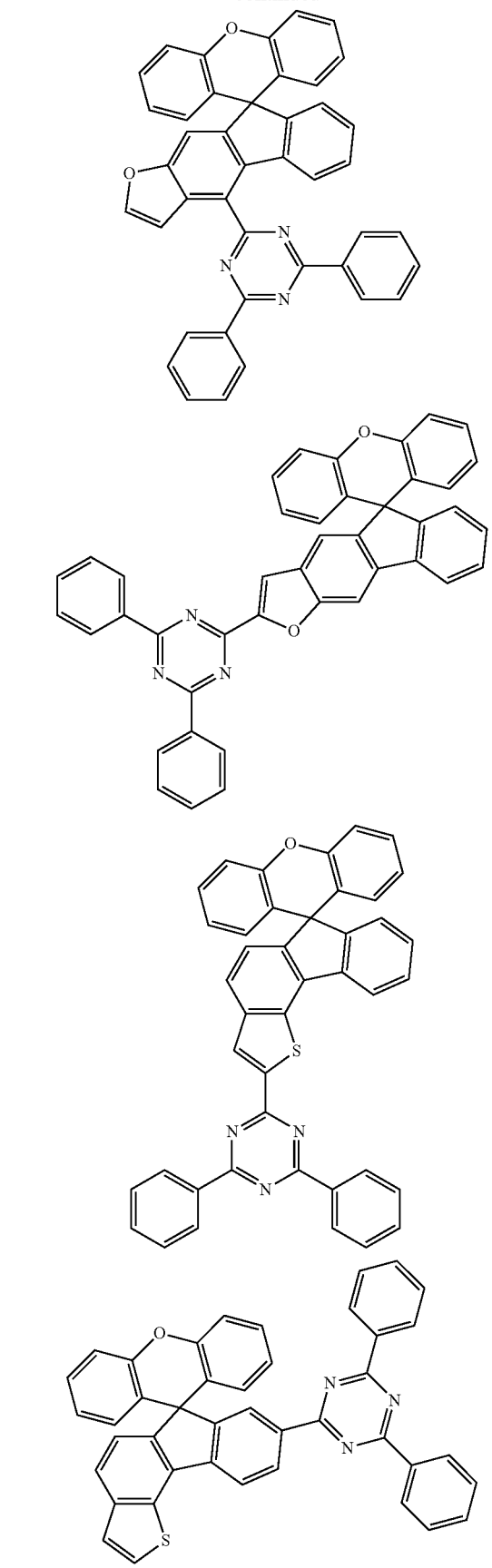

33
-continued
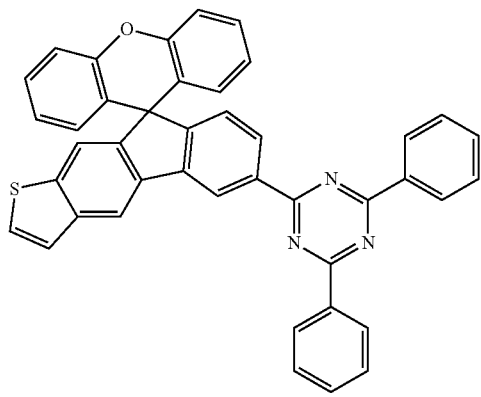
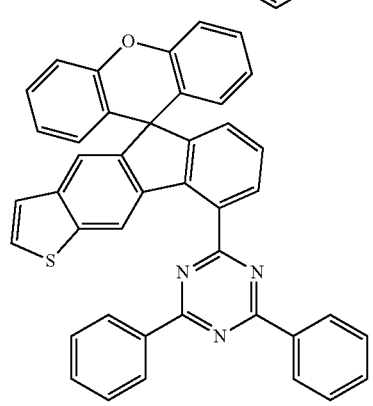
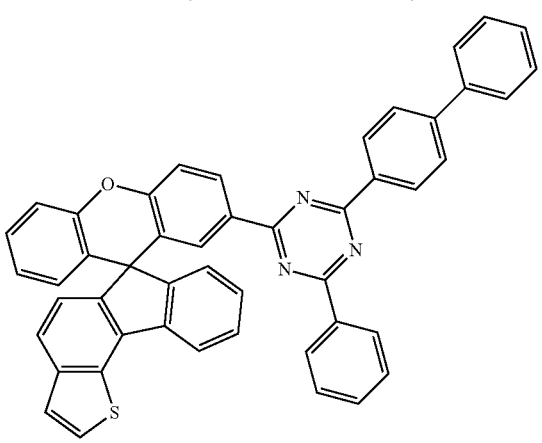
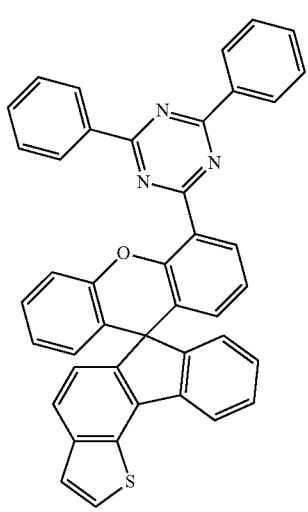
34
-continued
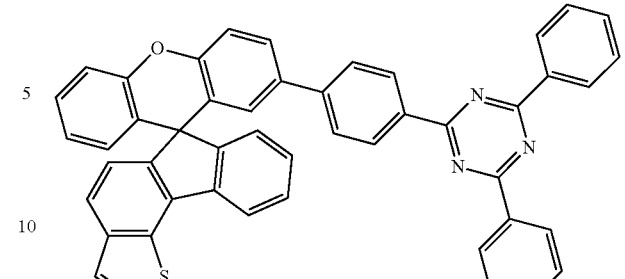
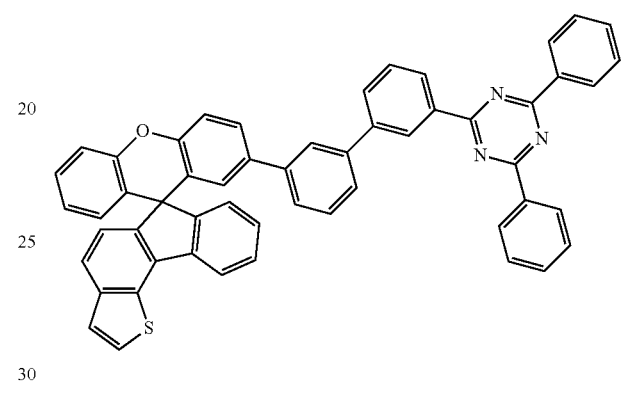
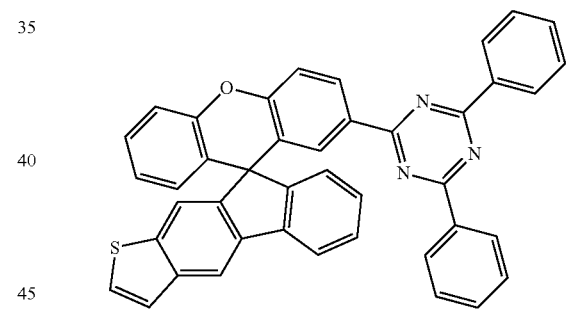
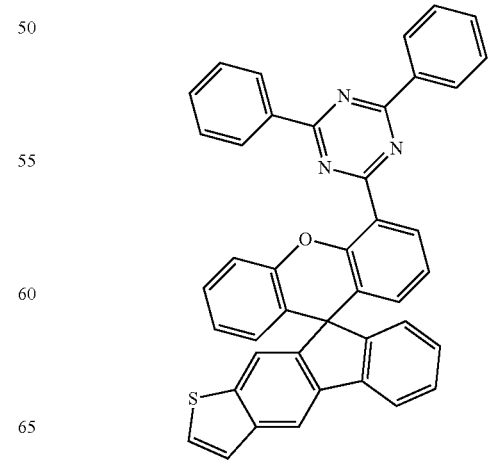

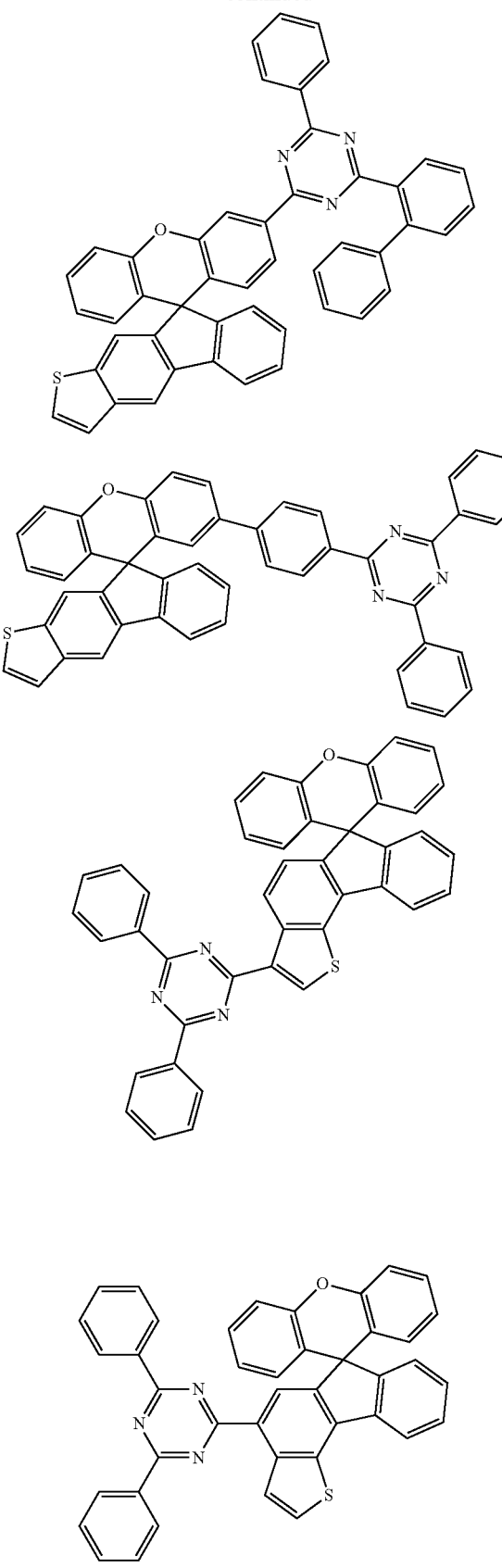
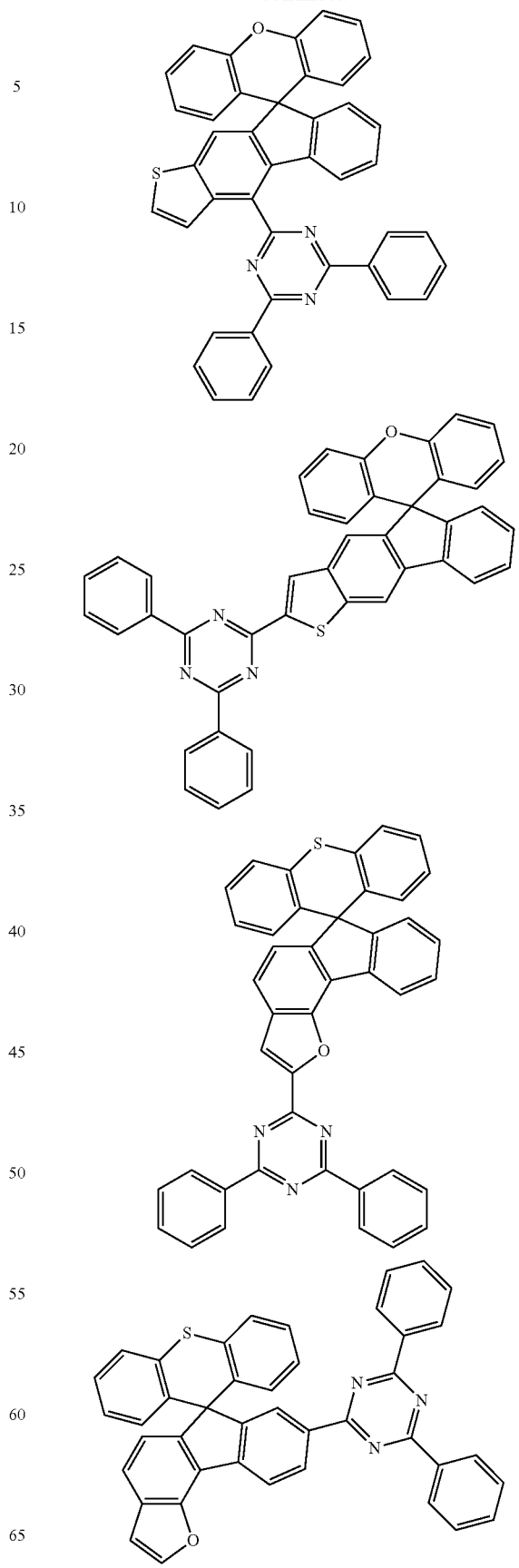

37
-continued
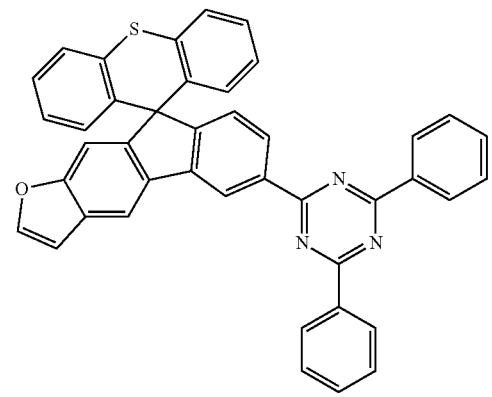
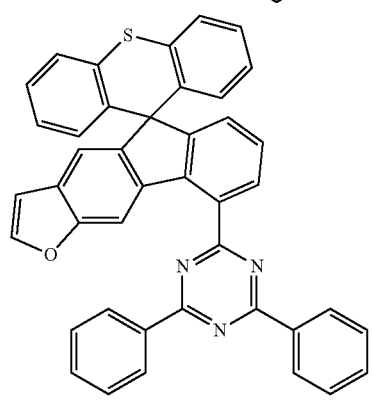
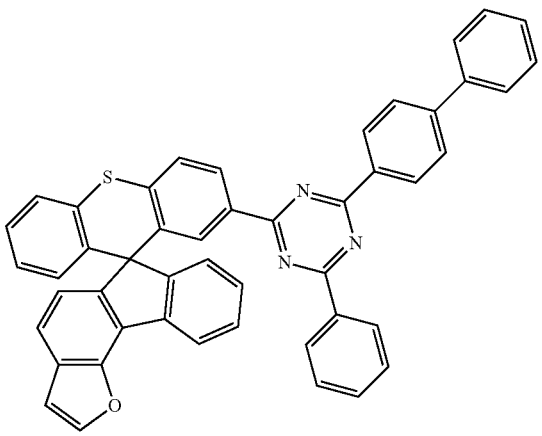
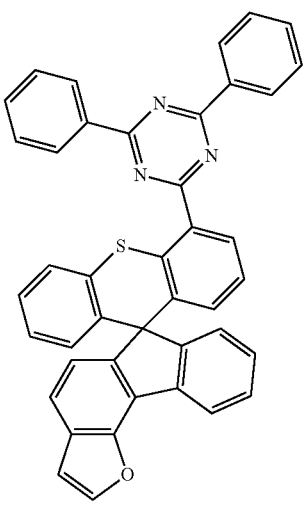
38
-continued
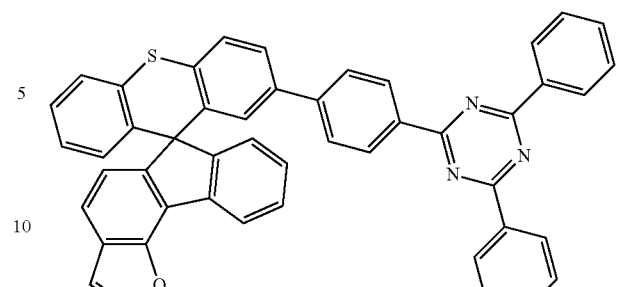
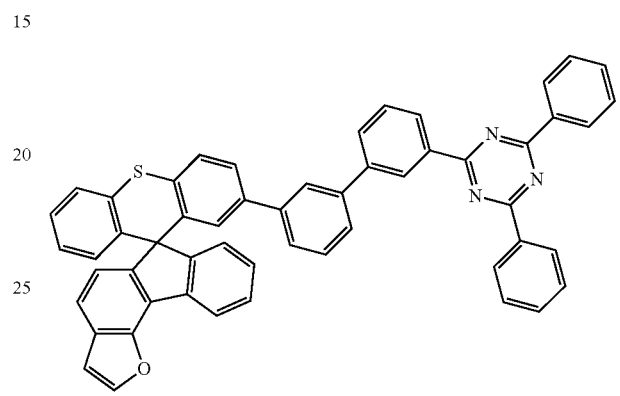
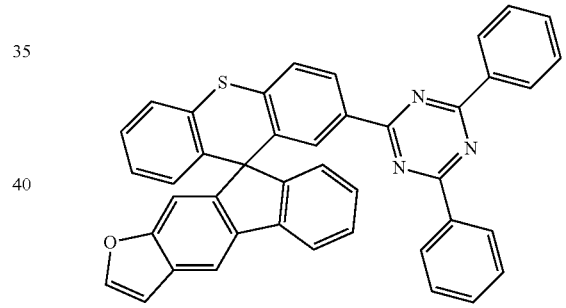
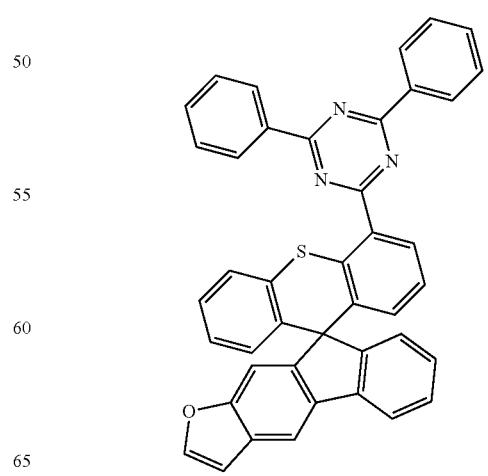

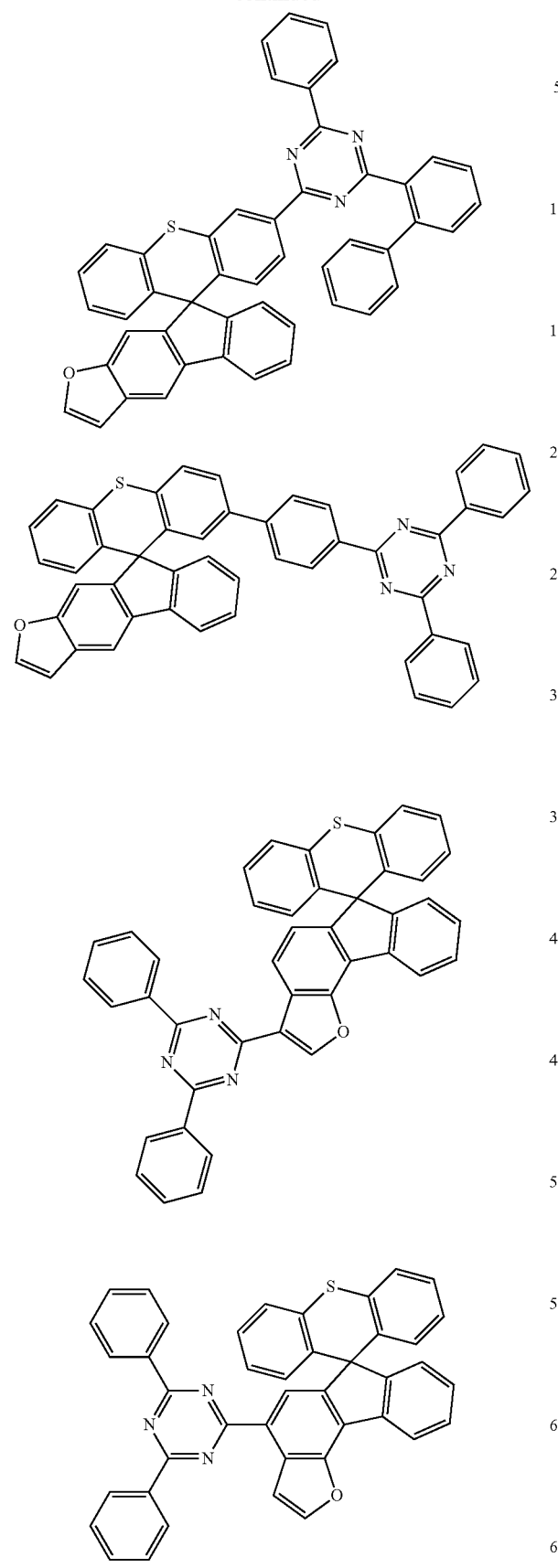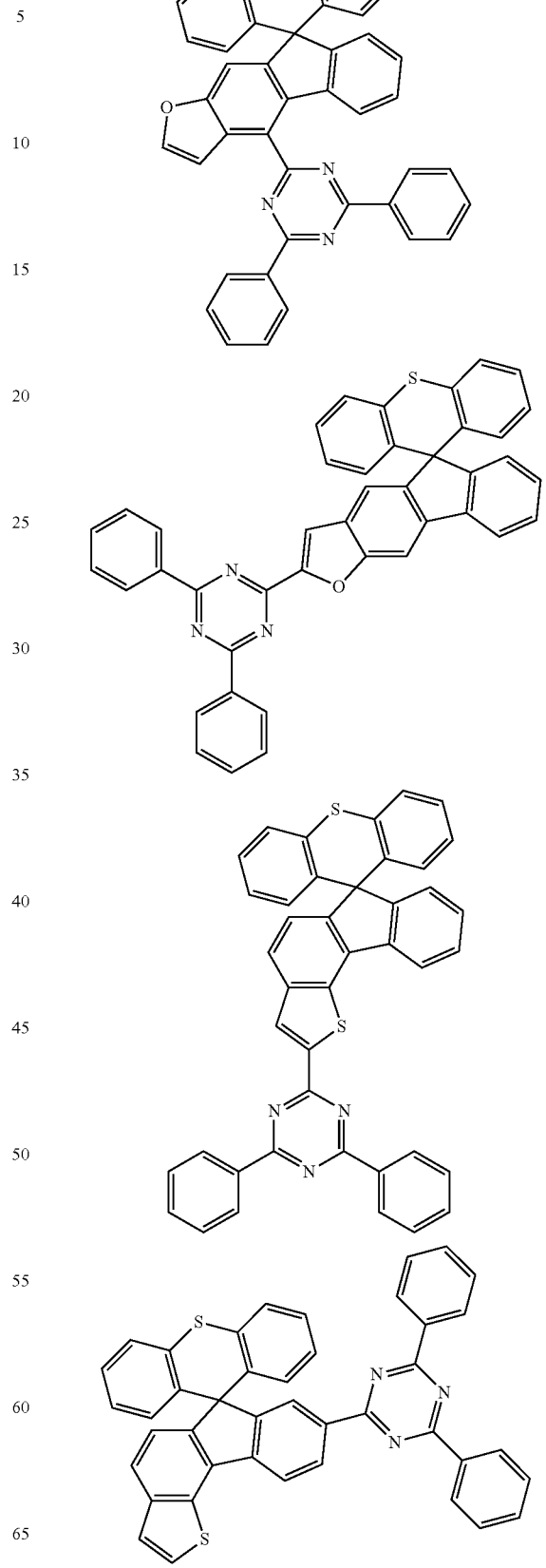

-continued
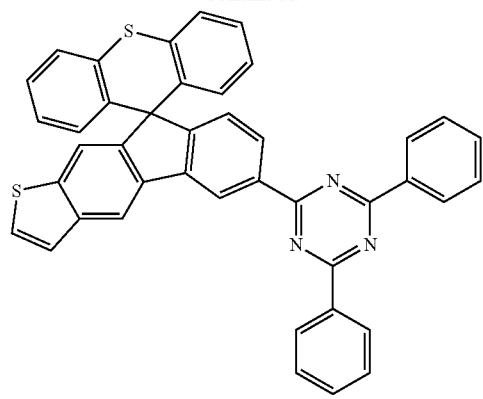
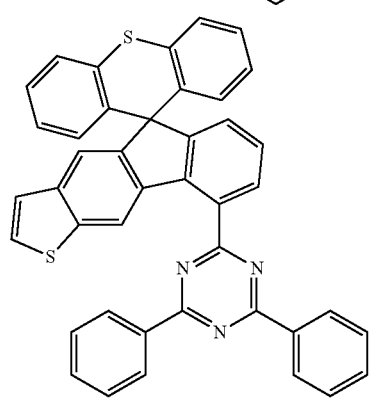
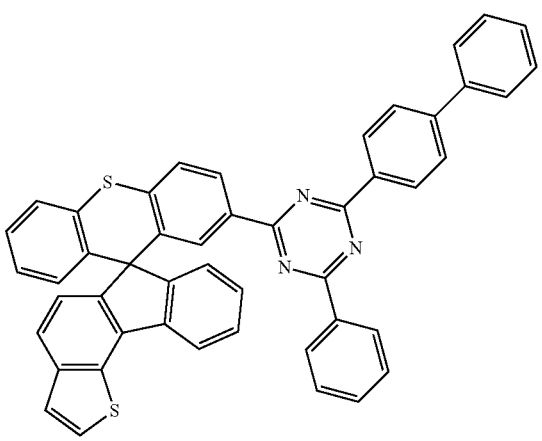
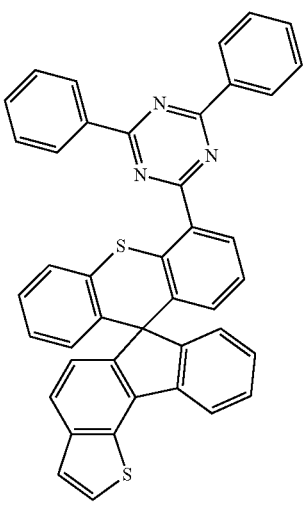
-continued
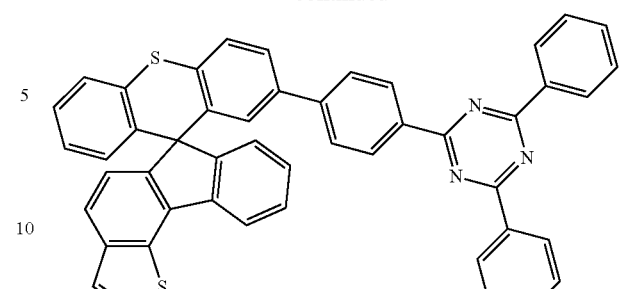
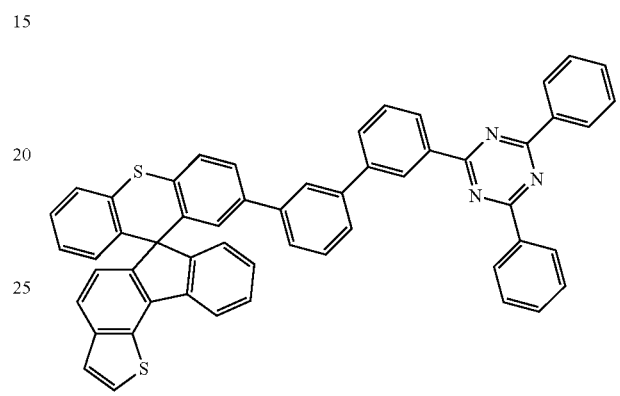
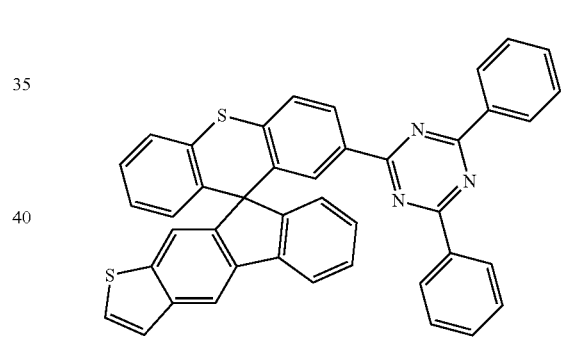
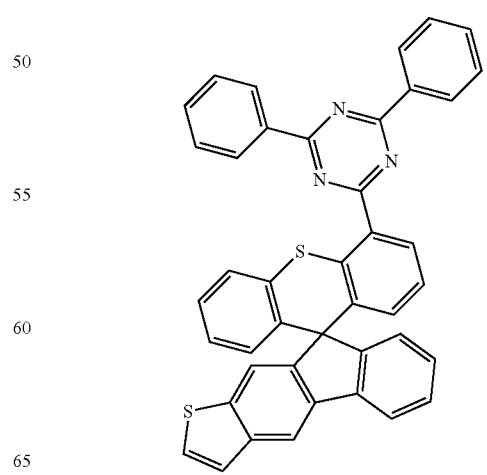

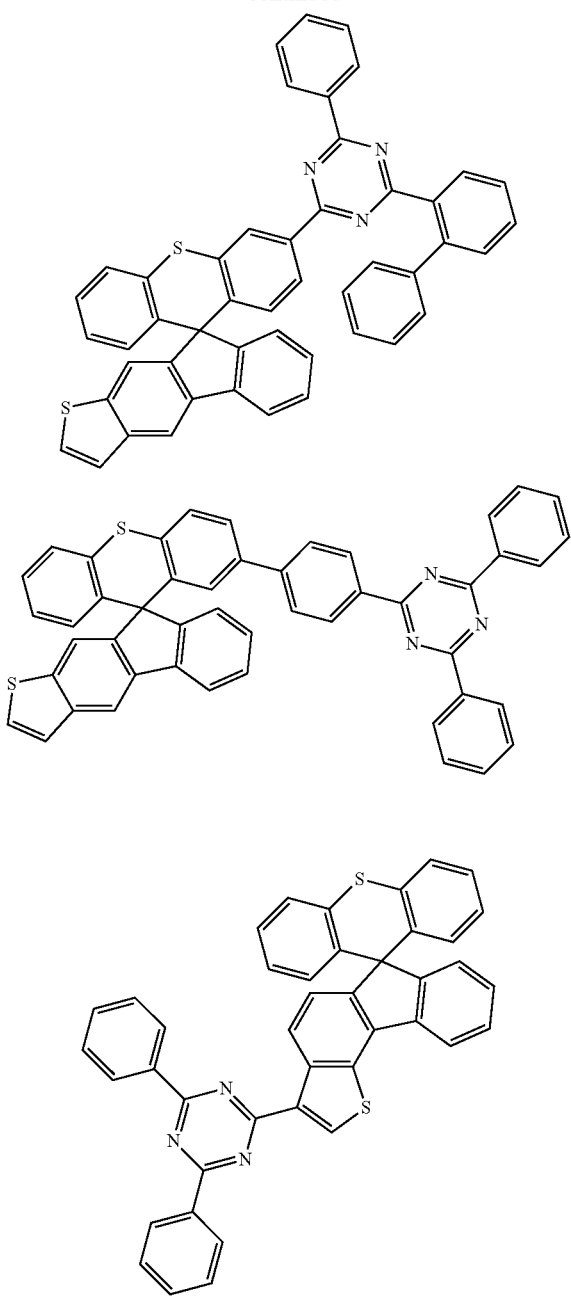
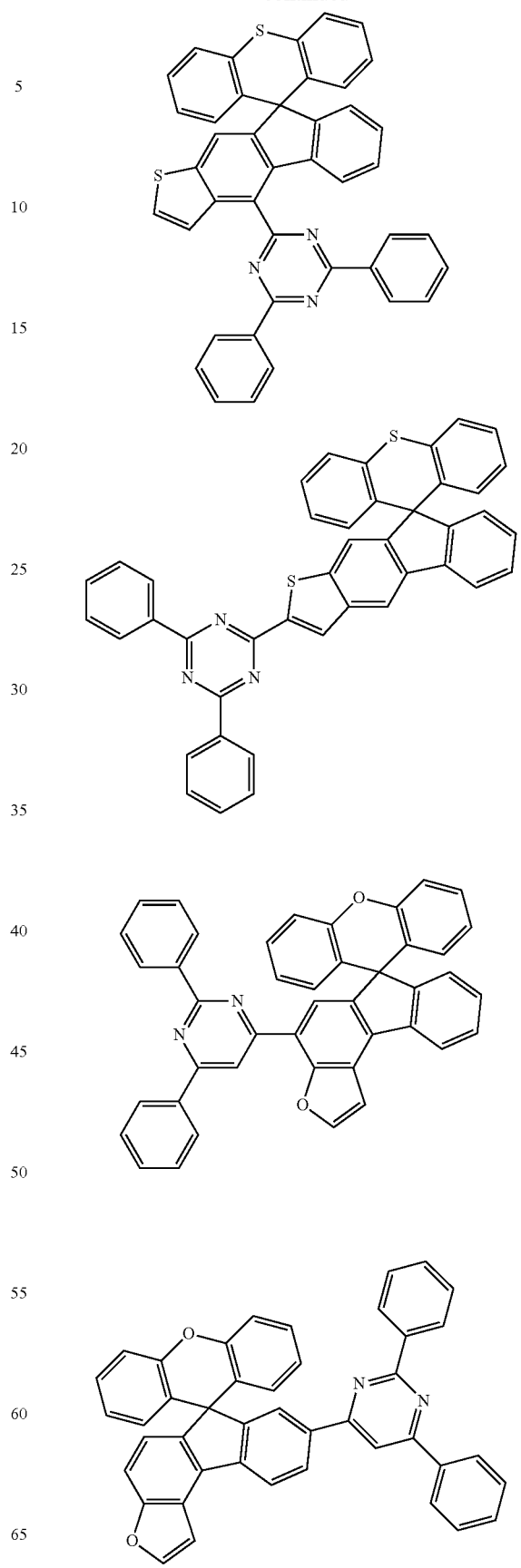

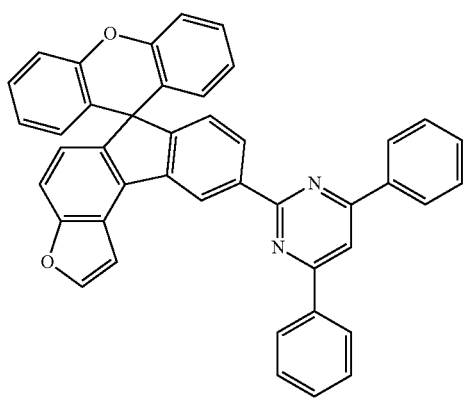
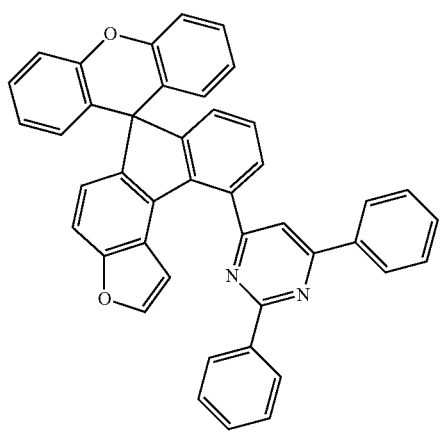
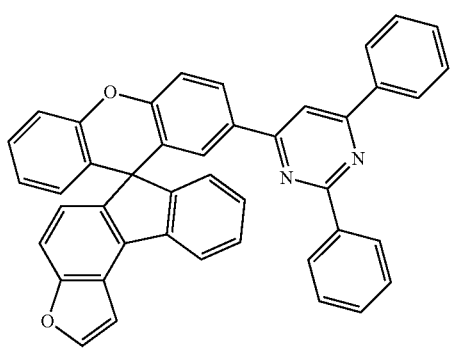
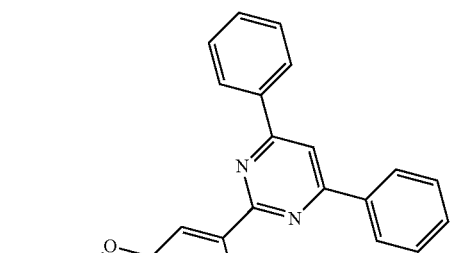
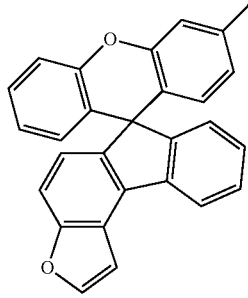
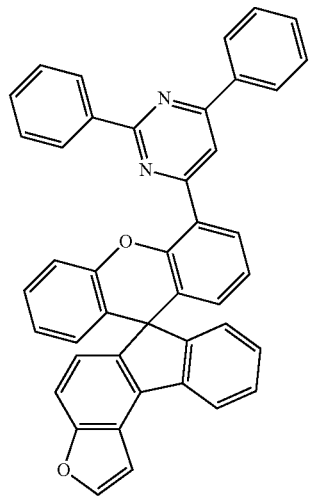
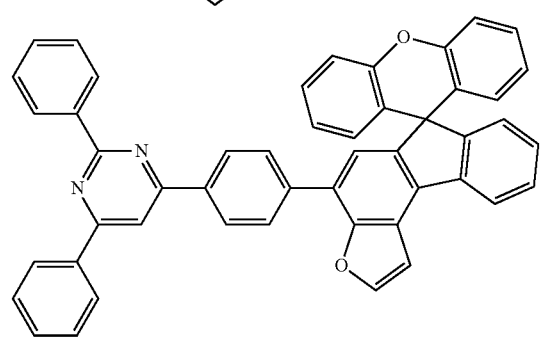
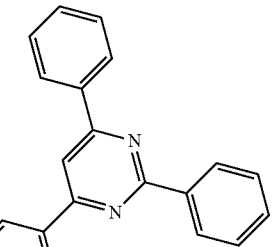
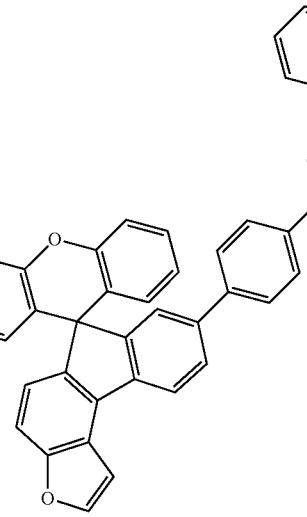
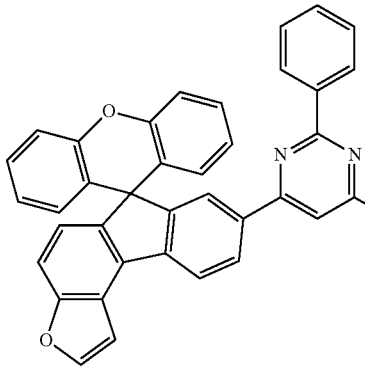

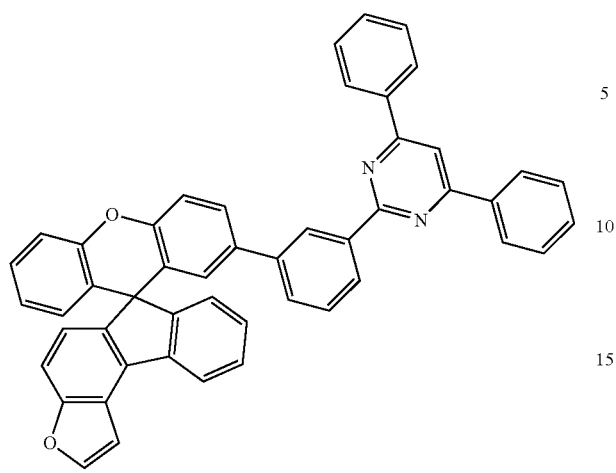
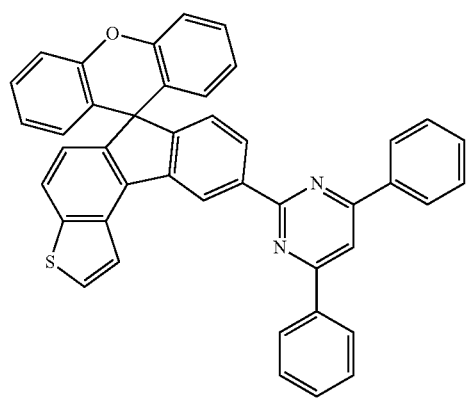
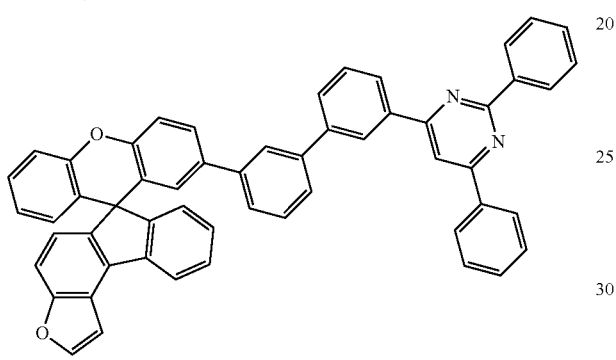
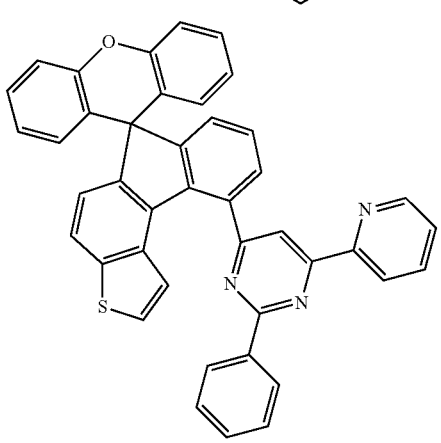
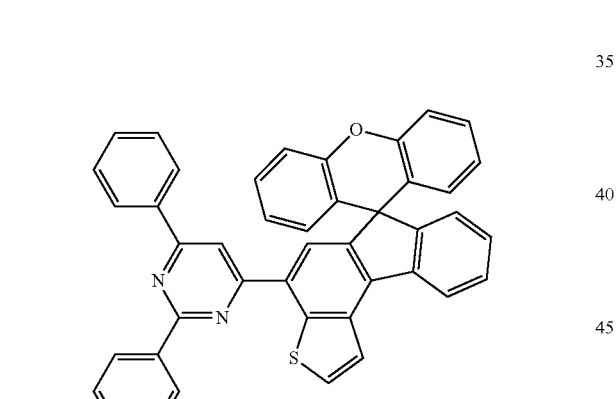
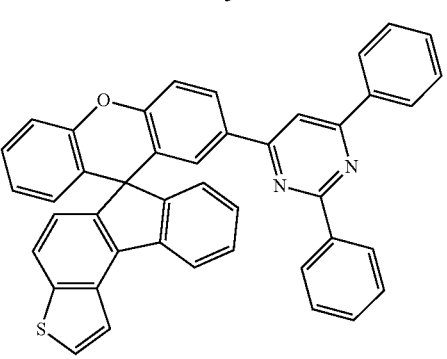
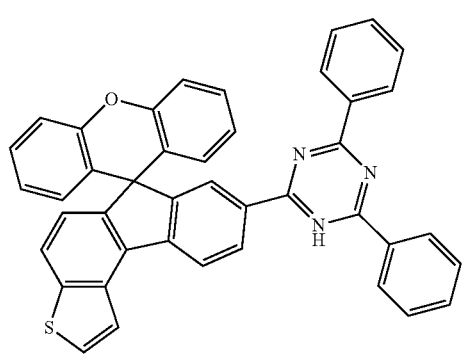
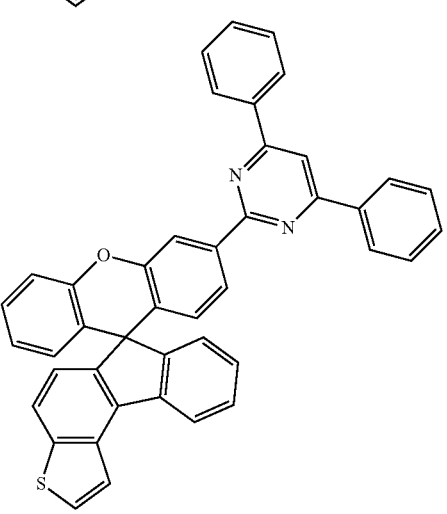

49
-continued
50
-continued
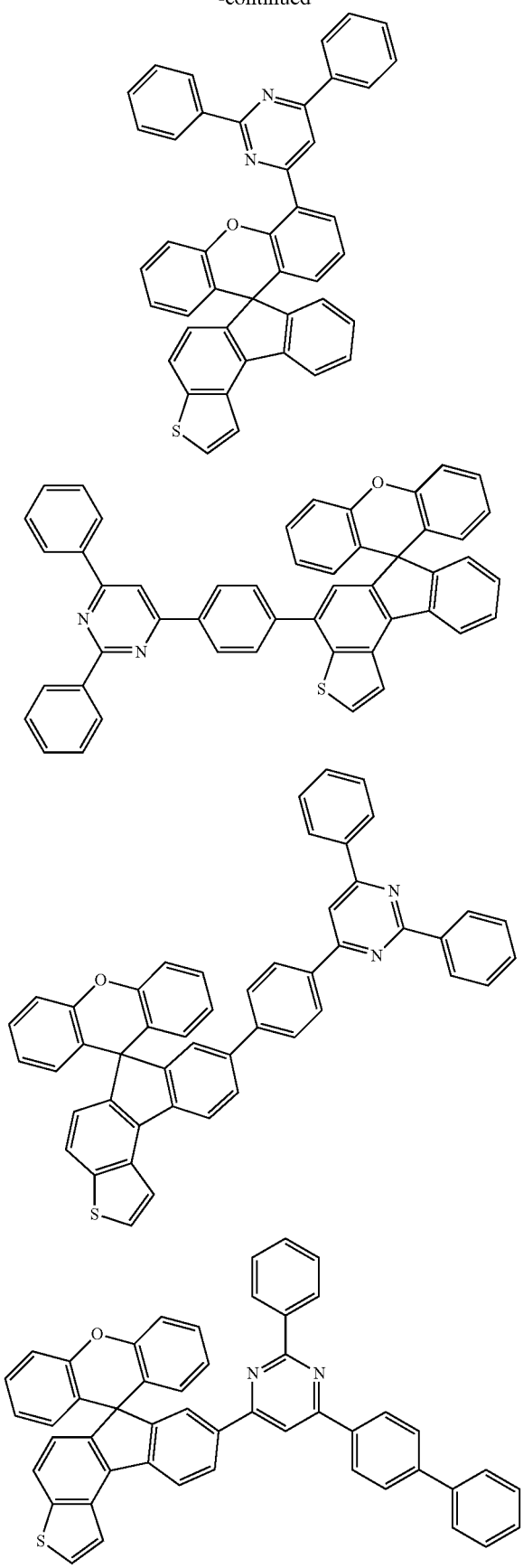
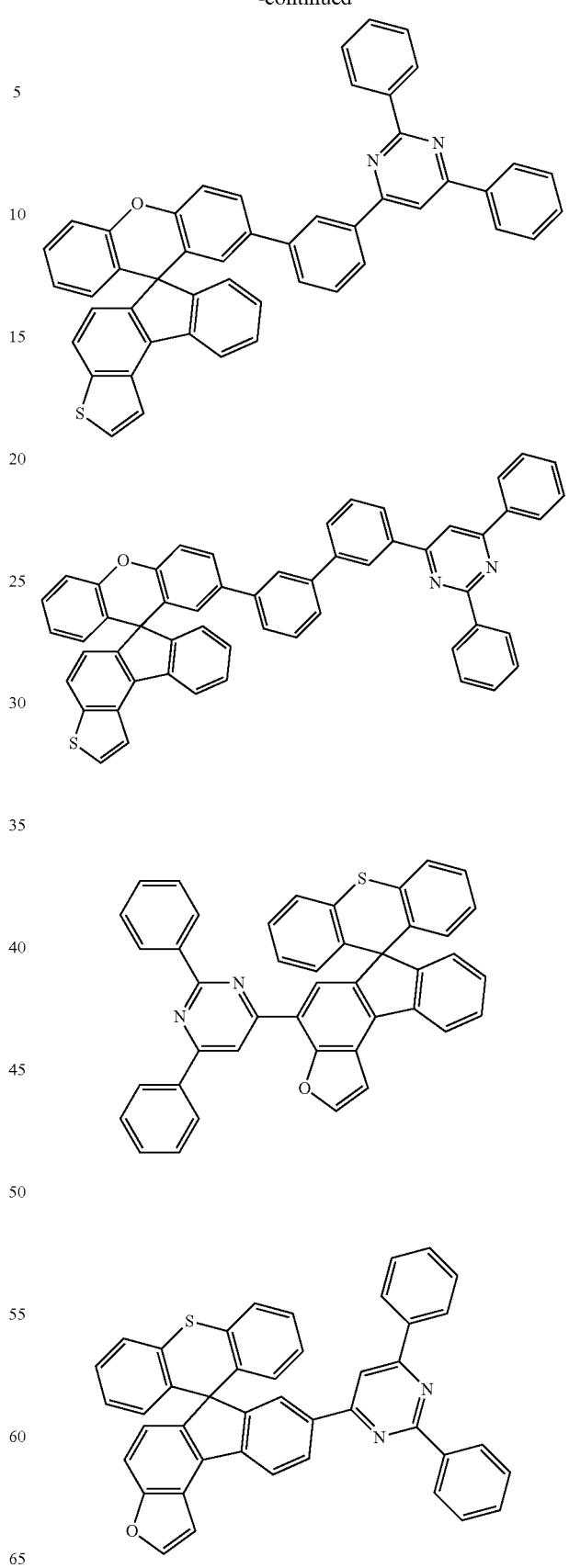

51
-continued
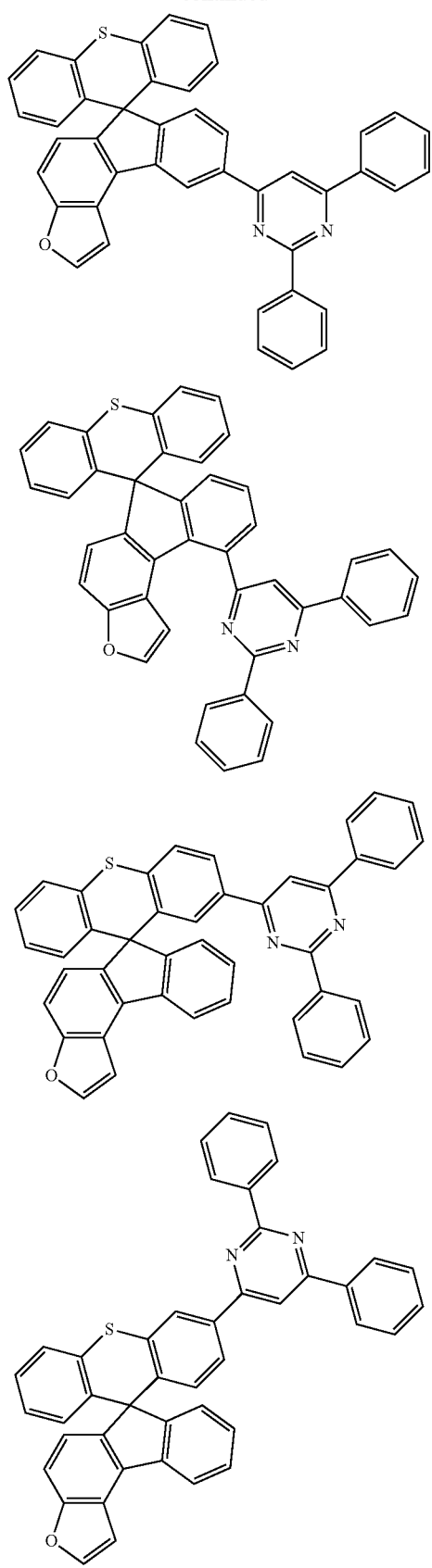
52
-continued
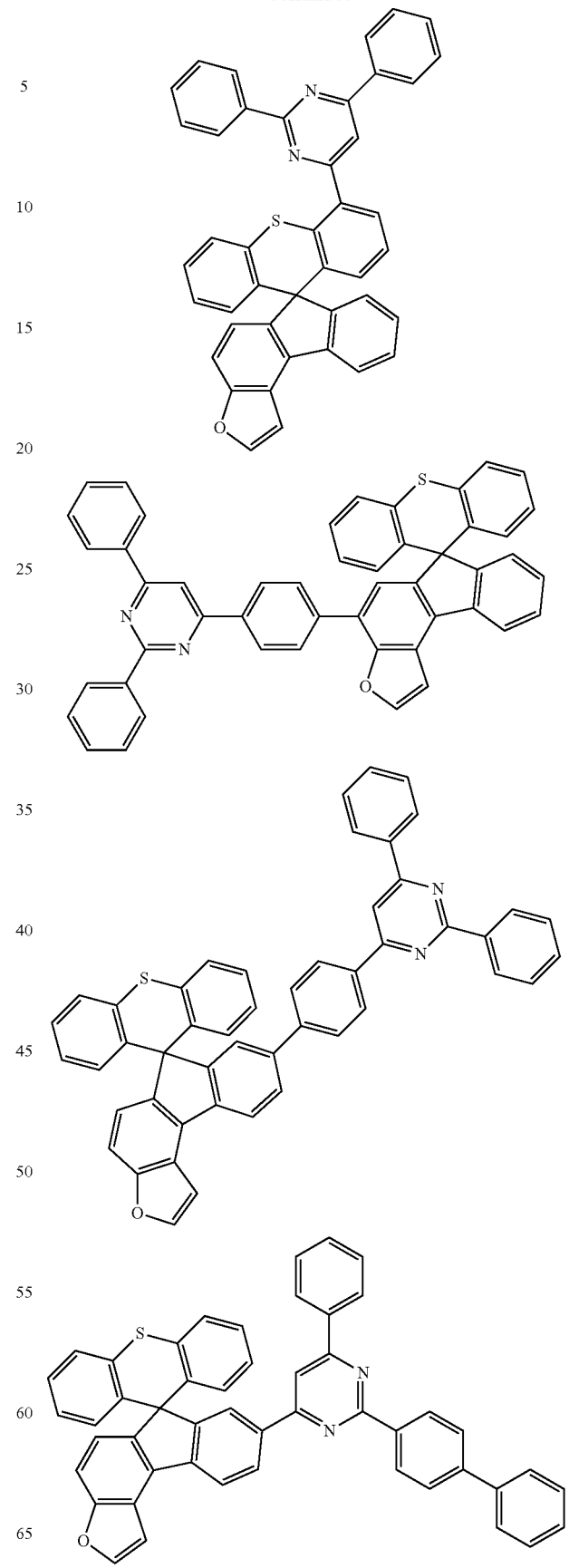

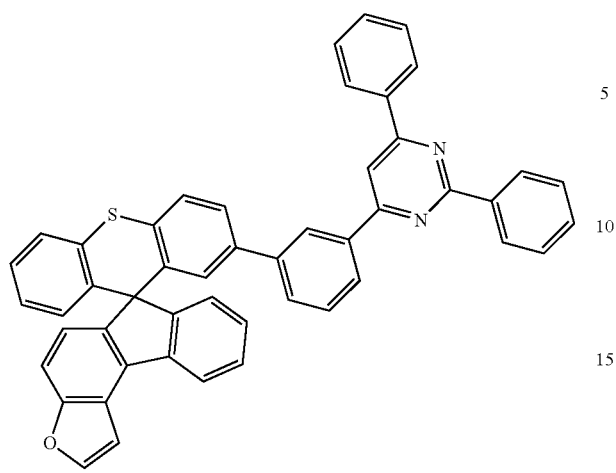
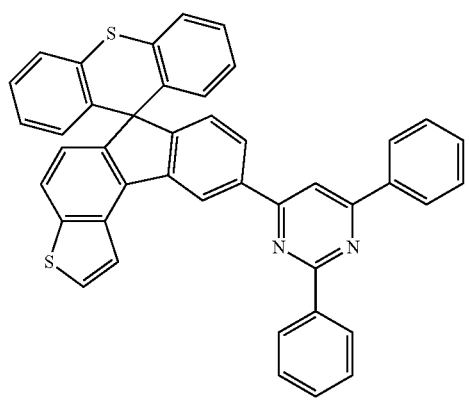
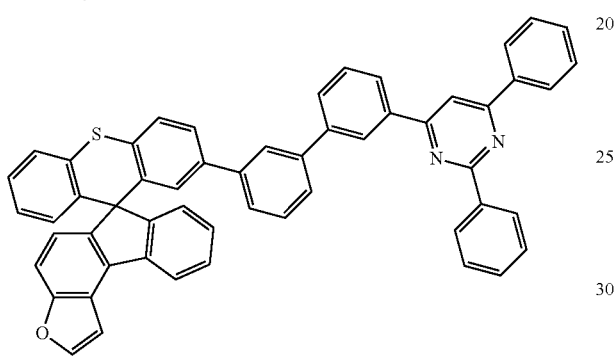
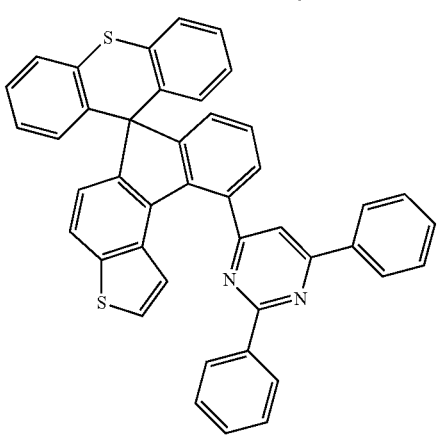
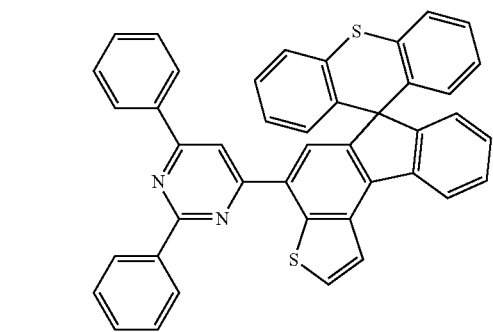
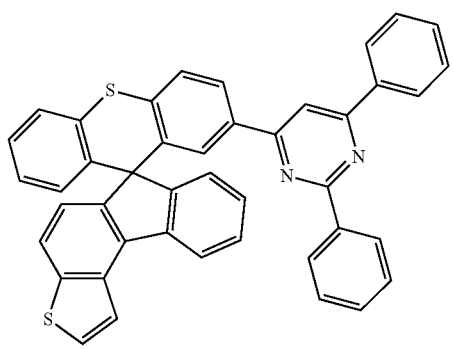
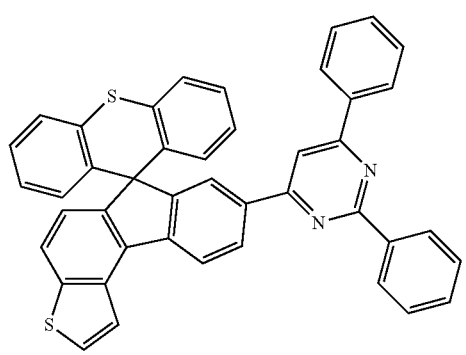
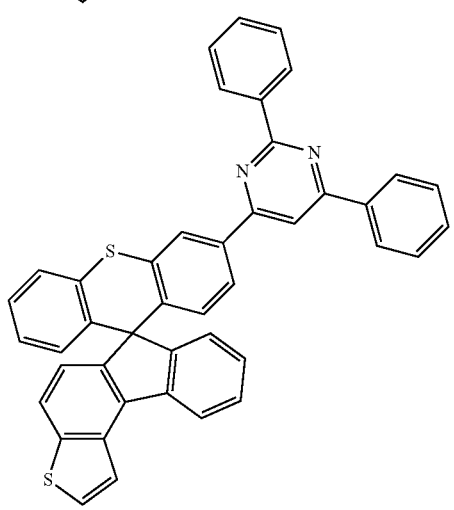

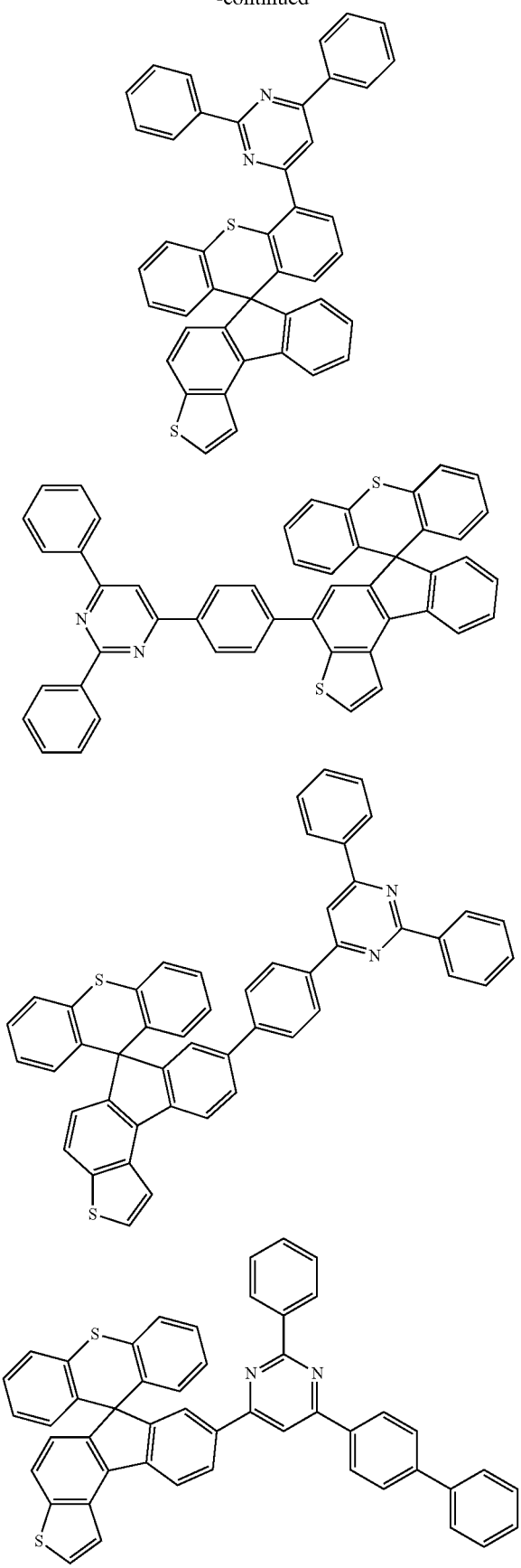
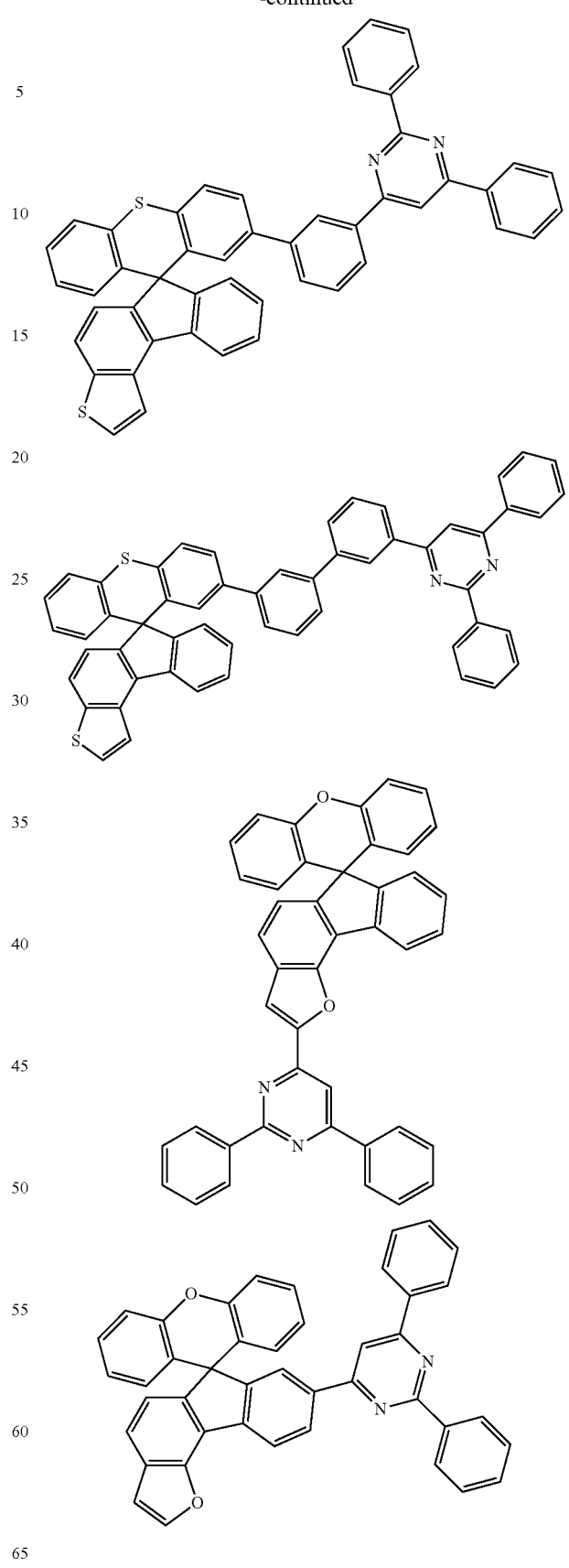

-continued
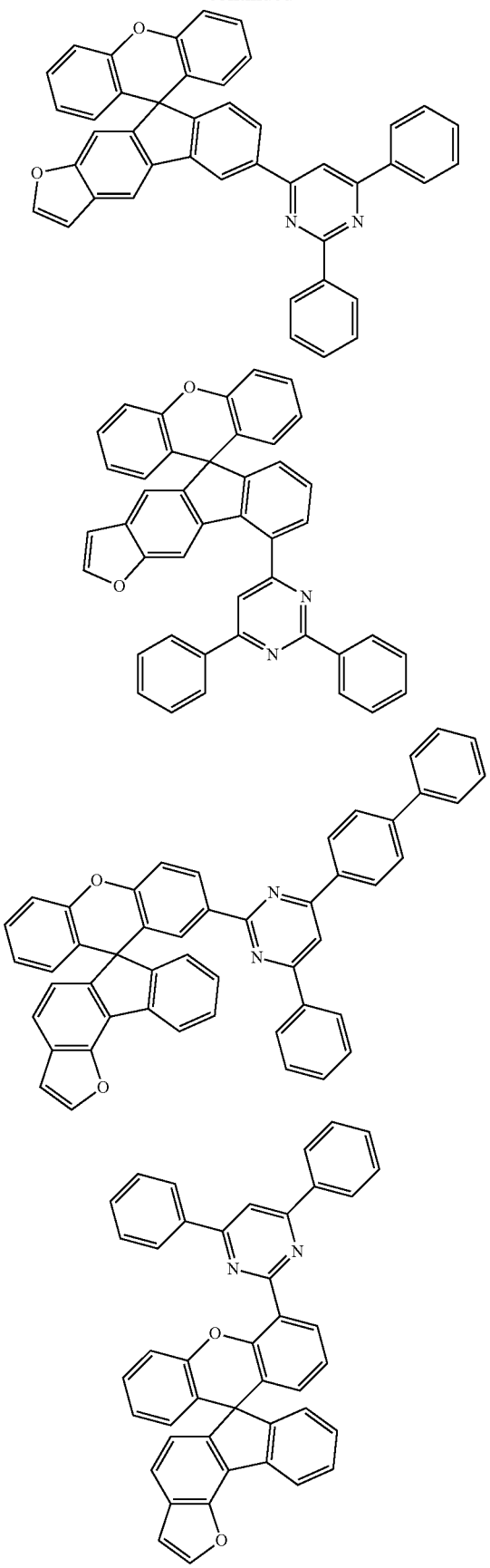
-continued
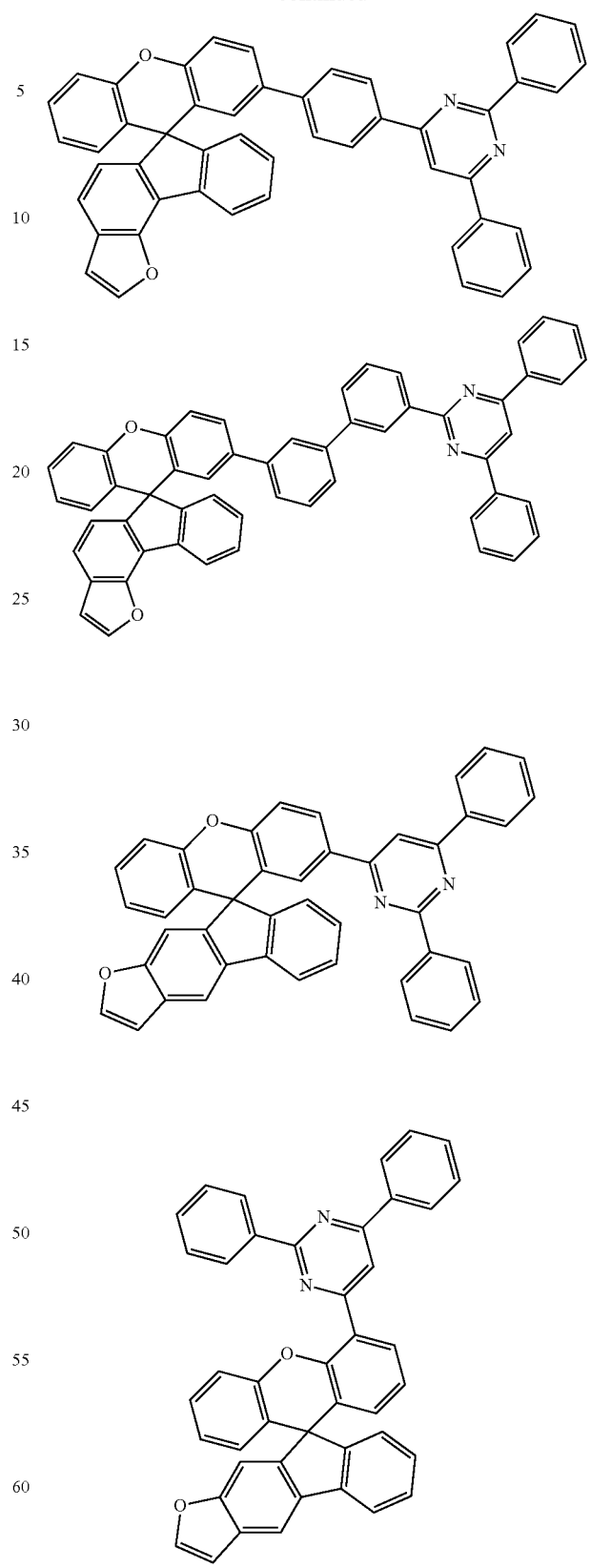

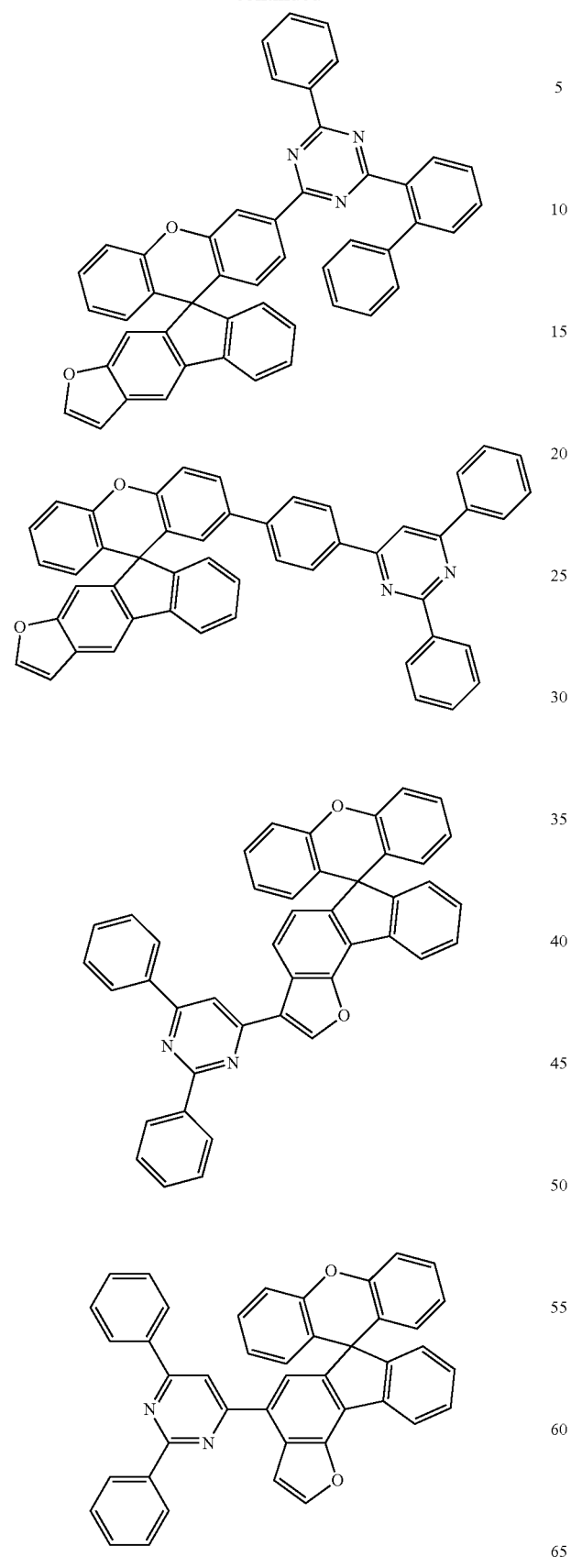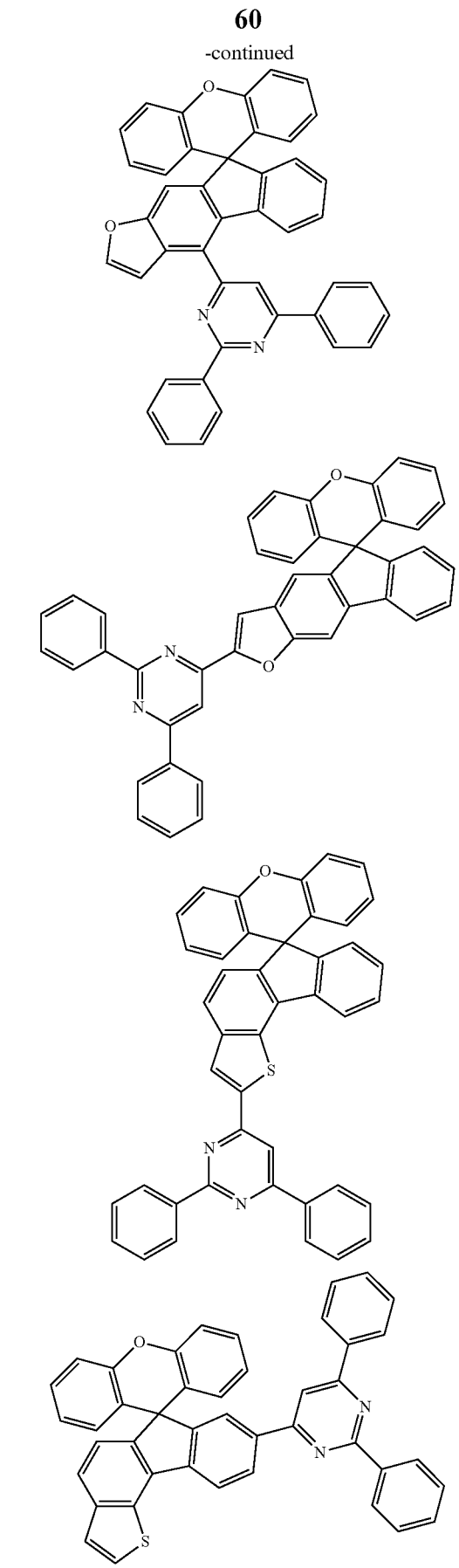

61
-continued
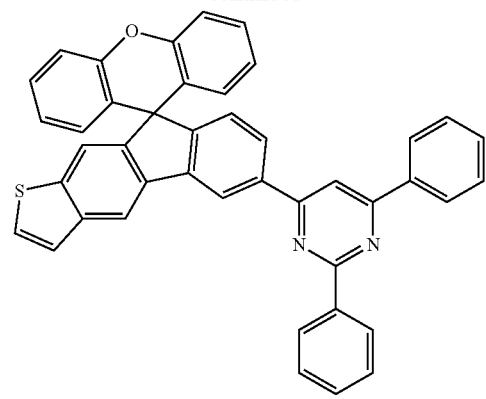
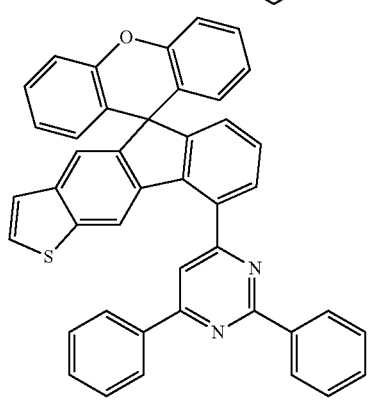
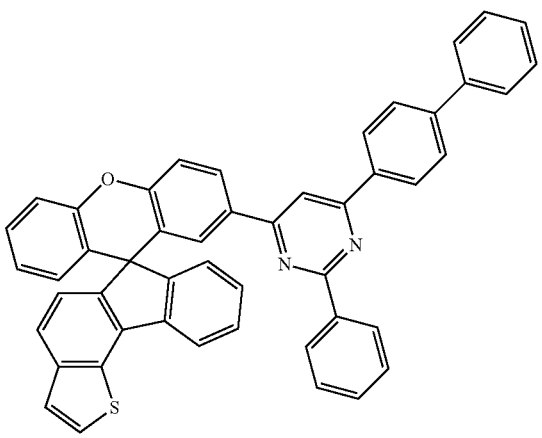
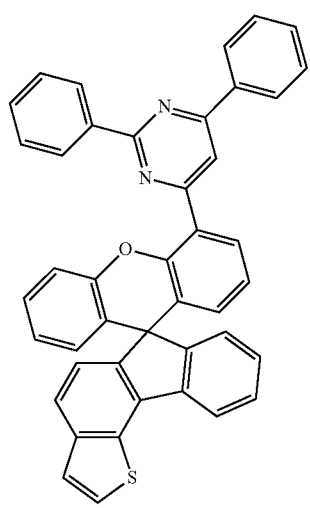
62
-continued
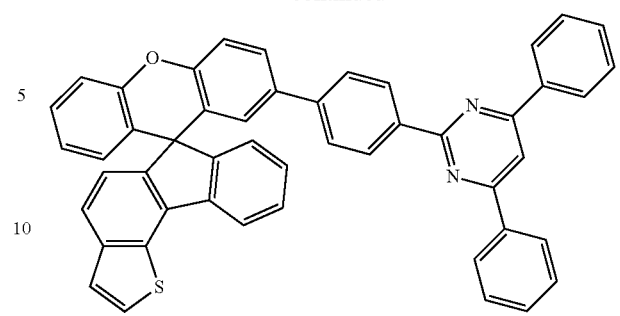
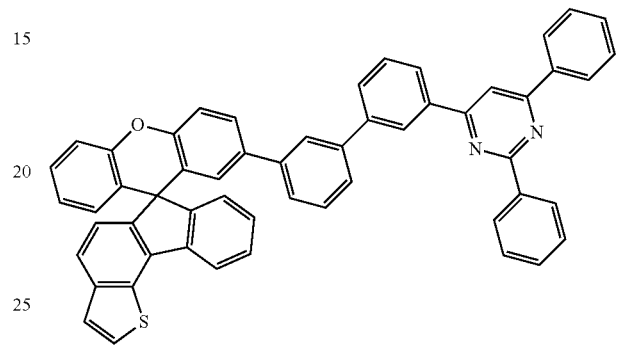
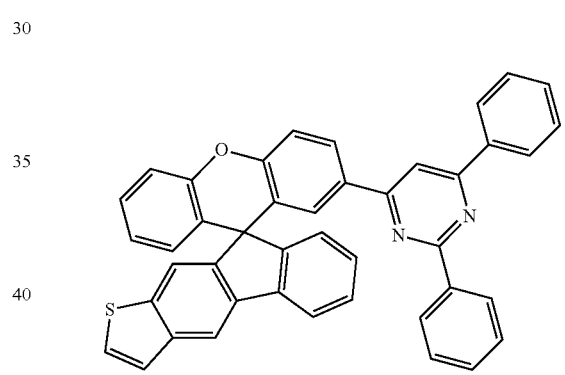
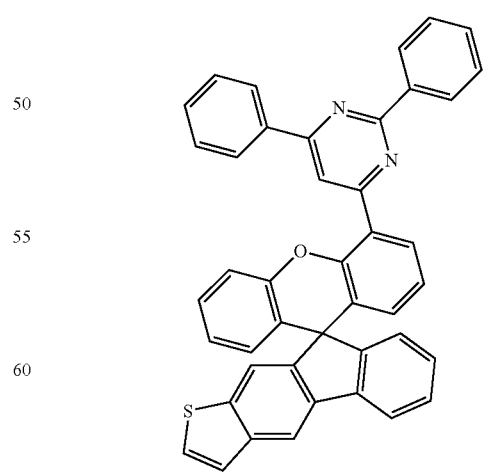

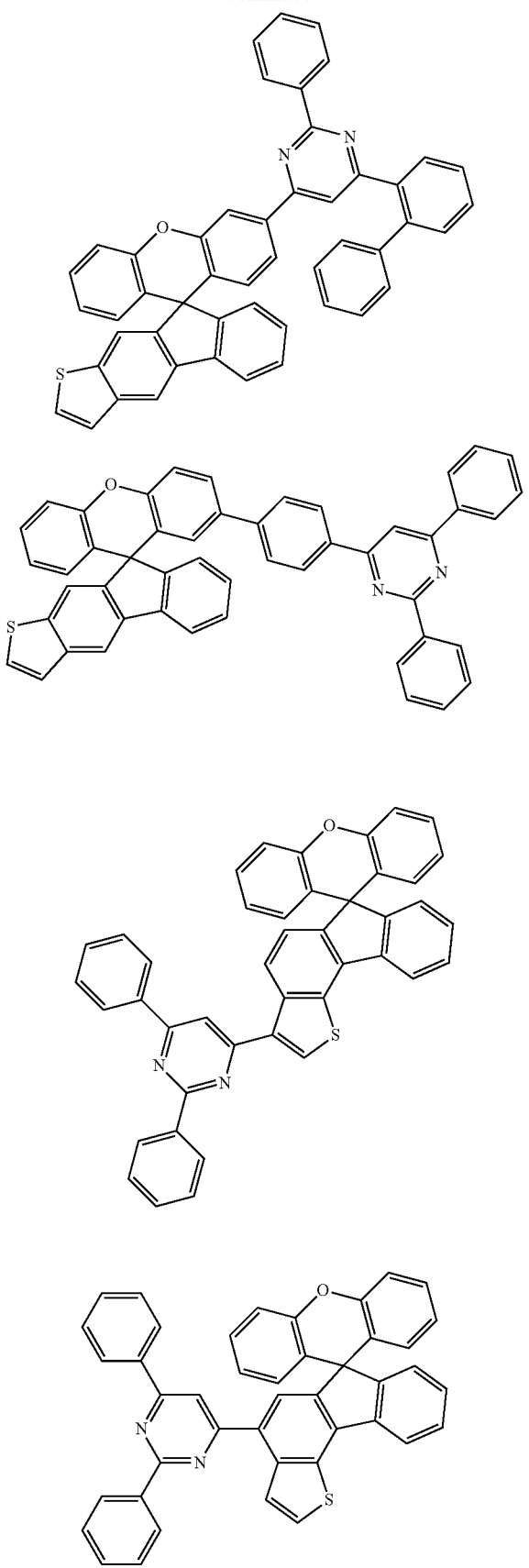
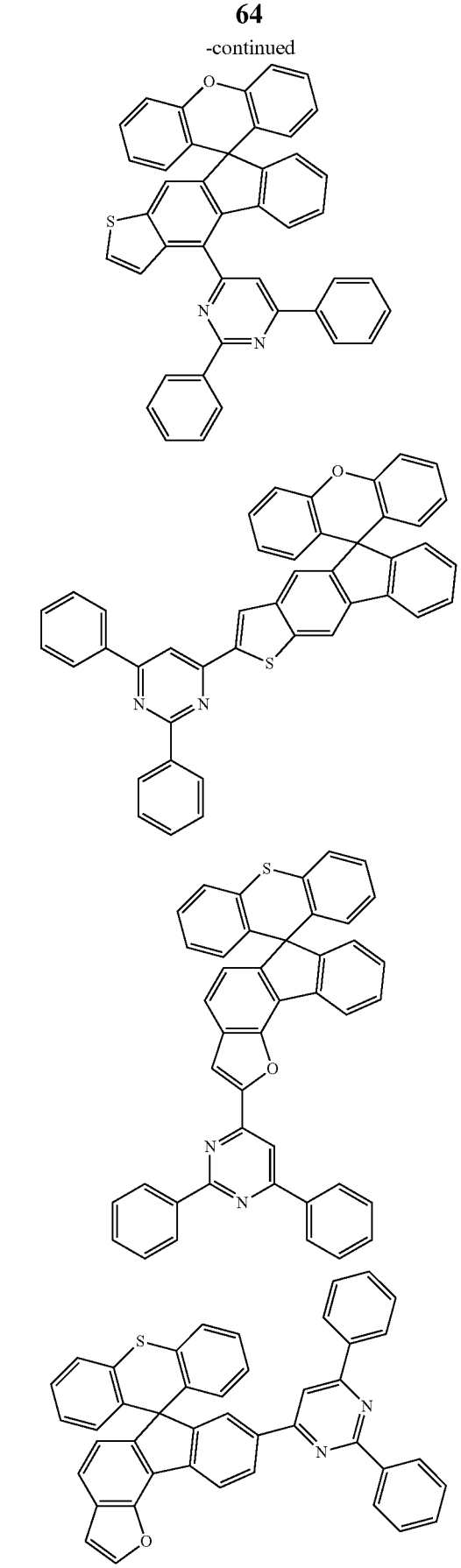

65
-continued
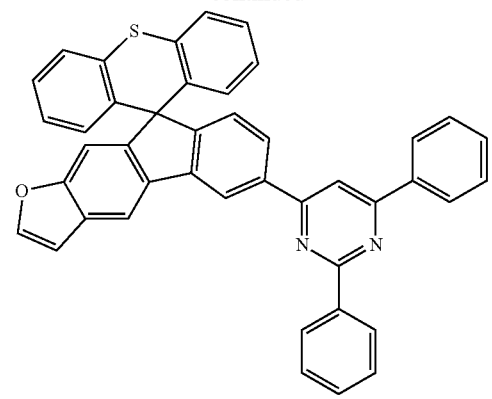
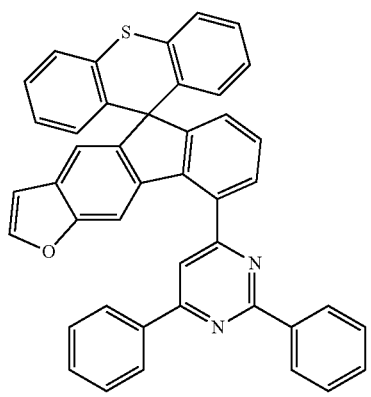
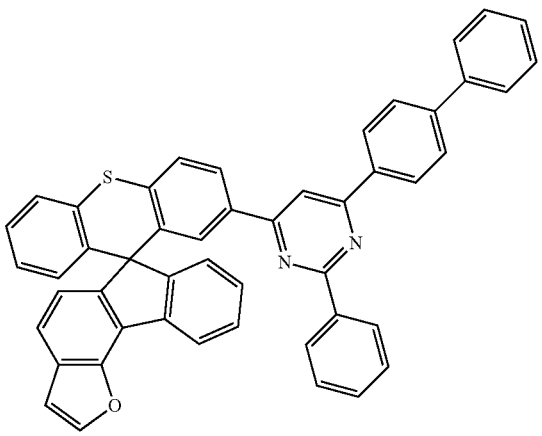
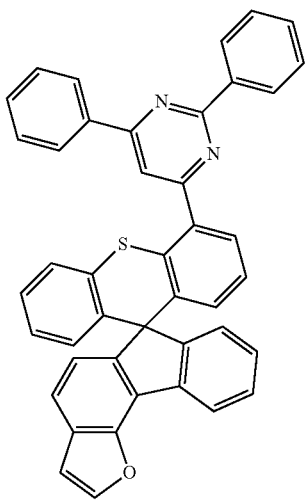
66
-continued
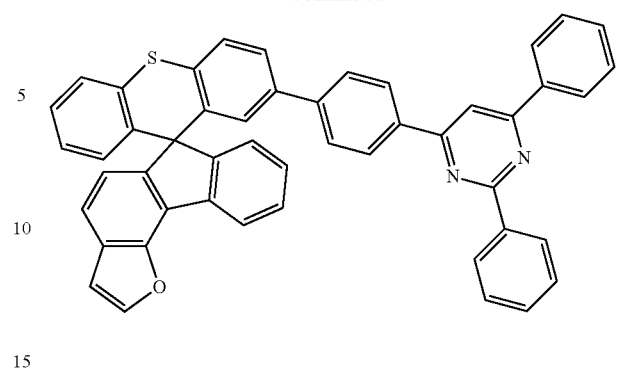
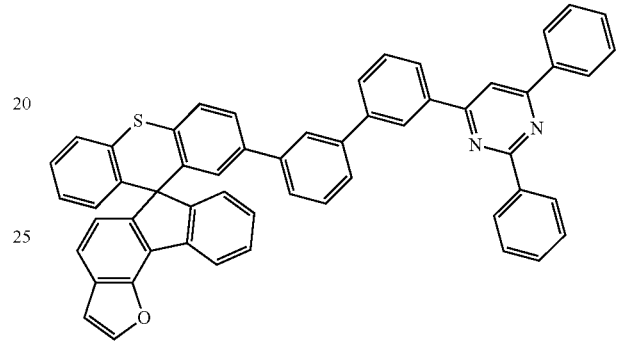
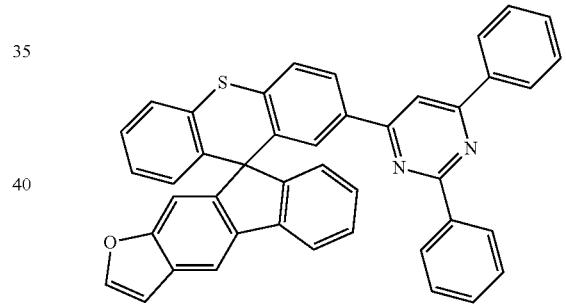
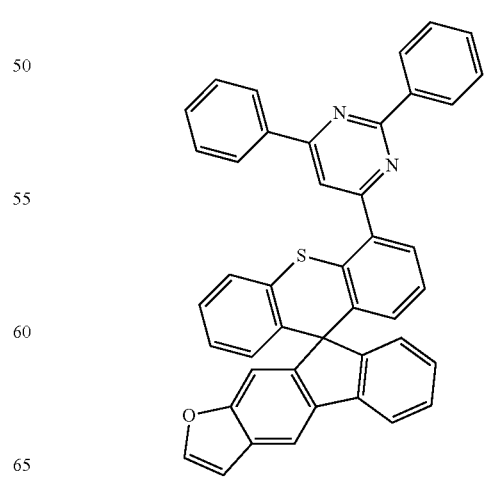

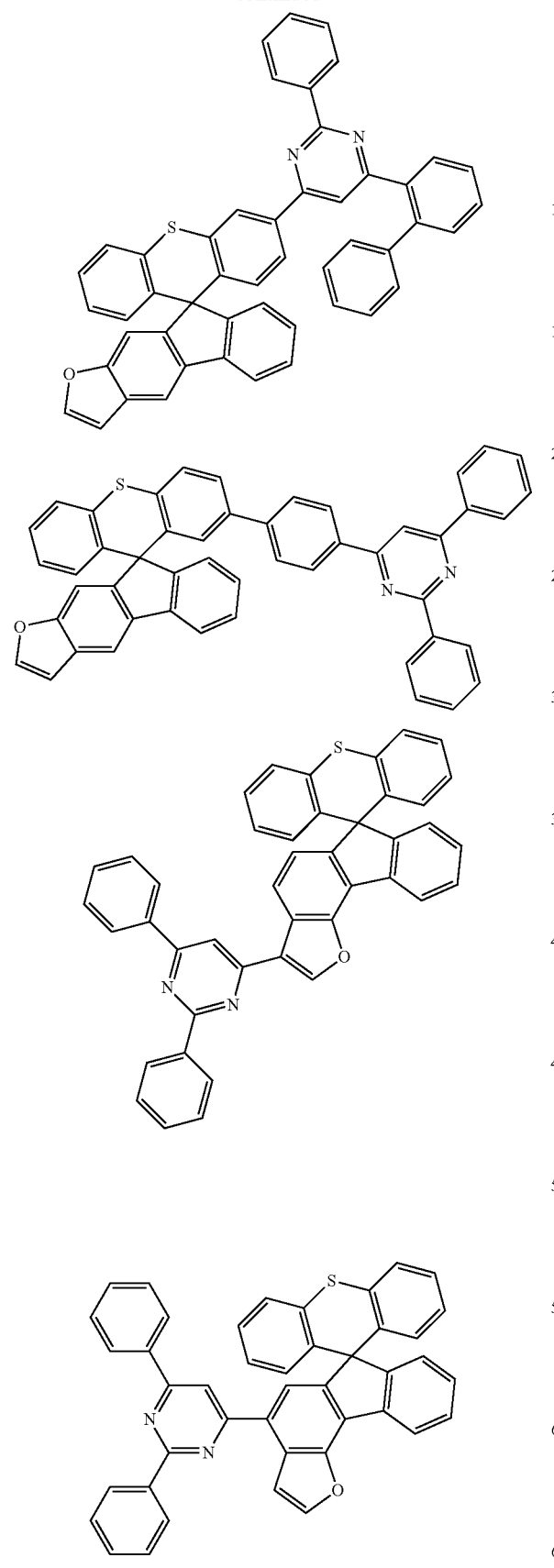
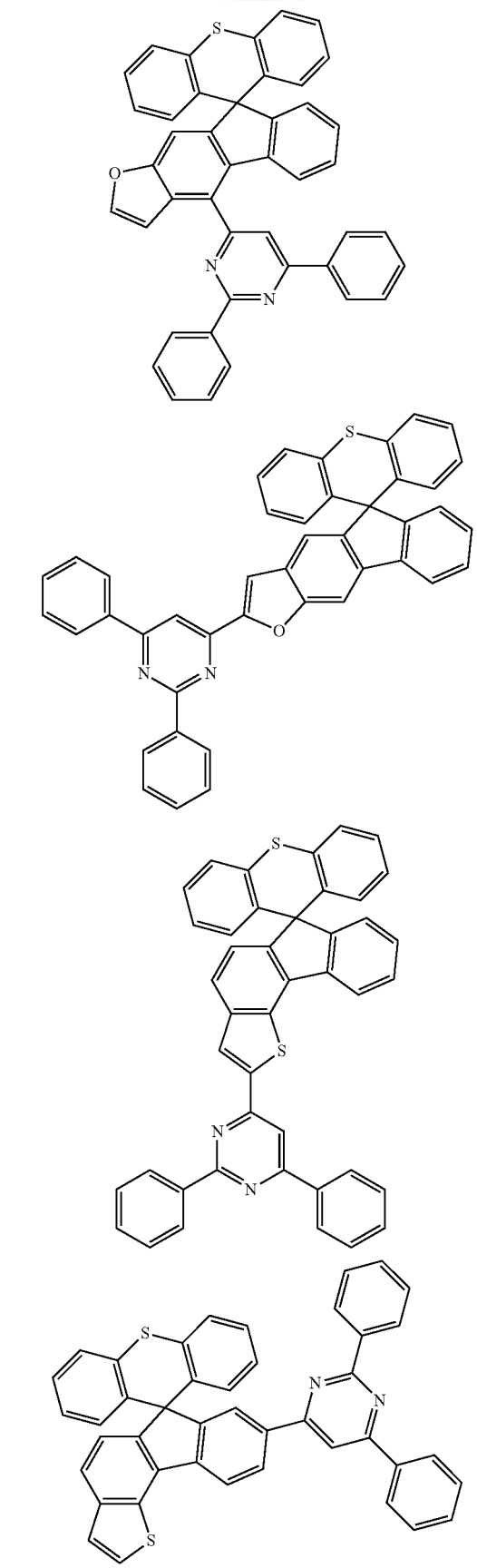

69
-continued
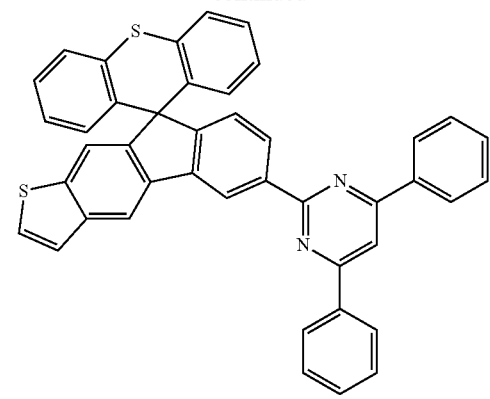
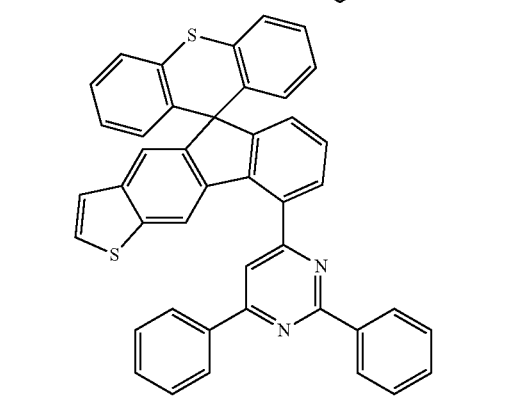
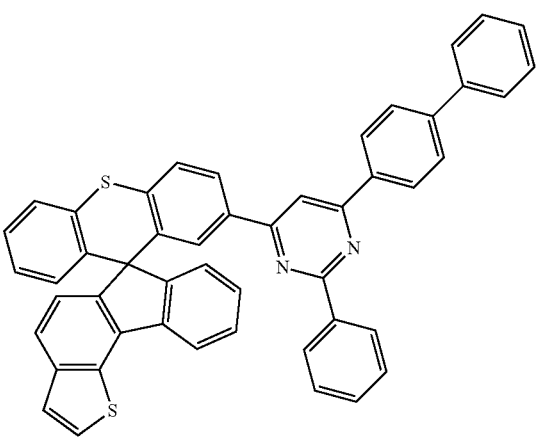
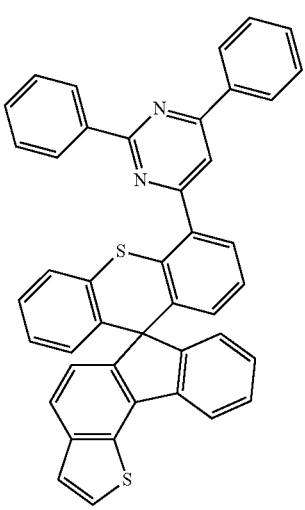
70
-continued
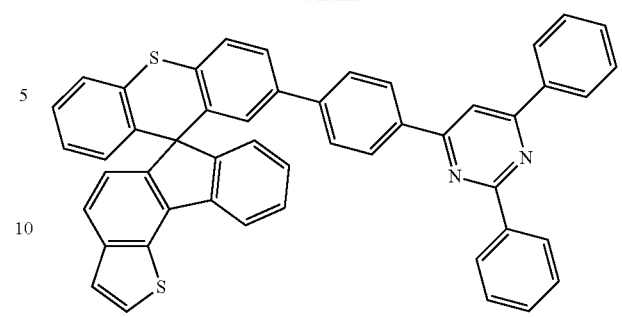
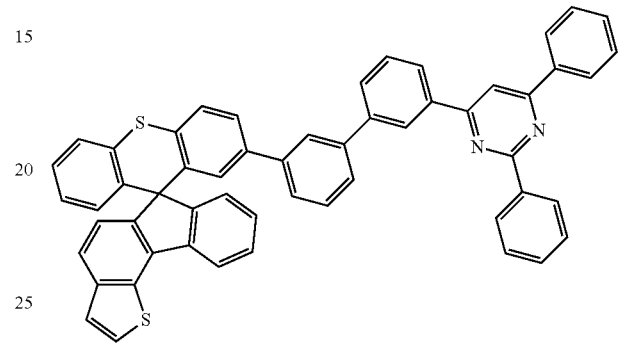
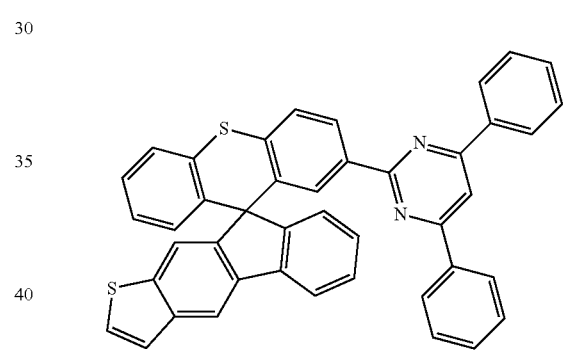
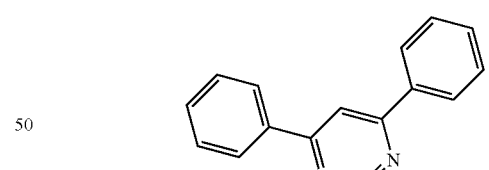
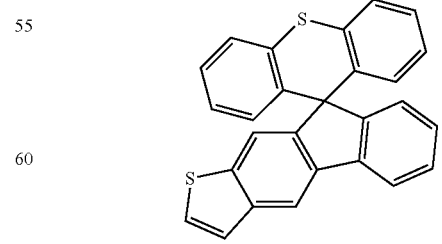

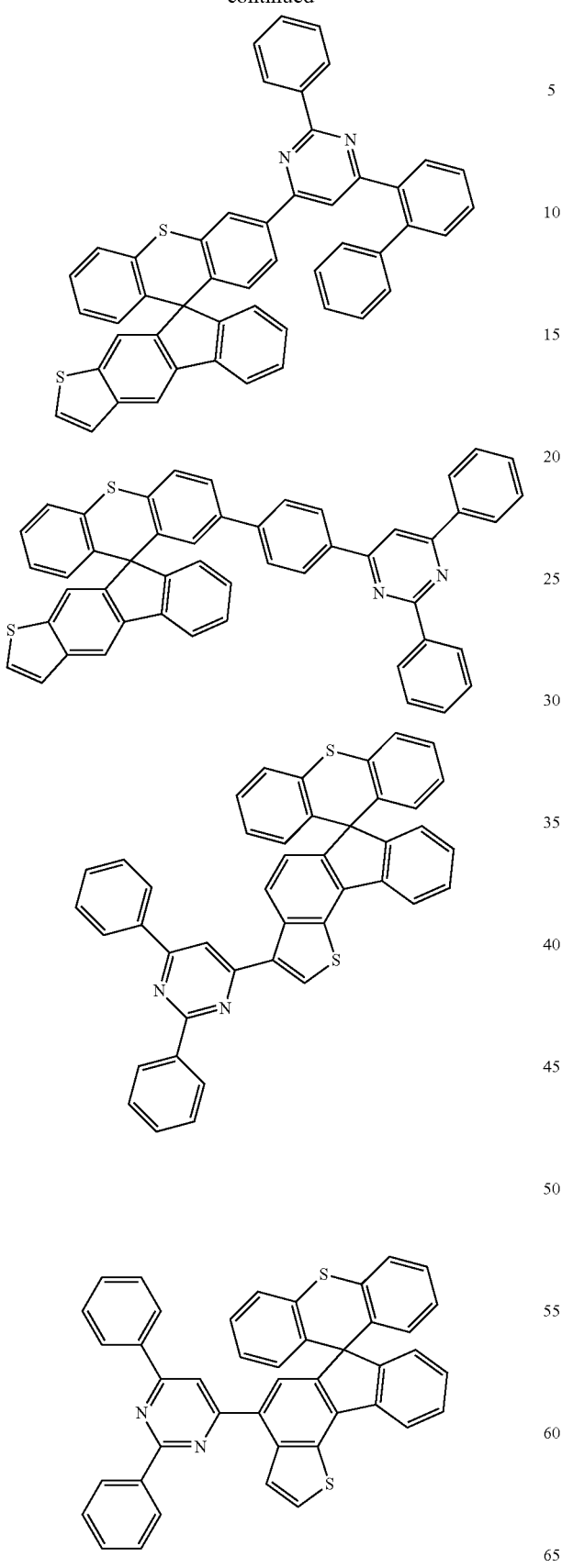
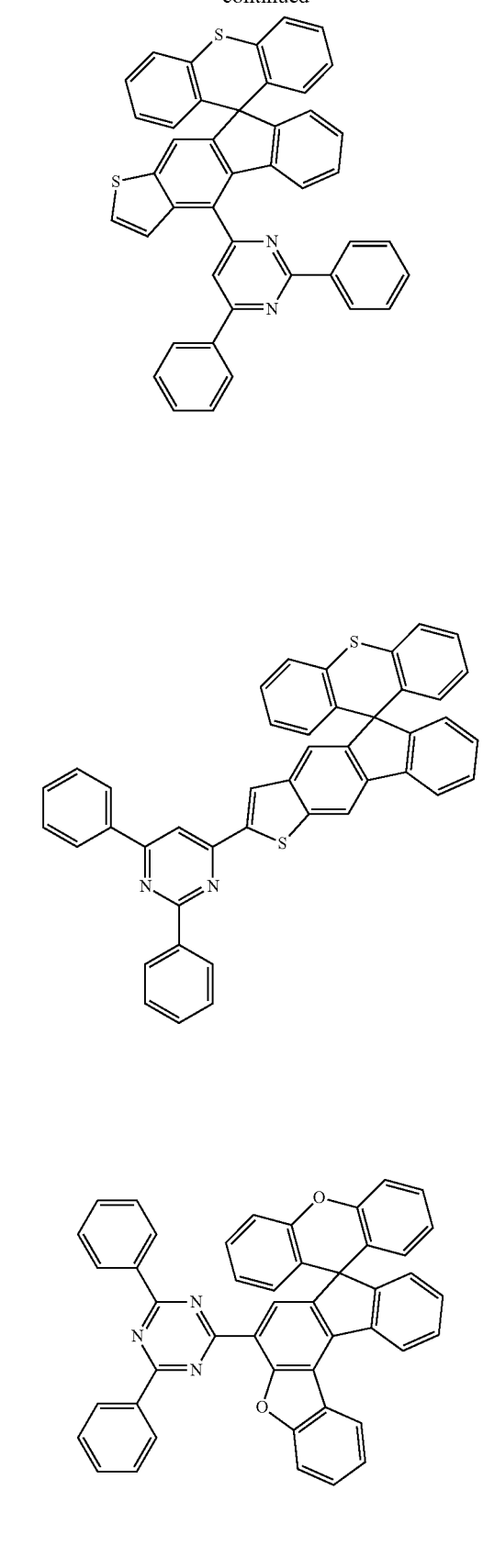

-continued
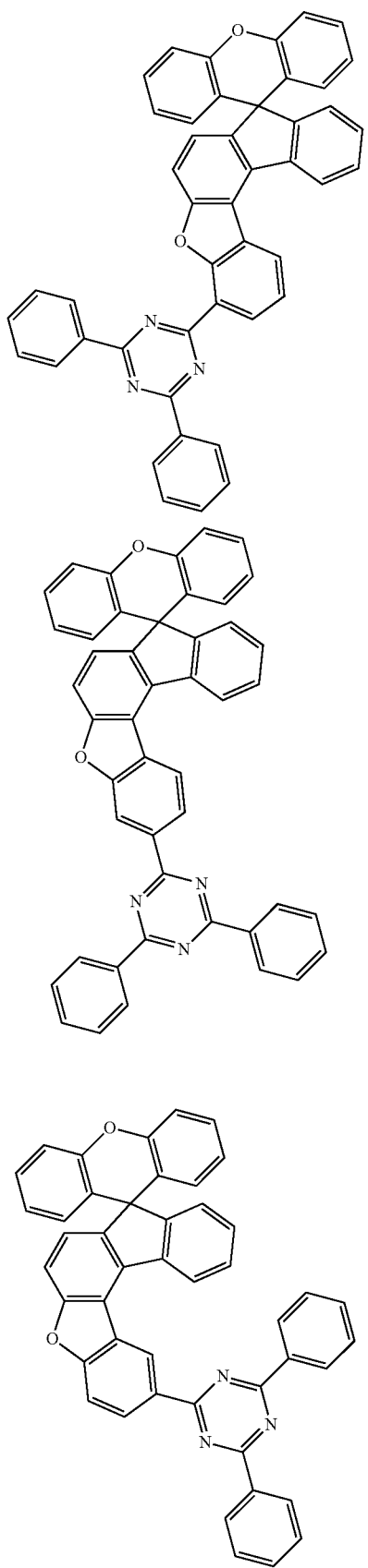
-continued
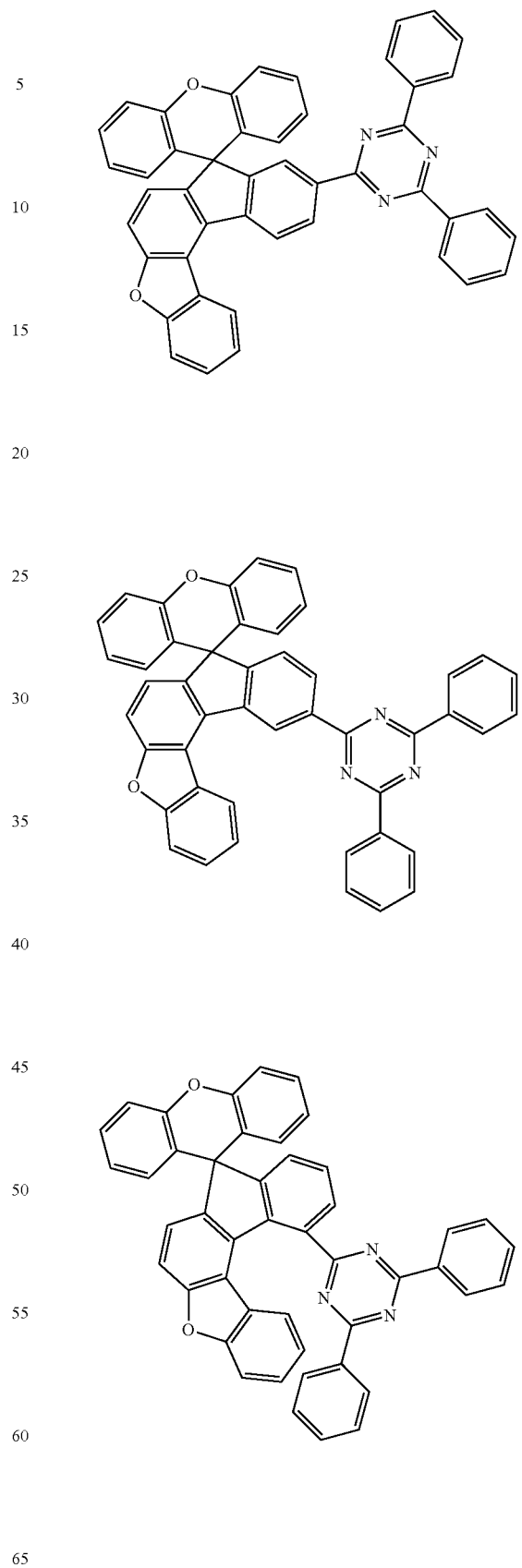

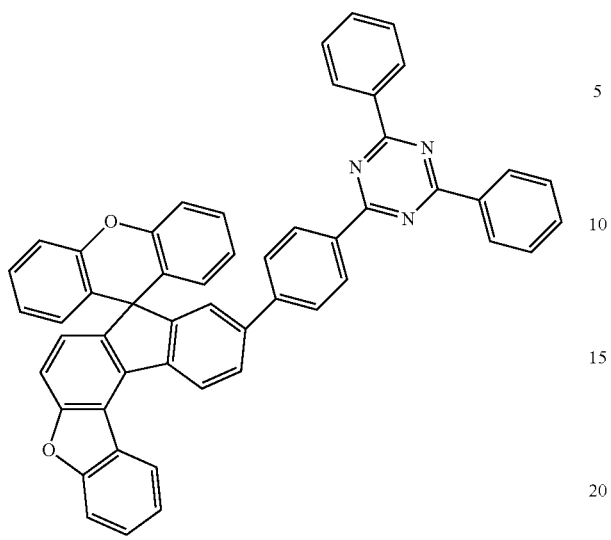
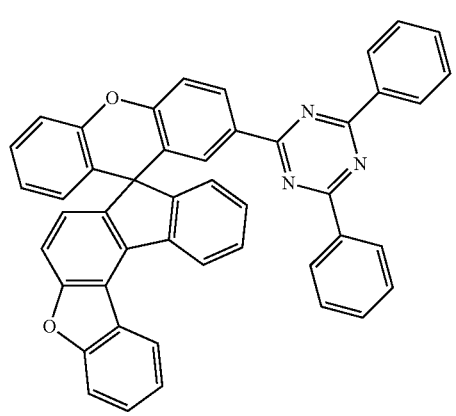
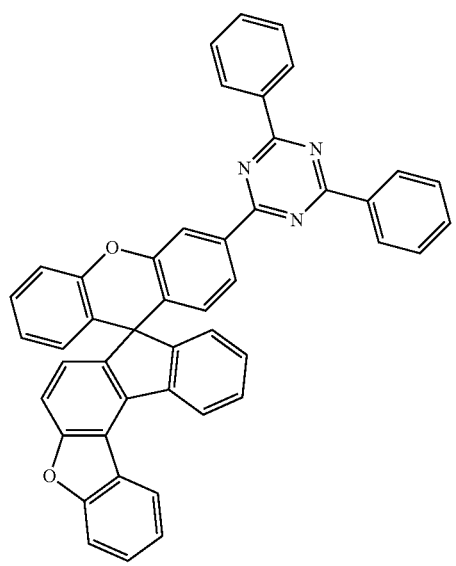
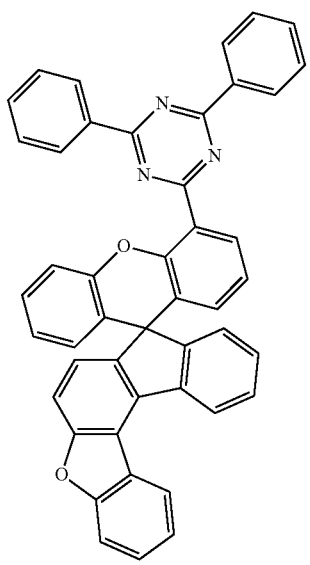
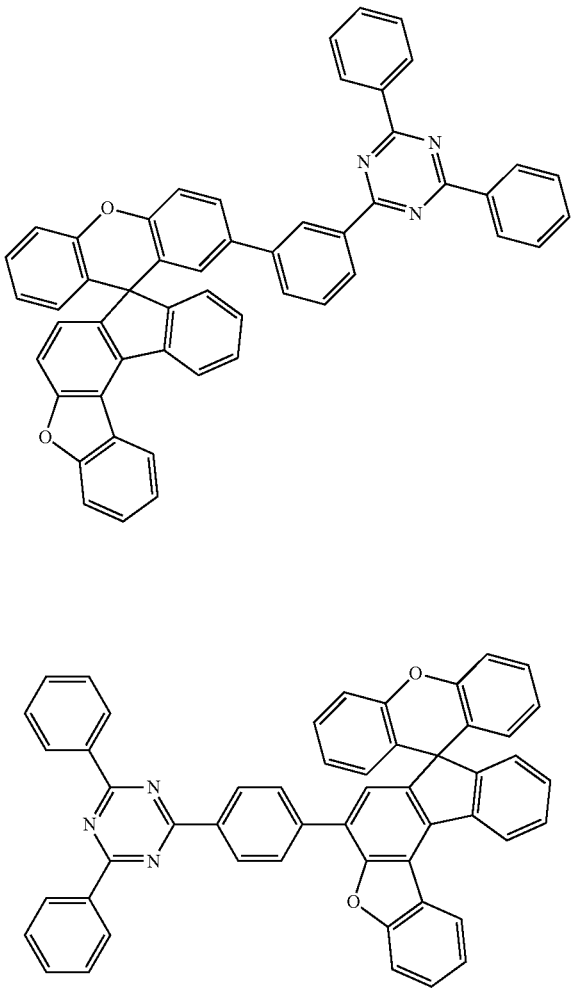

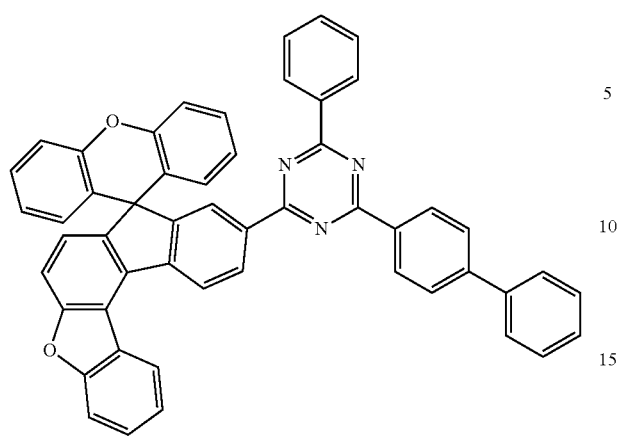
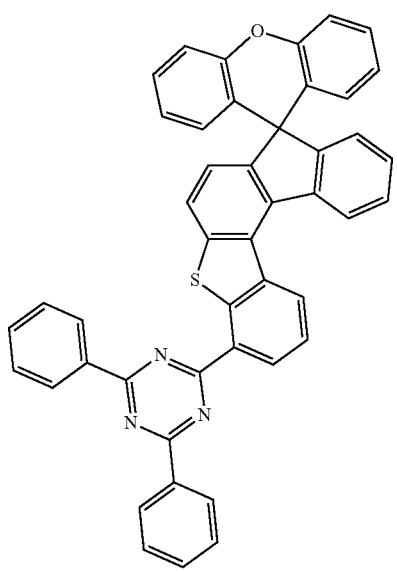
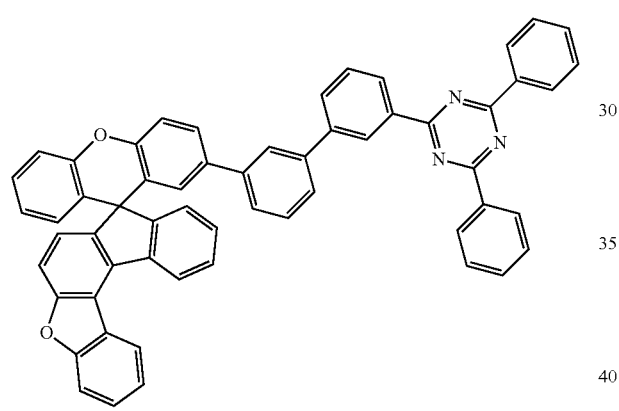
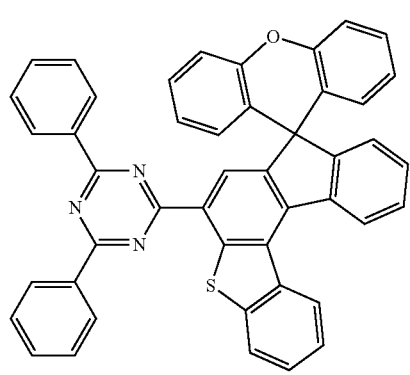
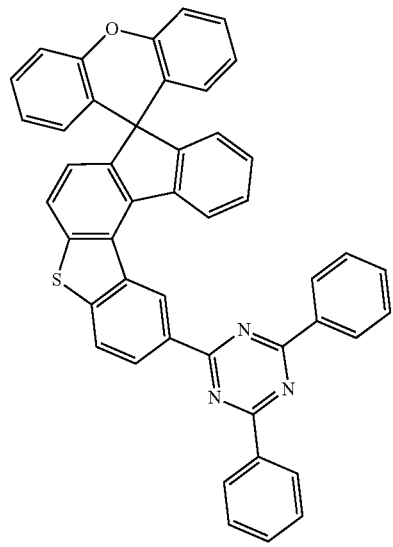

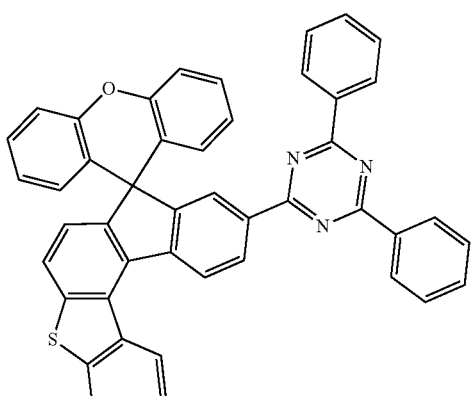
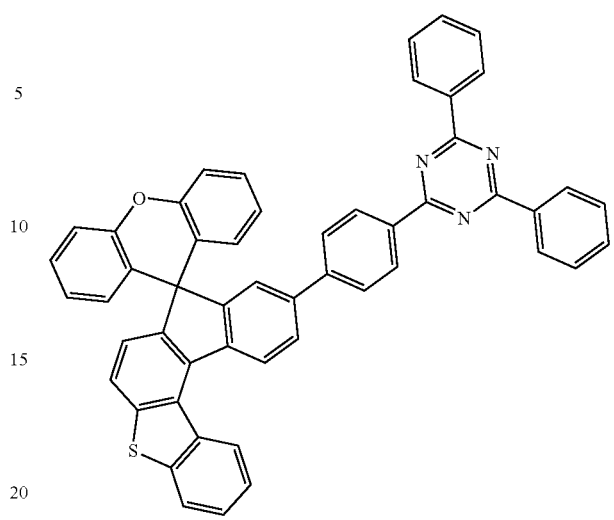
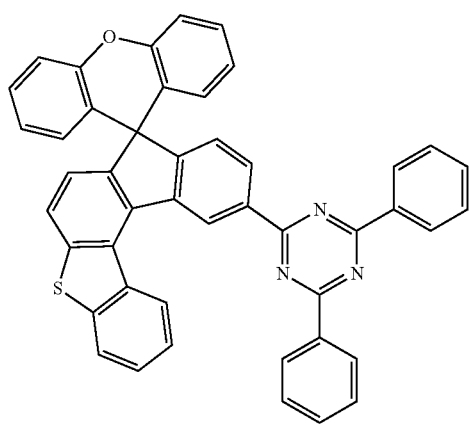
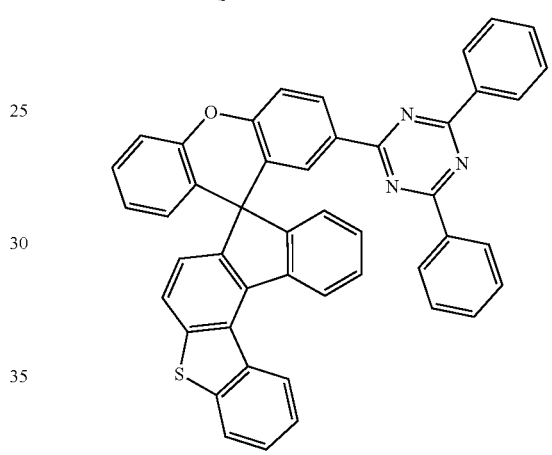
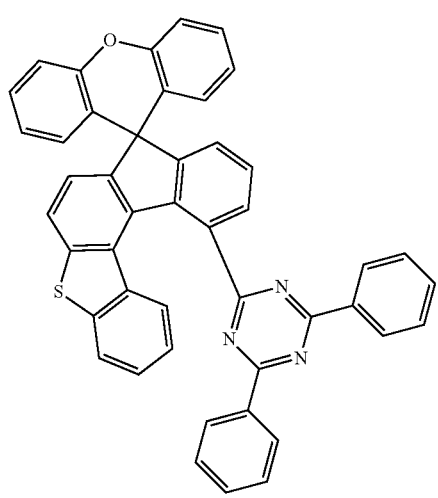
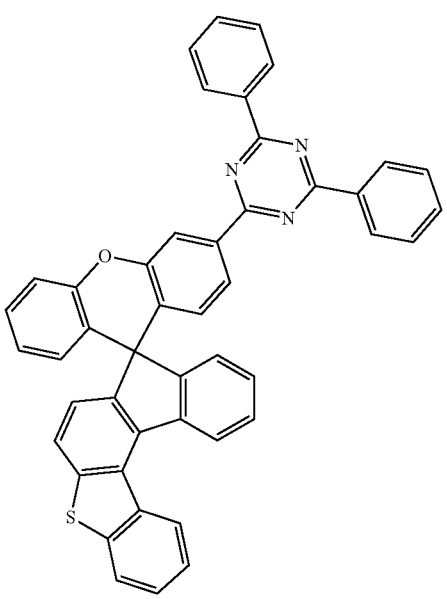

81
-continued
82
-continued
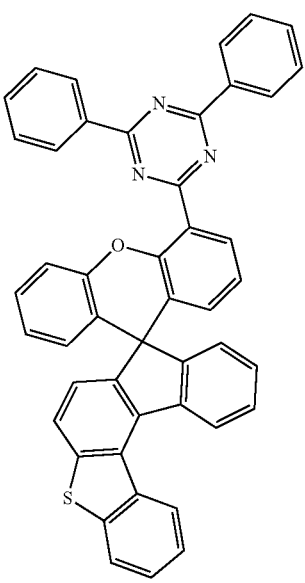
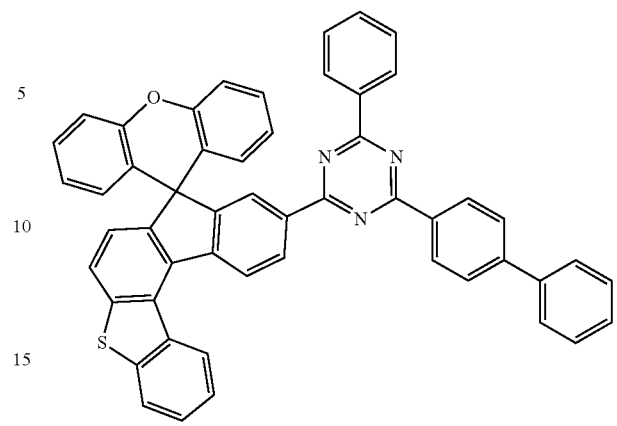
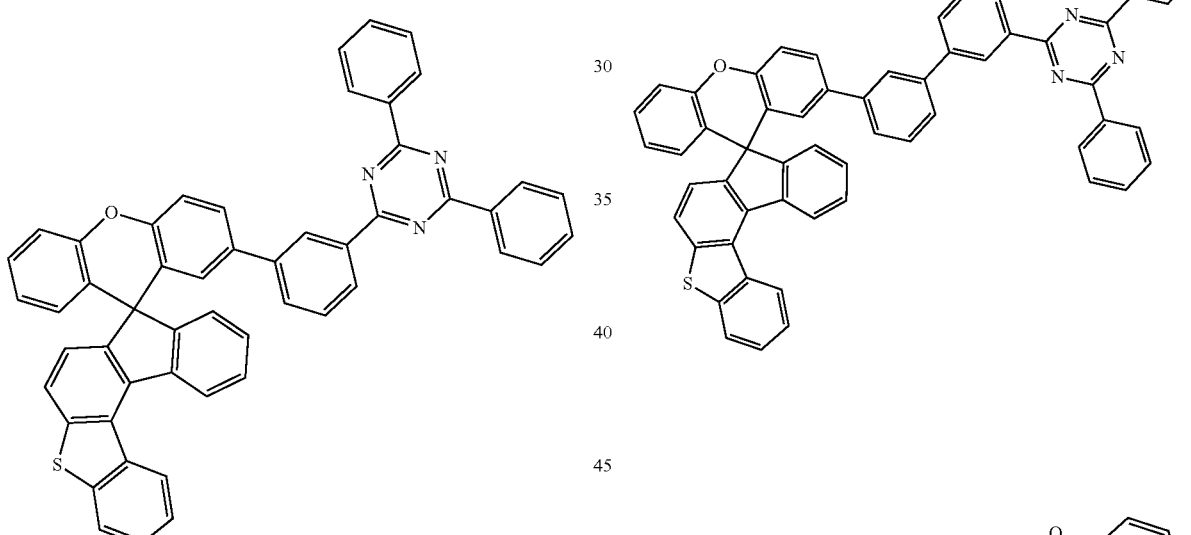
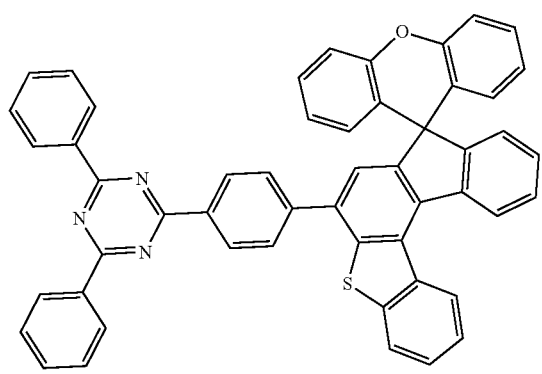

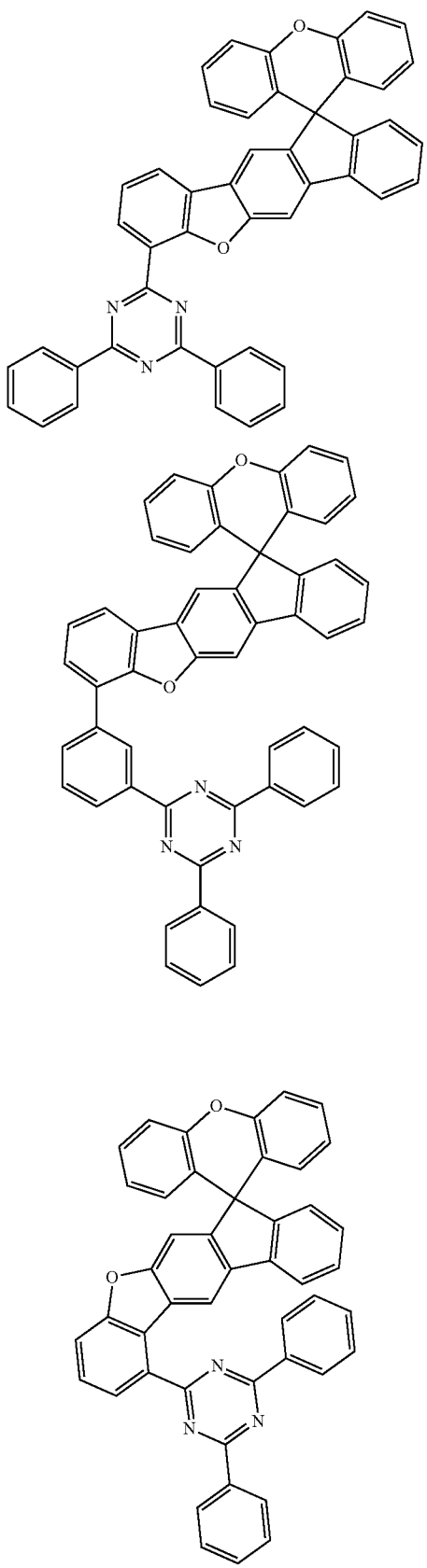
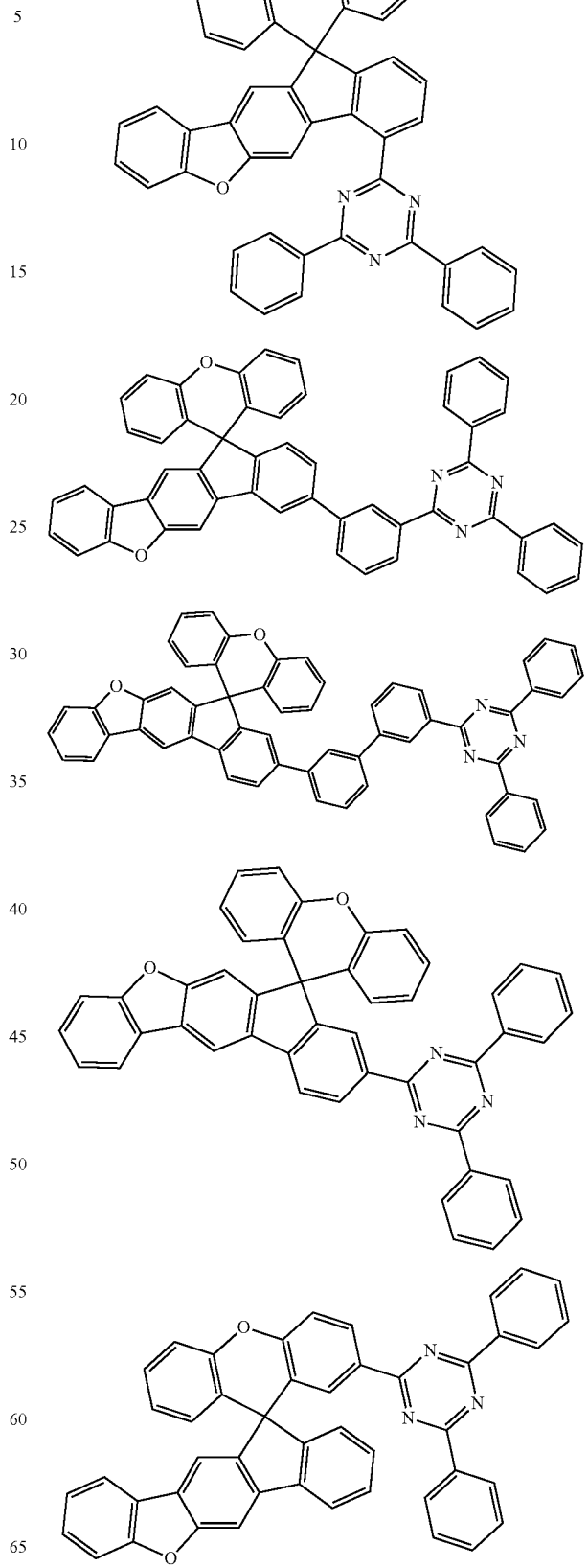

85
-continued
86
-continued
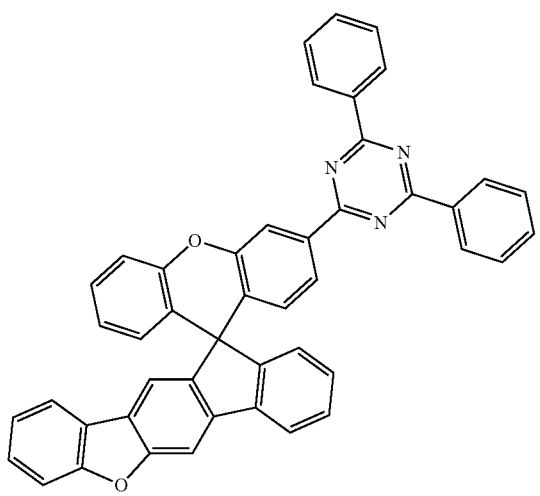
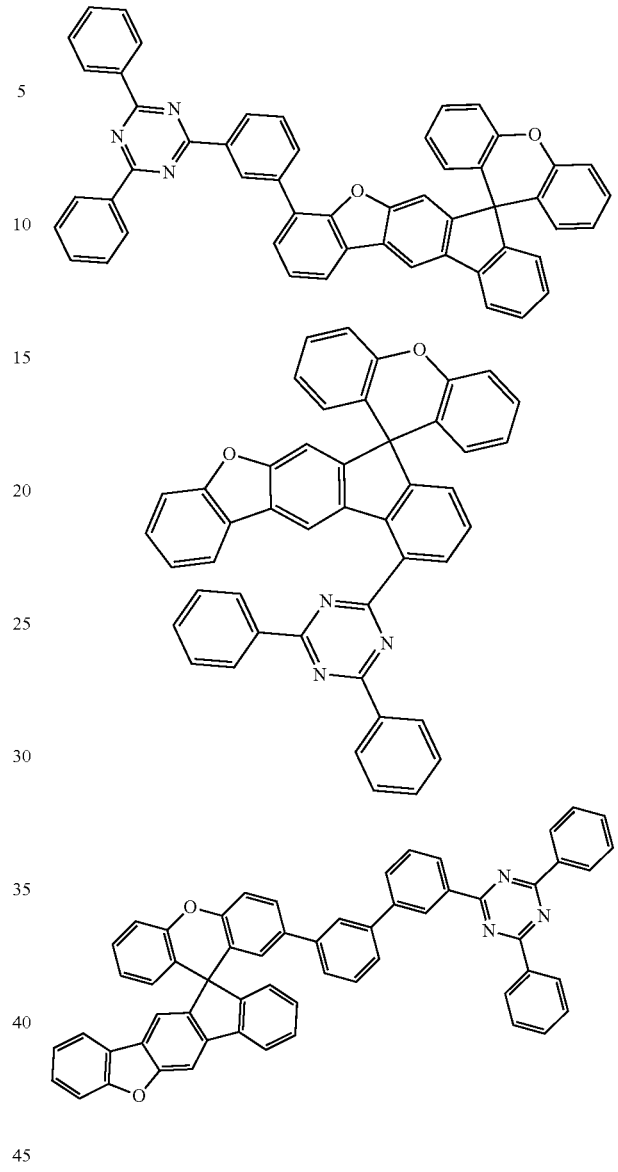
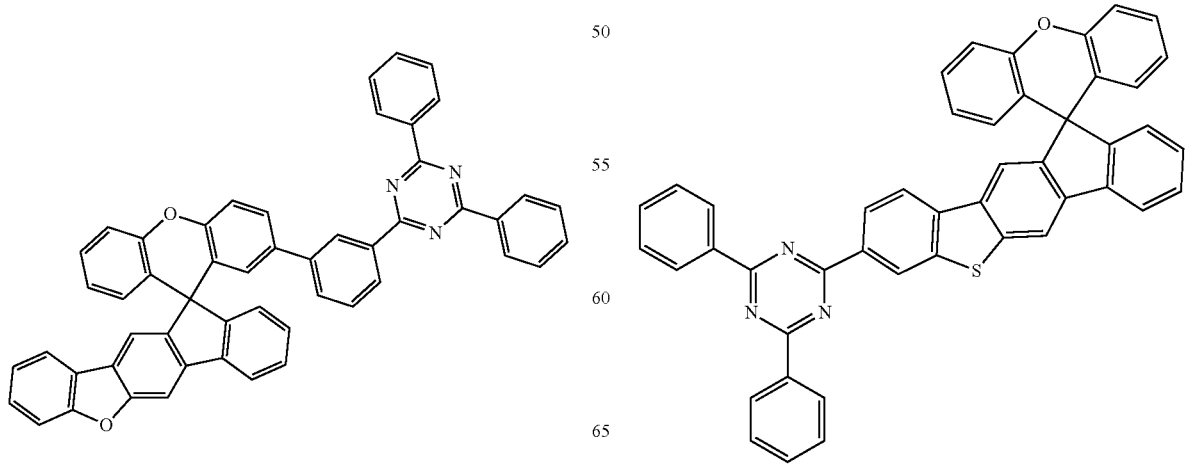

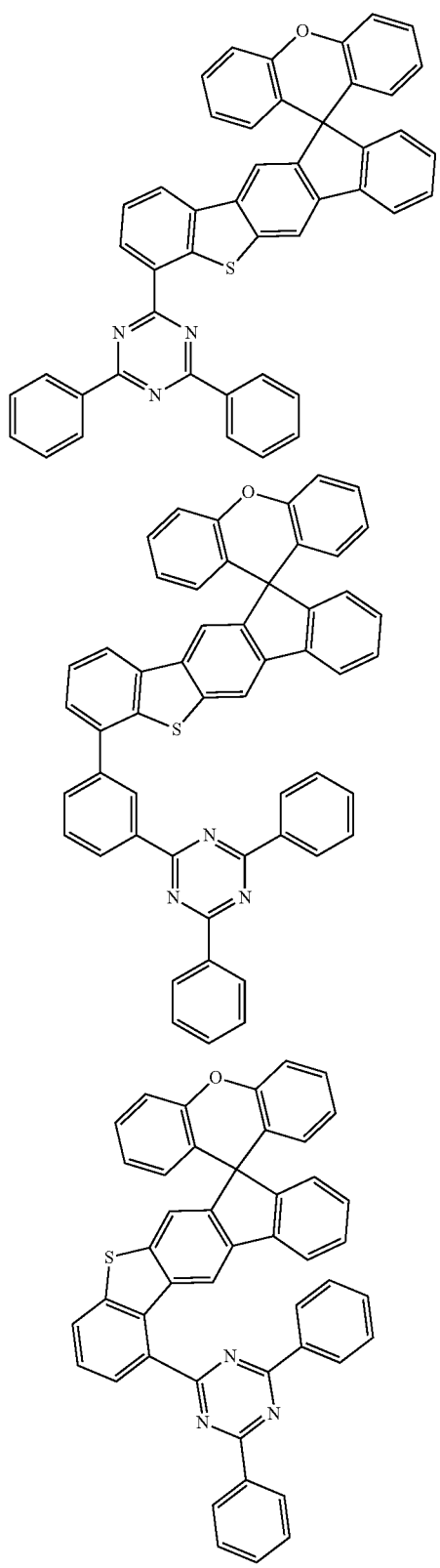
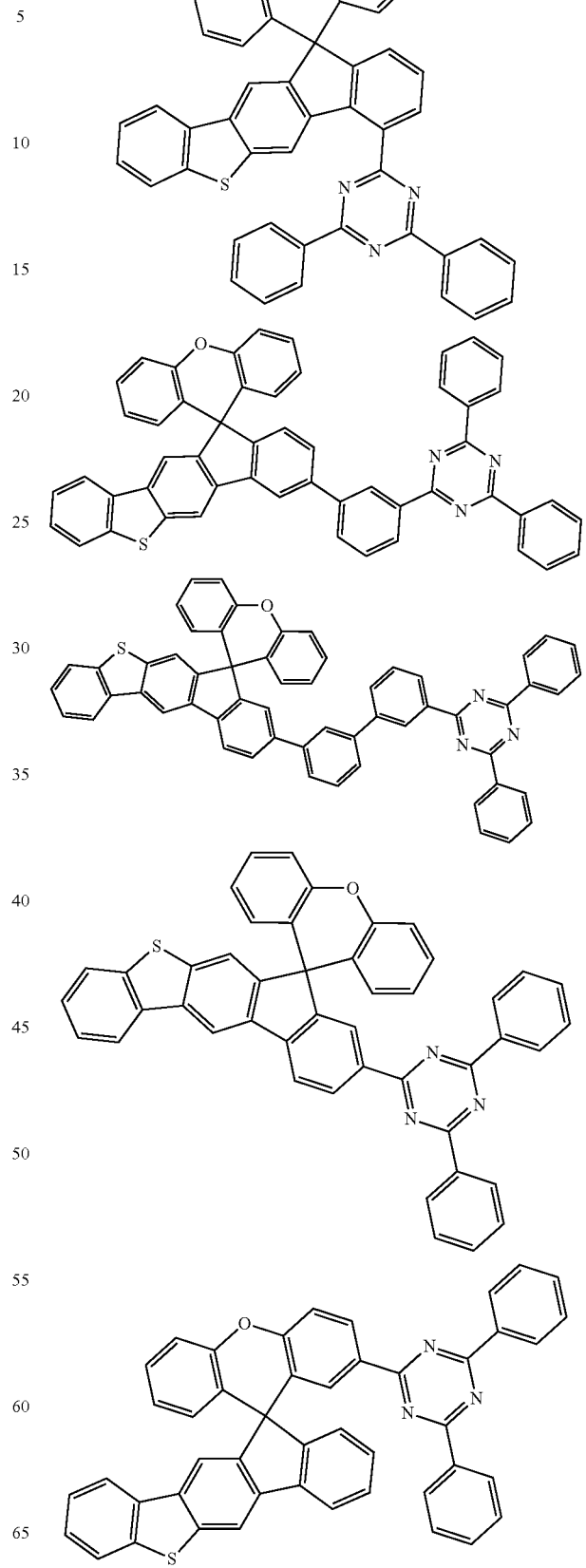

89
-continued
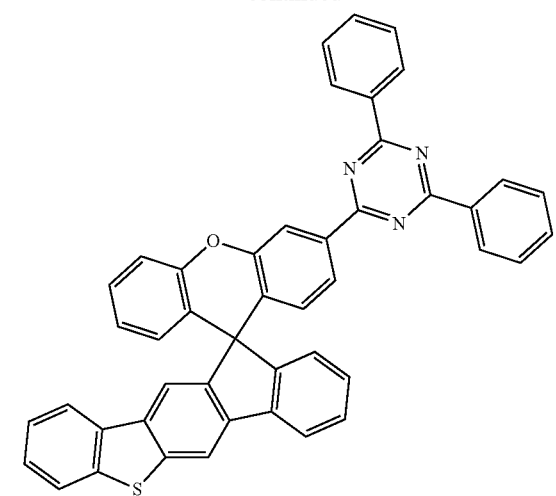
90
-continued
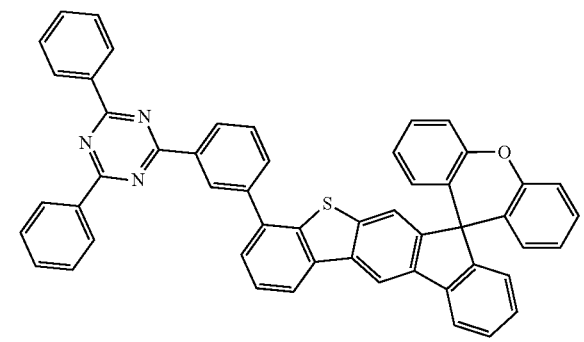
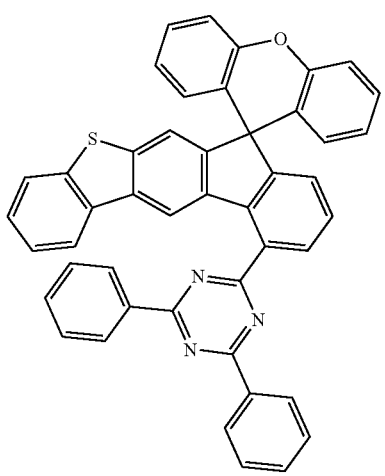
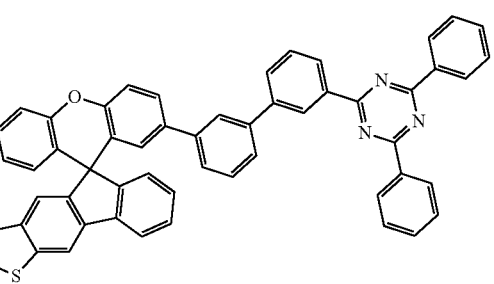
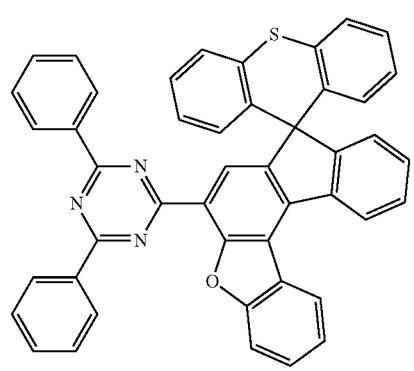

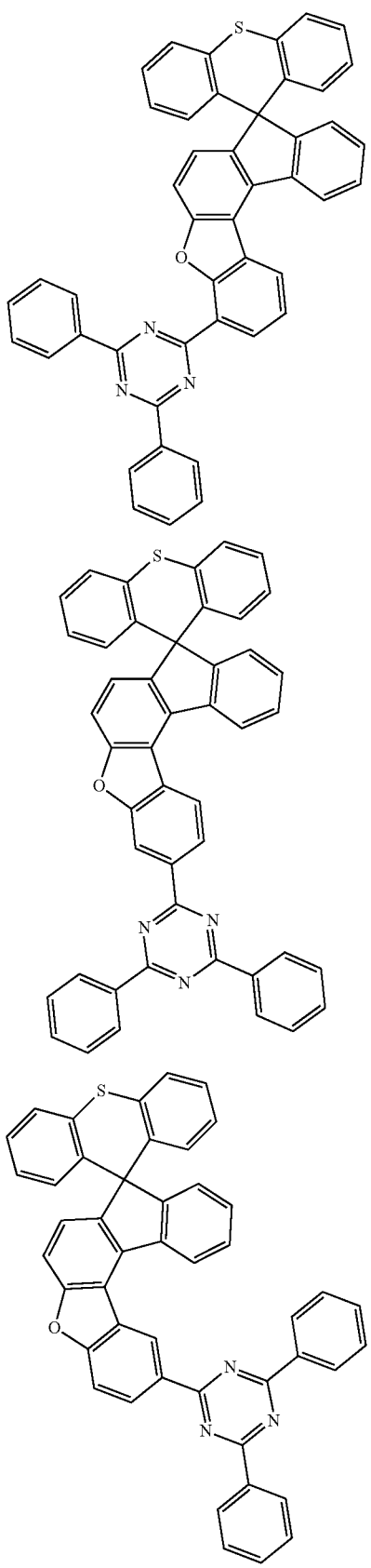
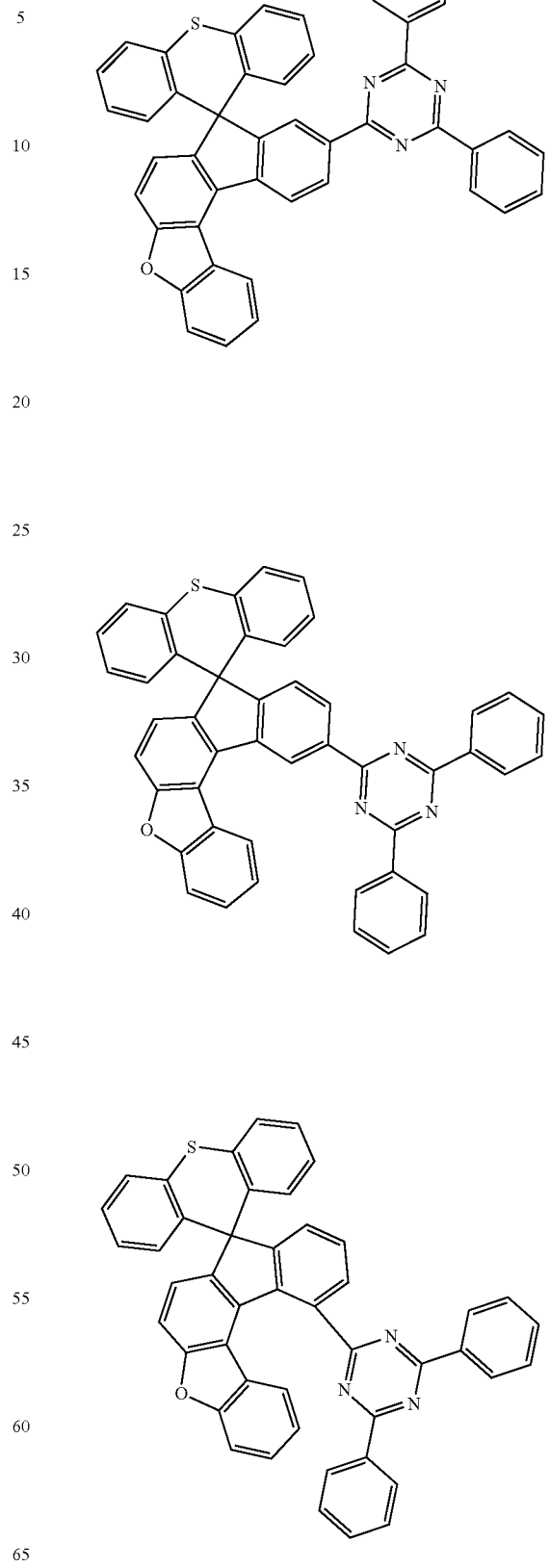

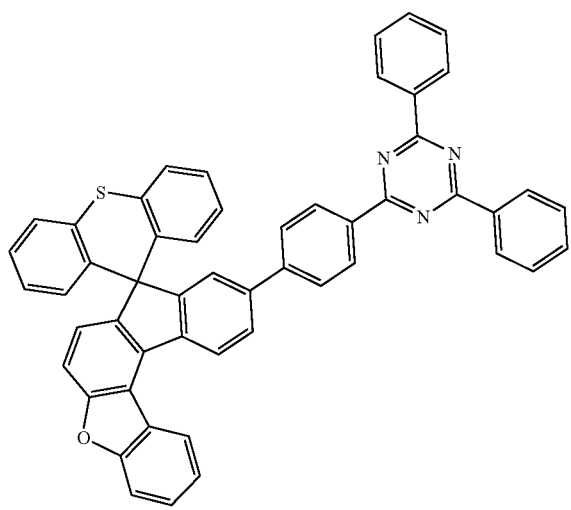
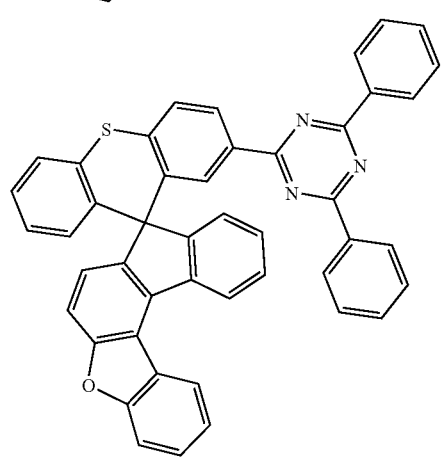
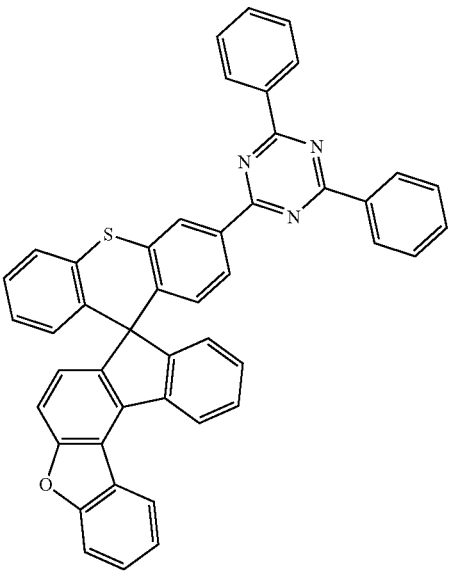
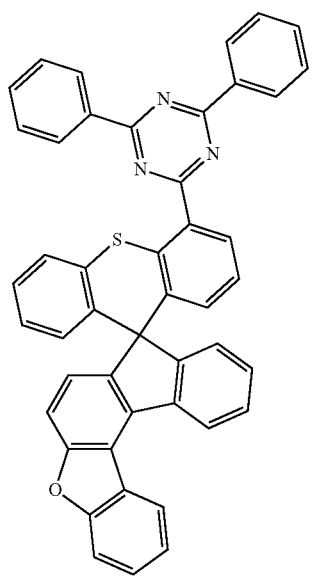
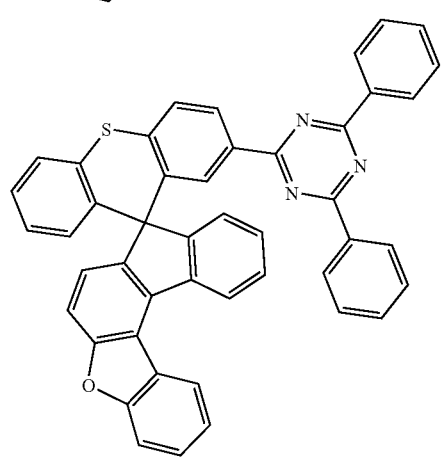
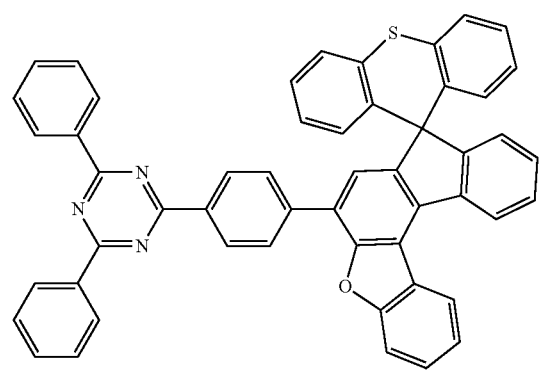

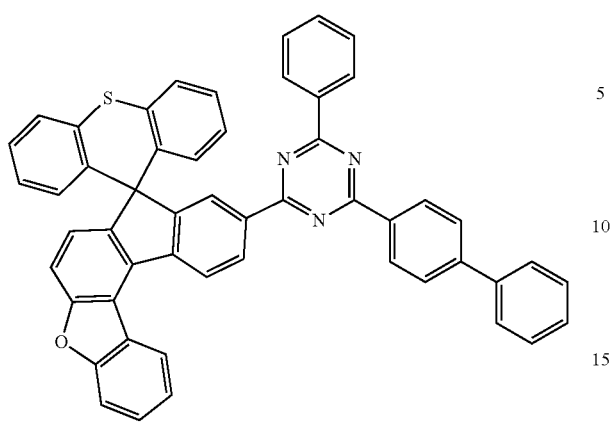
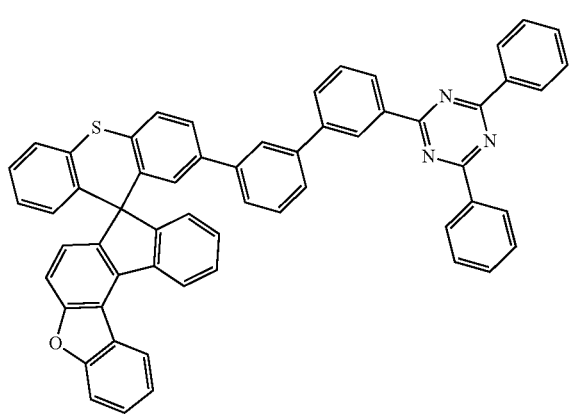
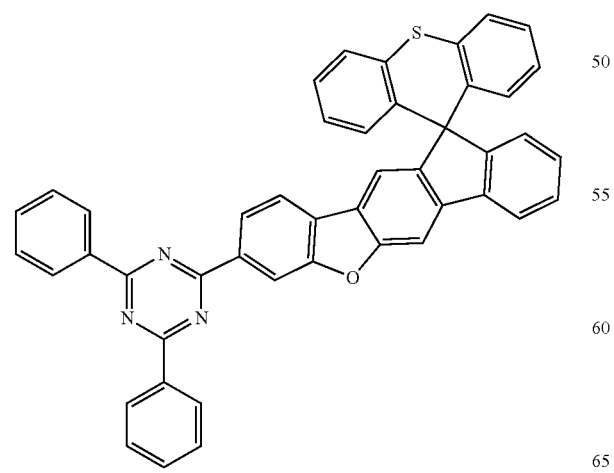
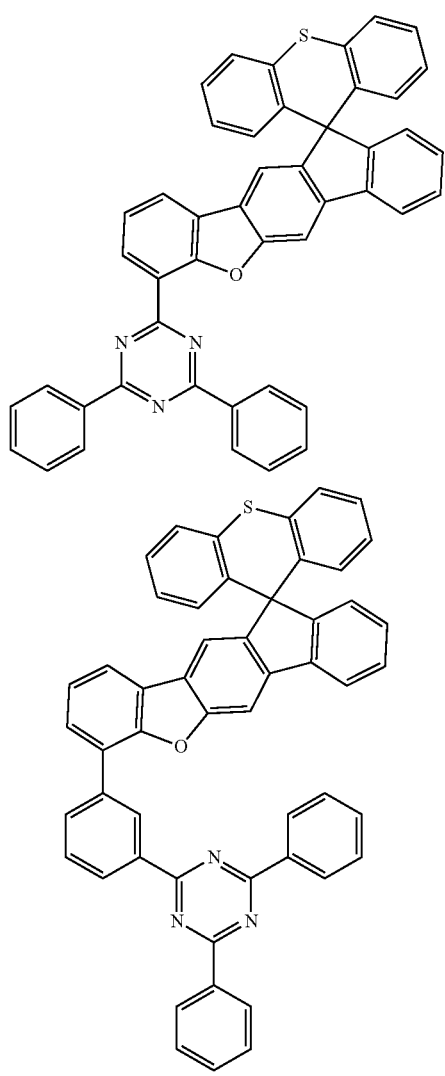
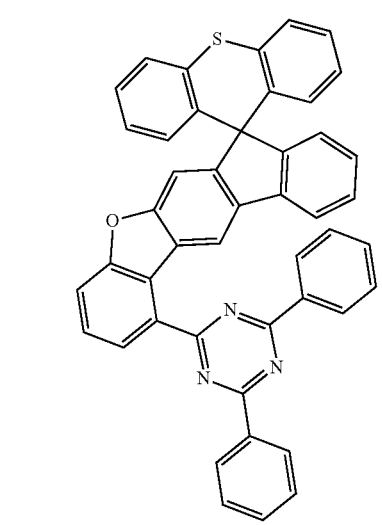

97
-continued
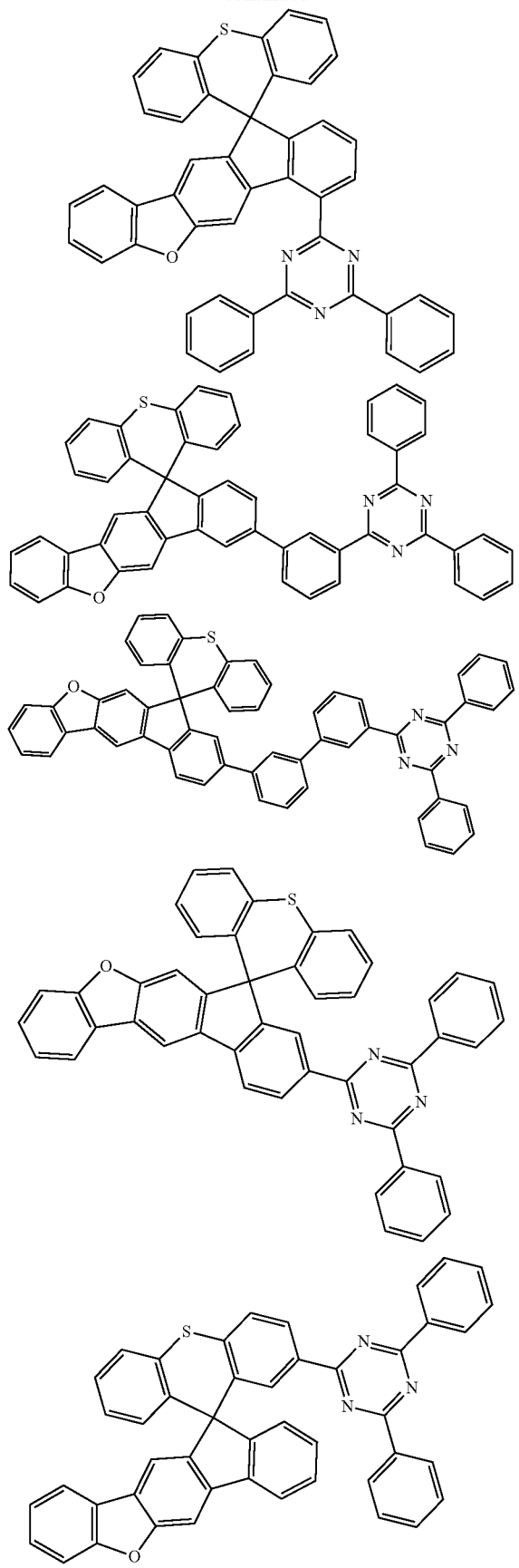
98
-continued
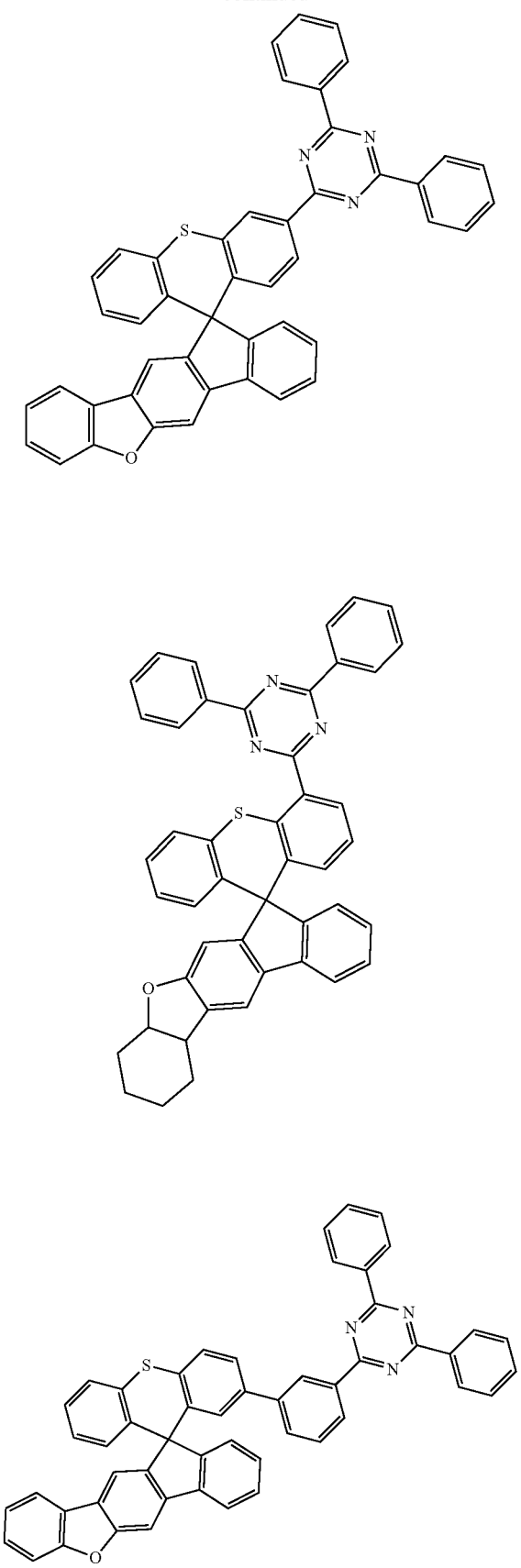

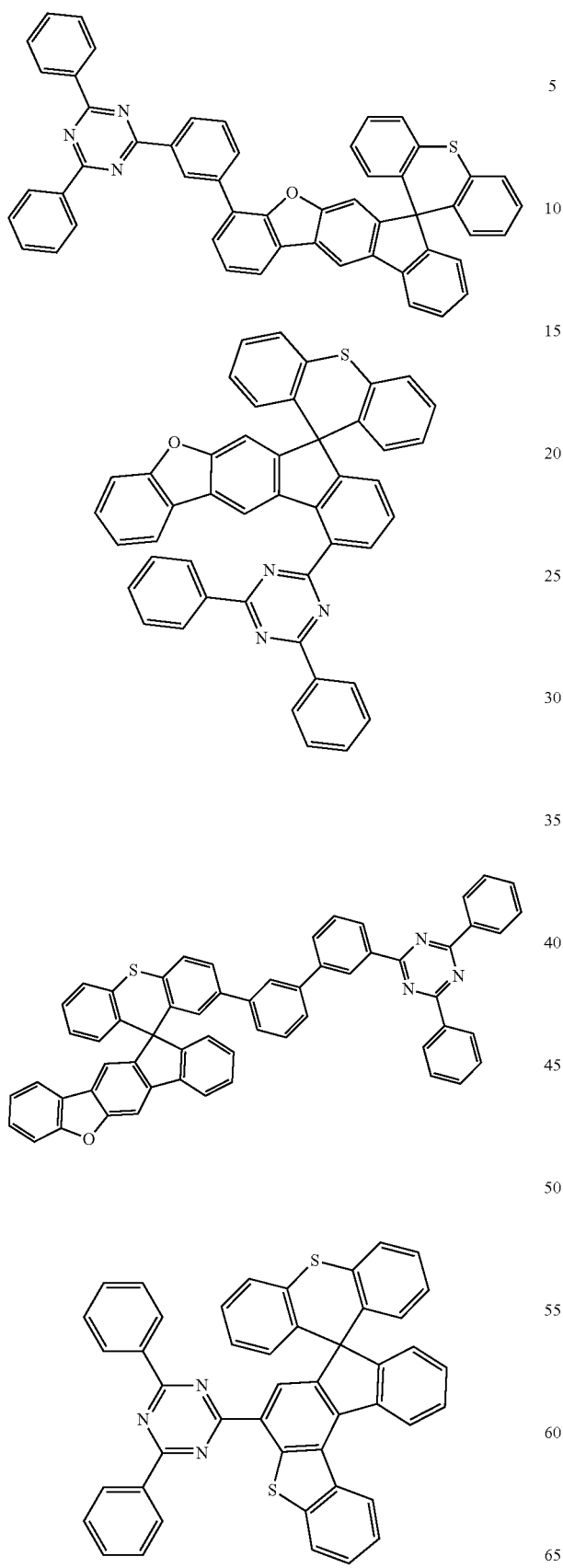
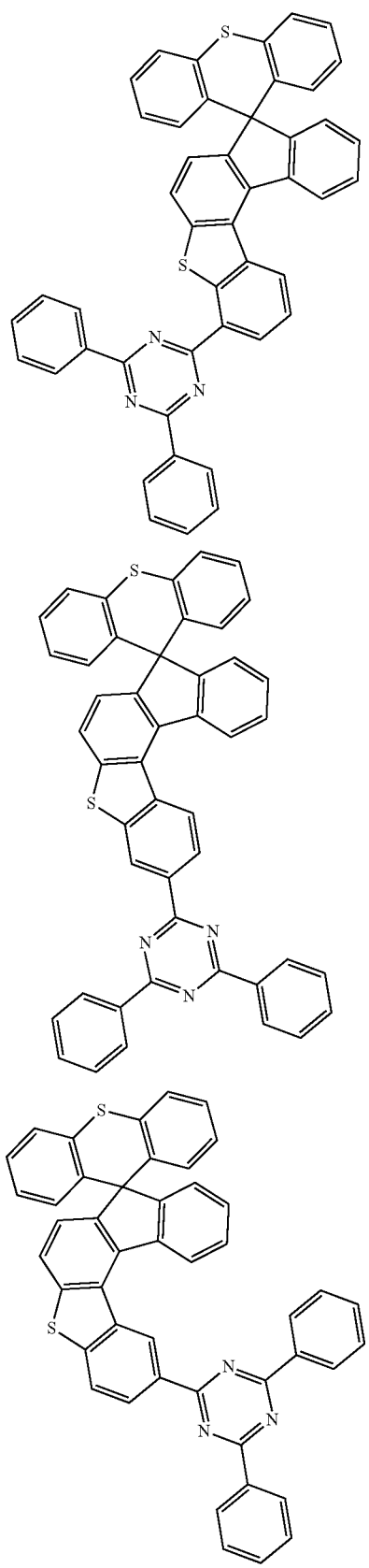

101
-continued
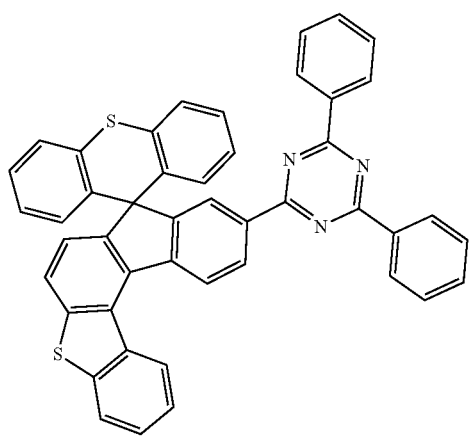
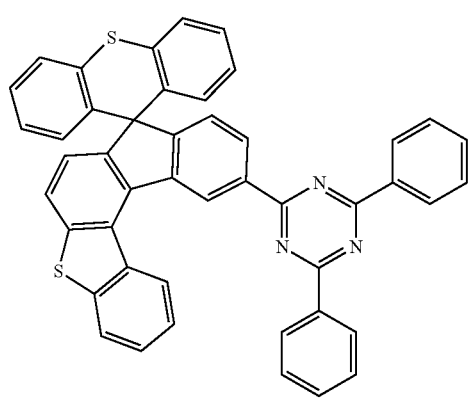
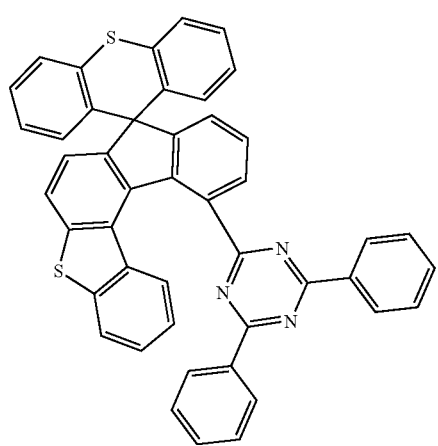
102
-continued
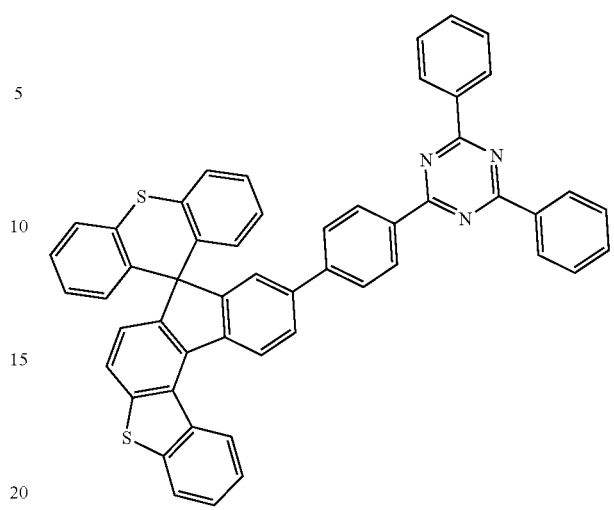
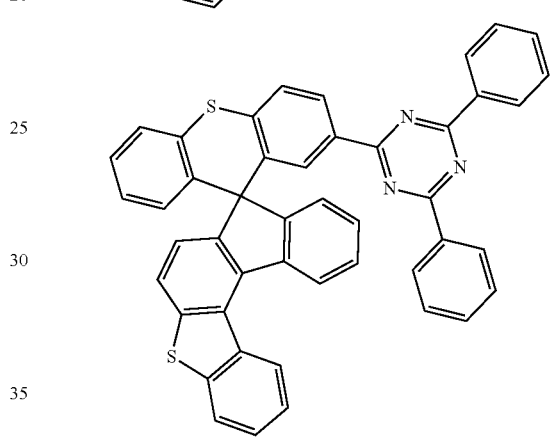
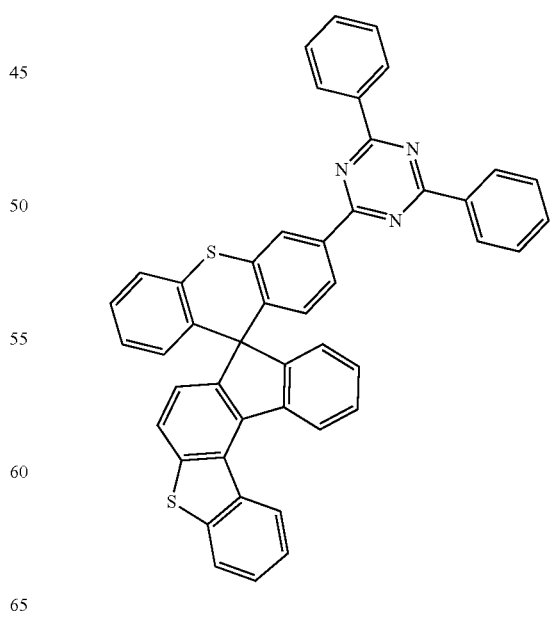

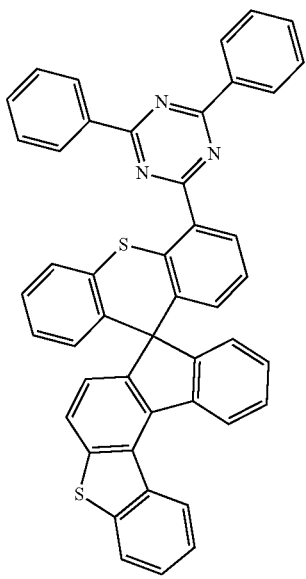
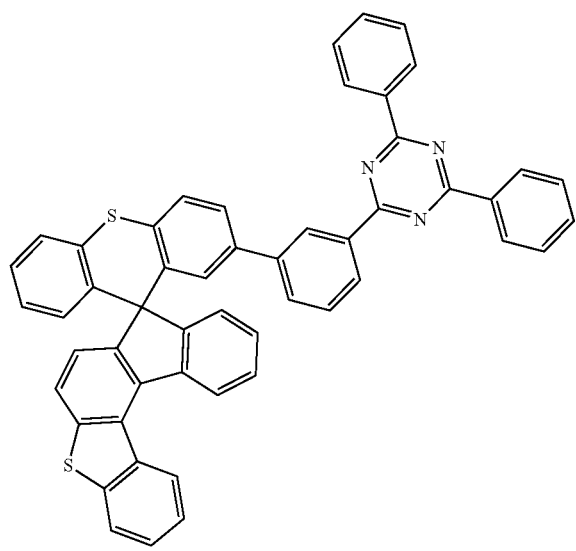
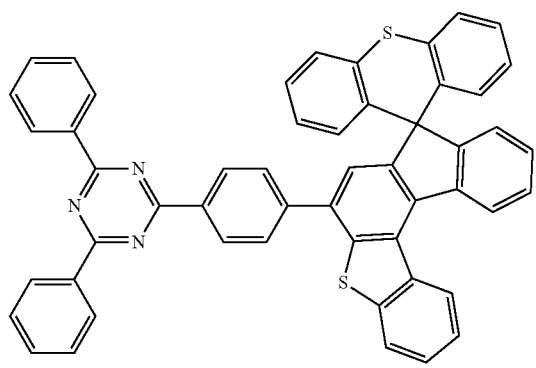
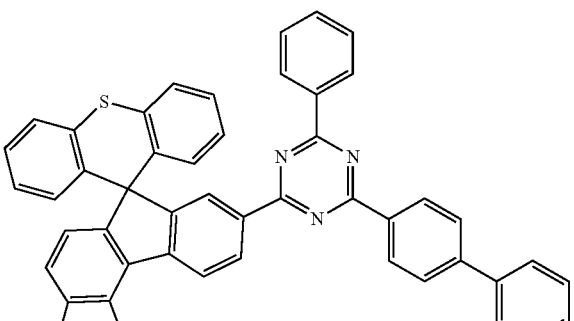
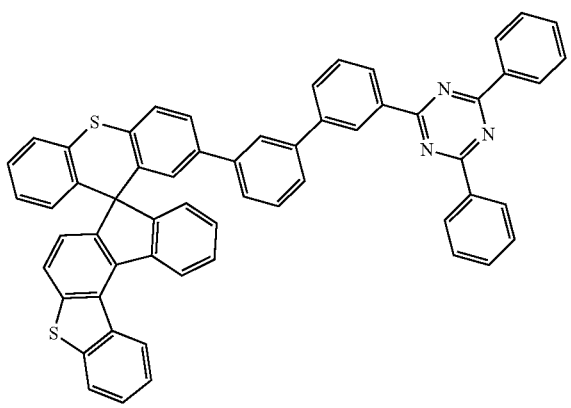
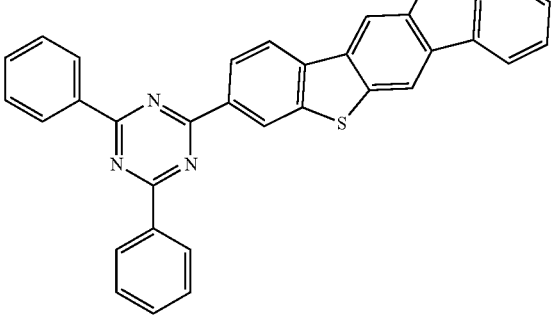

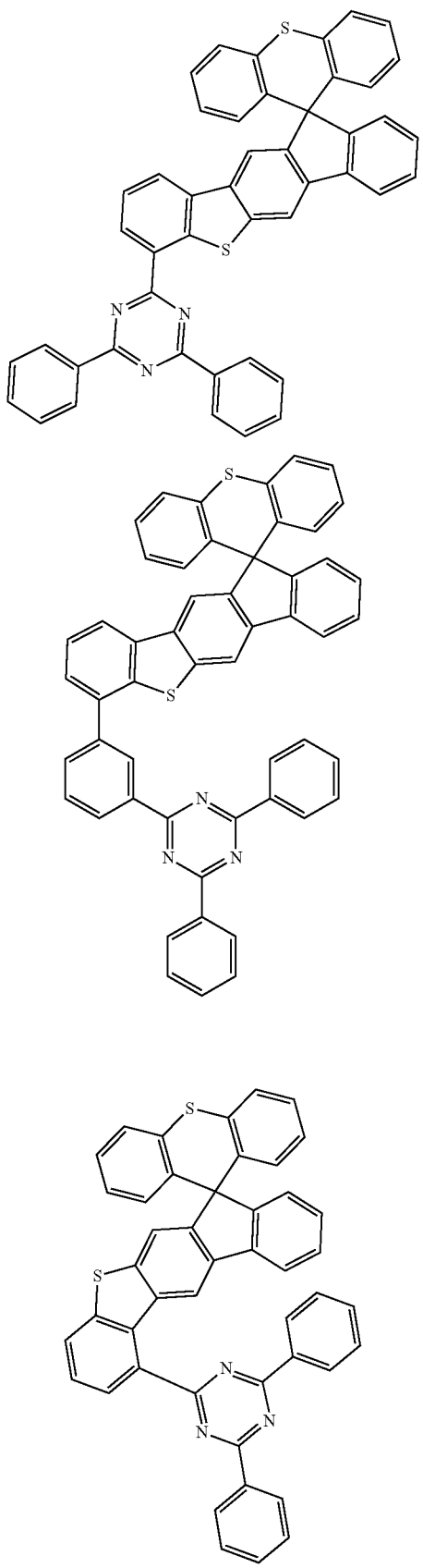
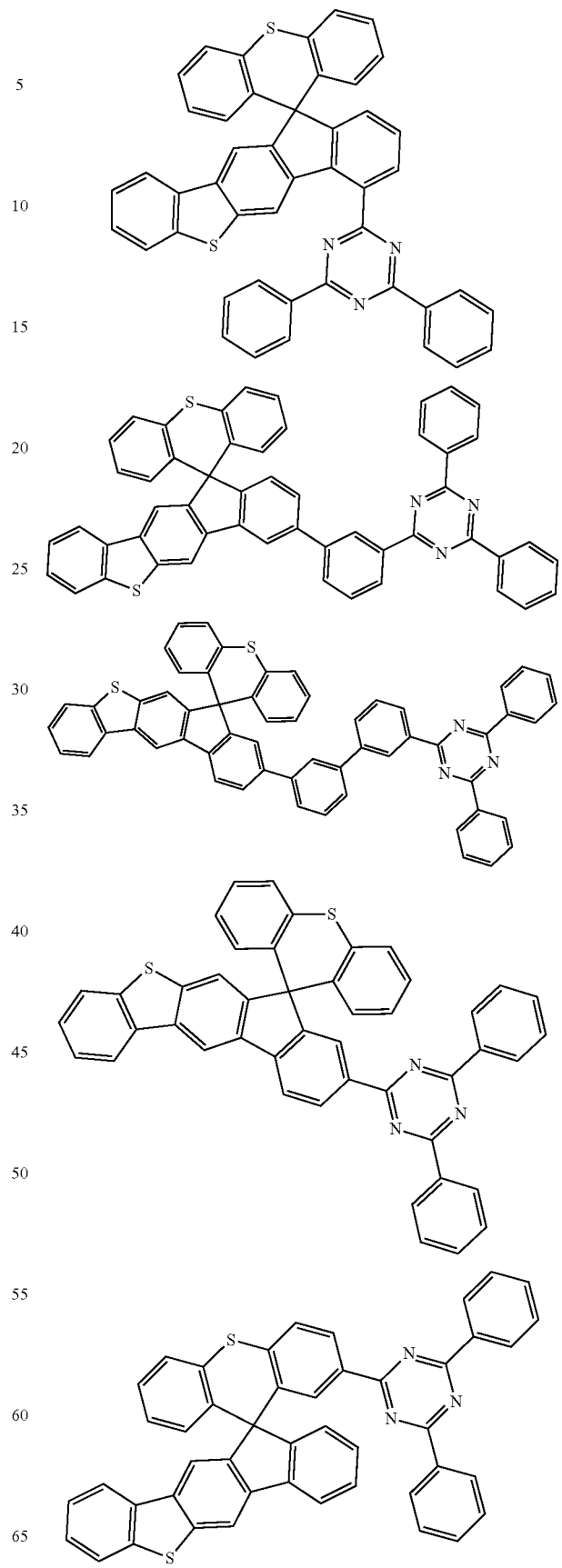

107
-continued
108
-continued
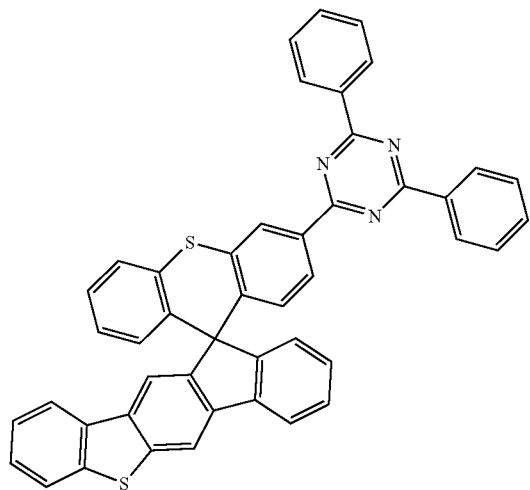
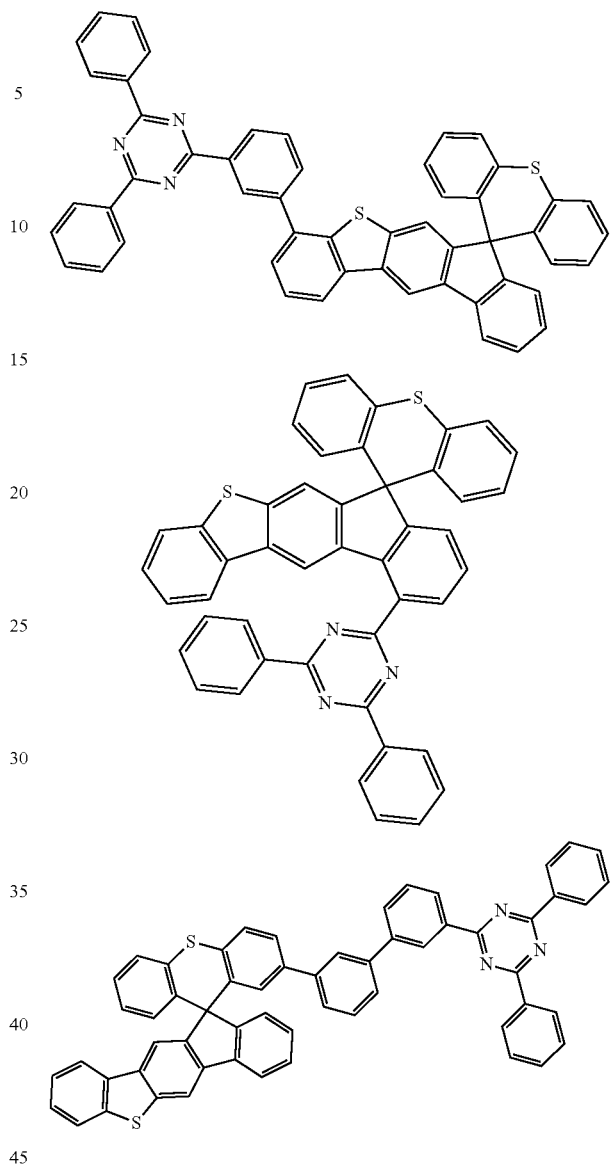
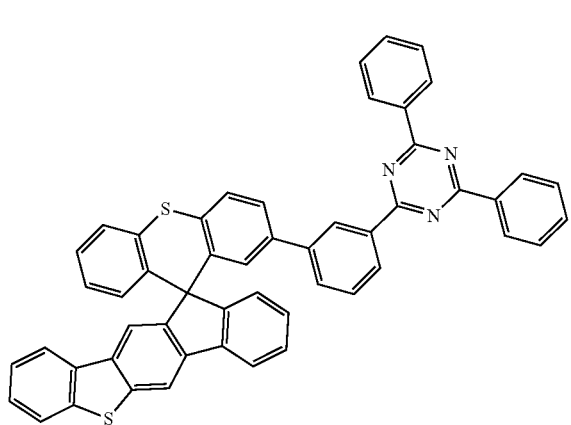
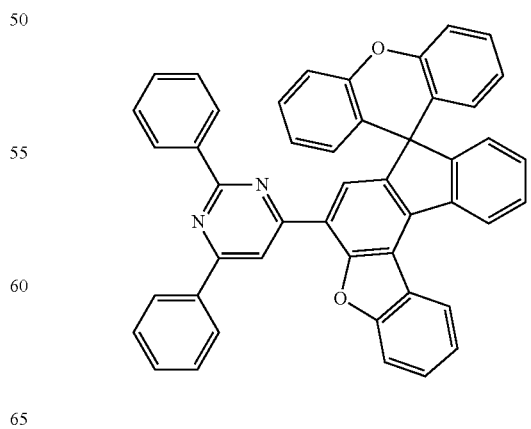

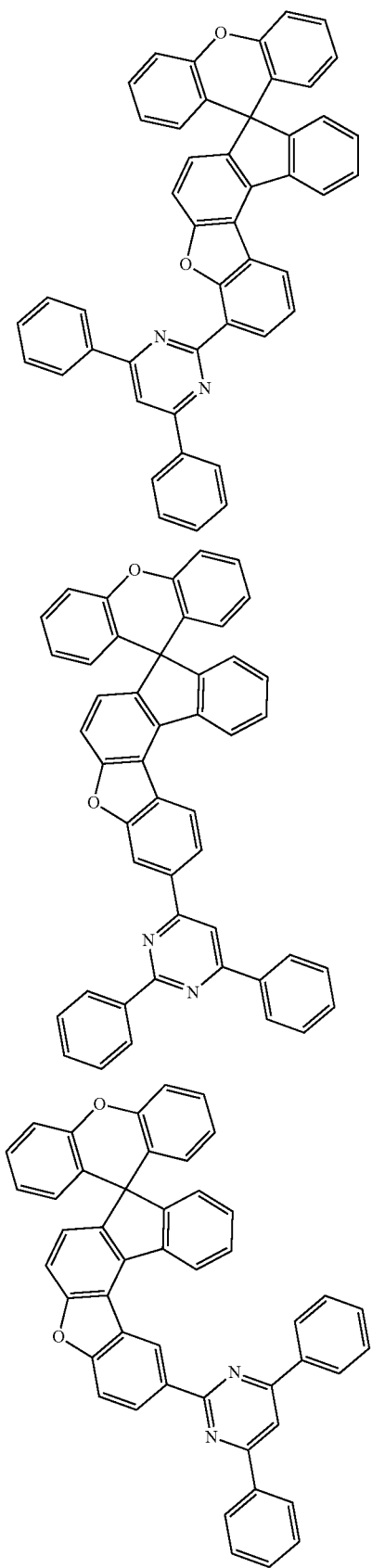
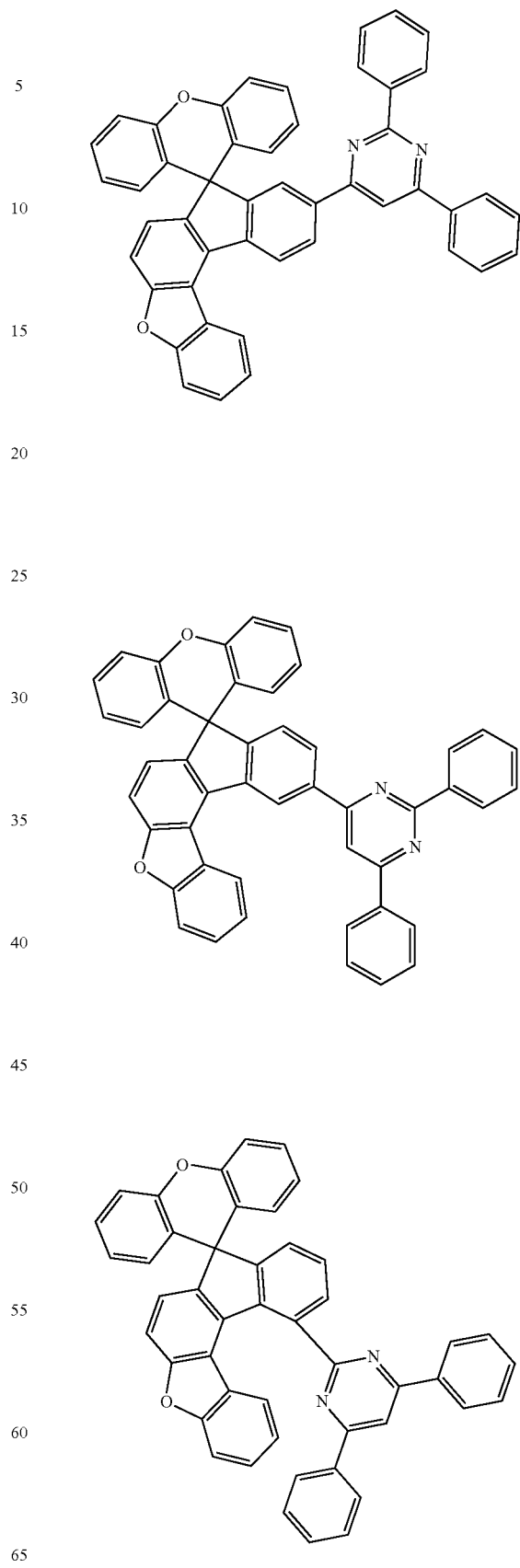

111
-continued
112
-continued
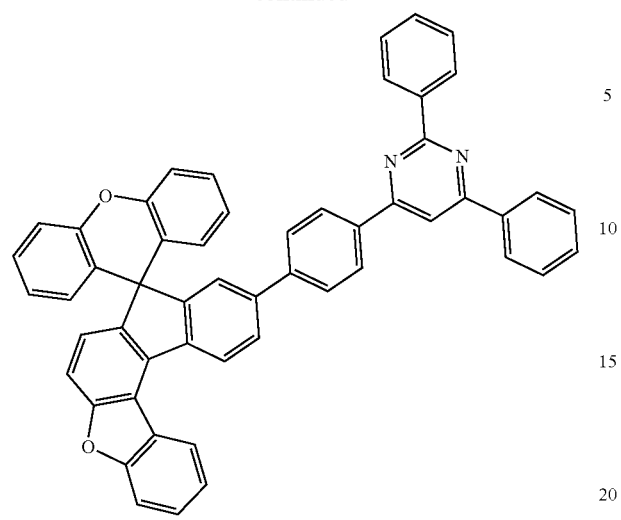
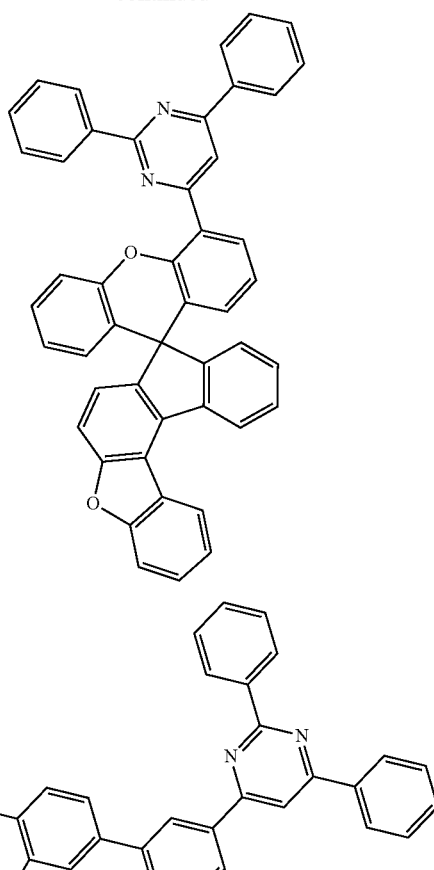
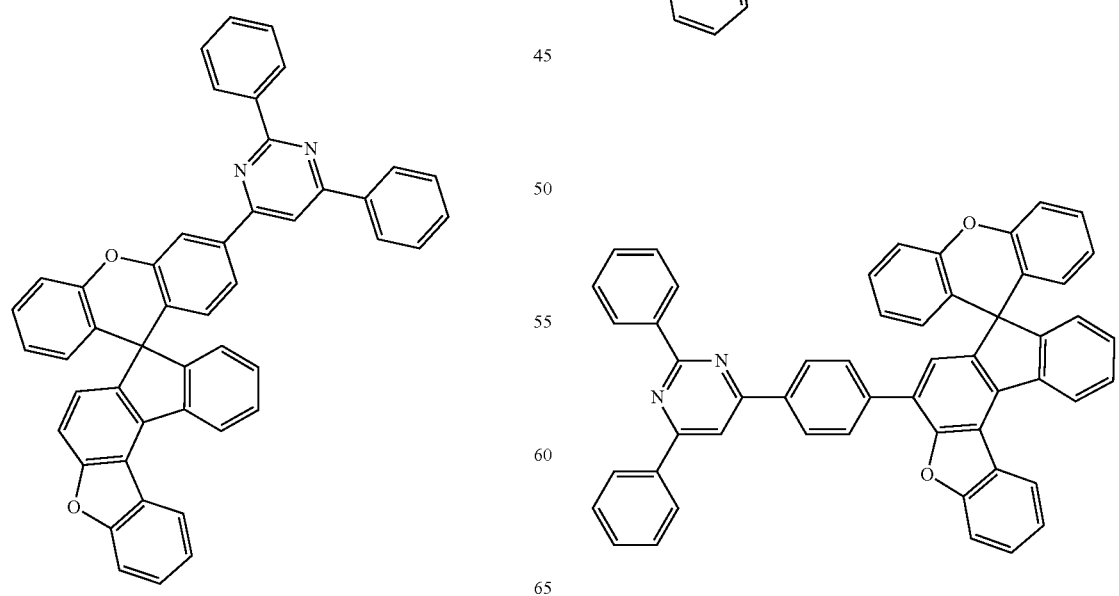

113
-continued
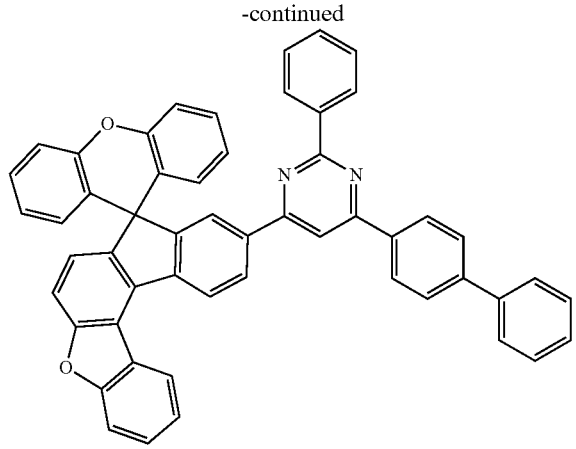
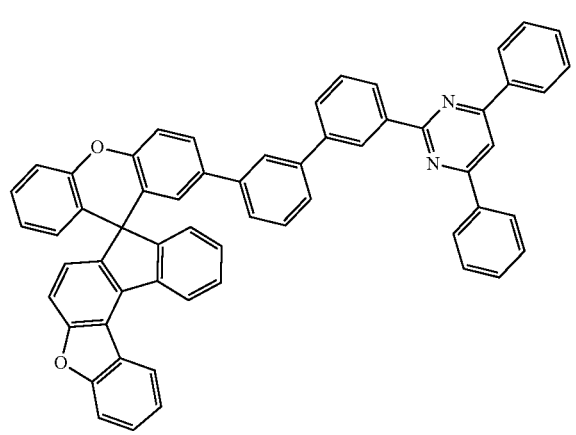
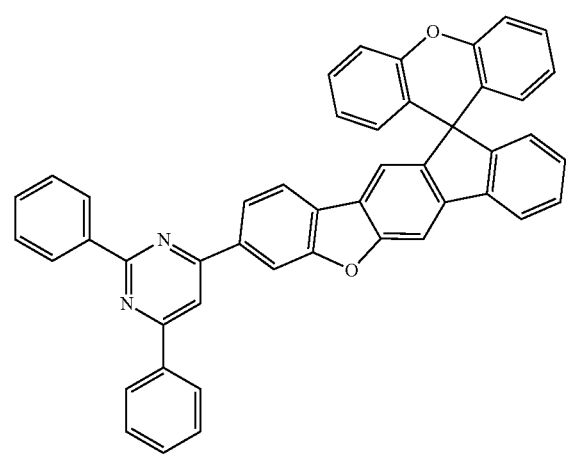
114
-continued
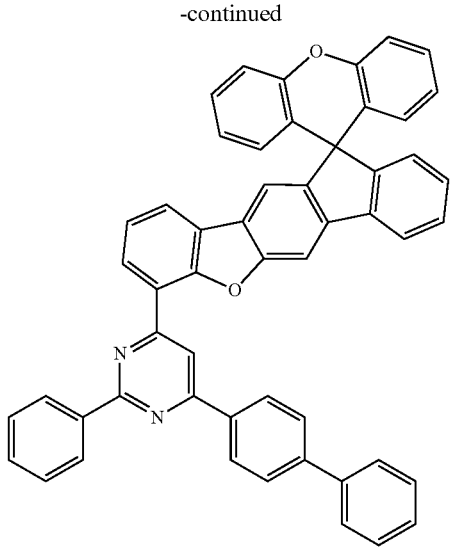
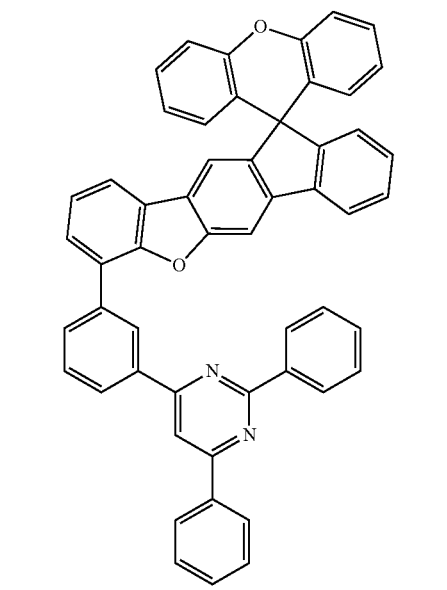
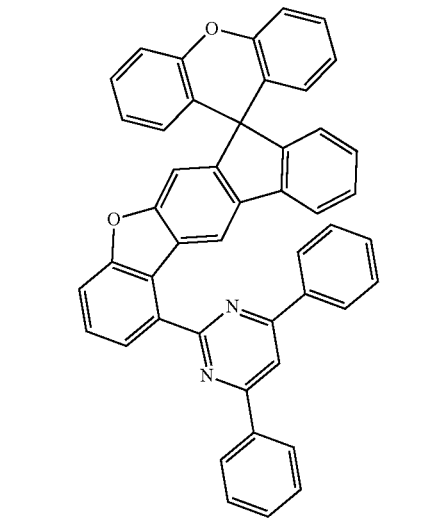

115
-continued
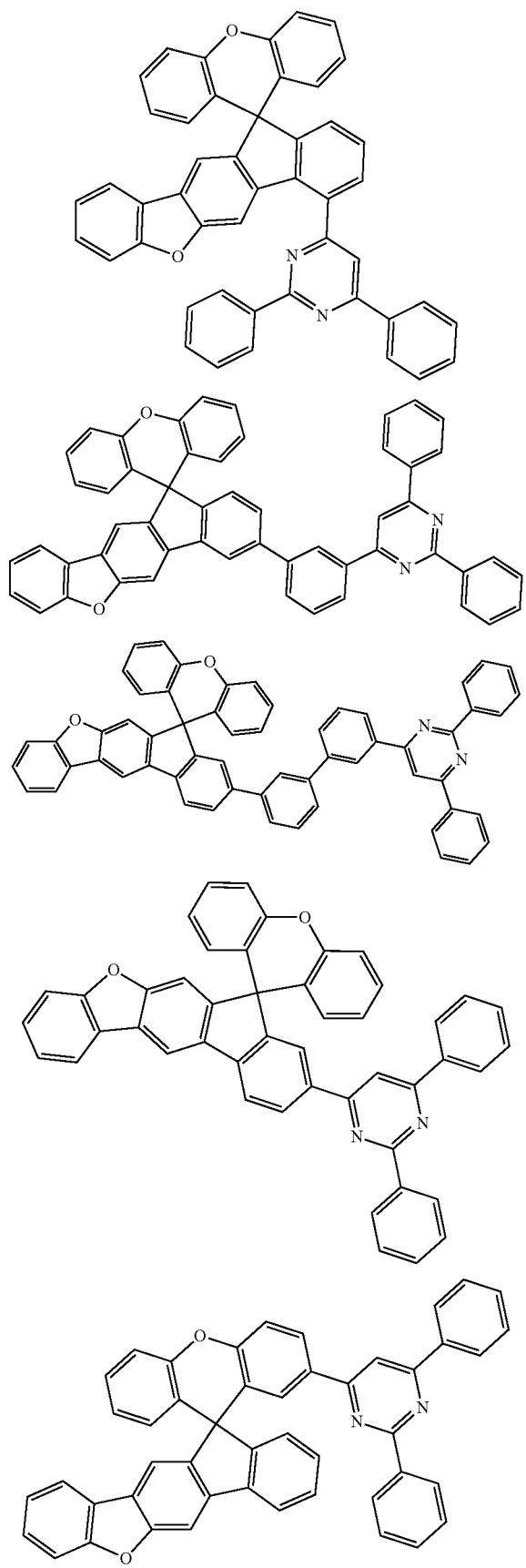
116
-continued
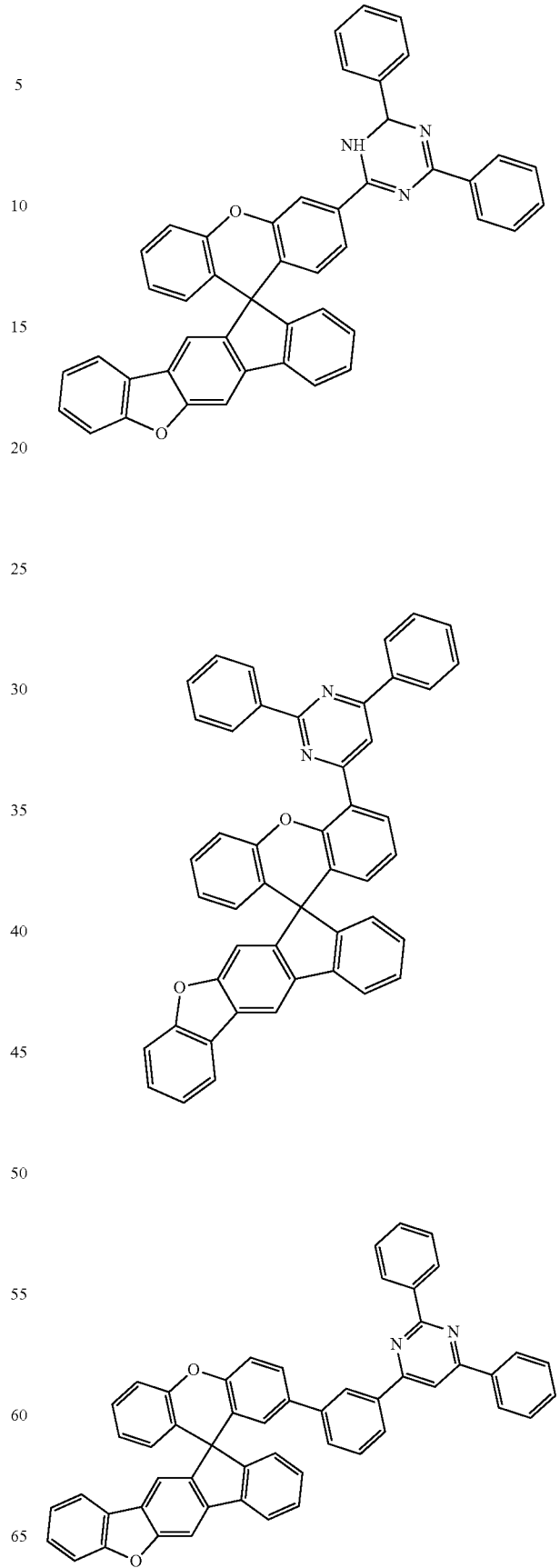

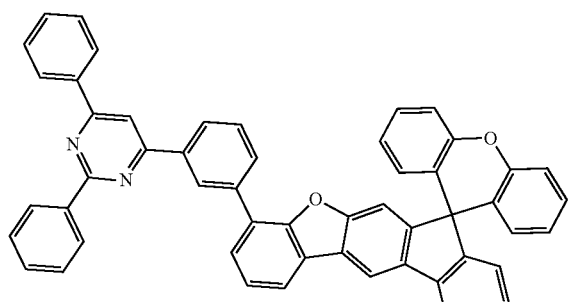
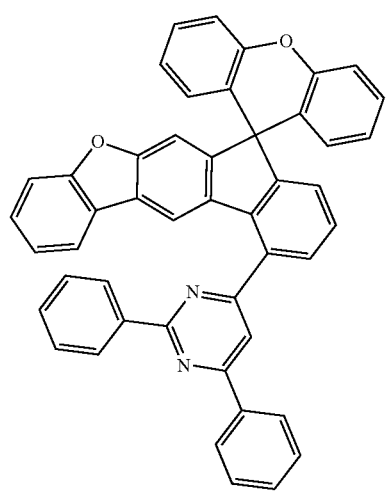
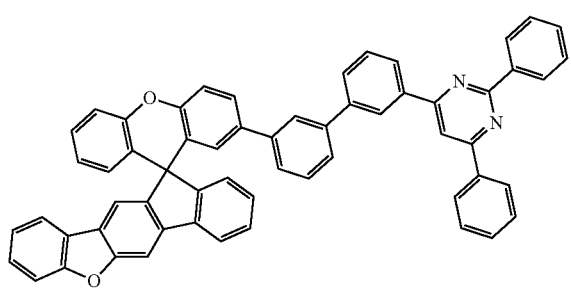
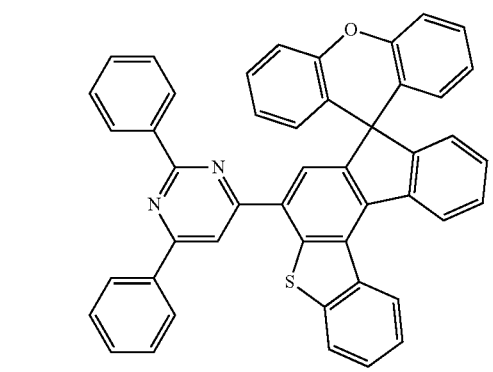
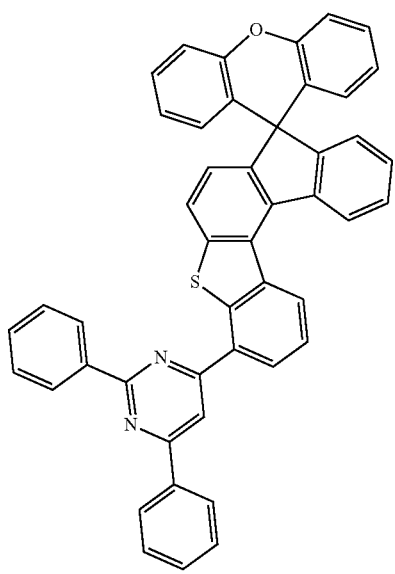
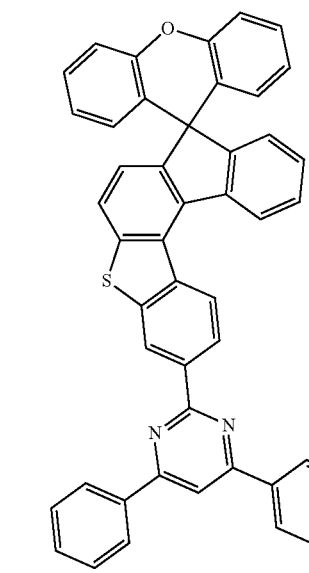
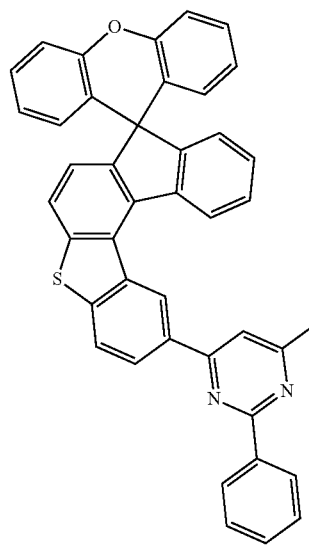

119
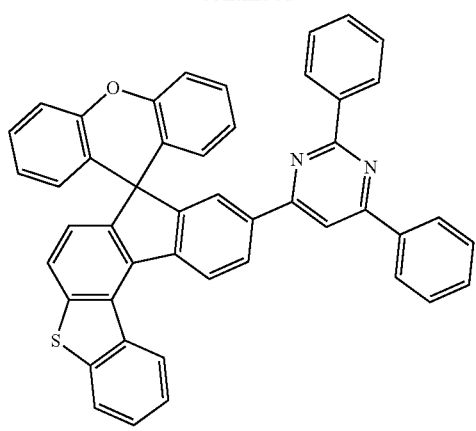
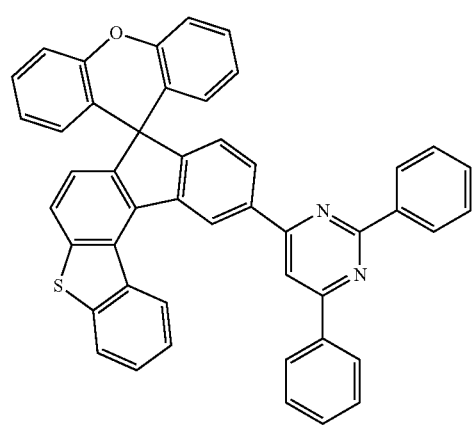
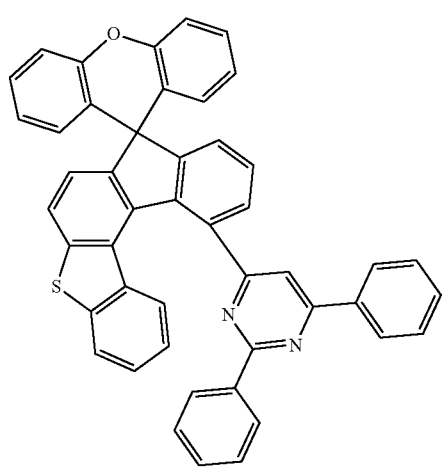
120
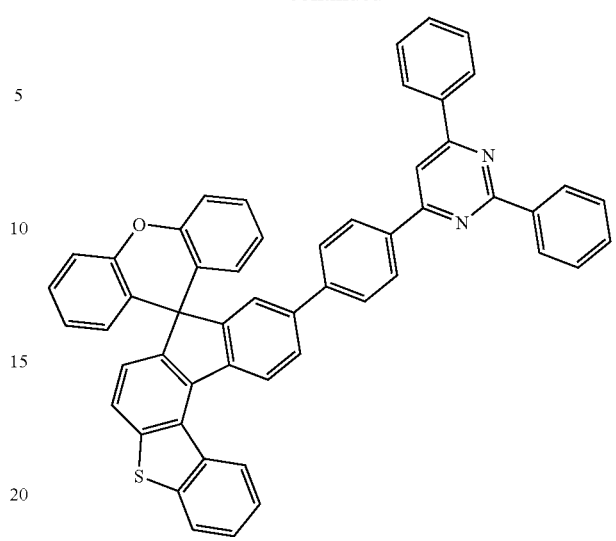
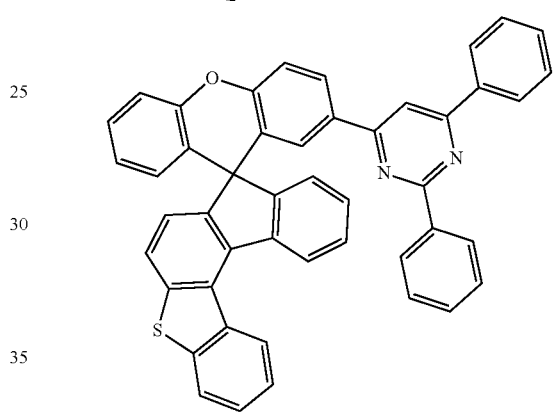
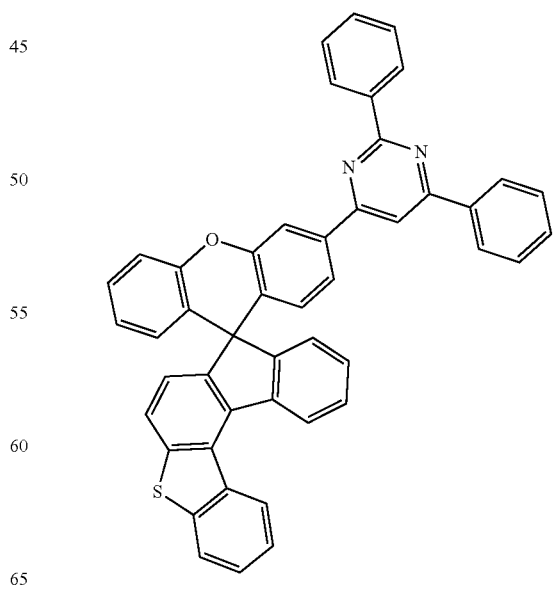

121
-continued
122
-continued
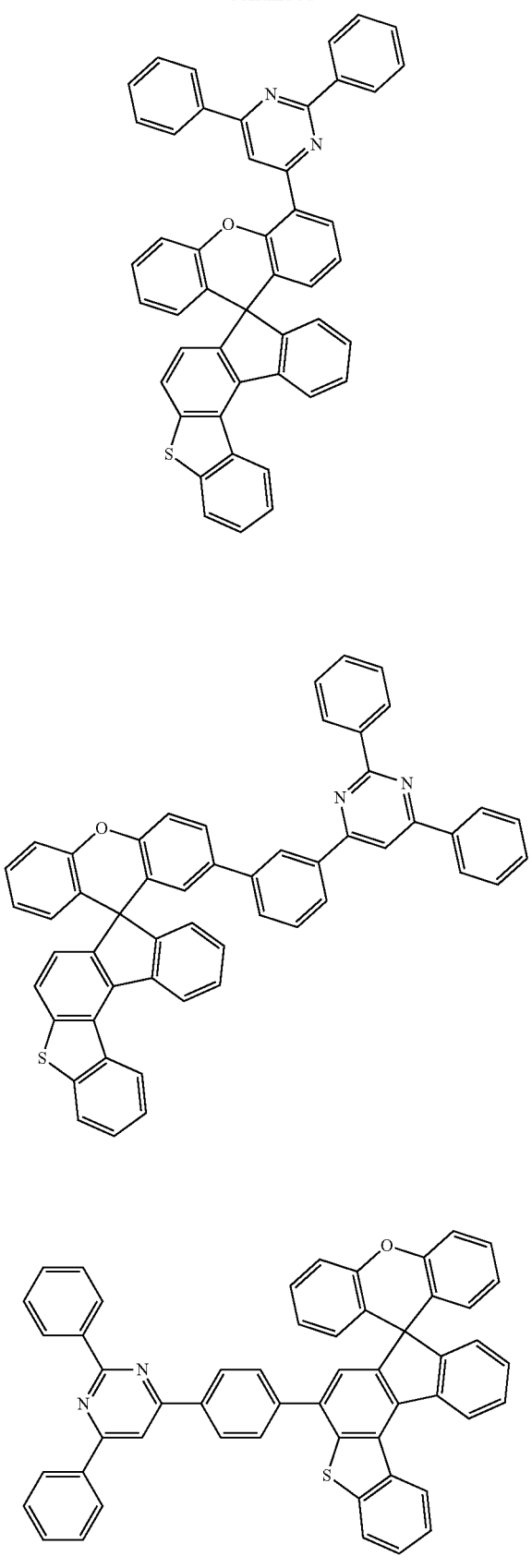
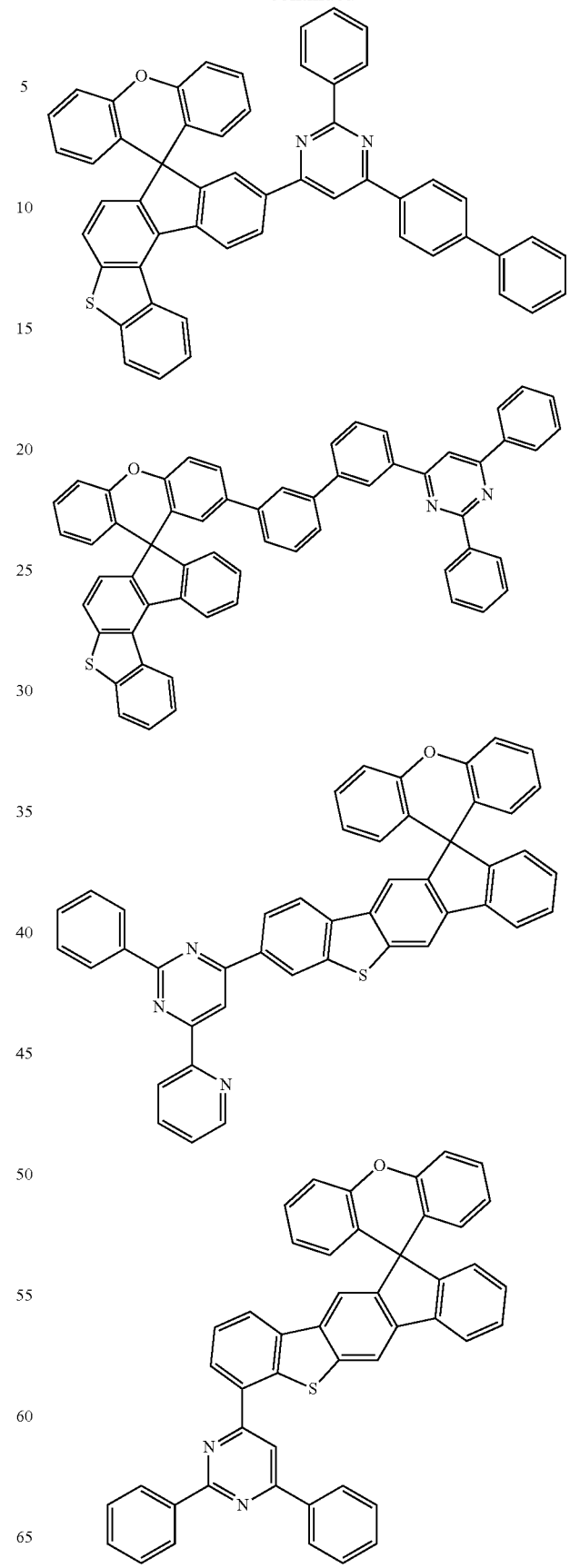

123
-continued
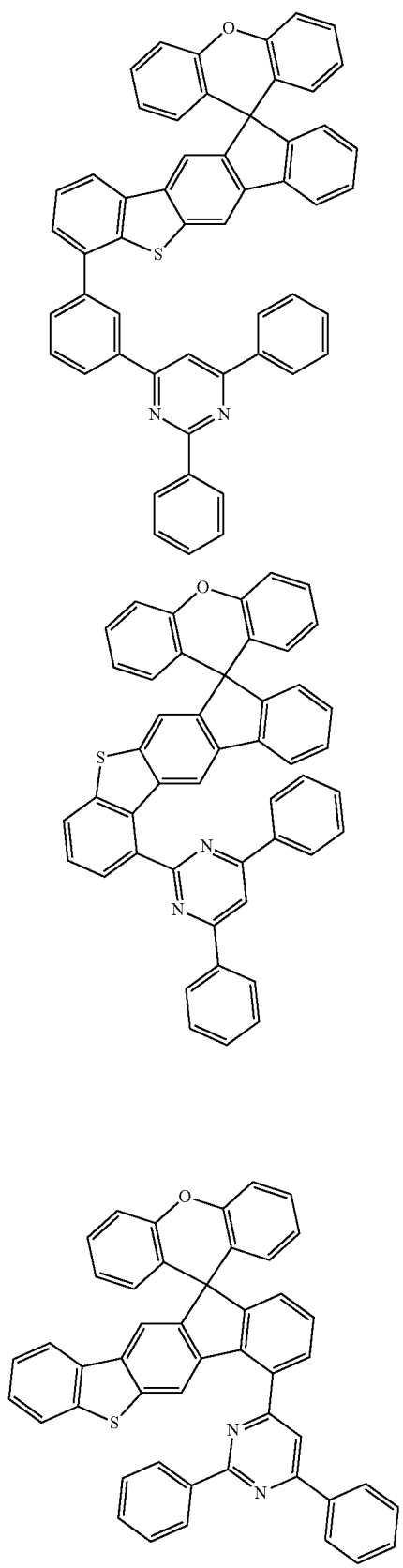
124
-continued
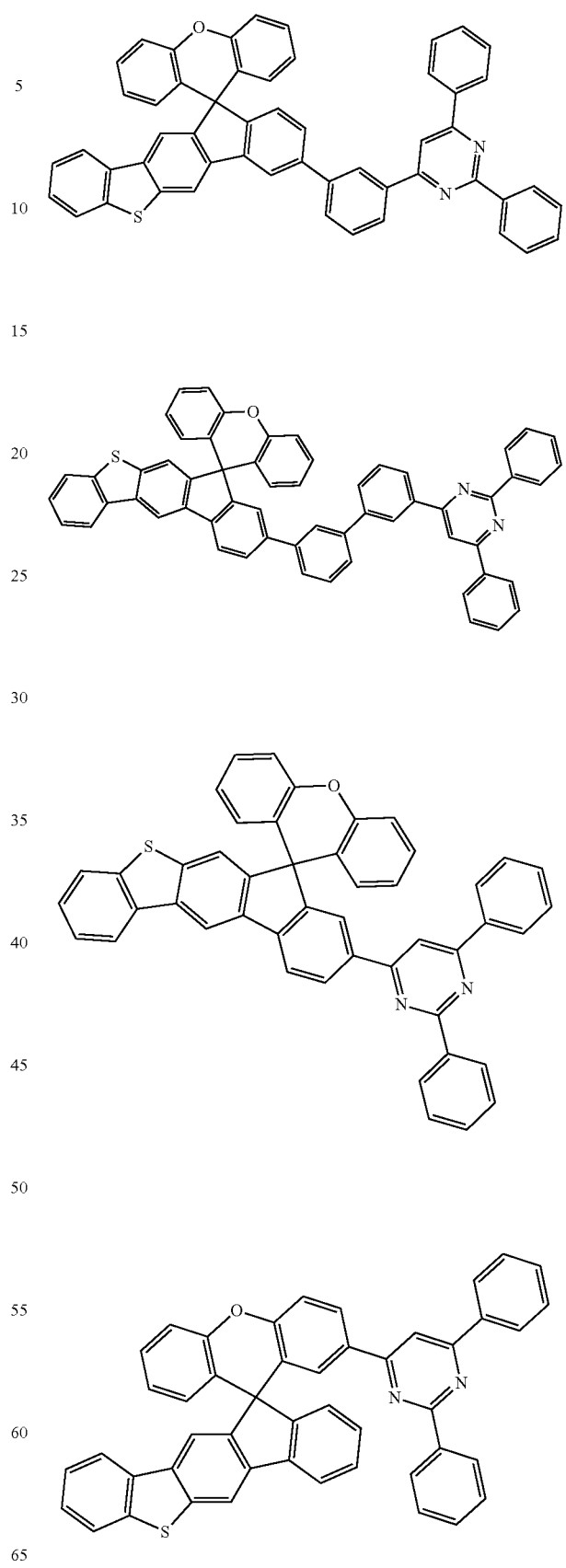

125
-continued
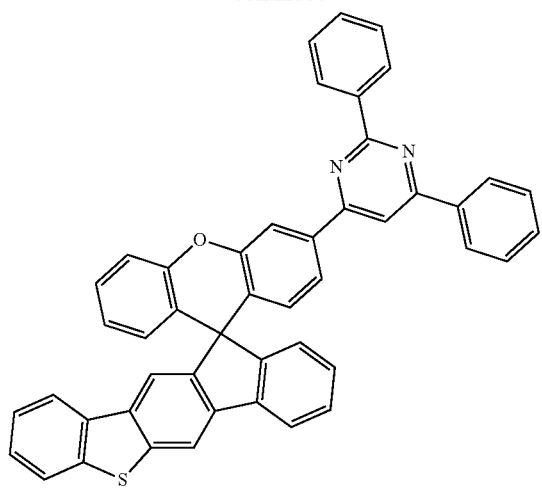
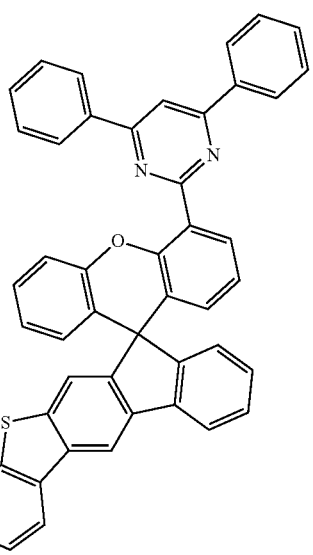
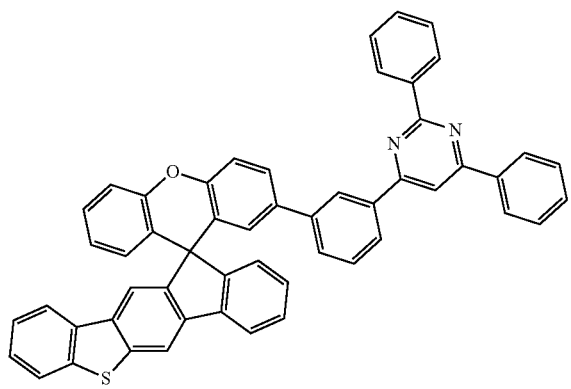
126
-continued
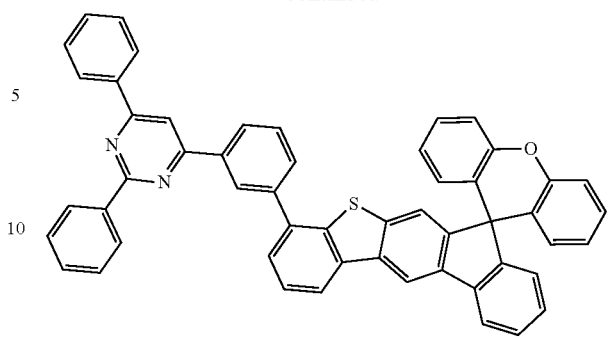
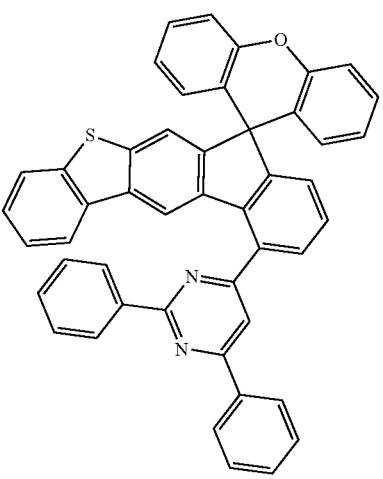
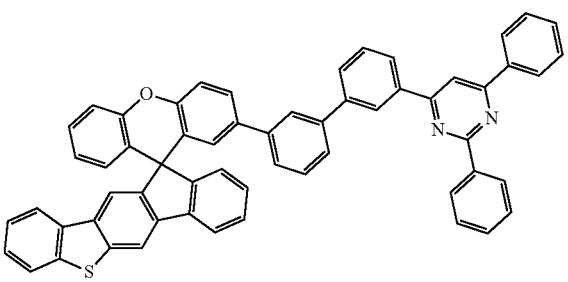
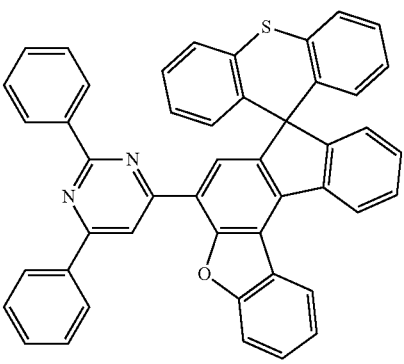

127
-continued
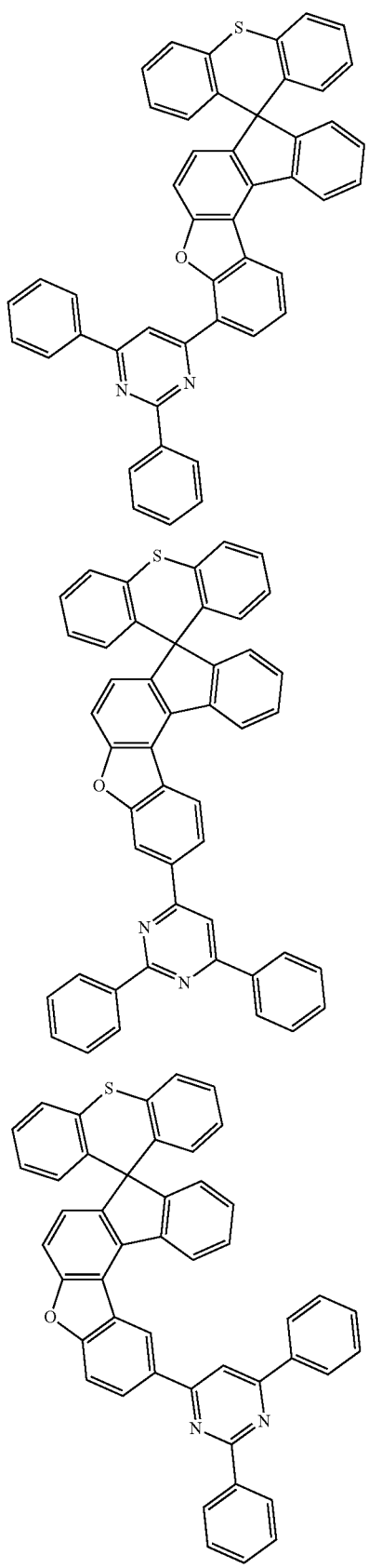
128
-continued
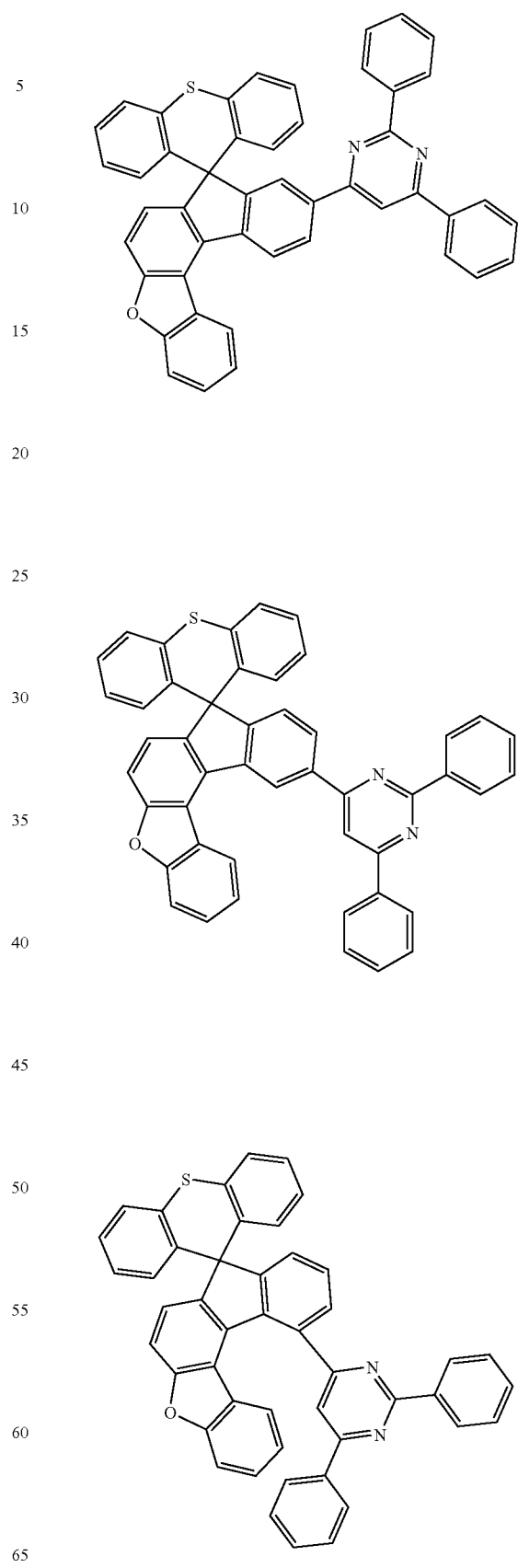

129
-continued
130
-continued
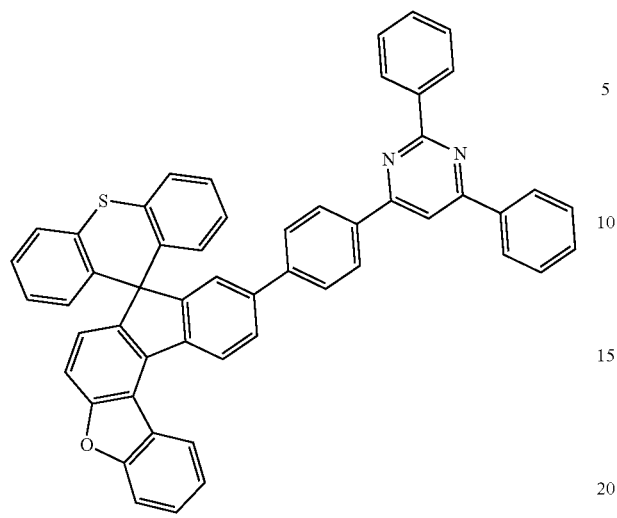
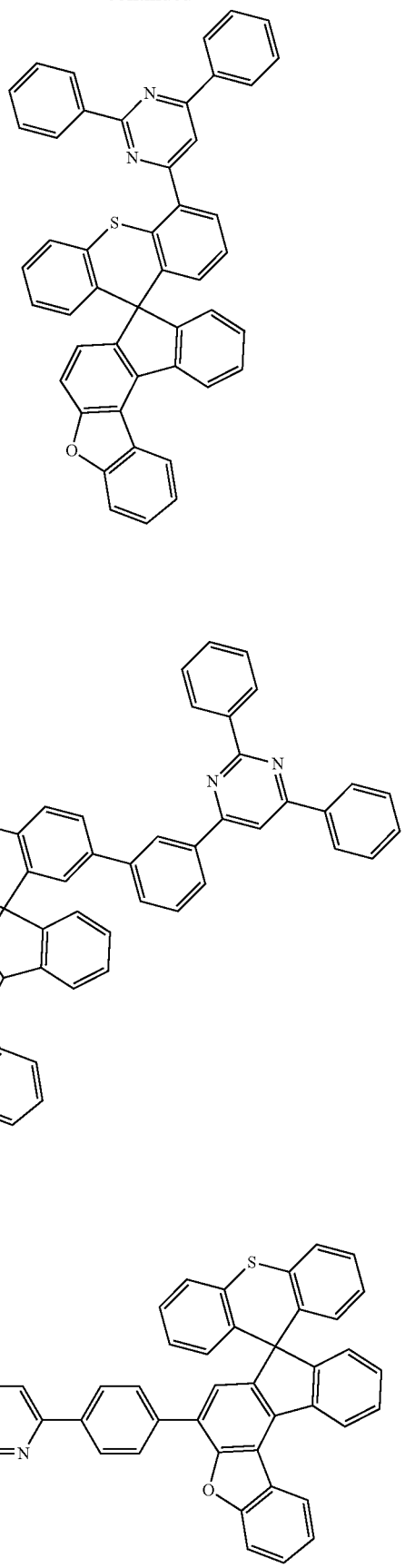

131
-continued
132
-continued
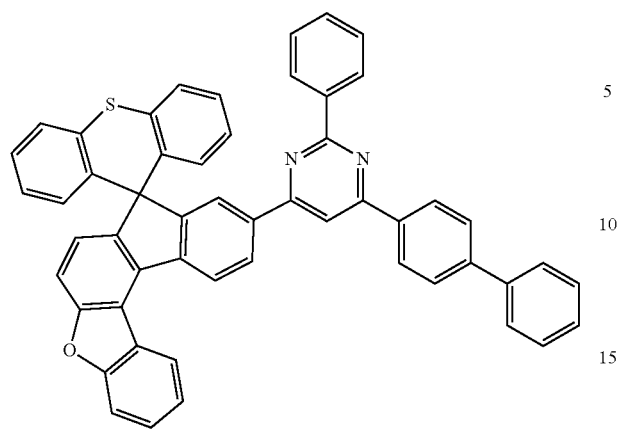
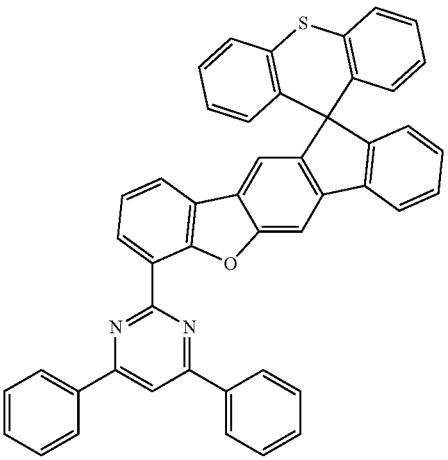
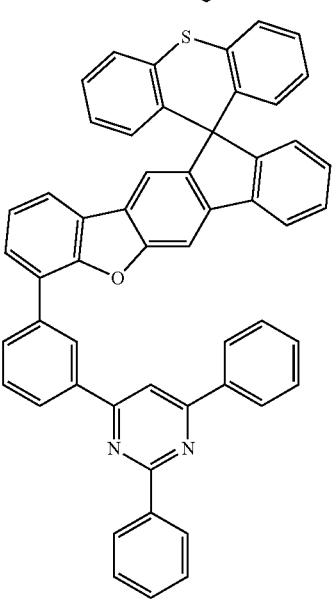
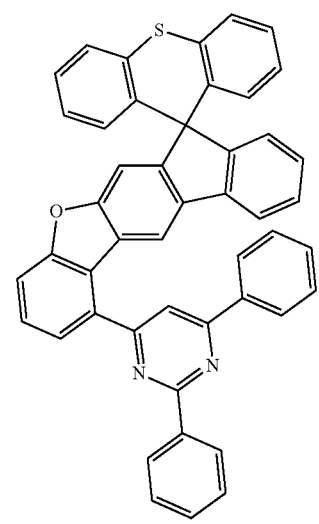

133
-continued
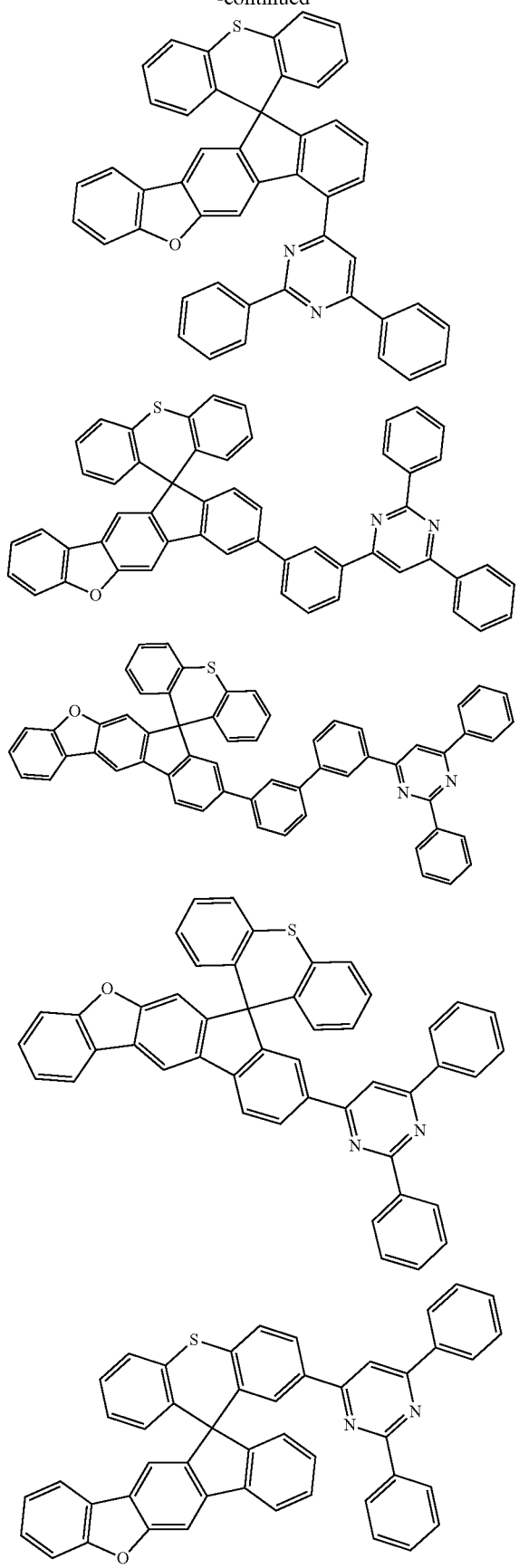
134
-continued
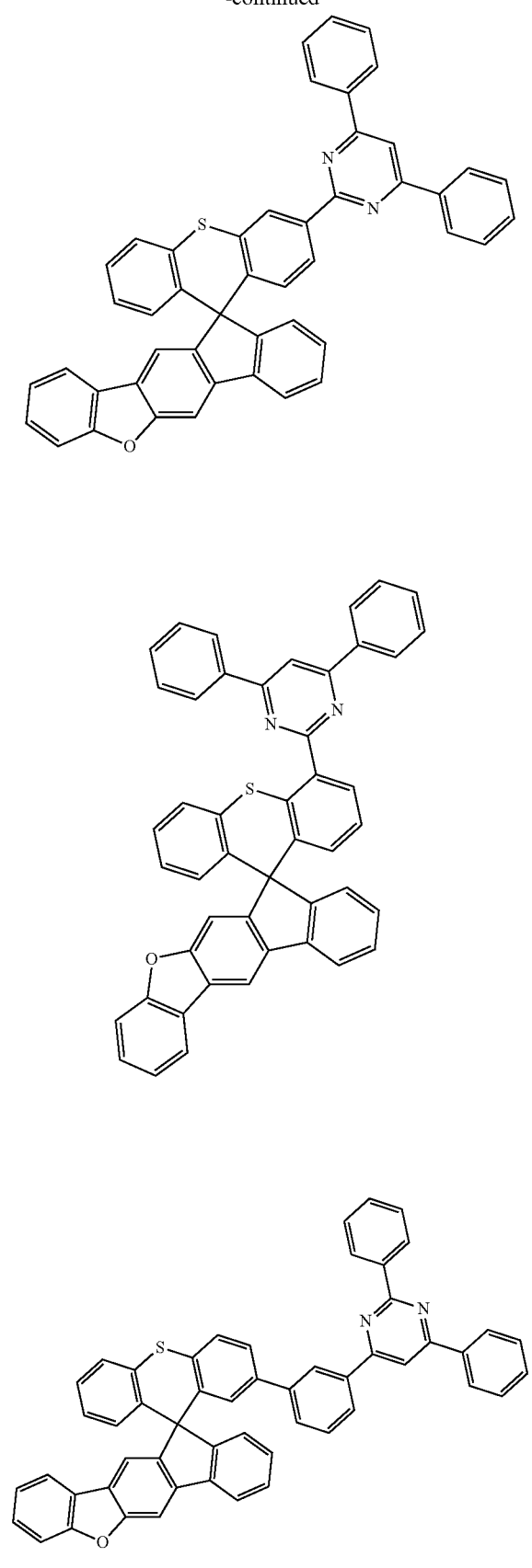

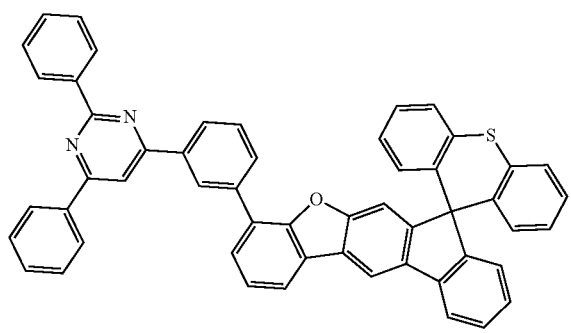
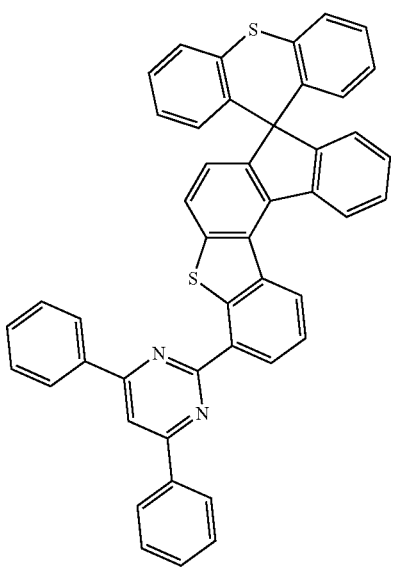
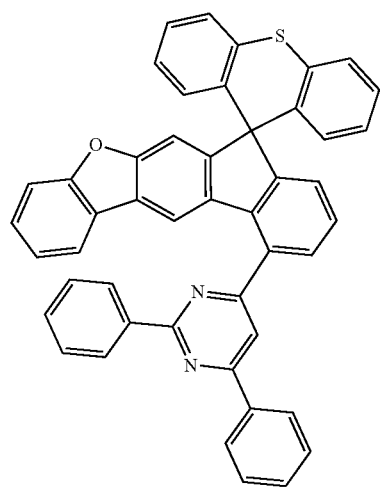
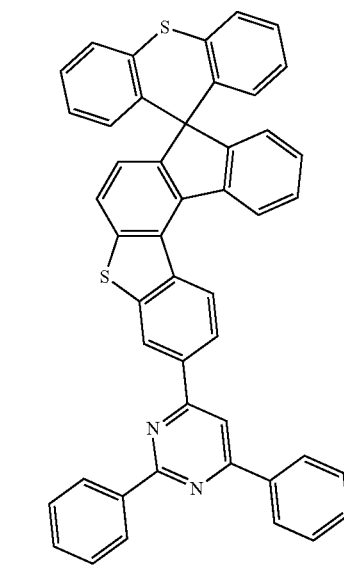
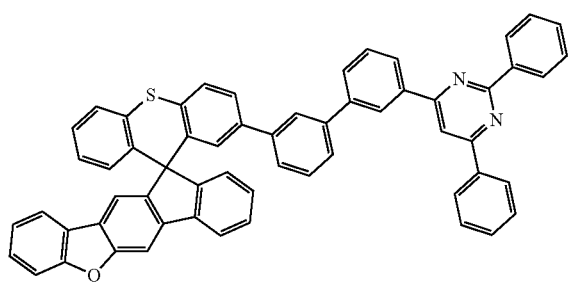
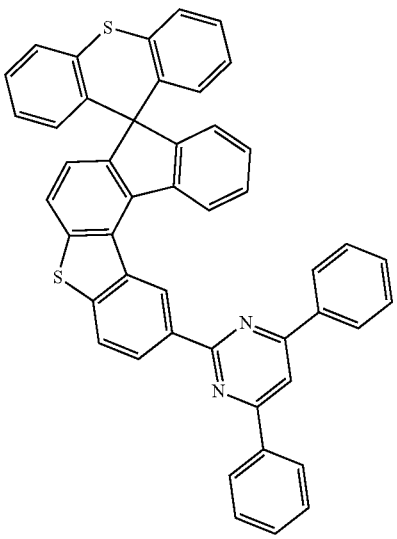
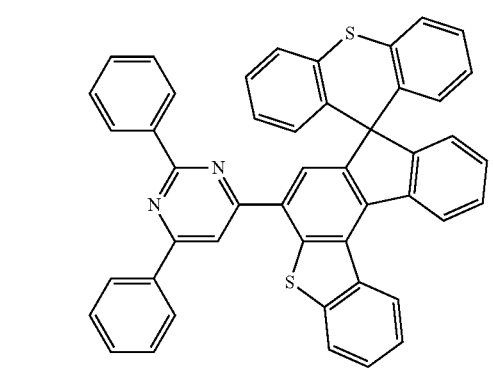

137
-continued
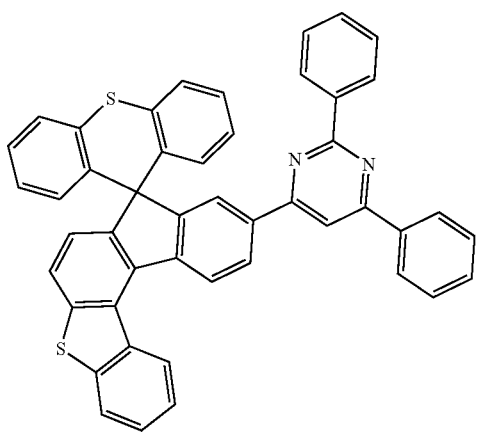
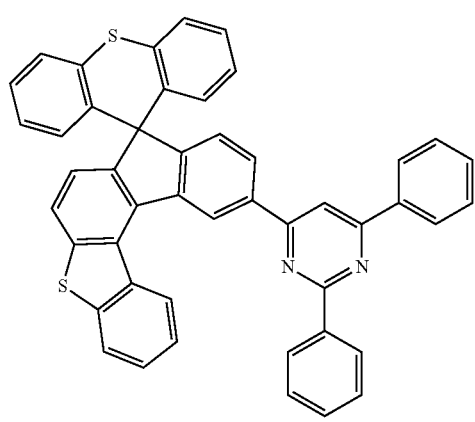
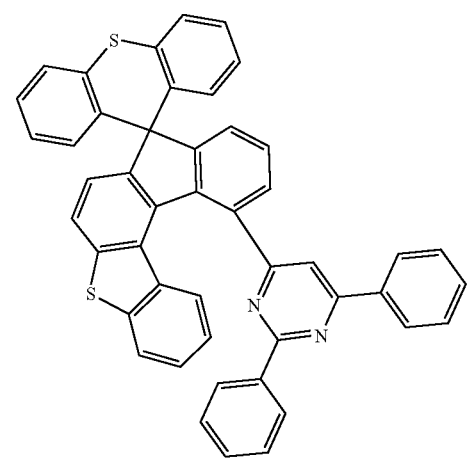
138
-continued
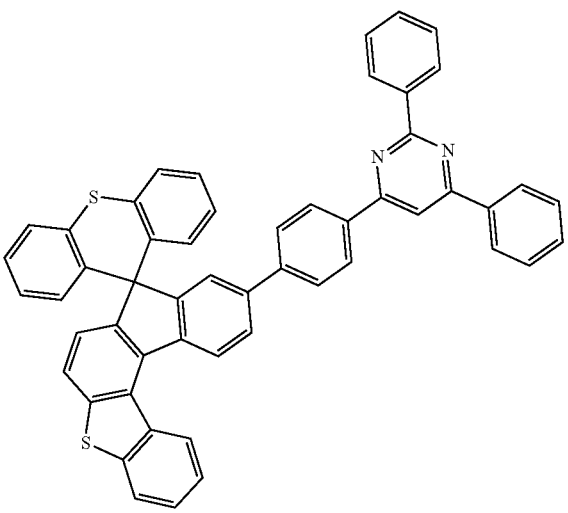
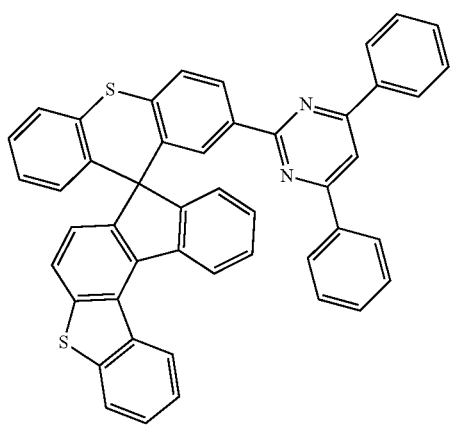
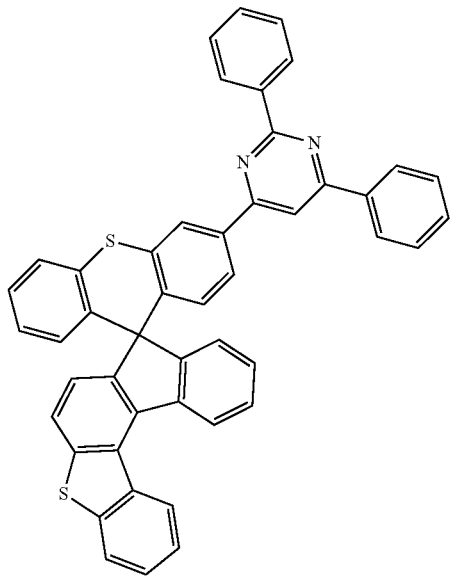

139
-continued
140
-continued
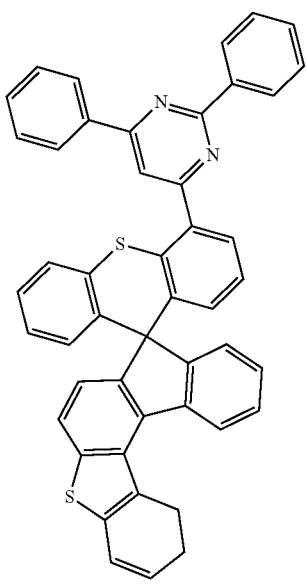 [SMILES: C1=Cc2sc3ccc4c(c3c2CC1)-c1ccccc1C41c2ccccc2Sc2c(-c3cc(-c4ccccc4)nc(-c4ccccc4)n3)cccc21]
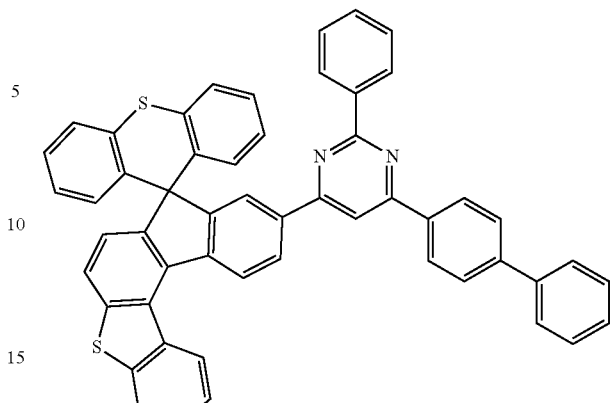
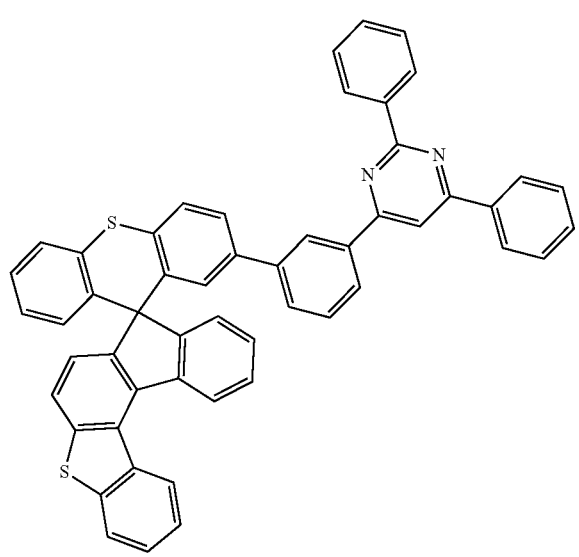
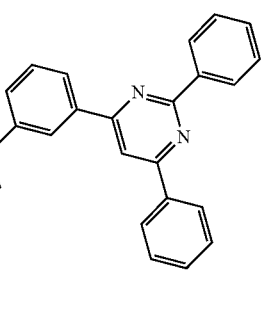
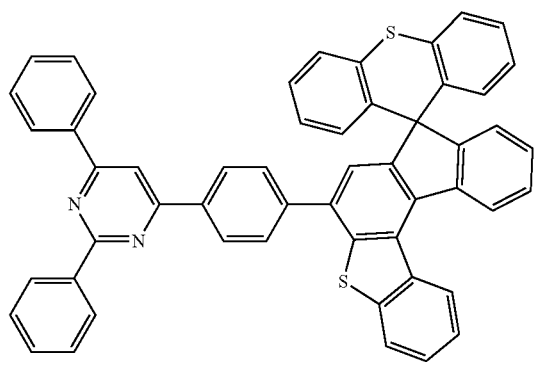
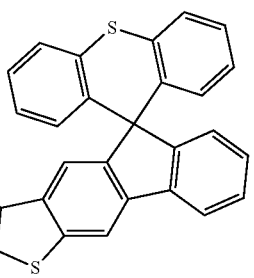

141
-continued
142
-continued
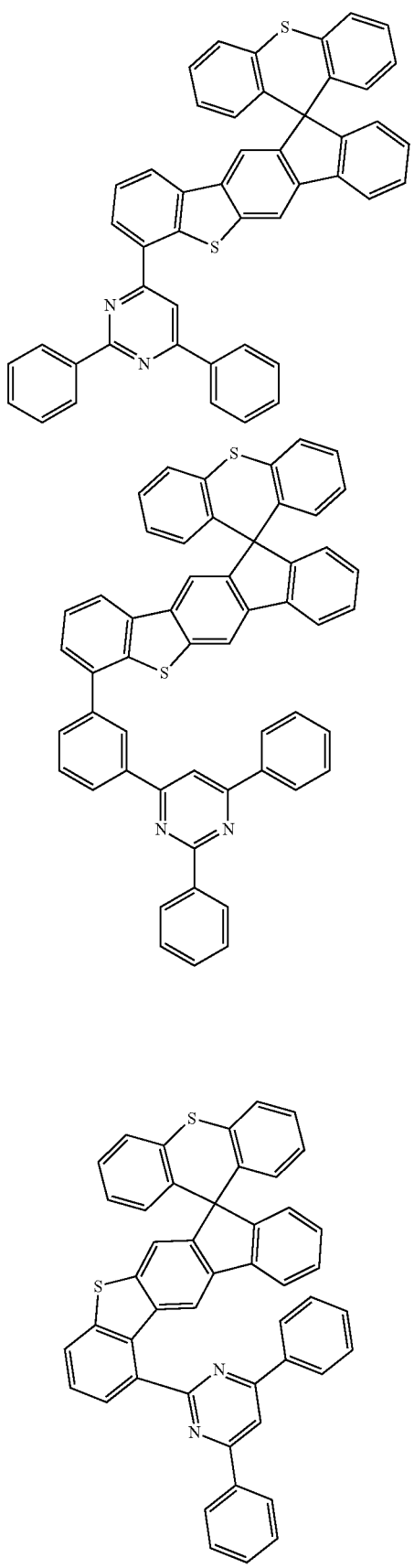
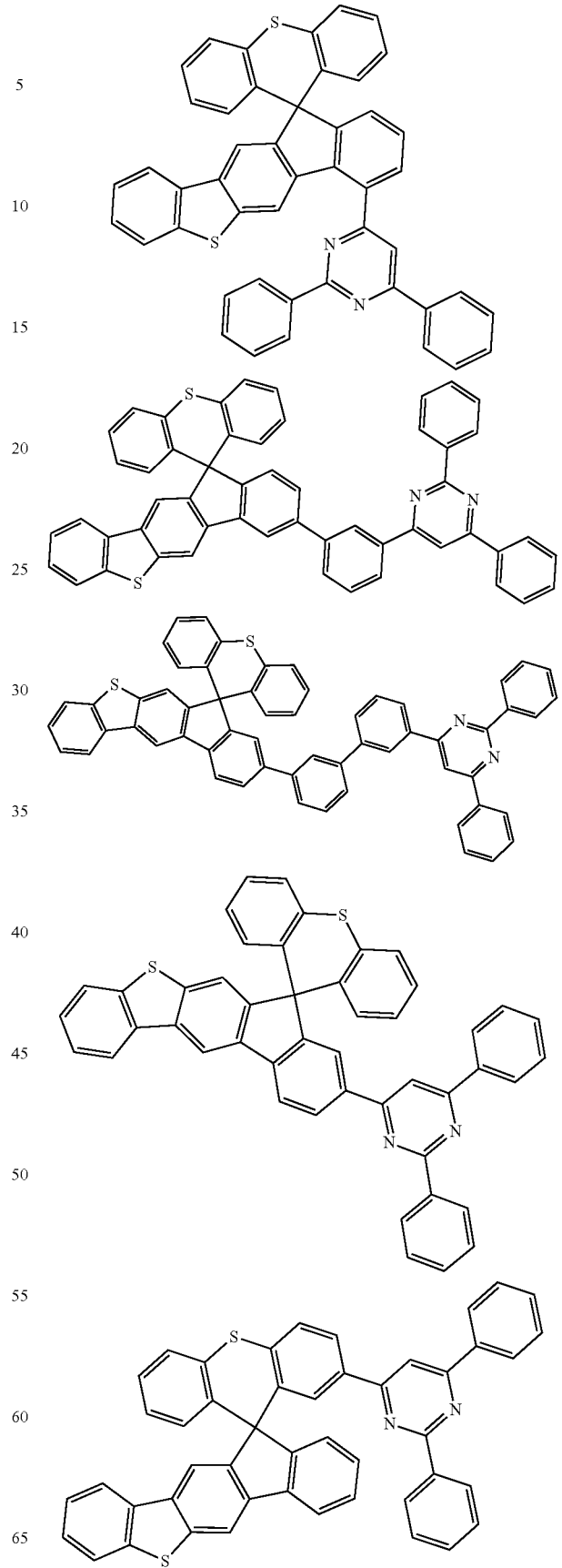

-continued

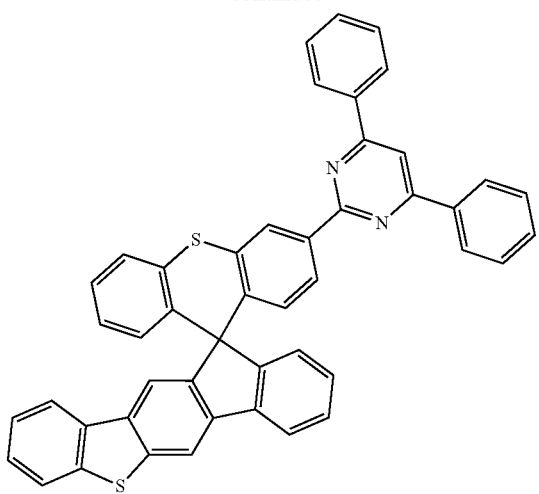

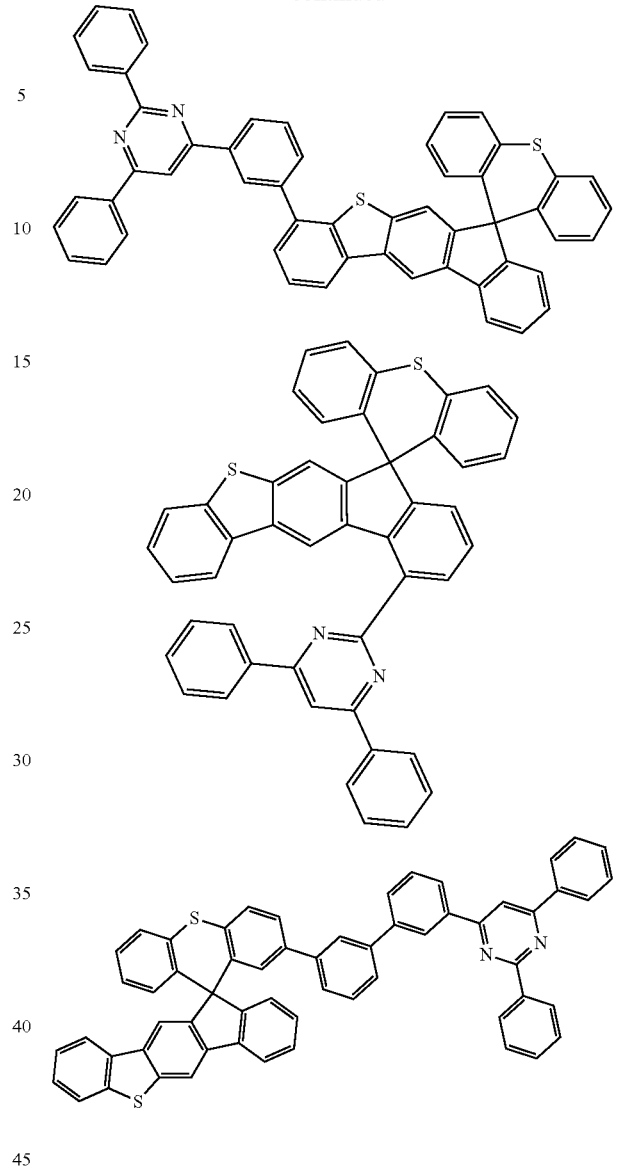

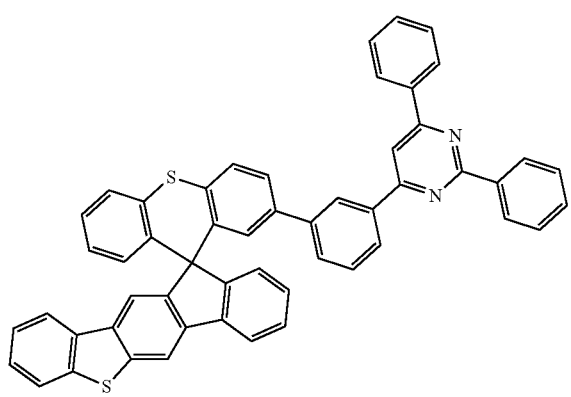

The compound represented by Chemical Formula 1 according to the present disclosure has a core structure in which a fluorene-based ring that is spiro-bonded to xanthene or thioxanthene forms an additional ring with furan or thiophene, in particular, it further has the structure of at least one triazine-based (triazine, pyrimidine) substituent and thus is superior in thermal stability and hole stability as compared with compounds which do not have said core structure and/or do not contain triazine-based substituents. Therefore, when applied to an organic light emitting device, the present compound can exhibit characteristics such as high efficiency, low driving voltage and long lifetime when applied to an organic light emitting device The compound represented by Chemical Formula 1 may be prepared according to the preparation method based on the reaction shown in the following Reaction Scheme 1.

[Reaction Scheme 1]

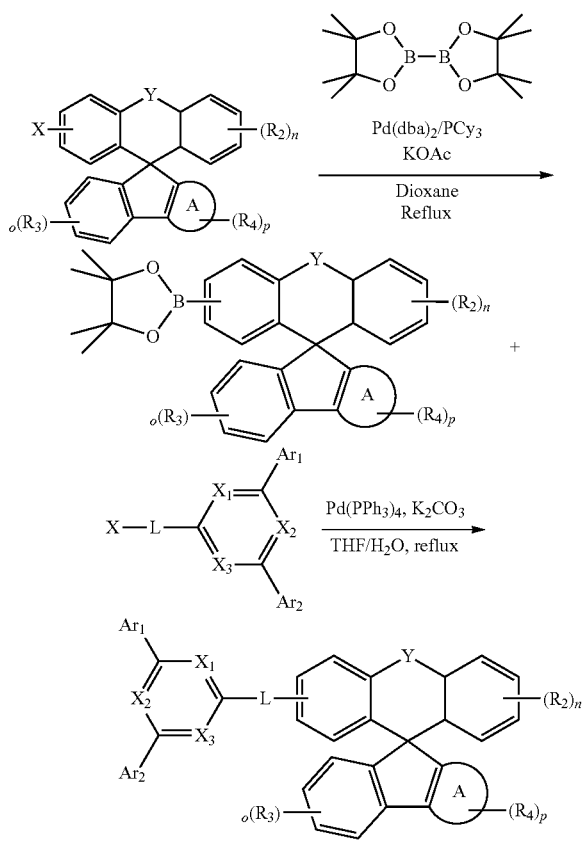

In Reaction Scheme 1, X is halogen atom, preferably bromo, or chloro. In addition, the other substituents are the same as defined above in Chemical Formula 1.

Reaction Scheme 1 is a Suzuki coupling reaction, which is preferably carried out in the presence of a palladium catalyst and a base, and the reactive group for the Suzuki coupling reaction can be modified as known in the art.

Reaction Scheme 1 illustrates the case where the substitution position of Chemical Formula 1 is substituted on the xanthene or thioxanthene side. In the compound represented by Chemical Formula 1, the position of each substituent may be prepared by appropriately changing the structure of the starting material with reference to Reaction Scheme 1. The above preparation method will be more specifically described in Preparation Examples to be described later.

In another embodiment of the disclosure, there is provided an organic light emitting device including a compound represented by Chemical Formula 1 described above. As an example, there is provided an organic light emitting device including a first electrode; a second electrode that is disposed to face the first electrode; and one or more organic material layers that are disposed between the first electrode and the second electrode, wherein one or more layers of the organic material layers include the compound represented by Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, or a layer simultaneously performing hole injection and transport, wherein the hole injection layer, the hole transport layer, or the layer simultaneously performing hole injection and transport include a compound represented by Chemical Formula 1.

Further, the organic material layer may include a light emitting layer, wherein the light emitting layer includes a compound represented by Chemical Formula 1.

Further, the organic material layer may include an electron transport layer, or an electron injection layer, wherein the electron transport layer, or the electron injection layer includes a compound represented by Chemical Formula 1.

Further, the electron transport layer, the electron injection layer, or the layer simultaneously performing electron injection and electron transport include a compound represented by Chemical Formula 1. In particular, the compound represented by Chemical Formula 1 according to the present disclosure has excellent thermal stability, a deep HOMO level of 6.0 eV or more, a high triplet energy (ET) and a hole stability. In addition, when the compound represented by Chemical Formula 1 is used in an organic material layer capable of simultaneously performing electron injection and electron transport, it can be used by mixing an n-type dopant used in the art.

In addition, the organic material layer may include a light emitting layer and an electron transport layer, wherein the electron transport layer may include a compound represented by Chemical Formula 1.

Further, the organic light emitting device according to the present disclosure may be a normal type organic light emitting device in which an anode, one or more organic material layers and a cathode are sequentially stacked on a substrate. Further, the organic light emitting device according to the present disclosure may be an inverted type organic light emitting device in which a cathode, one or more organic material layers and an anode are sequentially stacked on a substrate. For example, the structure of an organic light emitting device according to an embodiment of the present disclosure is illustrated in FIGS. 1 and 2.

FIG. 1 depicts an example of an organic light emitting device comprising a substrate 1, an anode 2, a light emitting layer 3, and a cathode 4. In such a structure, the compound represented by Chemical Formula 1 may be included in the light emitting layer.

FIG. 2 depicts an example of an organic light emitting device comprising a substrate 1, an anode 2, a hole injection layer 5, a hole transport layer 6, a light emitting layer 7, an electron transport layer 8 and a cathode 4. In such a structure, the compound represented by the chemical formula 1 may be included in one or more layers of the hole injection layer, the hole transport layer, the light emitting layer and the electron transport layer.

The organic light emitting device according to the present disclosure may be manufactured by materials and methods known in the art, except that one or more layers of the organic material layers include the compound represented by Chemical Formula 1. Moreover, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

Further, the compound represented by Chemical Formula 1 may be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene)(PPV)-based polymer; a spiro compound; polyfluorene, lubrene, and the like, but are not limited thereto.

The light emitting layer may include a host material and a dopant material. The host material may be a fused aromatic ring derivative, a heterocyclic-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material may be an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group and includes arylamino group-containing pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transport layer is a layer which receives electrons from an electron injection layer and transports the electrons to a light emitting layer, and as the electron transport material, materials capable of favorably receiving electrons from a cathode, moving the electrons to a light emitting layer, and having high mobility for the electrons are suitable. Specific examples thereof include: an Al complex of 8-hydroxyquinoline; a complex including $Alq_3$; an organic radical compound; a hydroxyflavone-metal complex, and the like, but are not limited thereto. The electron transport layer may be used together with any desired cathode material as used in the related art. In particular, appropriate examples of the cathode material are a typical material which has a low work function in which an aluminum layer or a silver layer follows. Specific examples thereof include cesium, barium, calcium, ytterbium, and samarium, and in each case, an aluminum layer or a silver layer follows.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a backside emission type, or a double-sided emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples. However, these examples are presented for illustrative purposes only, and are not intended to limit the scope of the present disclosure.

Preparation Example 1: Preparation of Compound E1

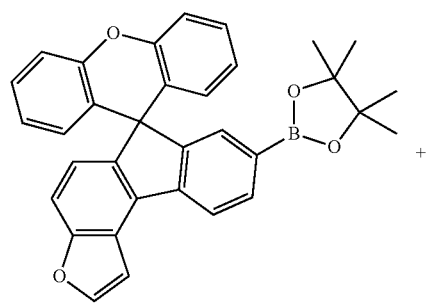

E1-A

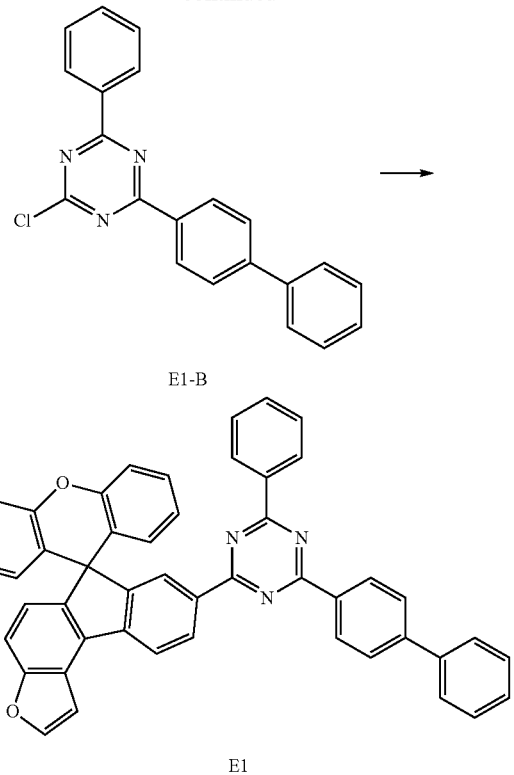

E1-B

E1

E1-A (20 g, 40.1 mmol) and E1-B (13.8 g, 40.1 mmol) were added to 400 ml of tetrahydrofuran under a nitrogen atmosphere, and the mixture was stirred and refluxed. Then, potassium carbonate (16.6 g, 120.4 mmol) was dissolved in 17 ml of water, added thereto, stirred sufficiently, and then tetrakistriphenyl-phosphinopalladium (1.4 g, 1.2 mmol) was added. After the reaction for 2 hours, the reaction mixture was cooled down to room temperature, and the resulting solid was filtered. The solid was added to and dissolved in 20 times its volume (546 mL) of chloroform, and washed twice with water. The organic layer was then separated, anhydrous magnesium sulfate was added, stirred and filtered. The filtrate was distilled under reduced pressure. The concentrated compound was recrystallized from chloroform and ethyl acetate to give a white solid compound E1 (20.7 g, yield: 76%).

MS[M+H]$^+$=680

Preparation Example 2: Preparation of Compound E2

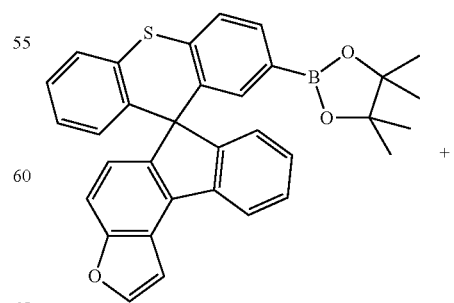

E2-A

-continued

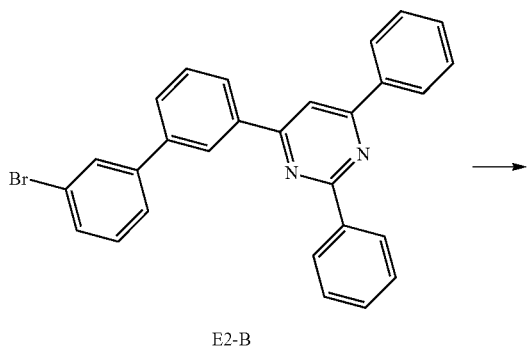

E2-B

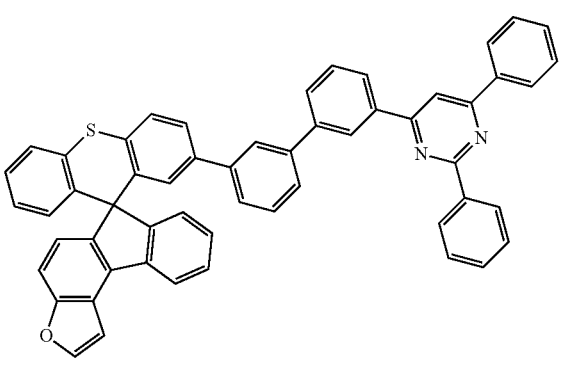

E2

A compound represented by Chemical Formula E2 was prepared in the same manner as in the preparation method of E1 in Preparation Example 1, except that E2-A was used instead of a starting material E1-A and E2-B was used instead of E1-B in Preparation Example 1.

MS[M+H]$^+$=787

Preparation Example 3: Preparation of Compound

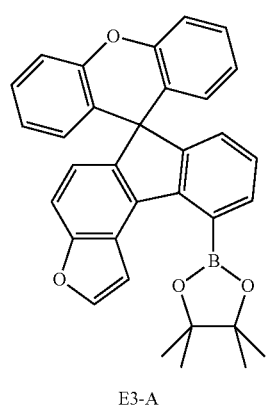

E3-A

-continued

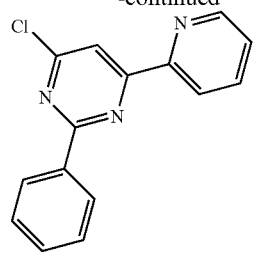

E3-B

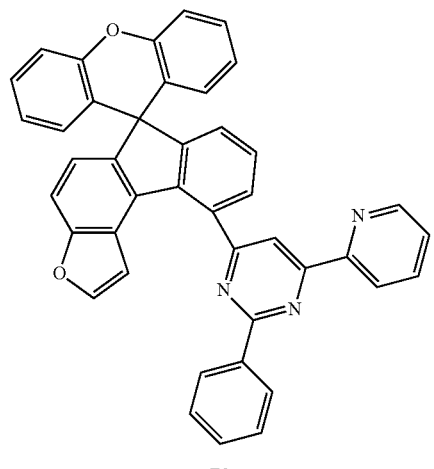

E3

A compound represented by Chemical Formula E3 was prepared in the same manner as in the preparation method of E1 in Preparation Example 1, except that E3-A was used instead of a starting material E1-A and E3-B was used instead of E1-B in Preparation Example 1.

MS[M+H]$^+$=620

Preparation Example 4: Preparation of Compound E4

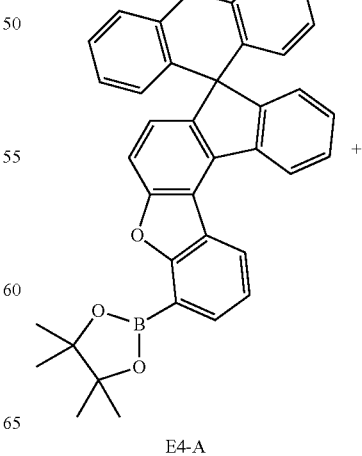

E4-A

-continued

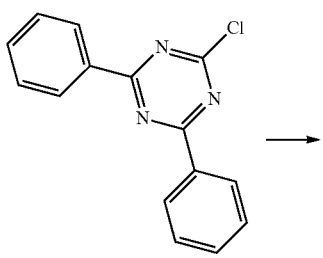

E4-B

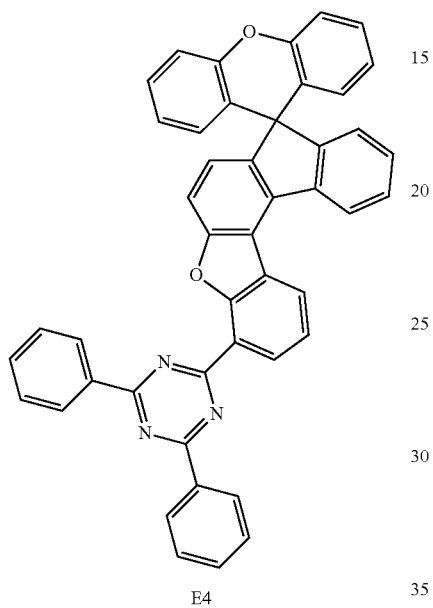

E4

A compound represented by Chemical Formula E4 was prepared in the same manner as in the preparation method of E1 in Preparation Example 1, except that E4-A was used instead of a starting material E1-A and E4-B was used instead of E1-B in Preparation Example 1.

MS[M+H]$^+$=654

Preparation Example 5: Preparation of Compound E5

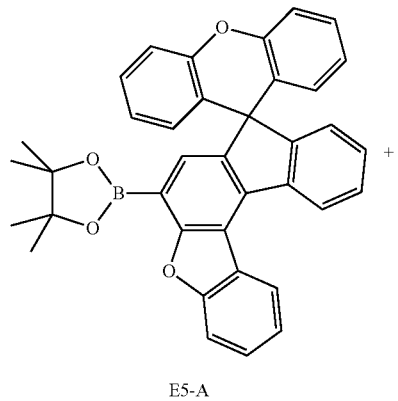

E5-A

-continued

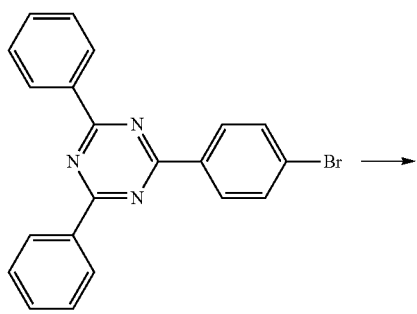

E5-B

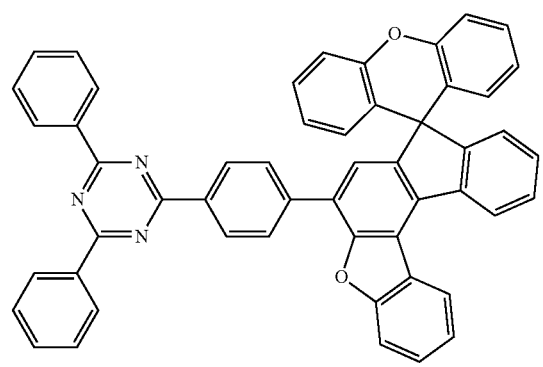

E5

A compound represented by Chemical Formula E5 was prepared in the same manner as in the preparation method of E1 in Preparation Example 1, except that E5-A was used instead of a starting material E1-A and E5-B was used instead of E1-B in Preparation Example 1.

MS[M+H]$^+$=730

Preparation Example 6: Preparation of Compound E6

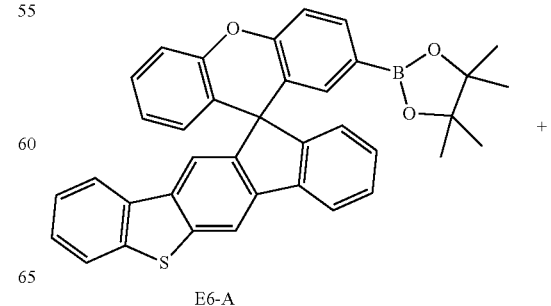

E6-A

-continued

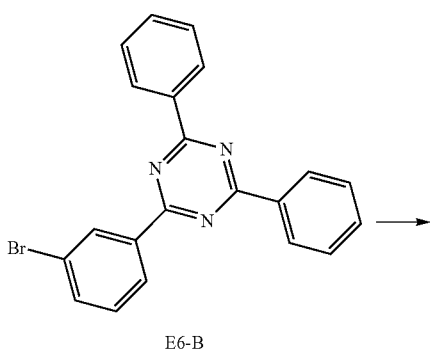

E6-B

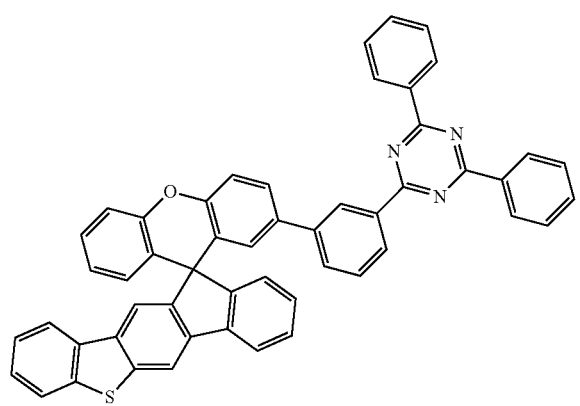

E6

A compound represented by Chemical Formula E6 was prepared in the same manner as in the preparation method of E1 in Preparation Example 1, except that E6-A was used instead of a starting material E1-A and E6-B was used instead of E1-B in Preparation Example 1.

MS[M+H]$^+$=746

Preparation Example 7: Preparation of Compound E7

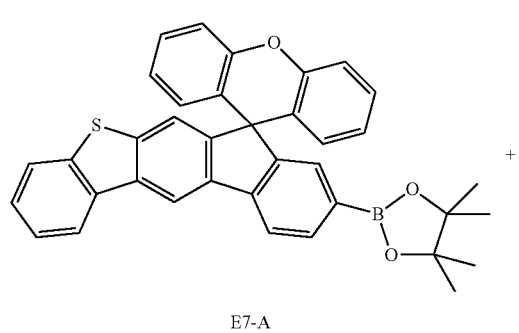

E7-A

-continued

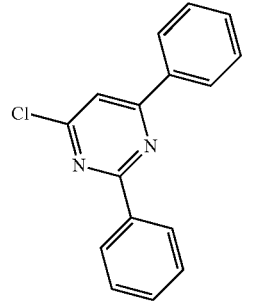

E7-B

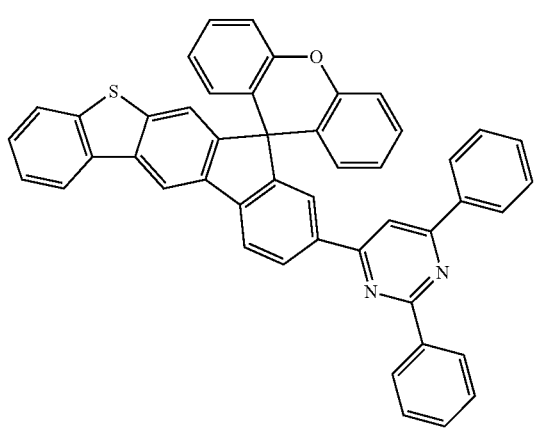

E7

A compound represented by Chemical Formula E7 was prepared in the same manner as in the preparation method of E1 in Preparation Example 1, except that E7-A was used instead of a starting material E1-A and E7-B was used instead of E1-B in Preparation Example 1.

MS[M+H]$^+$=669

Preparation Example 8: Preparation of Compound E8

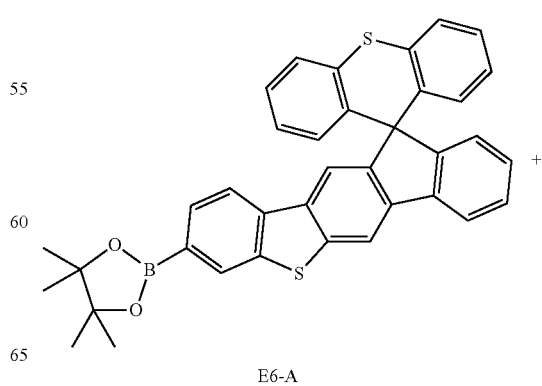

E6-A

-continued

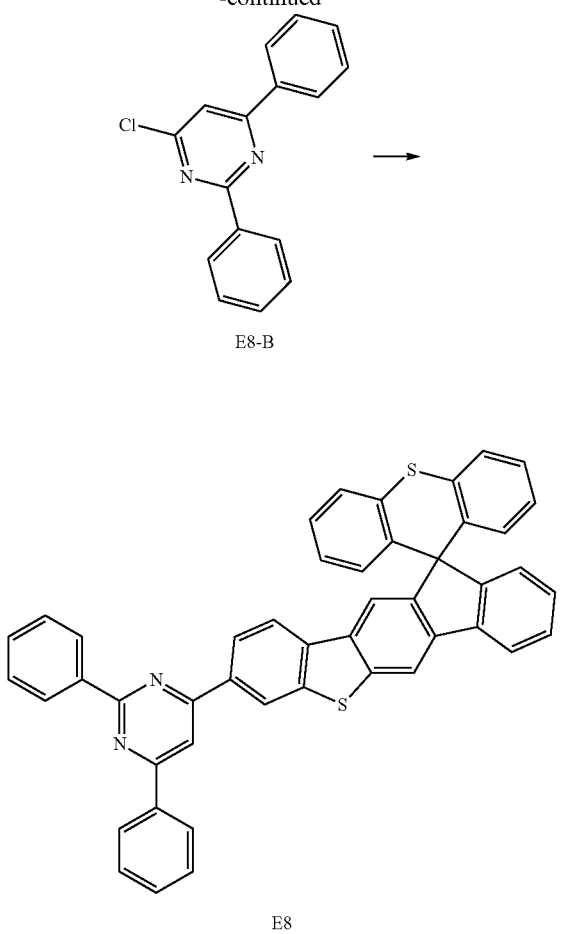

E8-B

E8

A compound represented by Chemical Formula E8 was prepared in the same manner as in the preparation method of E1 in Preparation Example 1, except that E8-A was used instead of a starting material E1-A and E8-B was used instead of E1-B in Preparation Example 1.

MS[M+H]$^+$=6 8 5

Preparation Example 9: Preparation of Compound E9

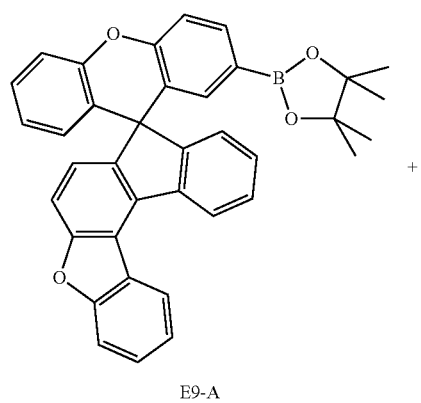

E9-A

+

-continued

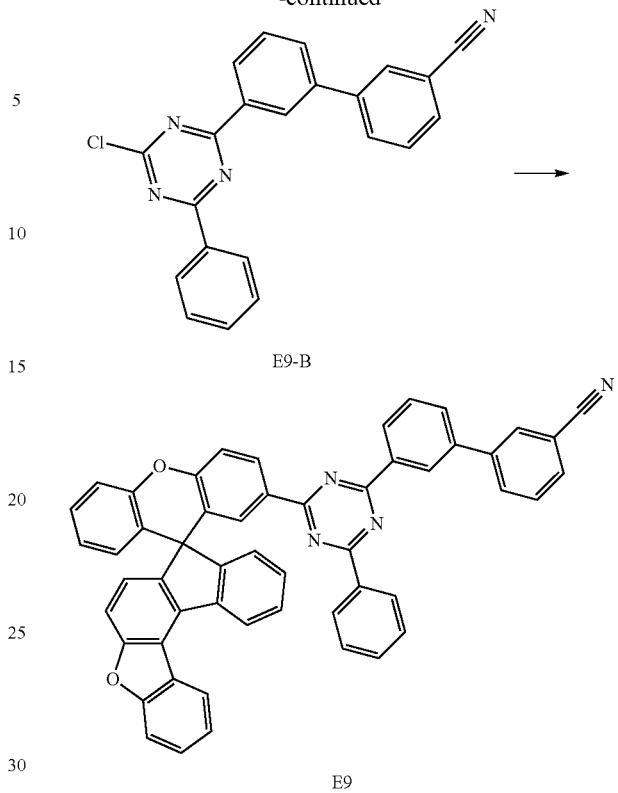

E9-B

E9

A compound represented by Chemical Formula E9 was prepared in the same manner as in the preparation method of E1 in Preparation Example 1, except that E9-A was used instead of a starting material E1-A and E9-B was used instead of E1-B in Preparation Example 1.

MS[M+H]$^+$=7 5 5

Preparation Example 10: Preparation of Compound E10

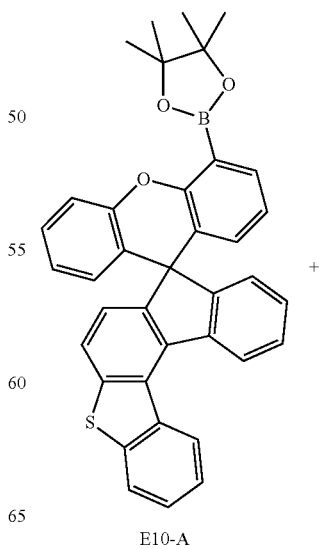

E10-A

+

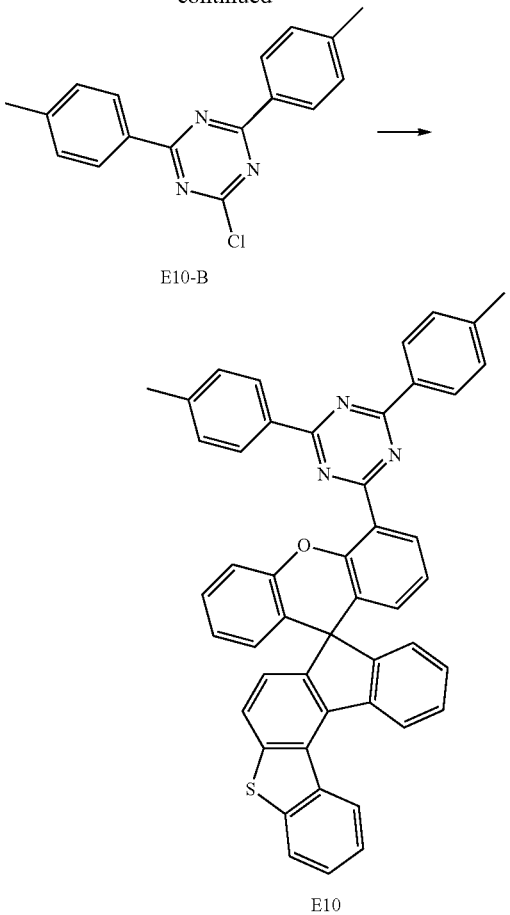

E10-B

E10

A compound represented by Chemical Formula E10 was prepared in the same manner as in the preparation method of E1 in Preparation Example 1, except that E10-A was used instead of a starting material E1-A and E10-B was used instead of E1-B in Preparation Example 1.

MS[M+H]$^+$=698

Example 1

A glass substrate on which ITO (indium tin oxide) was coated as a thin film to a thickness of 1,000 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, a compound HI-A below was thermally vacuum-deposited in a thickness of 600 Å to form a hole injection layer. A compound HAT below (50 Å) and a compound HT-A below (60 Å) were sequentially vacuum-deposited on the hole injection layer to form a first hole transport layer and a second hole transport layer.

Then, a compound BH below and a compound BD below were vacuum-deposited at a weight ratio of 25:1 to a thickness of 200 Å on the hole transport layer to form a light emitting layer.

A compound E1 of Preparation Example 1 and a compound LiQ below were vacuum-deposited at a weight ratio of 1:1 on the light emitting layer to form an electron injection and transport layer with a thickness of 350 Å. Lithium fluoride (LiF) and aluminum were sequentially deposited to have a thickness of 10 Å and 1,000 Å, respectively, on the electron injection and transport layer, thereby forming a cathode.

In the above-mentioned process, the vapor deposition rate of the organic material was maintained at 0.4 to 0.9 Å/sec, the deposition rates of lithium fluoride and aluminum of the cathode were maintained at 0.3 Å/sec and at 2 Å/sec, respectively, and the degree of vacuum during the deposition was maintained at $1\times10^{-7}$ to $5\times10^{-5}$ torr, thereby manufacturing an organic light emitting device.

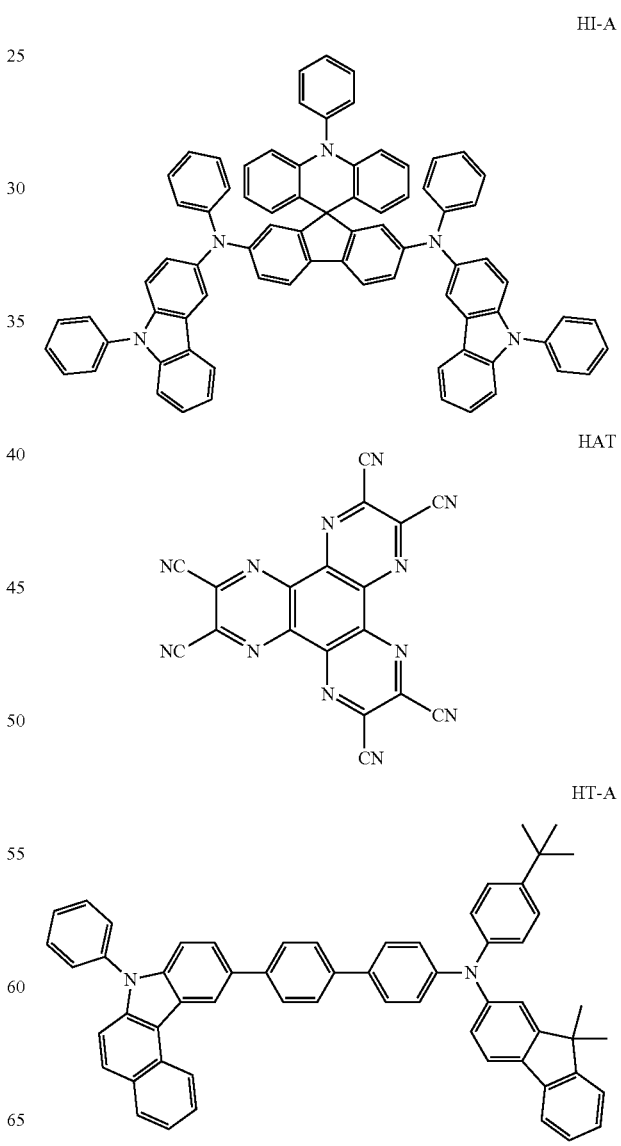

HI-A

HAT

HT-A

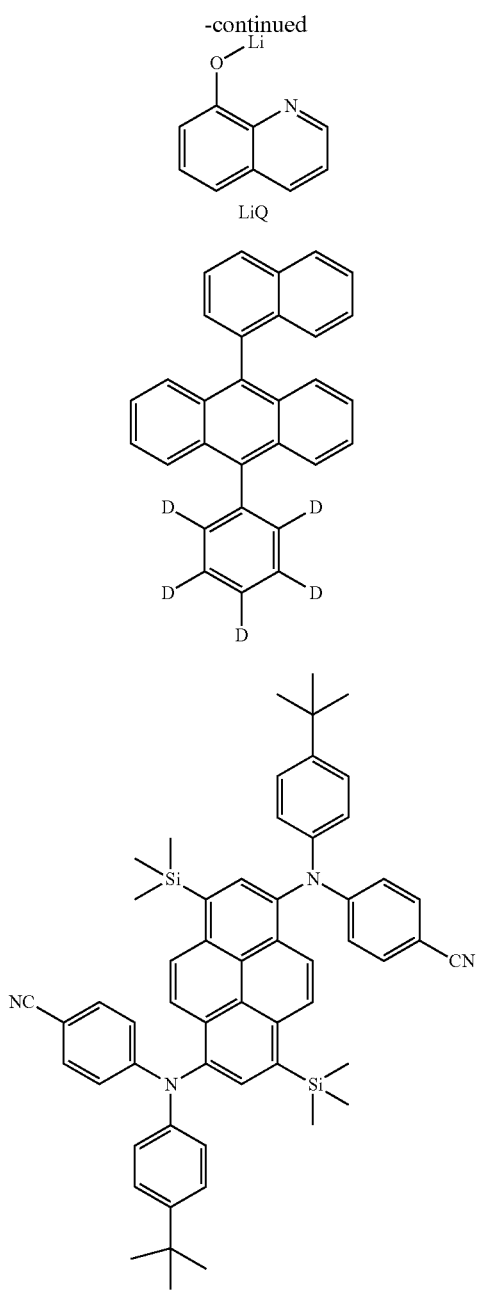
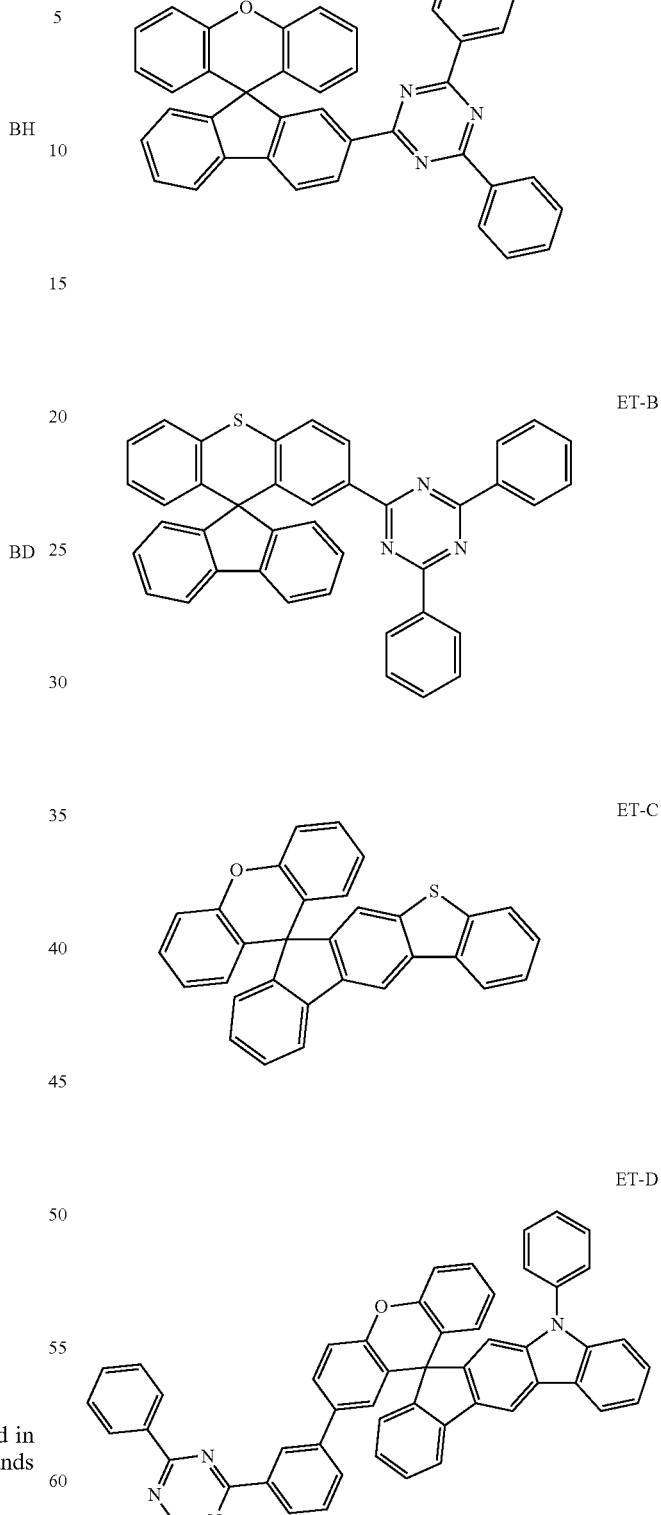
Examples 2 to 10
The organic light emitting devices were manufactured in the same manner as in Example 1, except that Compounds E2 to E10 were used instead of Compound E1.
Comparative Examples 1 to 8
The organic light emitting devices was manufactured in the same manner as in Example 1, except that the Compounds ET-A to ET-H were used instead of Compound E1.

-continued

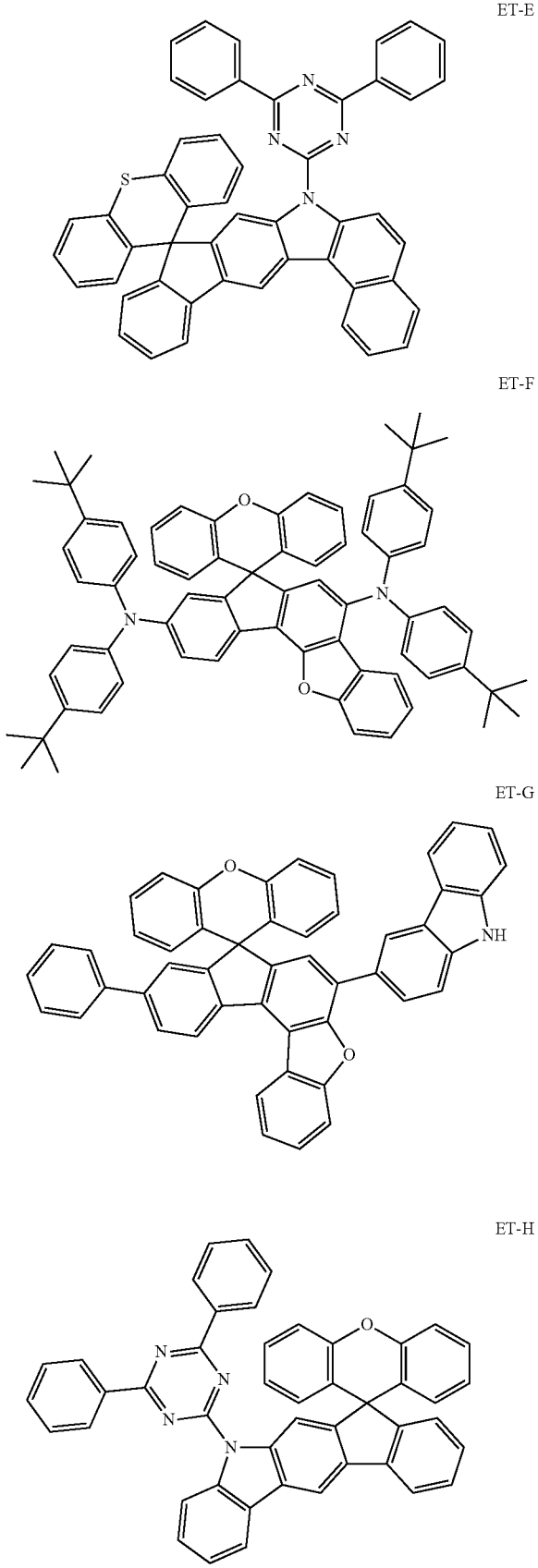

Experimental Example

For the organic light emitting devices manufactured in Examples 1 to 10 and Comparative Examples 1 to 8, the driving voltage and light emitting efficiency were measured at a current density of 10 mA/cm² and the time (T90) required for the luminance to be reduced to 90% of the initial luminance was measured at a current density of 20 mA/cm². The results are shown in Table 1 below.

TABLE 1

| Category (Compound) | Voltage (V@10 mA/cm²) | Efficiency (cd/A@10 mA/cm²) | Color Coordinate (x, y) | Lifetime (h) (T90 at 20 mA/cm²) |
|---|---|---|---|---|
| Example 1 (E1) | 4.59 | 5.04 | (0.142, 0.096) | 212 |
| Example 2 (E2) | 4.72 | 5.29 | (0.142, 0.096) | 150 |
| Example 3 (E3) | 4.49 | 5.14 | (0.142, 0.096) | 174 |
| Example 4 (E4) | 4.61 | 4.94 | (0.142, 0.096) | 246 |
| Example 5 (E5) | 4.47 | 5.13 | (0.142, 0.096) | 199 |
| Example 6 (E6) | 4.68 | 5.16 | (0.142, 0.097) | 180 |
| Example 7 (E7) | 4.45 | 5.19 | (0.142, 0.096) | 163 |
| Example 8 (E8) | 4.46 | 5.12 | (0.142, 0.096) | 176 |
| Example 9 (E9) | 4.71 | 4.91 | (0.142, 0.096) | 258 |
| Example 10 (E10) | 4.61 | 4.98 | (0.142, 0.097) | 226 |
| Comparative Example 1 (ET-A) | 4.56 | 4.69 | (0.142, 0.096) | 115 |
| Comparative Example 2 (ET-B) | 4.61 | 4.64 | (0.142, 0.096) | 118 |
| Comparative Example 3 (ET-C) | 5.12 | 3.53 | (0.142, 0.096) | 108 |
| Comparative Example 4 (ET-D) | 5.00 | 4.34 | (0.142, 0.096) | 160 |
| Comparative Example 5 (ET-E) | 5.09 | 3.99 | (0.142, 0.096) | 172 |
| Comparative Example 6 (ET-F) | 5.22 | 3.21 | (0.142, 0.096) | 90 |
| Comparative Example 7 (ET-G) | 5.19 | 3.39 | (0.142, 0.096) | 94 |
| Comparative Example 8 (ET-H) | 5.14 | 3.87 | (0.142, 0.096) | 170 |

As described in Table 1 above, the compound represented by Chemical Formula 1 according to the present disclosure may be used in an organic material layer capable of simultaneously performing electron injection and electron transport of an organic light emitting device.

When comparing Examples with Comparative Examples 1 and 2 in Table 1, the compound represented by Chemical Formula 1 according to the present disclosure was shown to be remarkably excellent in terms of the lifetime of the organic light emitting device compared to compounds in which fluorene-based ring spiro-bonded to xanthene or thioxanthene did not form an additional ring with furan or thiophene.

In addition, when comparing Examples with Comparative Examples 3 and 6 to 7, the compound represented by Chemical Formula 1 according to the present disclosure including an additional triazine-based substituent was shown to be remarkably superior in terms of the efficiency and lifetime of the organic light emitting device compared to the unsubstituted compound.

Further, when comparing Examples with Comparative Examples 4, 5 and 8, the compound represented by Chemical Formula 1 according to the present disclosure was remarkably excellent in terms of the efficiency of the organic light emitting device compared to a compound in which a fluorene ring spiro-bonded to xanthene or thioxanthene forms an additional carbazole ring.

| [Description of Reference Numerals] | |
|---|---|
| 1: substrate | 2: anode |
| 3: light emitting layer | 4: cathode |
| 5: hole injection layer | 6: hole transport layer |
| 7: light emitting layer | |
| 8: electron transport layer | |

The invention claimed is:

1. A compound represented by Chemical Formula 1:

[Chemical Formula 1]

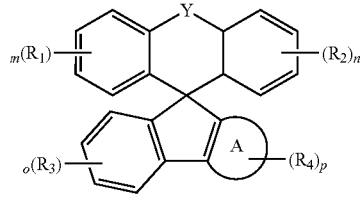

wherein, in Chemical Formula 1,

Y is O or S,

A is a benzofuran ring, a benzothiophene ring, dibenzofuran ring or dibenzothiophene ring, $R_1$, $R_2$, $R_3$ and $R_4$ are each independently a substituent represented by Chemical Formula 2, and m, n, o and p are each independently 0 or 1, and at least one thereof is 1,

[Chemical Formula 2]

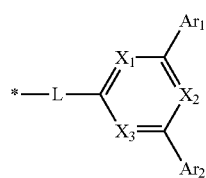

wherein, in Chemical Formula 2,

L is a single bond or a $C_{6-30}$ arylene, $X_1$, $X_2$ and $X_3$ are each independently N or CR', and at least two thereof are N, each R' is independently hydrogen, deuterium, or $C_{1-10}$ alkyl, and $Ar_1$ and $Ar_2$ are each independently $C_{6-30}$ aryl or pyridyl, and they are independently unsubstituted or substituted with a nitrile group, a $C_{1-10}$ alkyl, or a $C_{1-10}$ alkoxy.

2. The compound according to claim 1, wherein the compound is any one selected from compounds represented by Chemical Formulas 3 to 18:

[Chemical Formula 3]

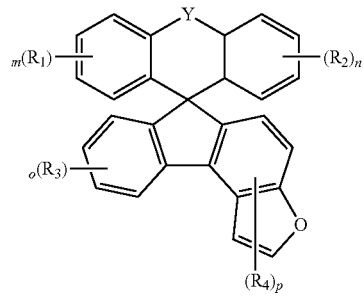

[Chemical Formula 4]

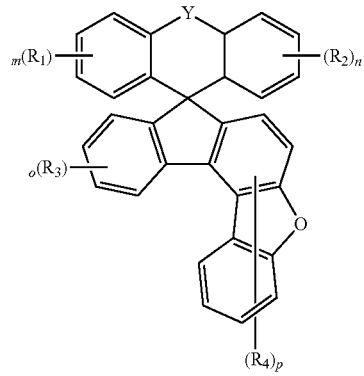

[Chemical Formula 5]

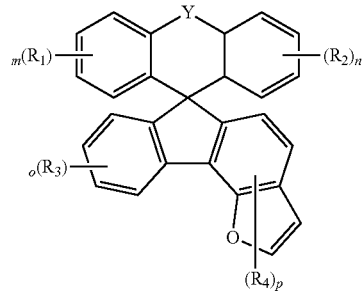

[Chemical Formula 6]

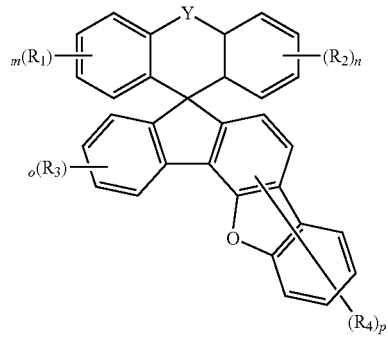

[Chemical Formula 7]
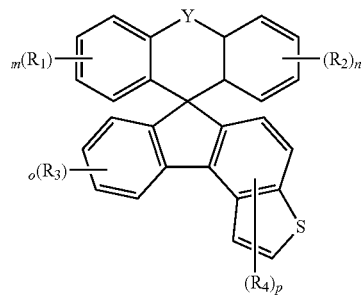
[Chemical Formula 8]
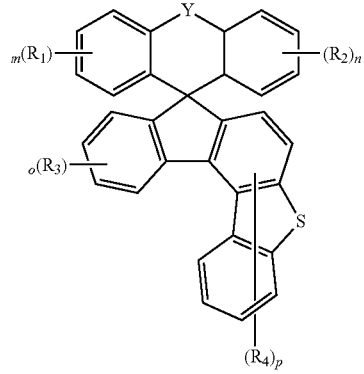
[Chemical Formula 9]
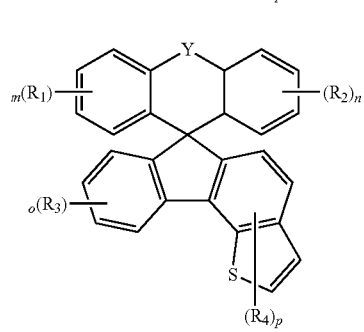
[Chemical Formula 10]
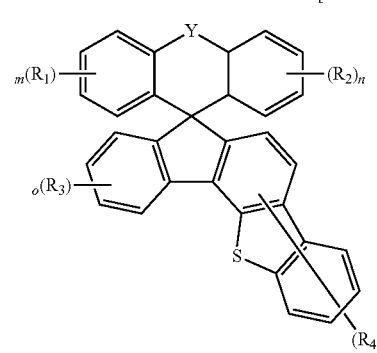
[Chemical Formula 11]
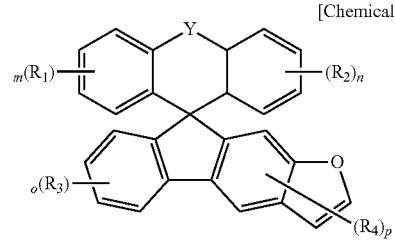
[Chemical Formula 12]
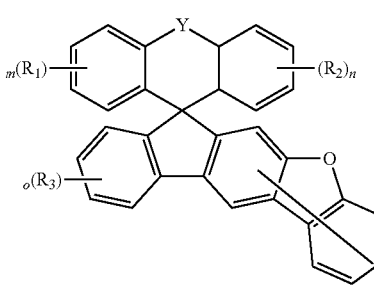
[Chemical Formula 13]
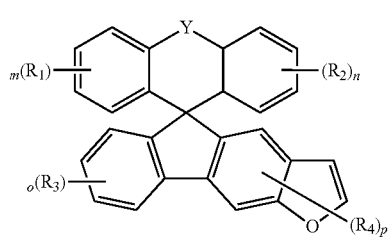
[Chemical Formula 14]
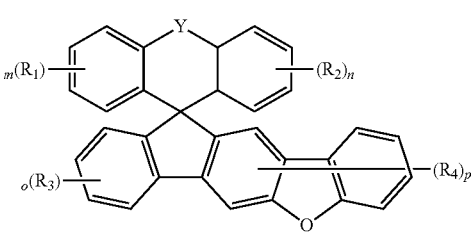
[Chemical Formula 15]
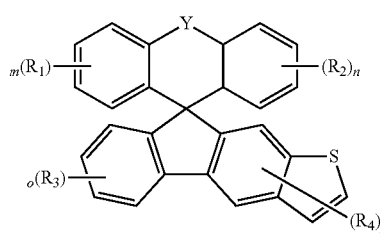
[Chemical Formula 16]
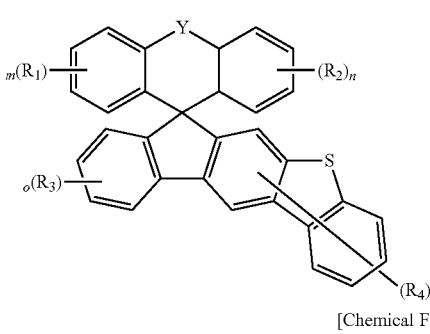
[Chemical Formula 17]
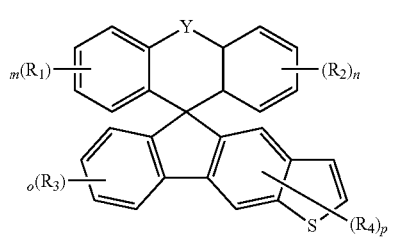

[Chemical Formula 18]

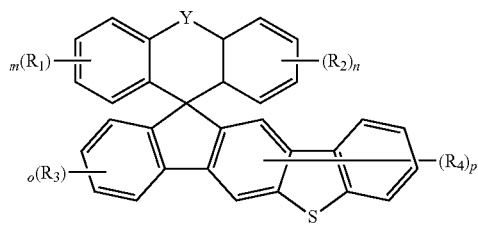

wherein, in Chemical Formulas 3 to 18, $Y$, $R_1$, $R_2$, $R_3$, $R_4$, m, n, o and p are the same as defined in claim 1.

3. The compound according to claim 1, wherein

L is a single bond, phenylene or biphenylylene.

4. The compound according to claim 1, wherein $Ar_1$ and $Ar_2$ are each independently phenyl, biphenylyl, naphthyl, terphenylyl, dimethylfluorenyl, diphenylfluorenyl or pyridyl, and are each independently unsubstituted or substituted with cyano, $C_{1-10}$ alkyl or $C_{1-10}$ alkoxy.

5. The compound according to claim 1, wherein $Ar_1$ and $Ar_2$ are each independently phenyl, biphenylyl, naphthyl or pyridyl, and are each independently unsubstituted or substituted with cyano, $C_{1-10}$ alkyl or $C_{1-10}$ alkoxy.

6. The compound according to claim 1, wherein

R' is hydrogen.

7. The compound according to claim 1, wherein the compound represented by Chemical Formula 1 is any one selected from the group consisting of the following:

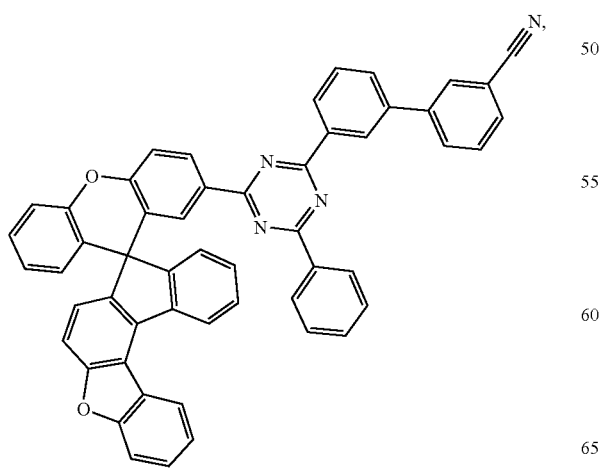

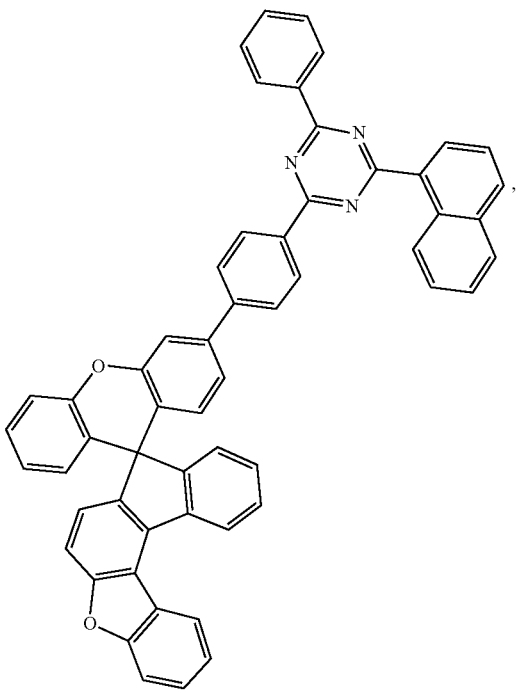

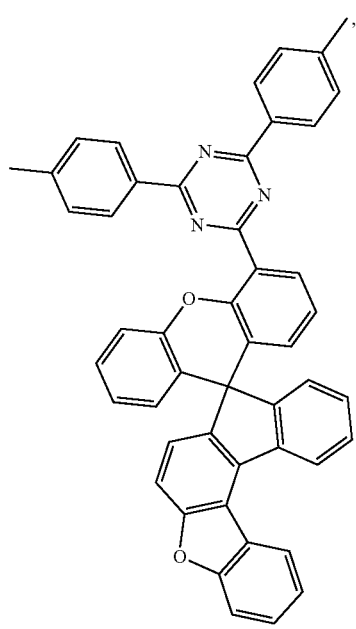

171
-continued
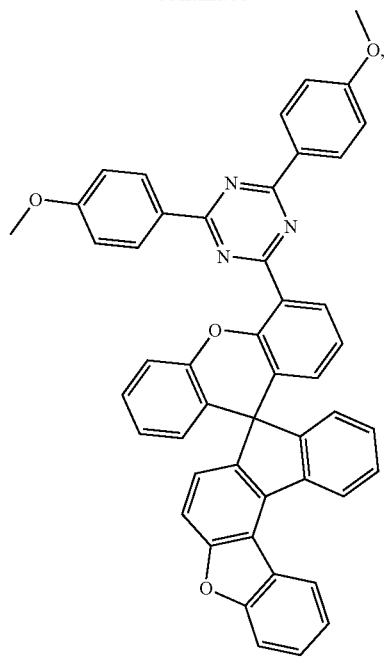
172
-continued
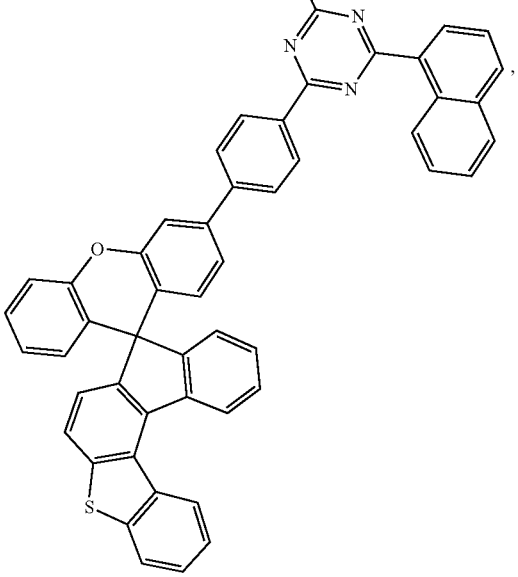
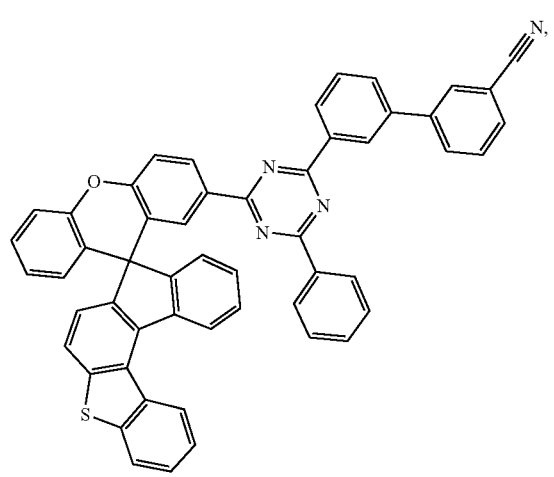
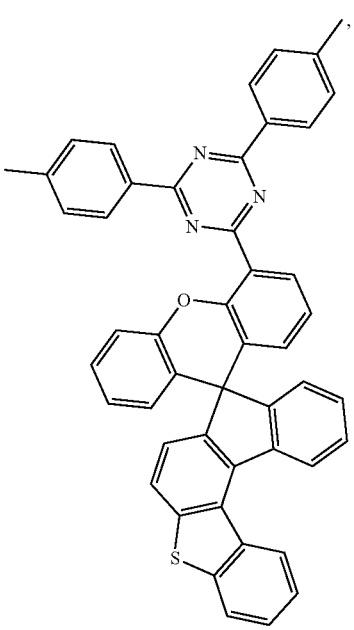

173
-continued
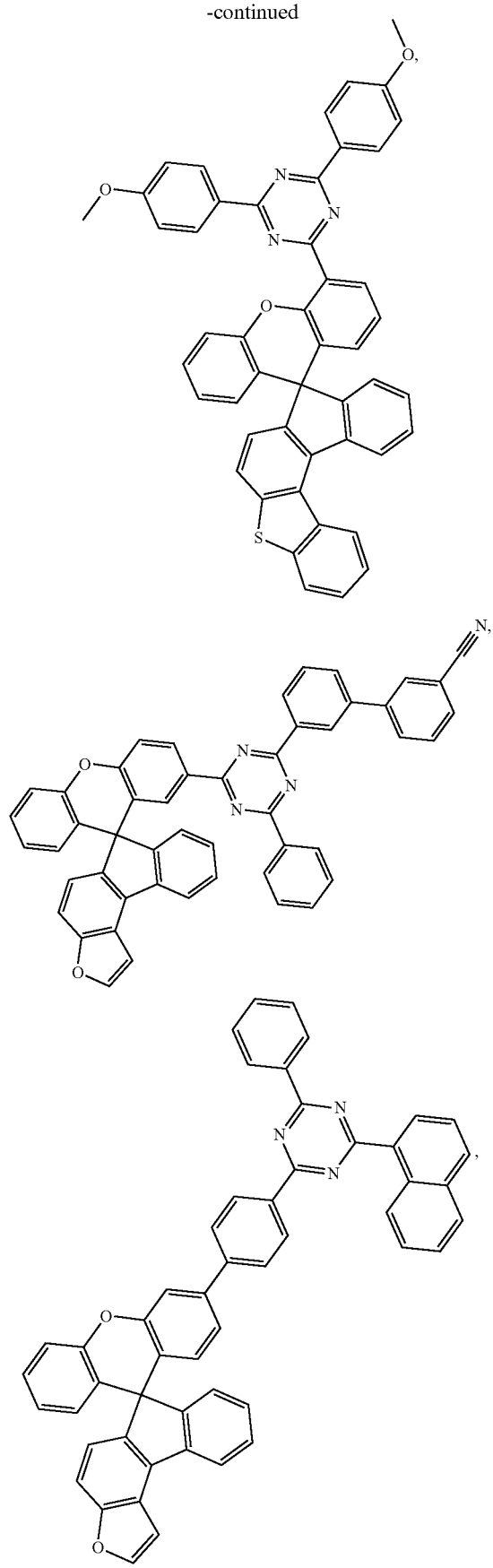
174
-continued
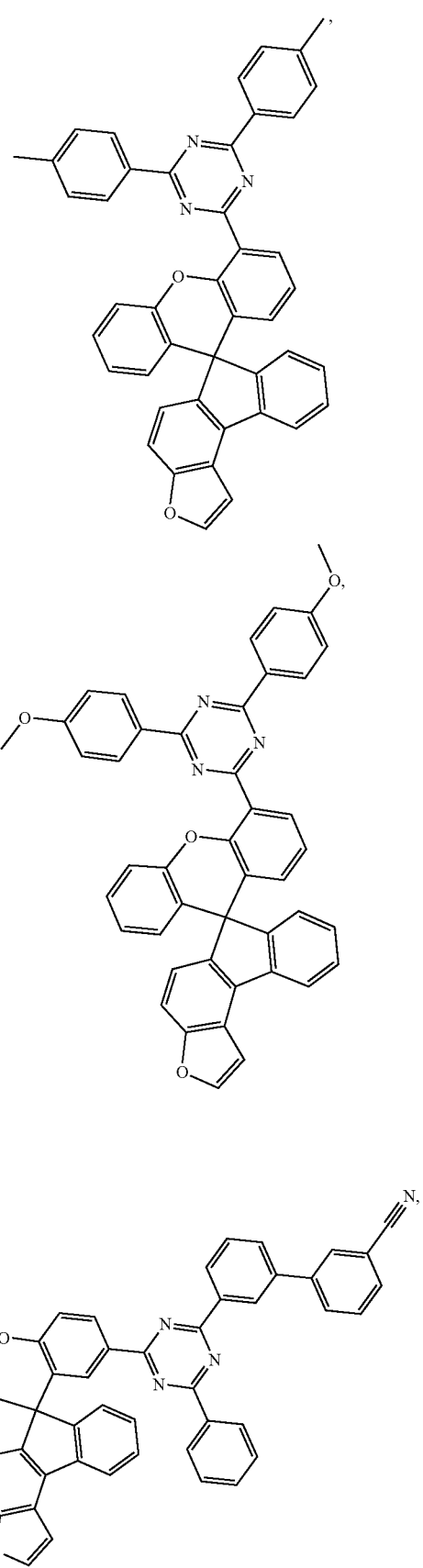

175
-continued
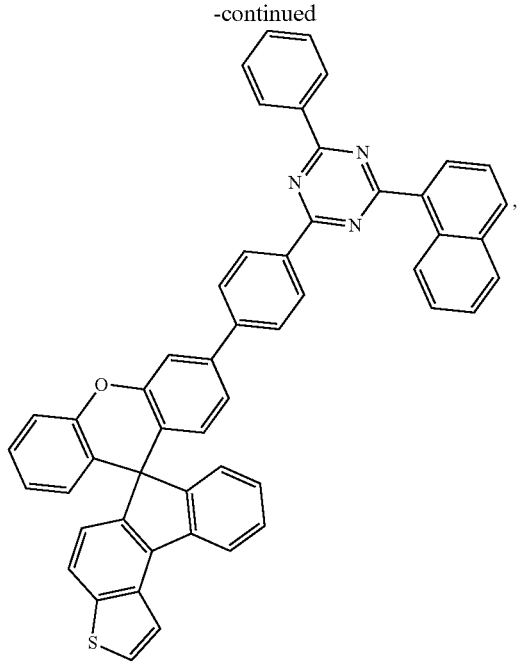
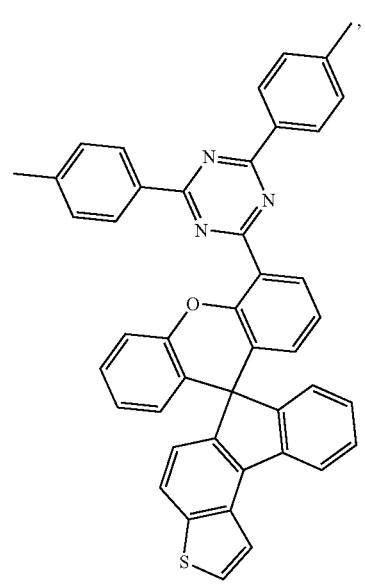
176
-continued
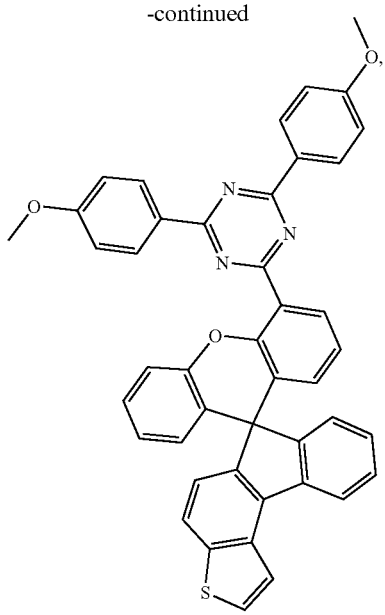
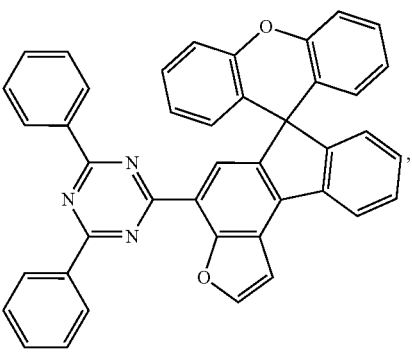
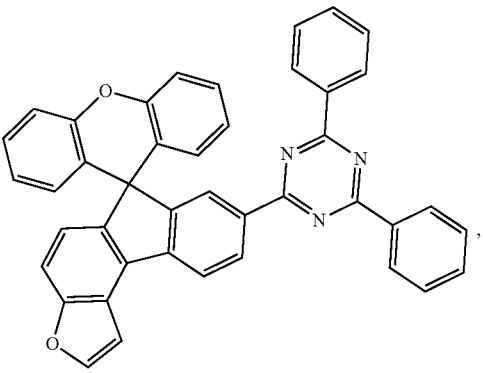
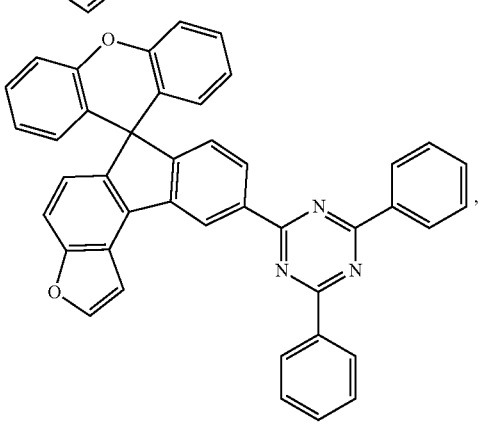

177
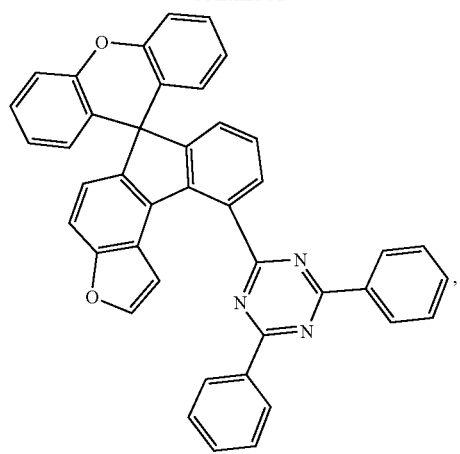
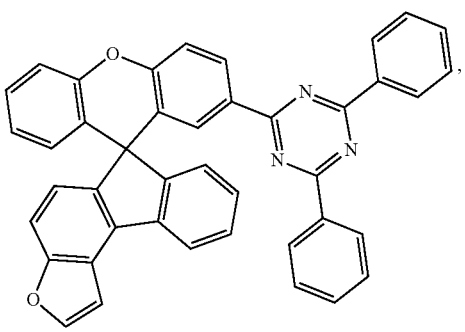
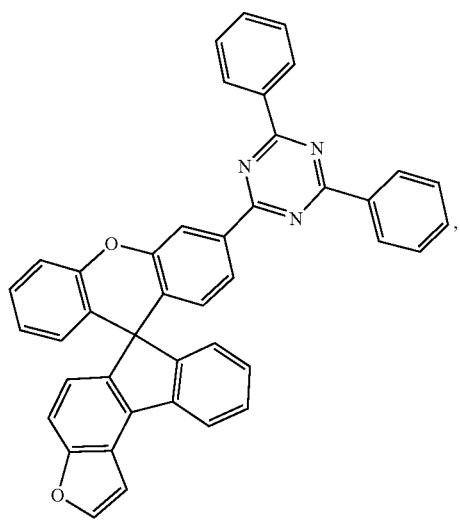
178
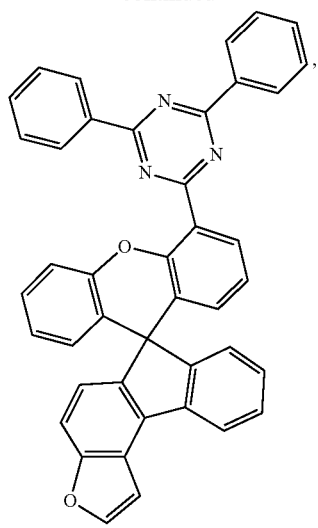
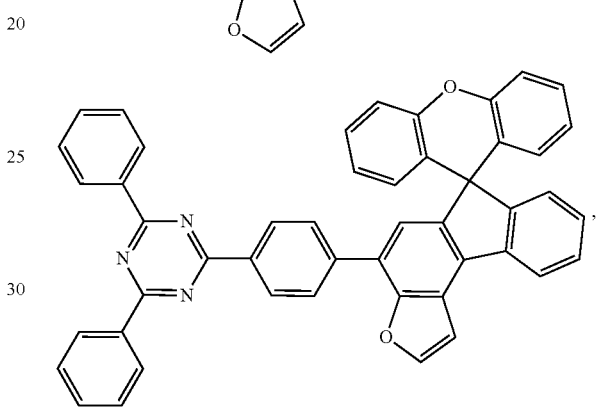
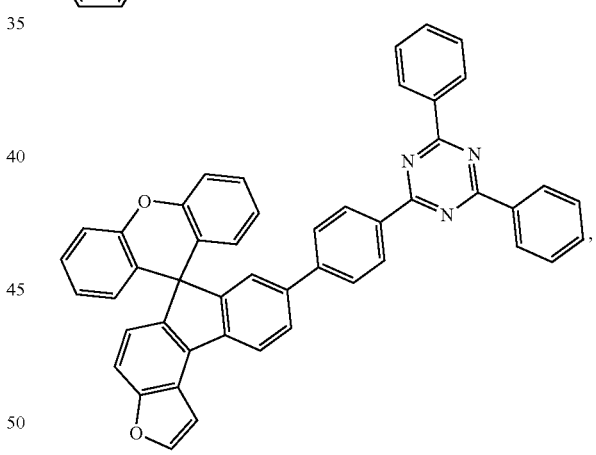
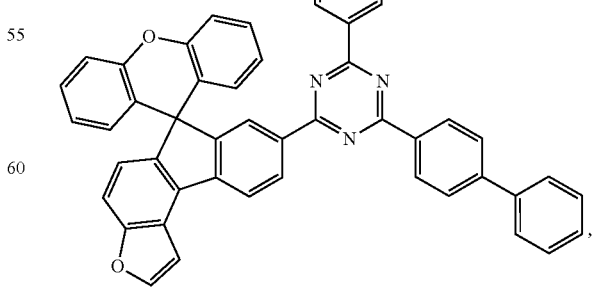

179
-continued
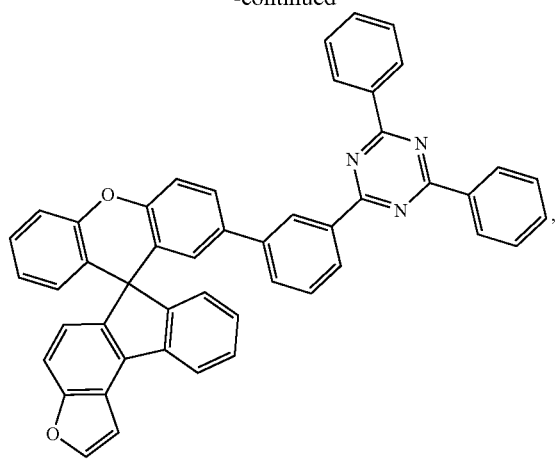
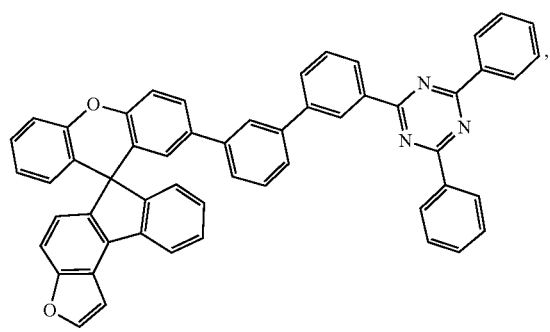
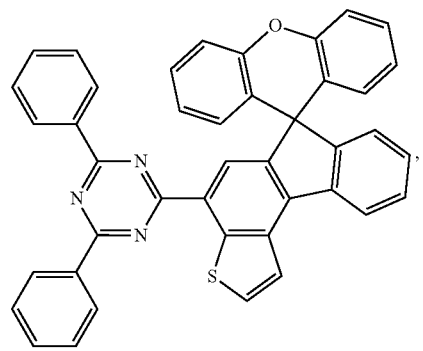
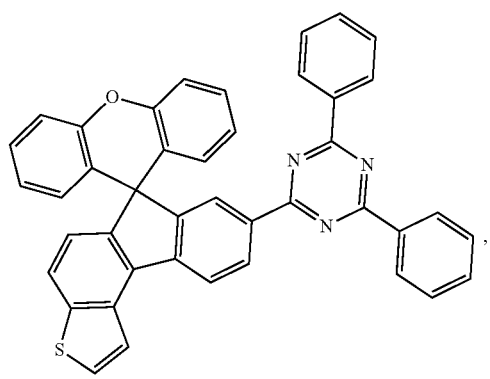
180
-continued
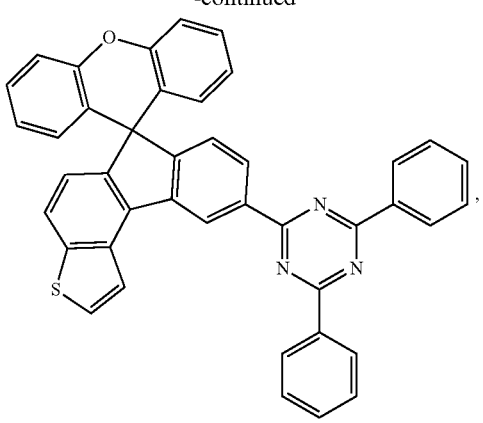
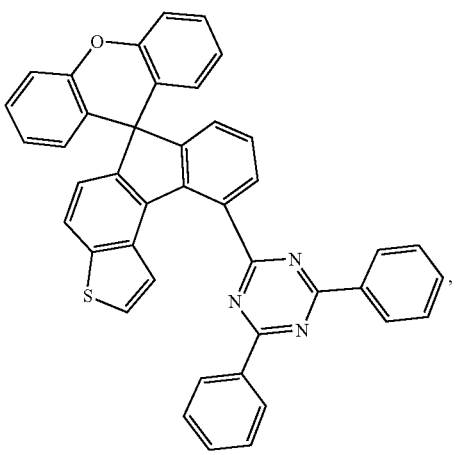
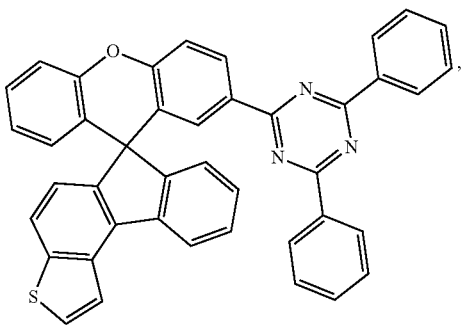
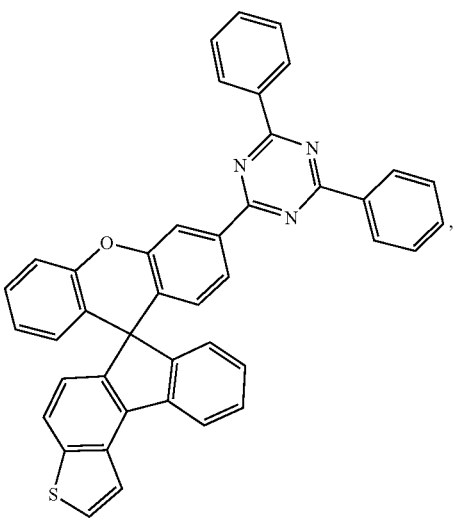

-continued
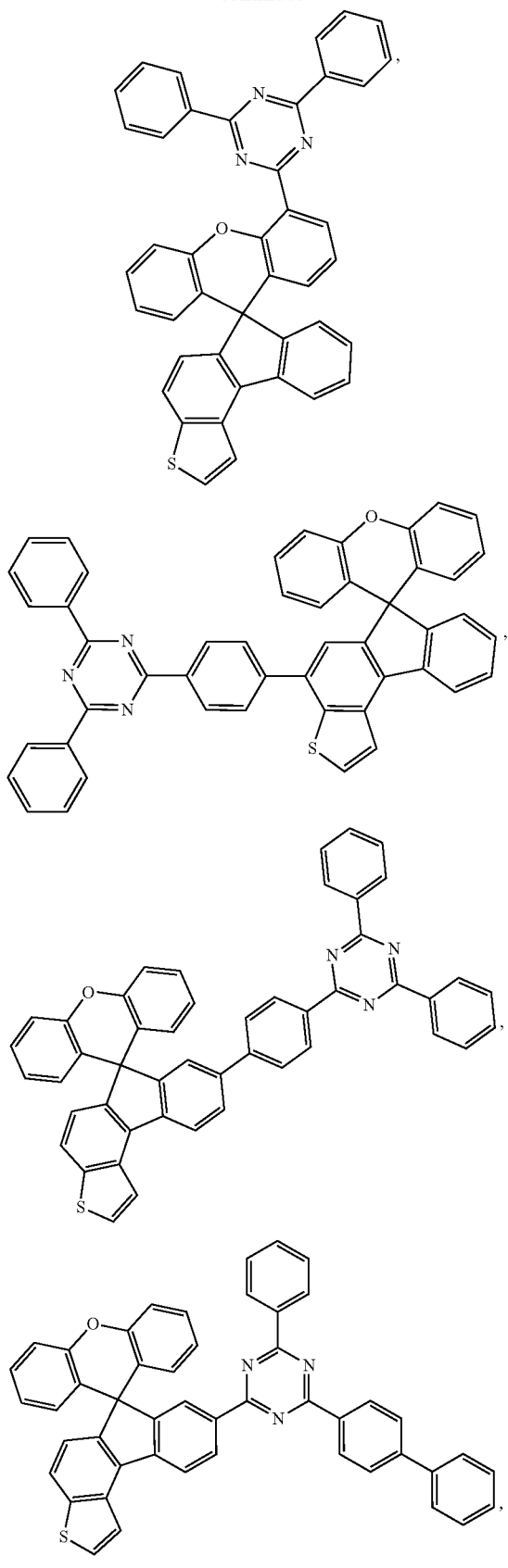
-continued
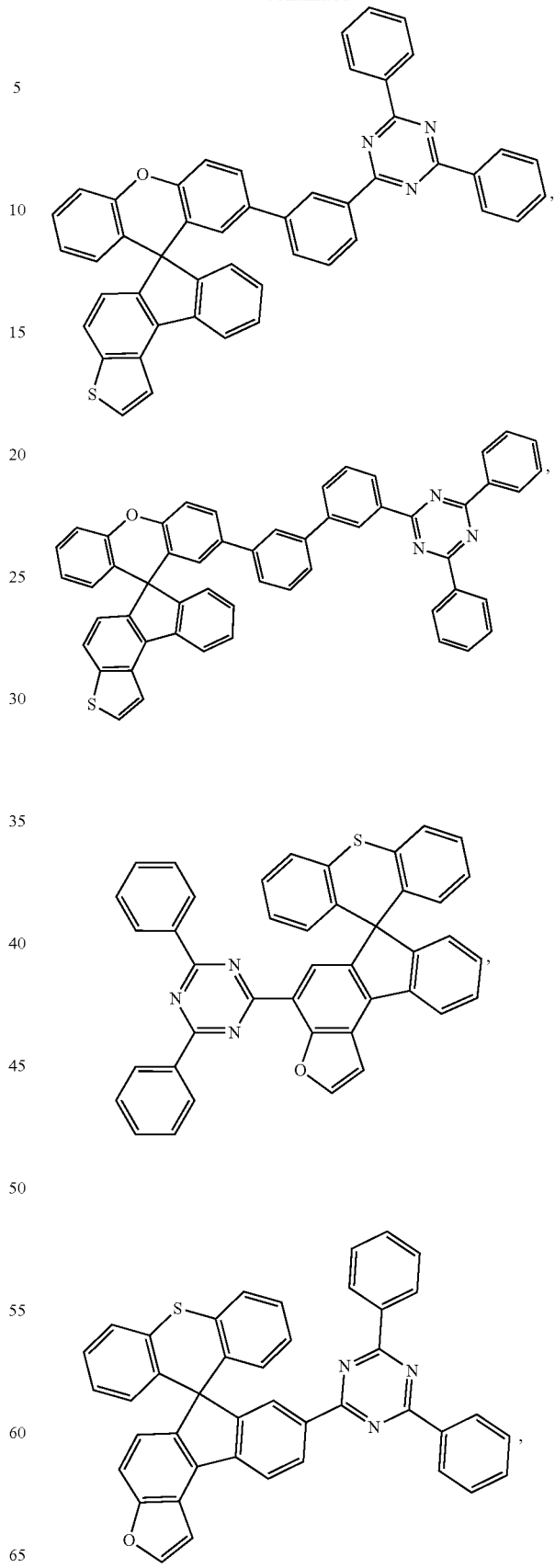

-continued
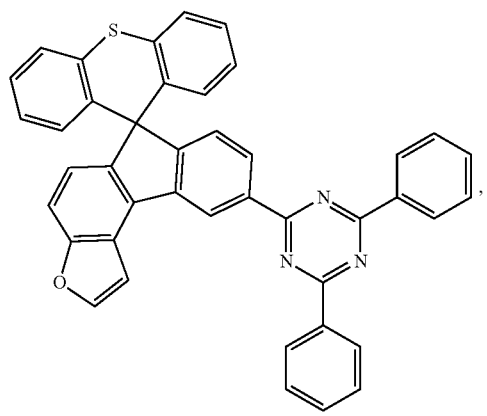
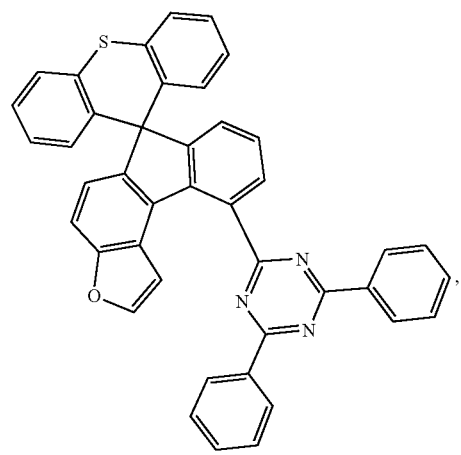
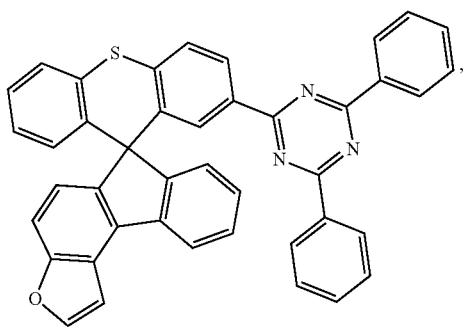
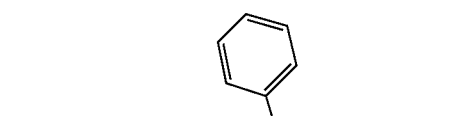
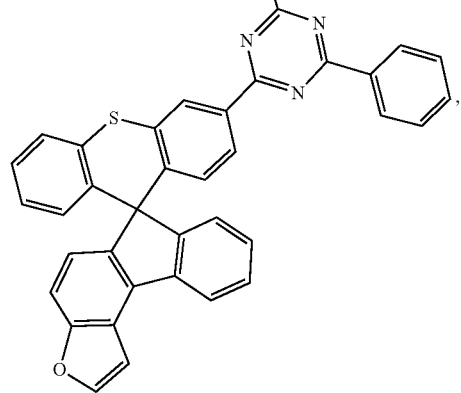
-continued
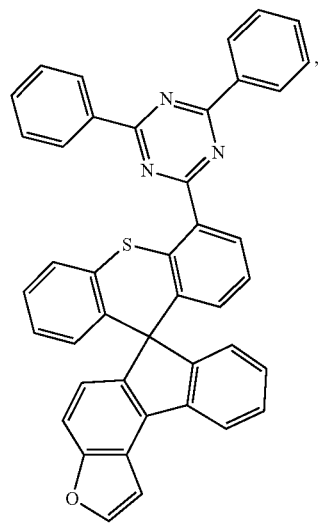
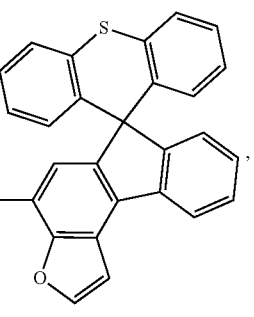
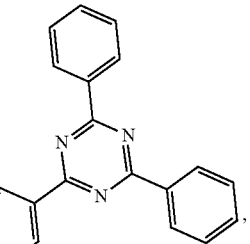
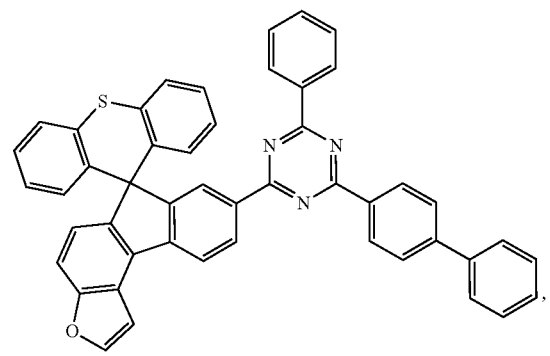

-continued
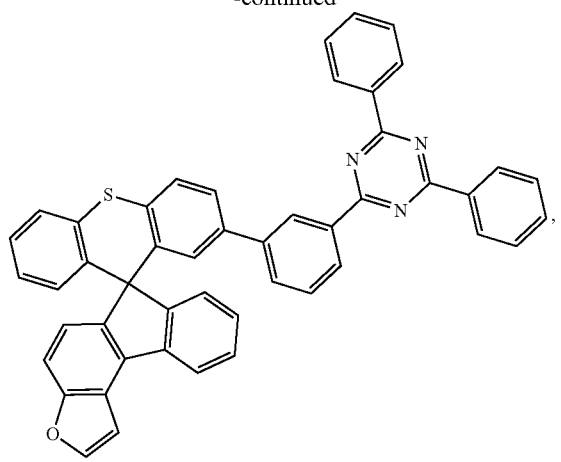
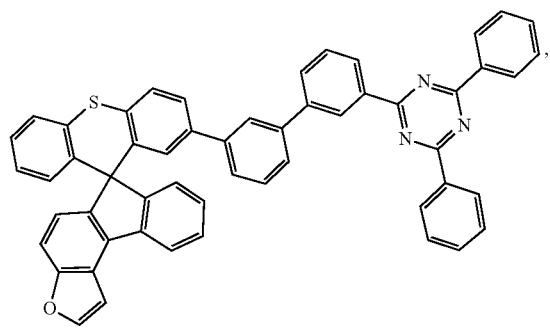
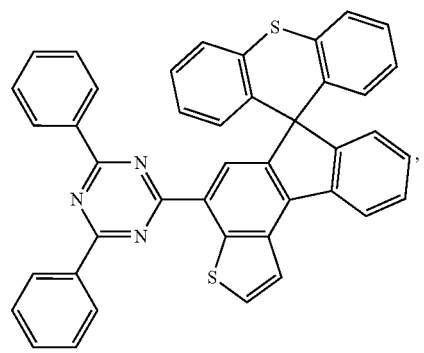
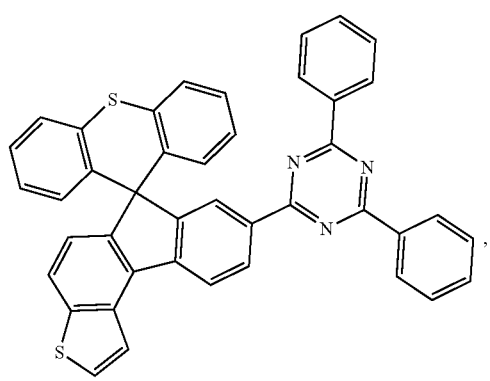
-continued
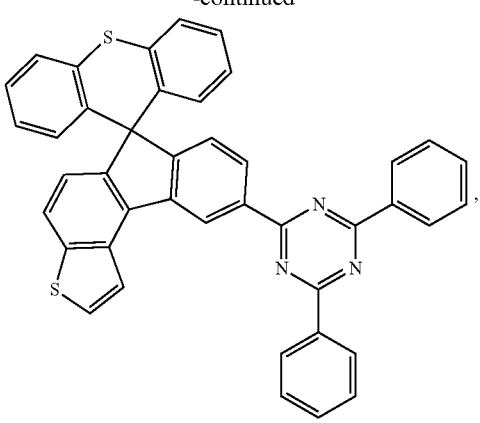
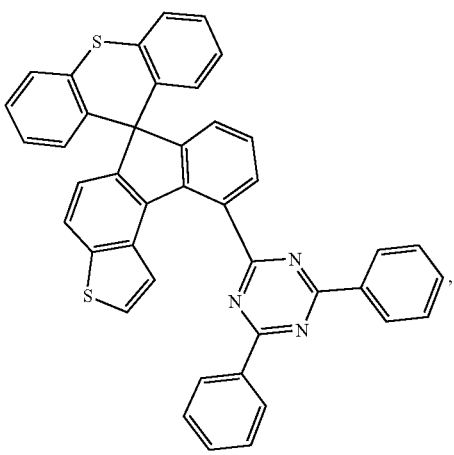
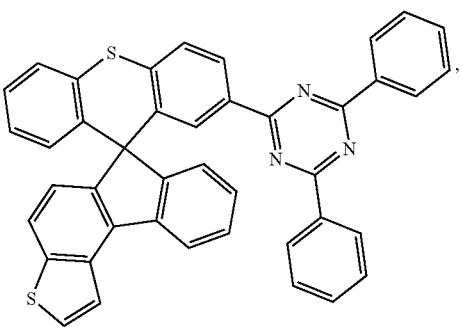
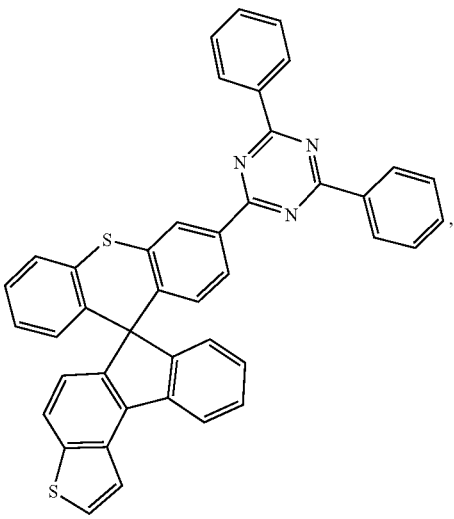

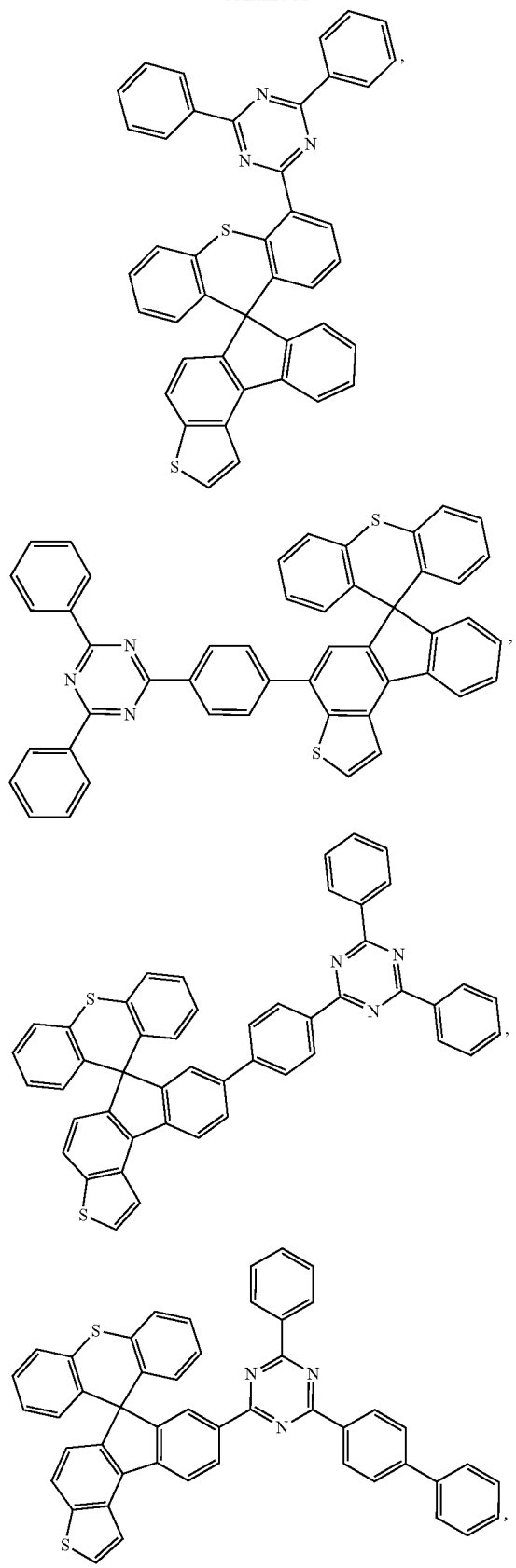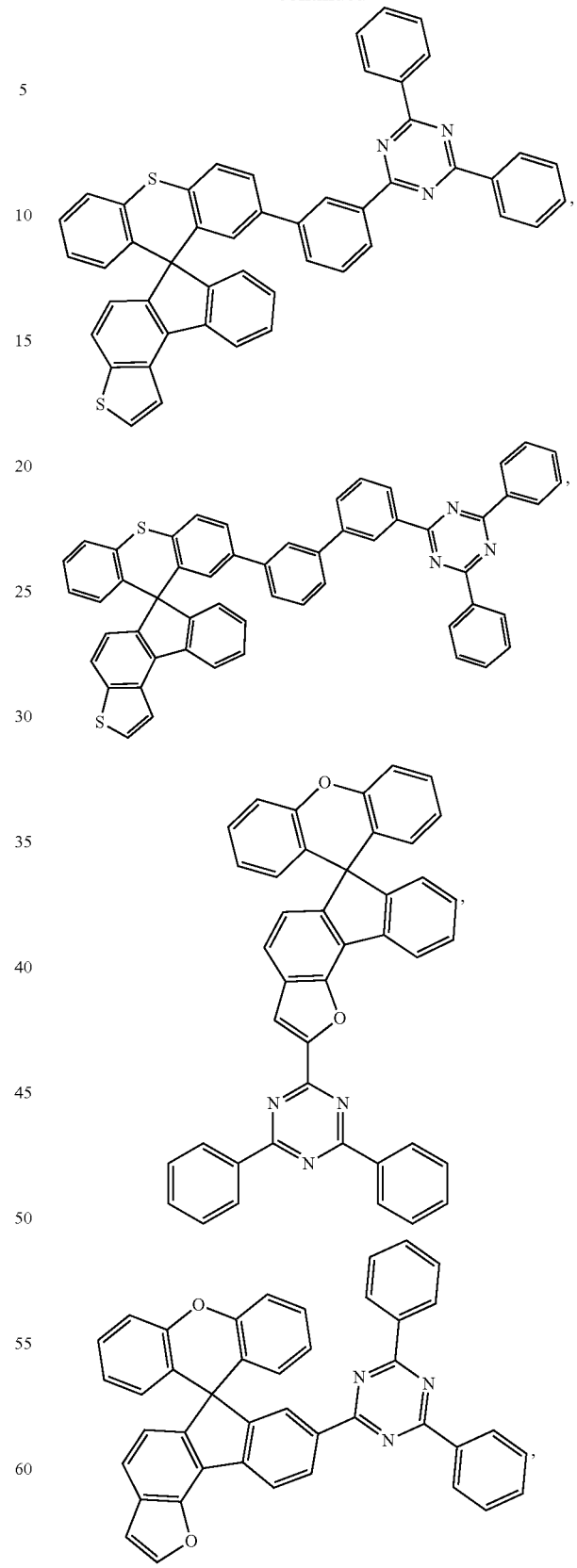

189
-continued
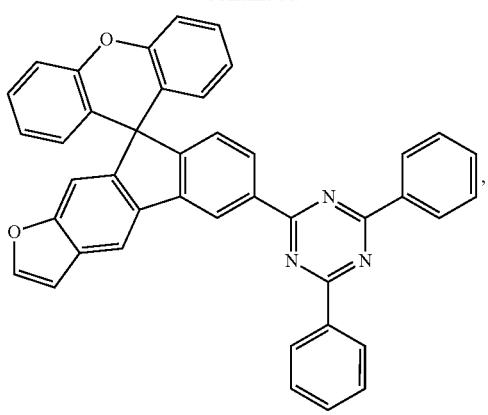
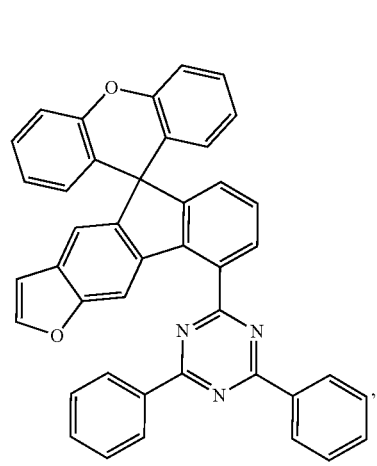
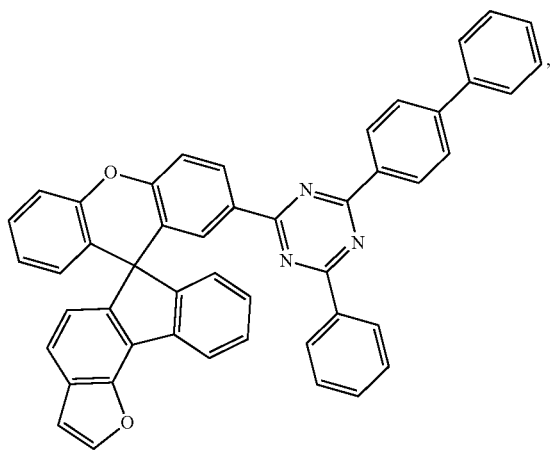
190
-continued
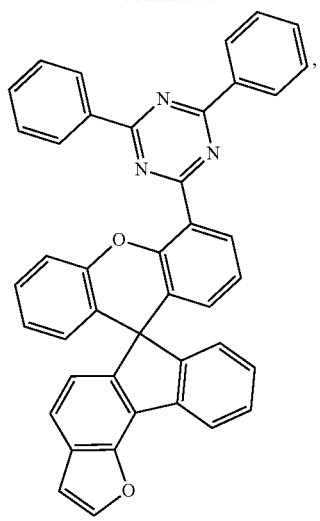
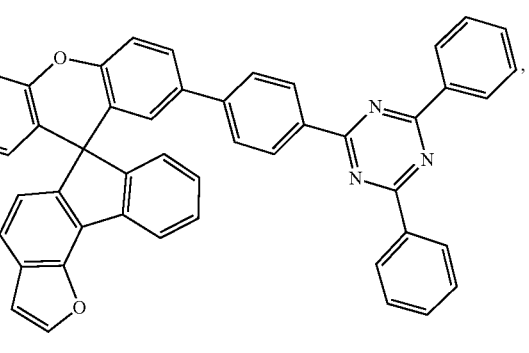
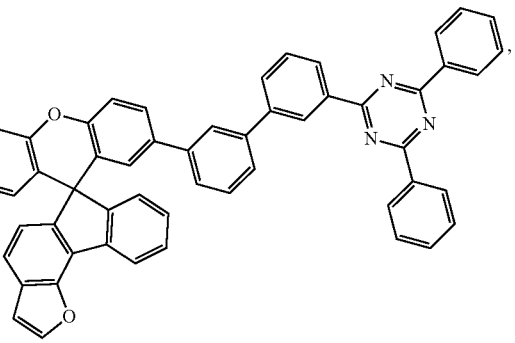
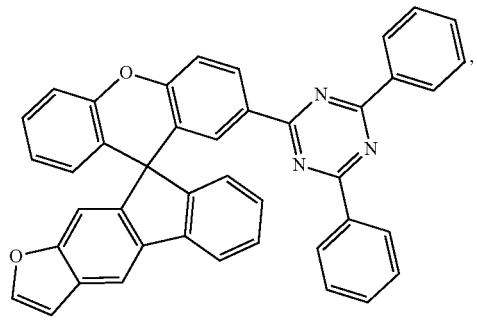

191
-continued
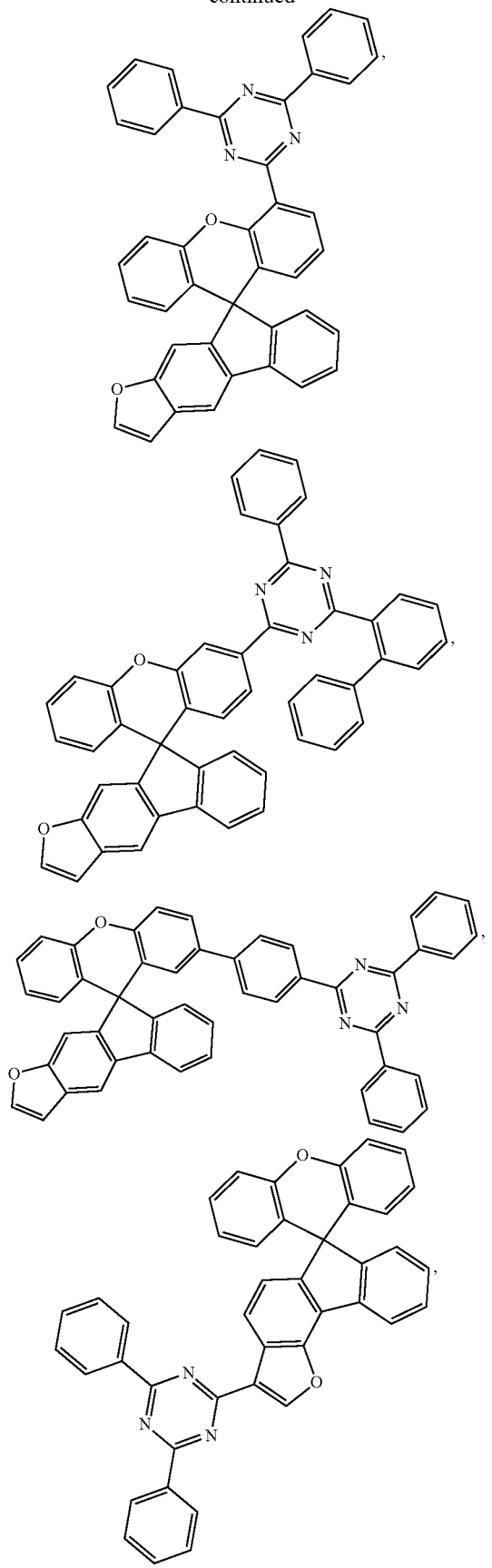
192
-continued
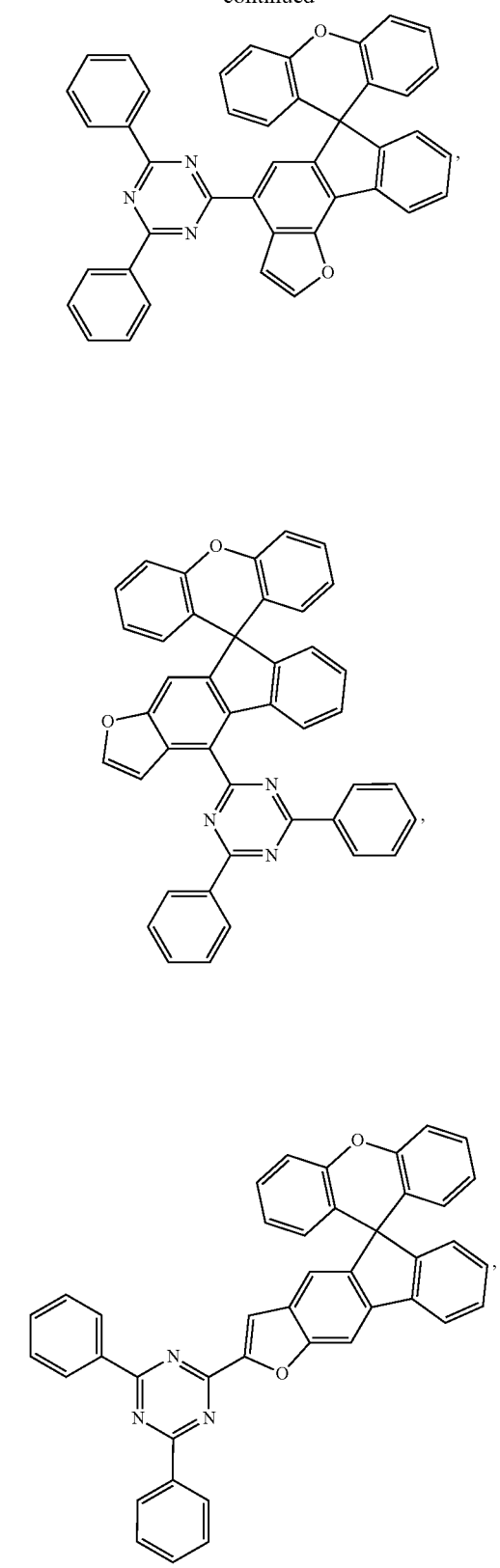

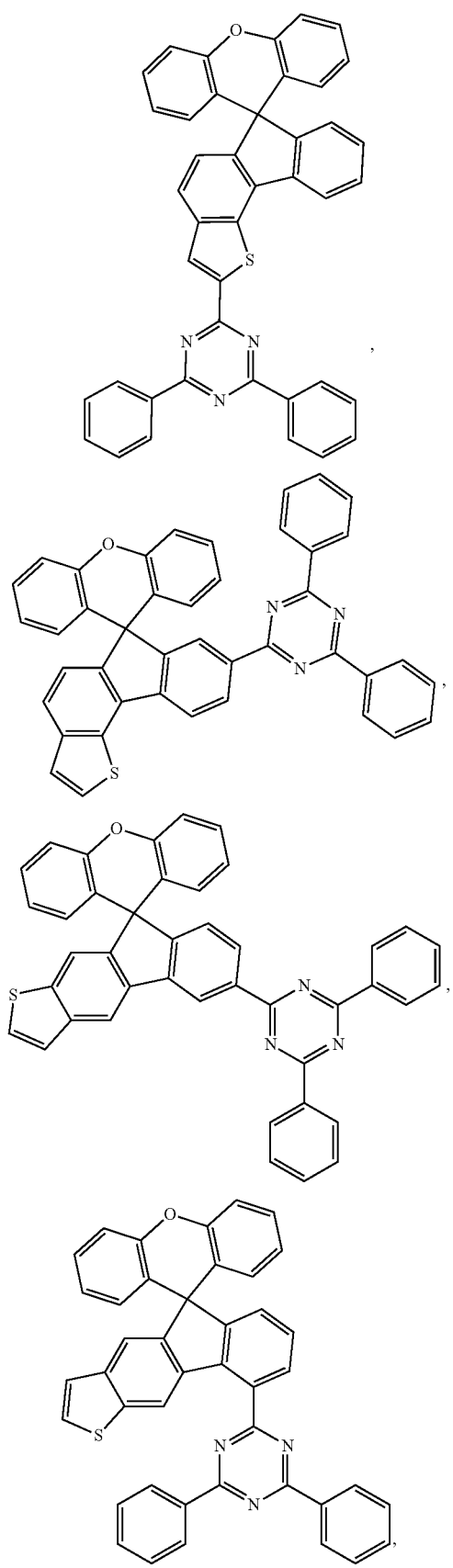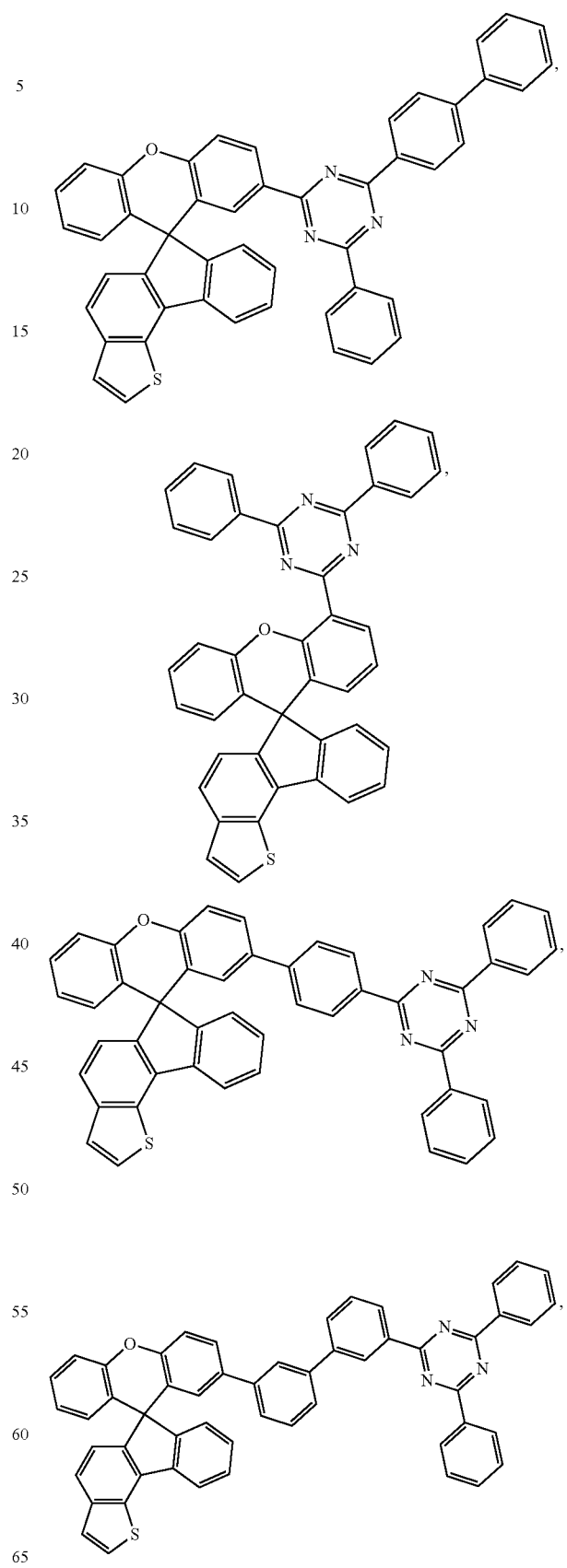

-continued
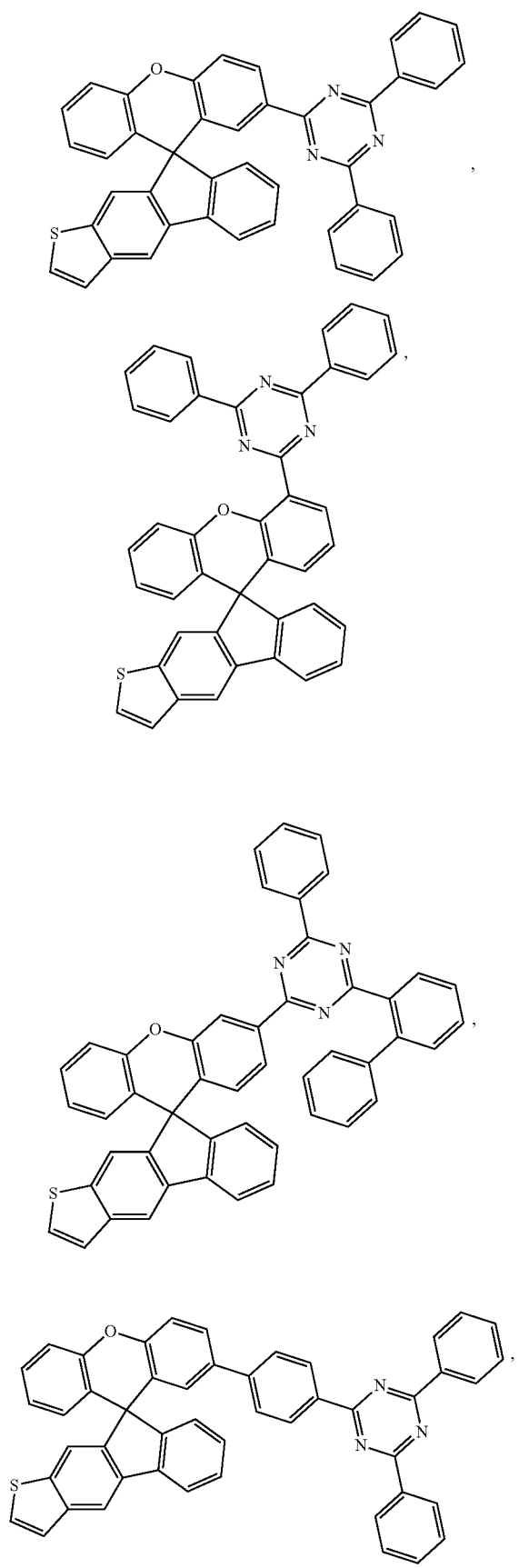
-continued
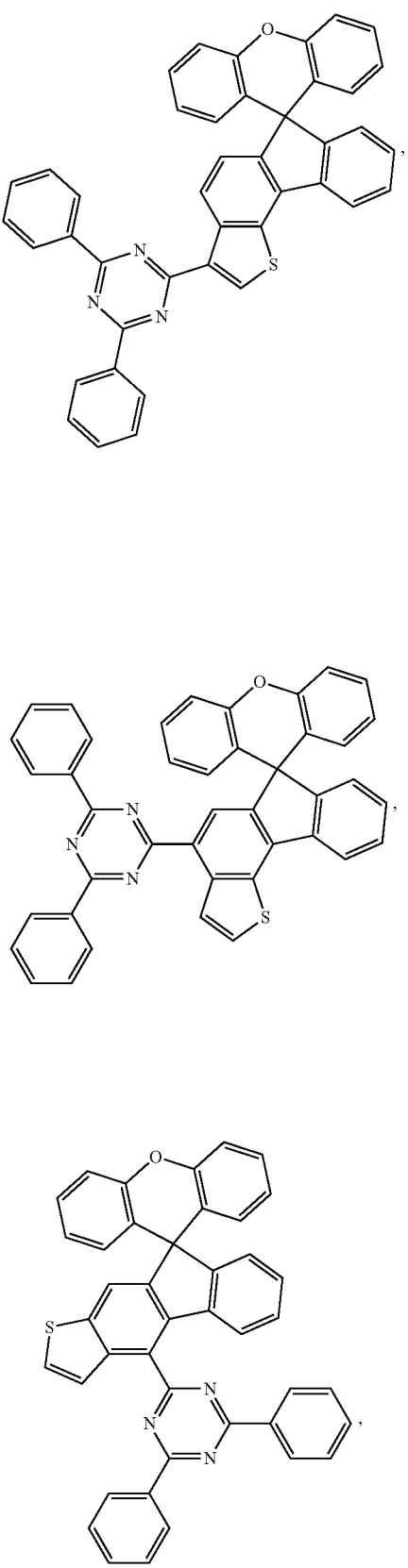

197
-continued
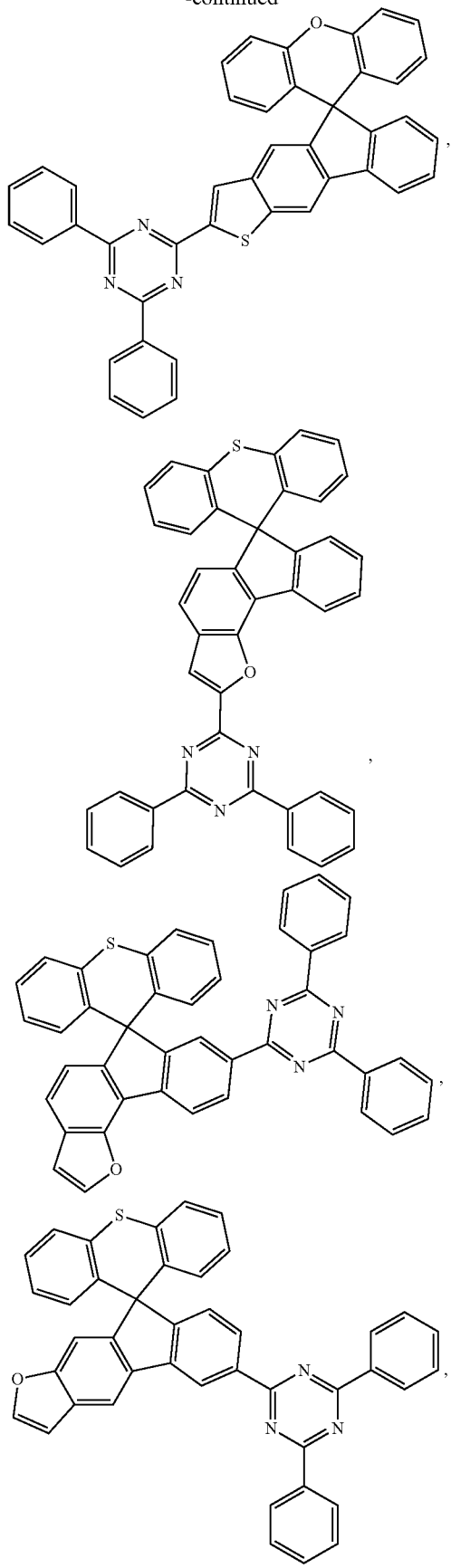
198
-continued
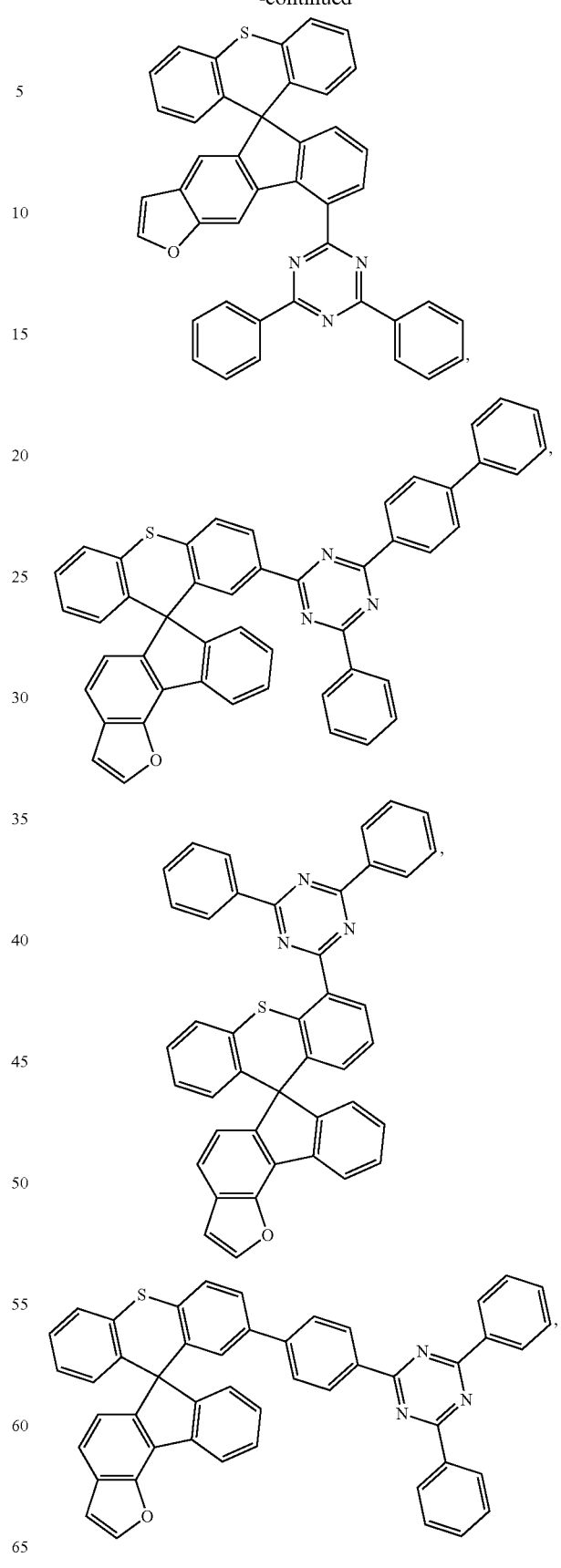

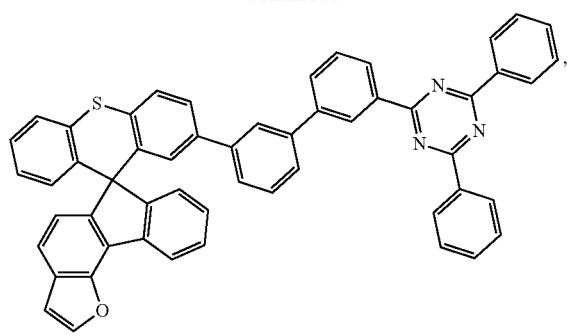
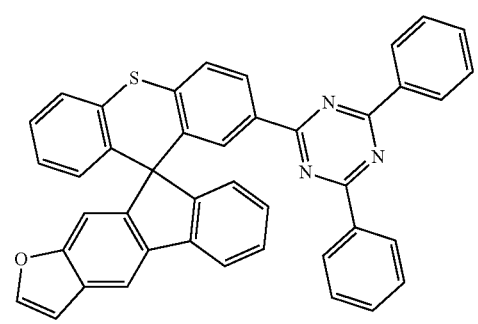
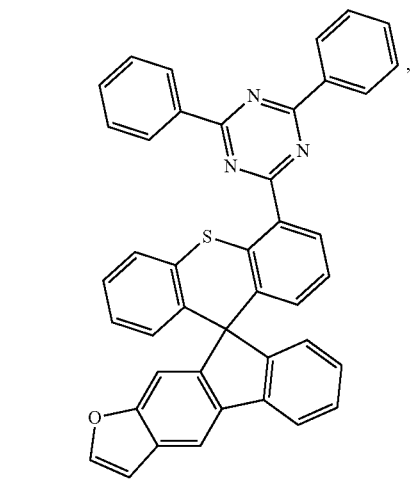
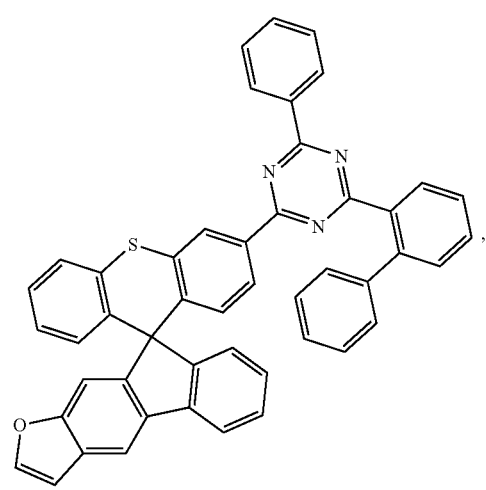
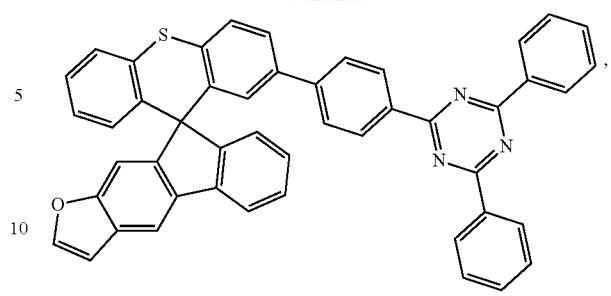
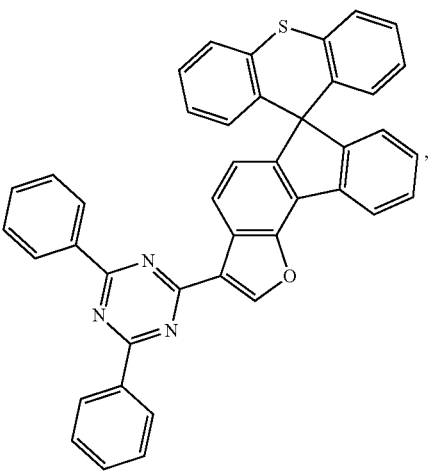
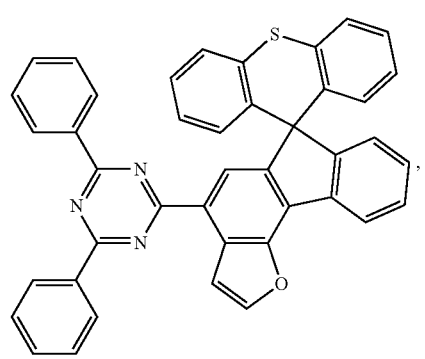
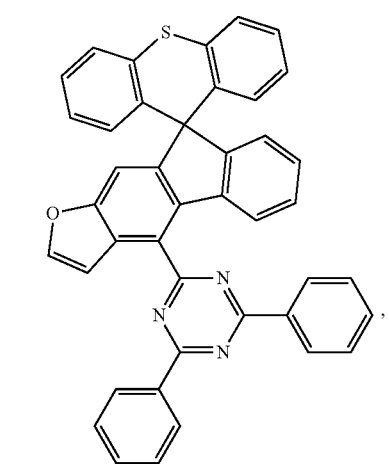

201
-continued
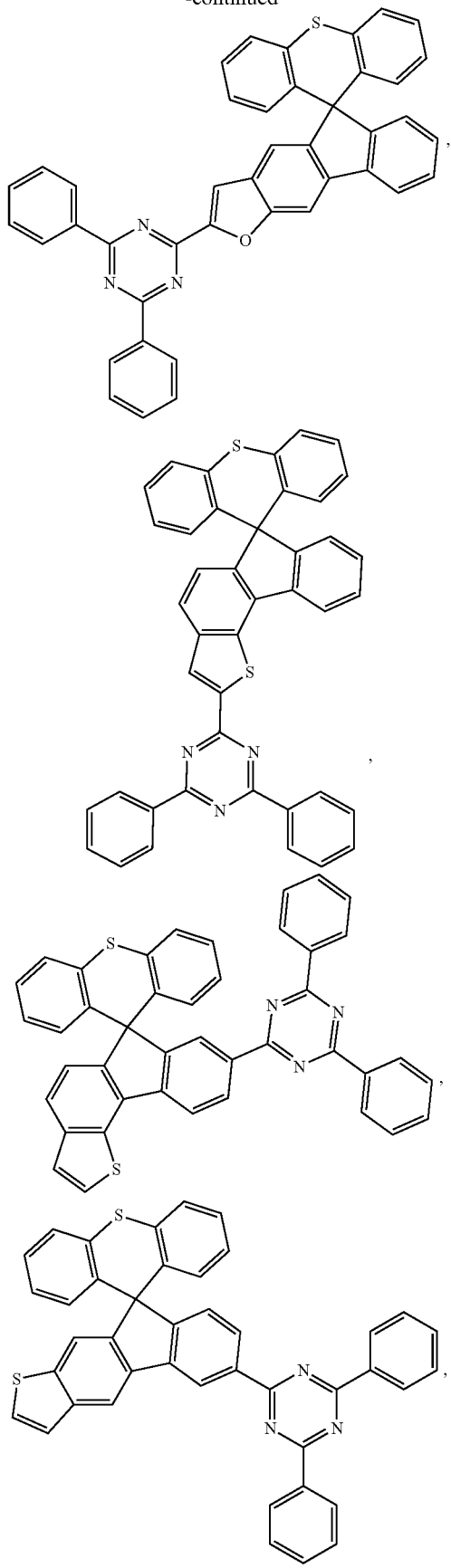
202
-continued
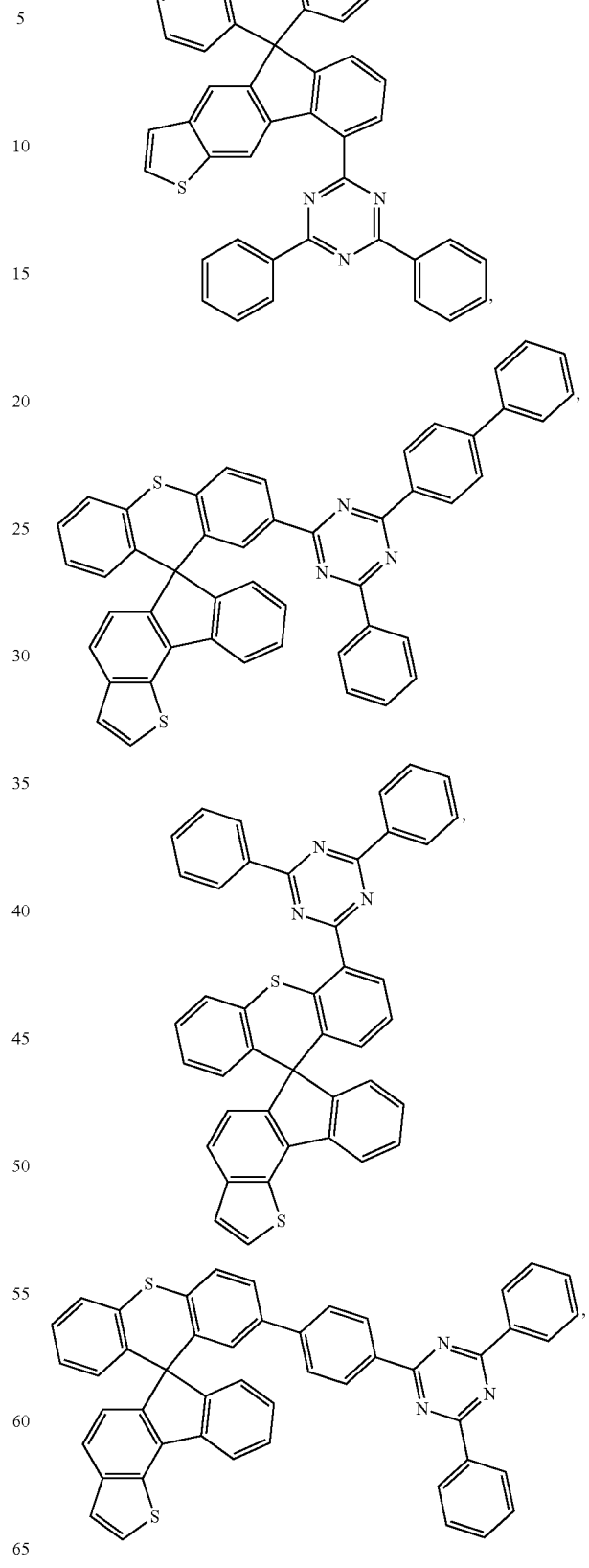

203
-continued
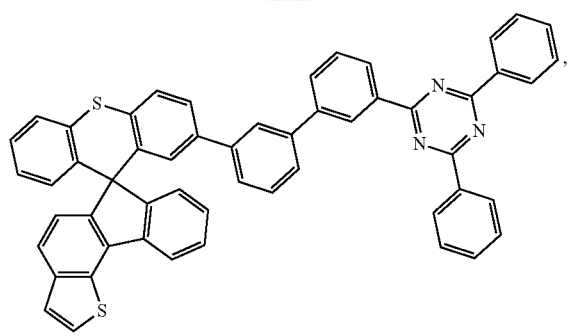
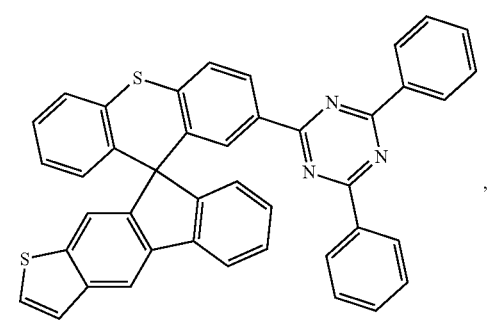
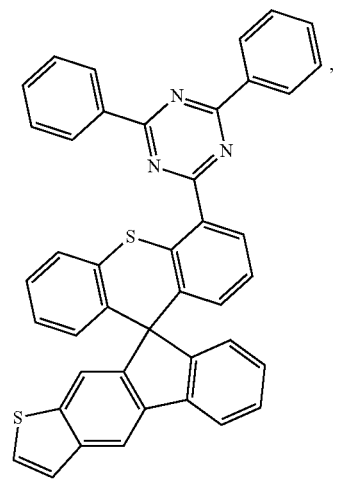
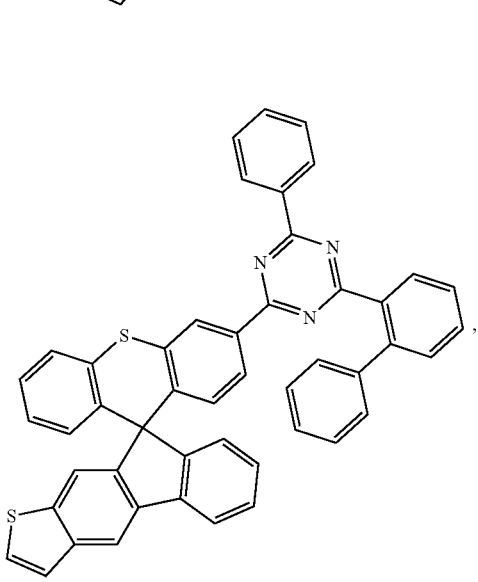
204
-continued
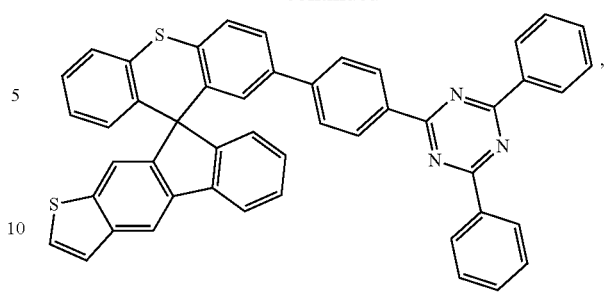
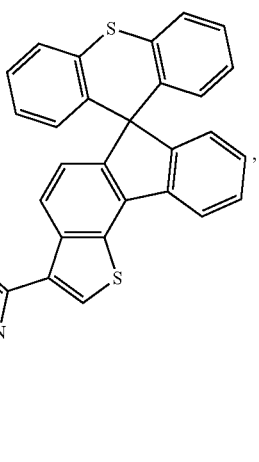
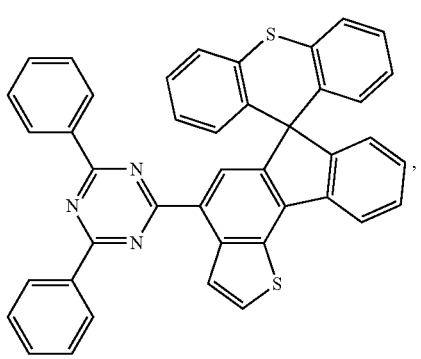
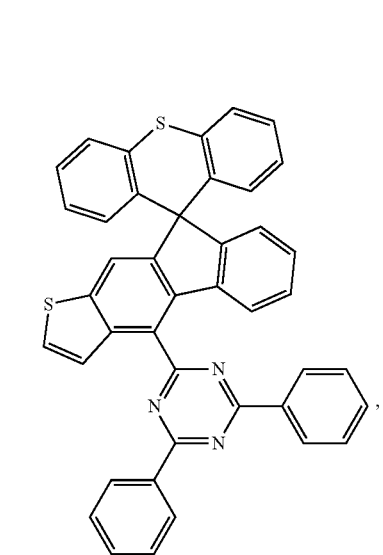

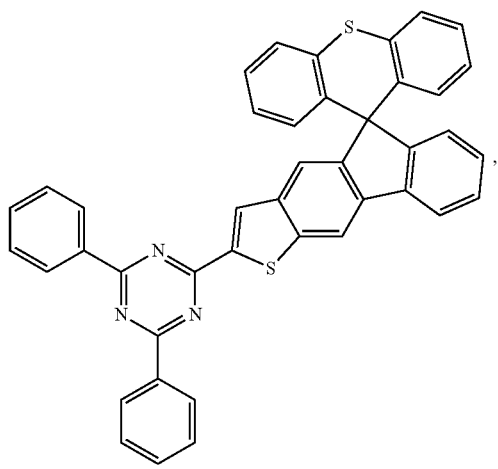
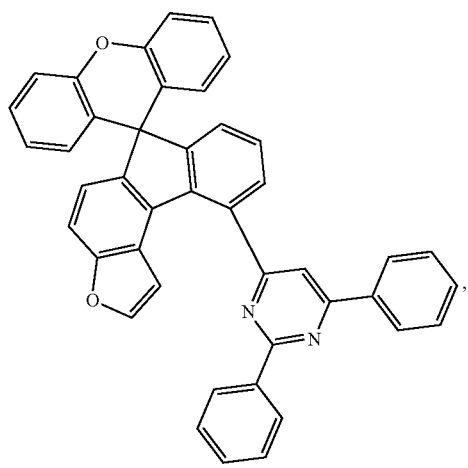
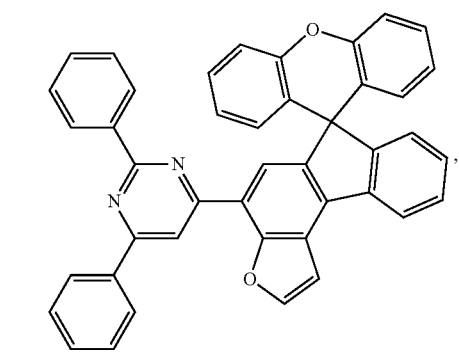
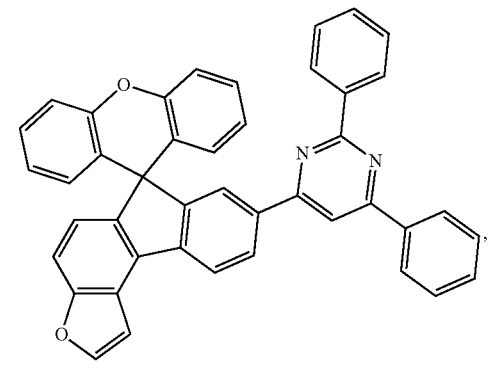
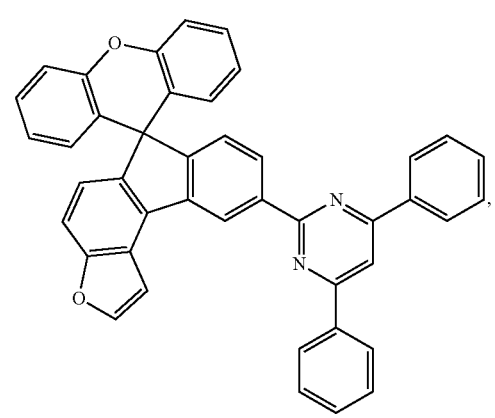

207
-continued
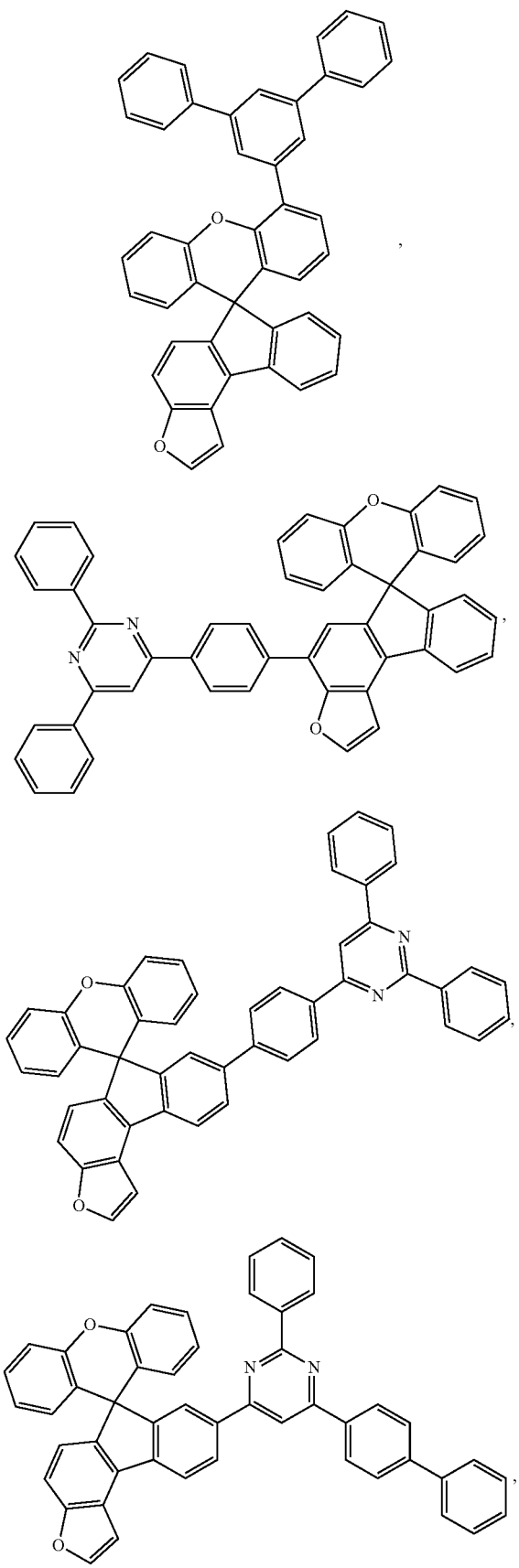
208
-continued
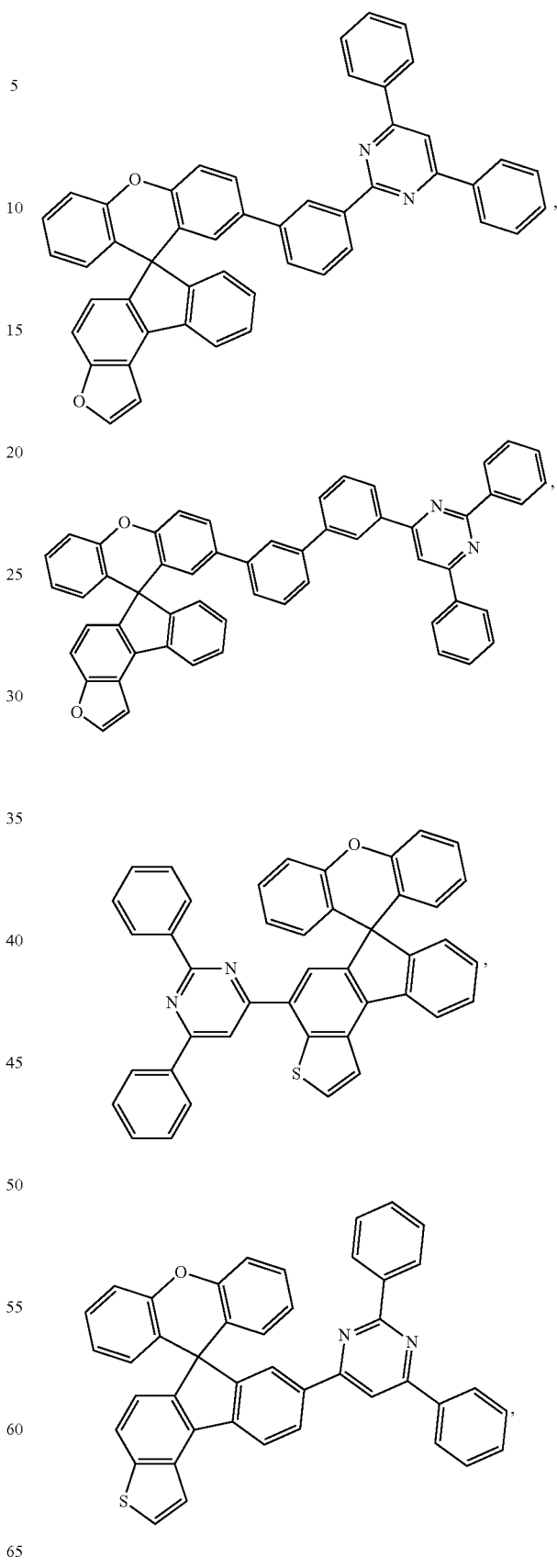

209
-continued
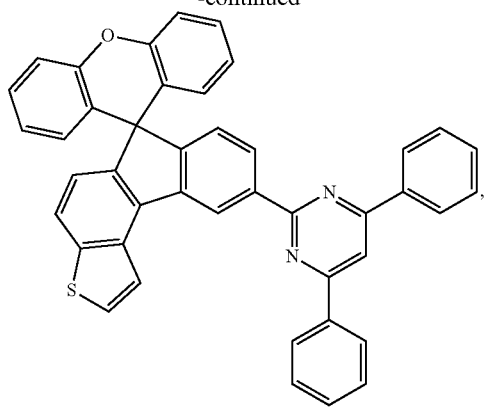
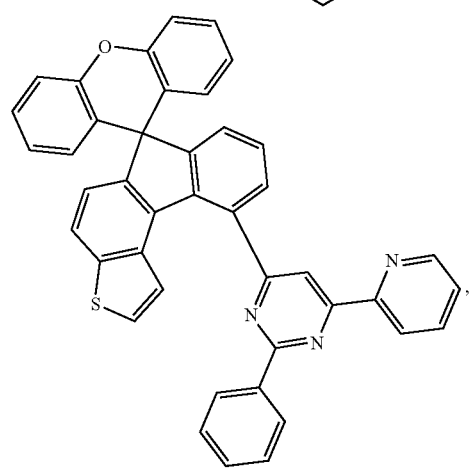
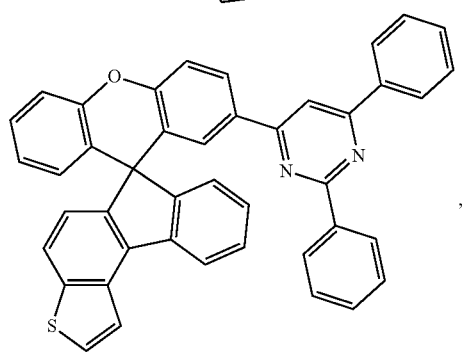
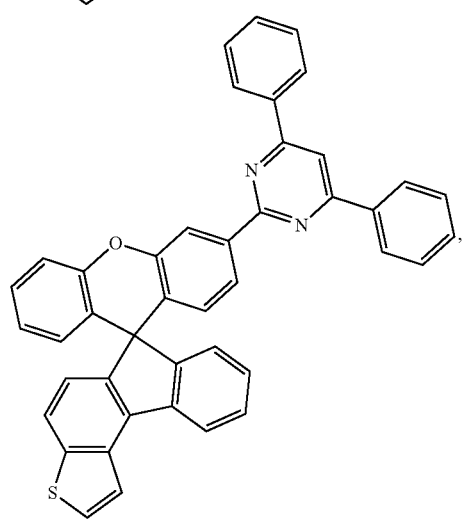
210
-continued
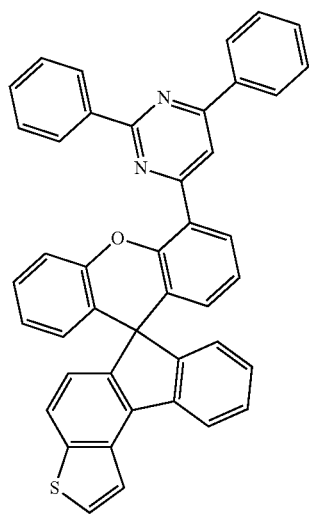
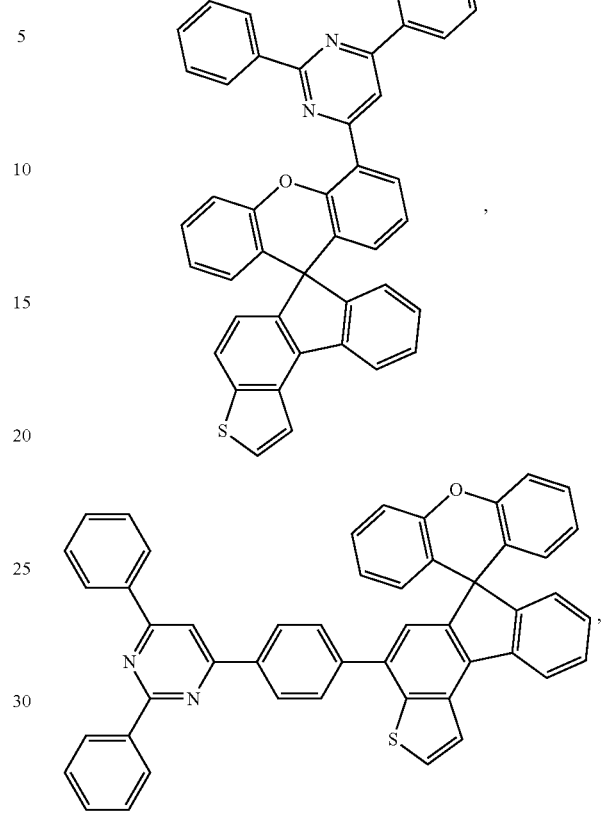
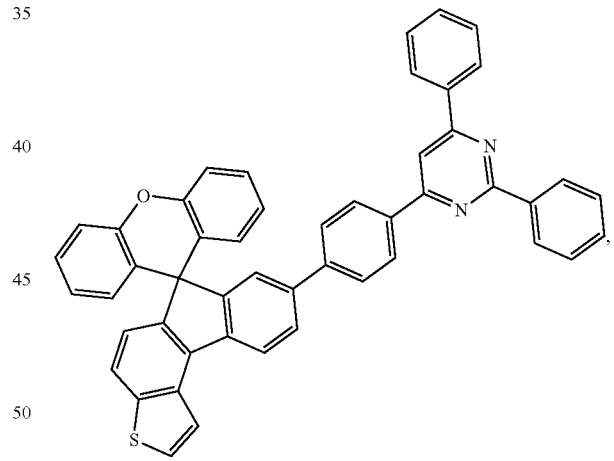
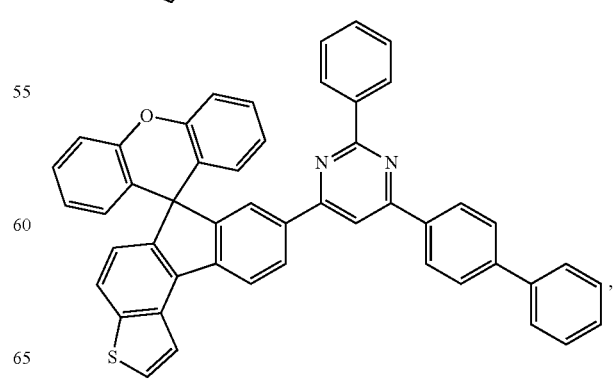

211
-continued
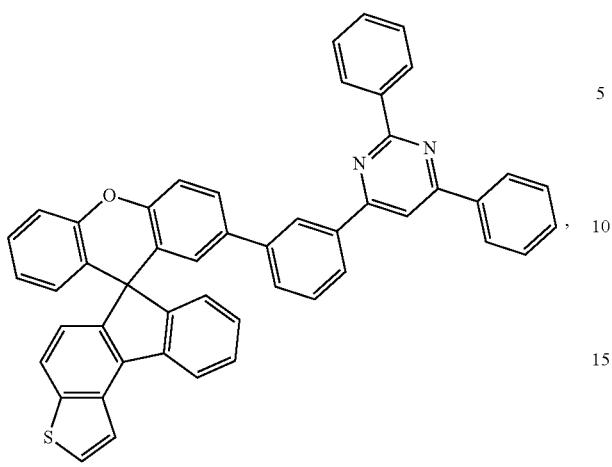
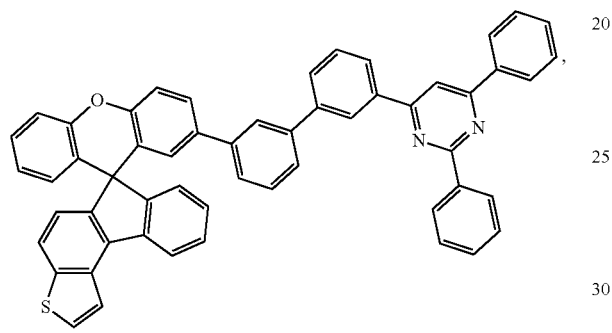
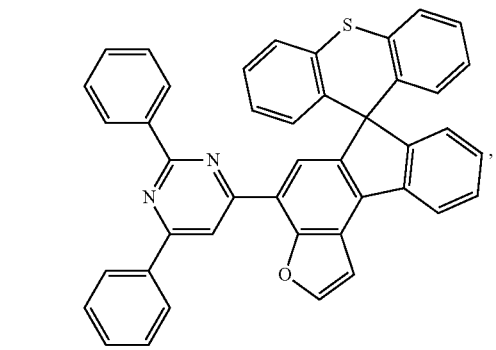
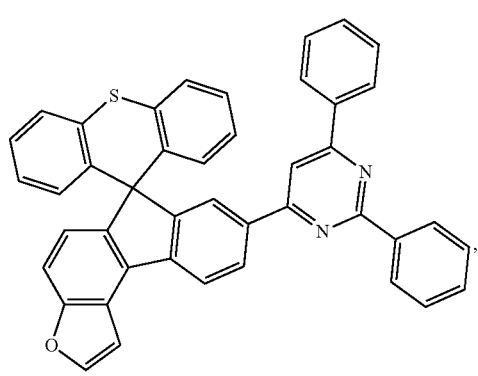
212
-continued
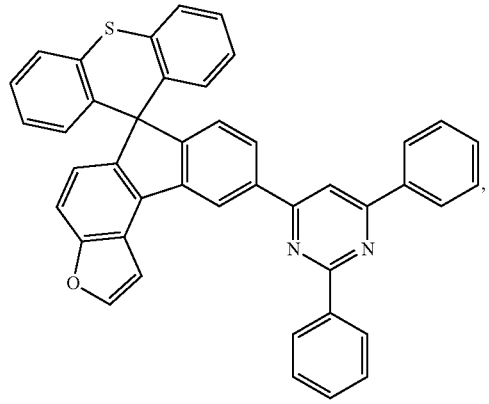
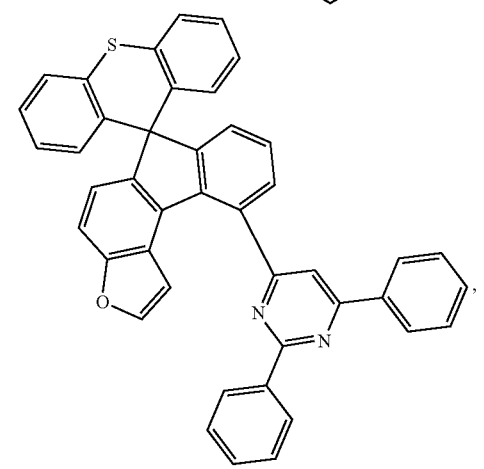
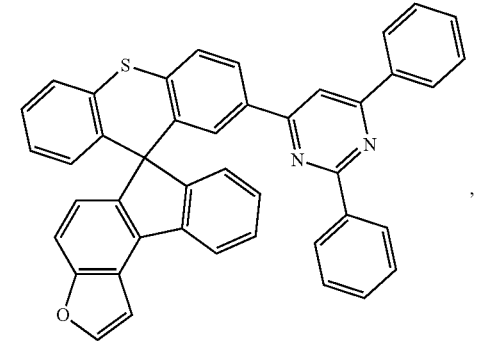
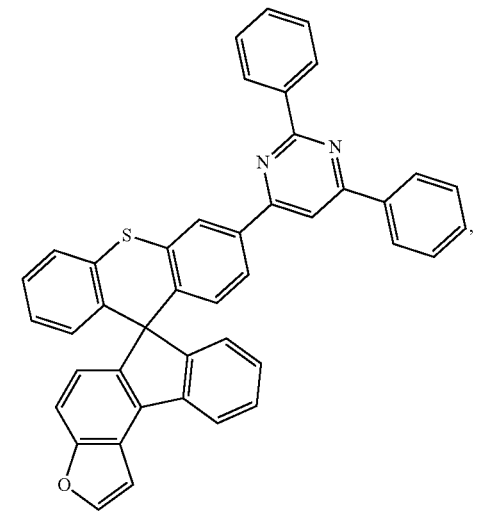

213
-continued
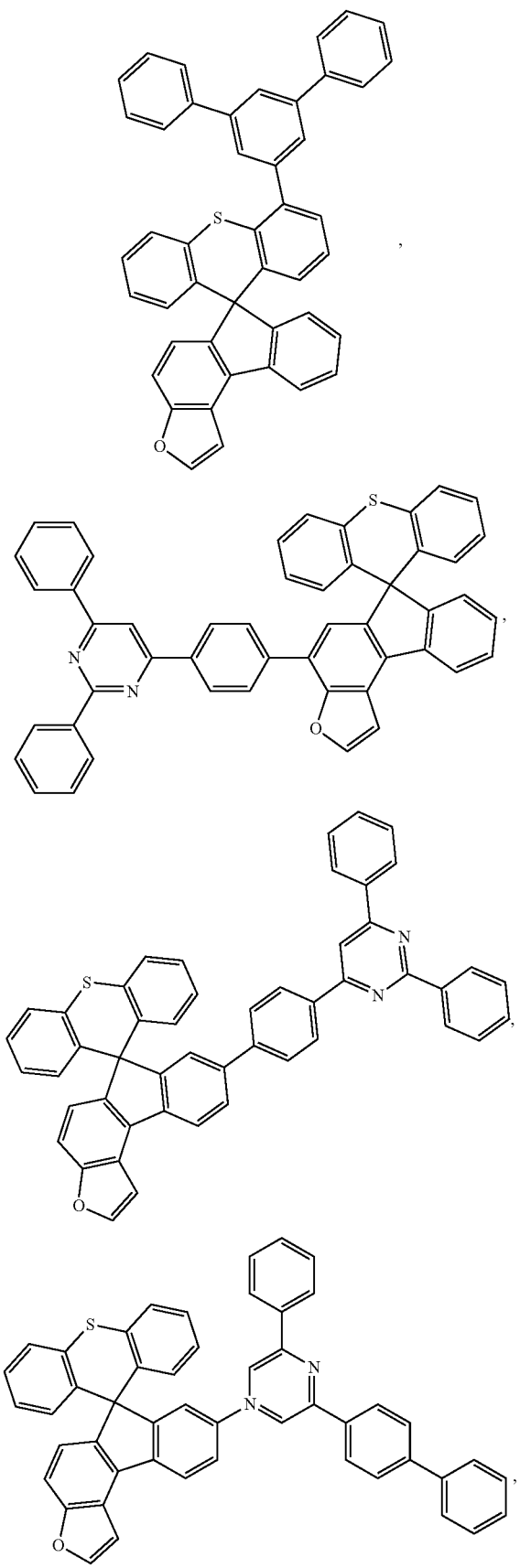
214
-continued
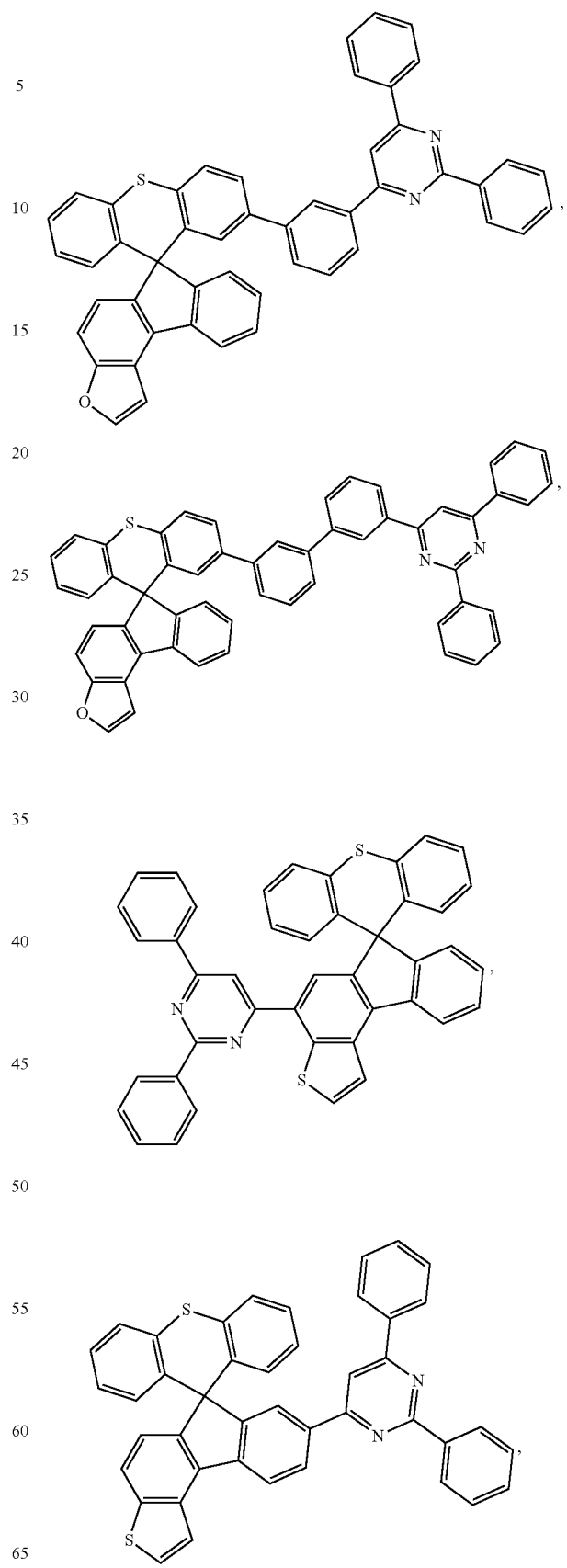

215
-continued
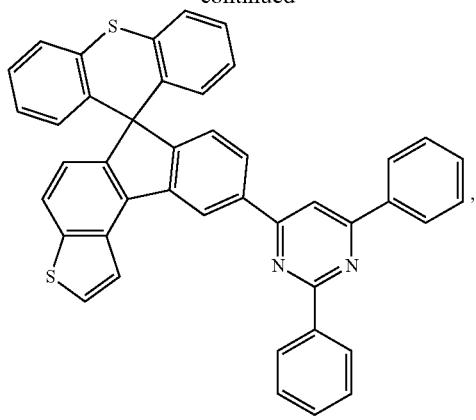
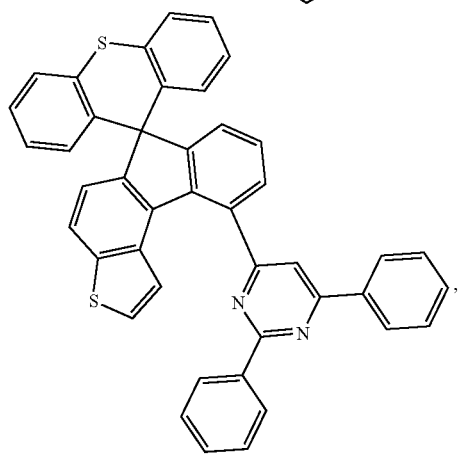
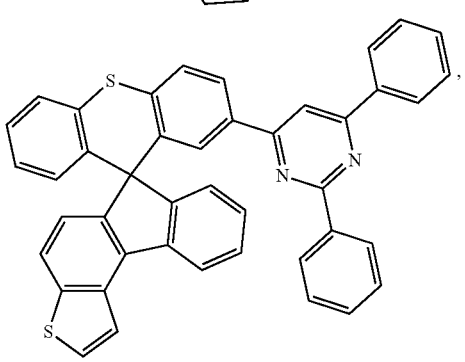
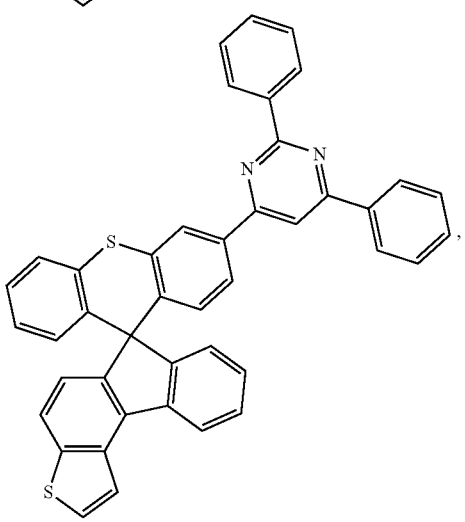
216
-continued
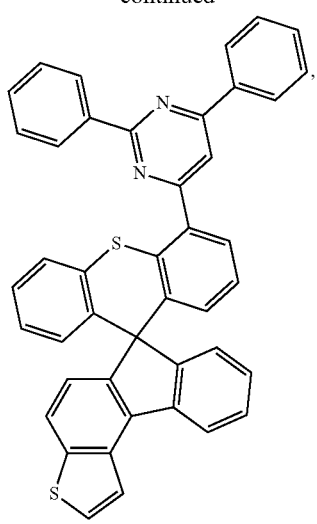
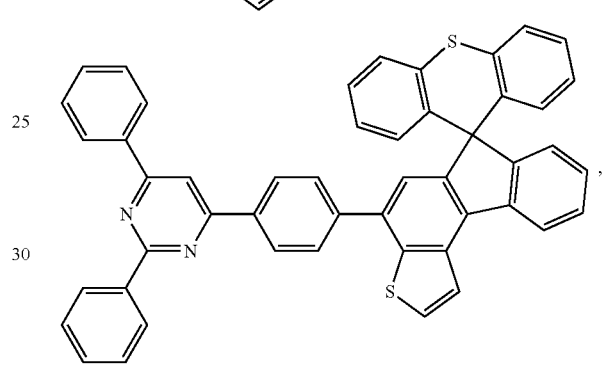
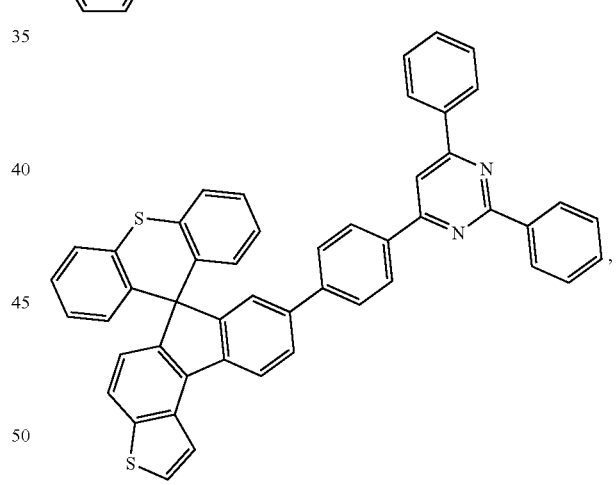
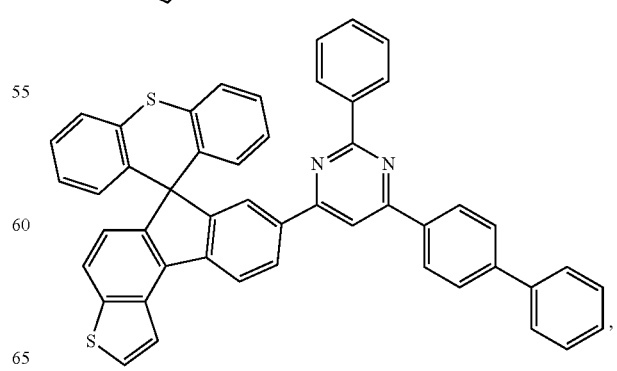

217
-continued
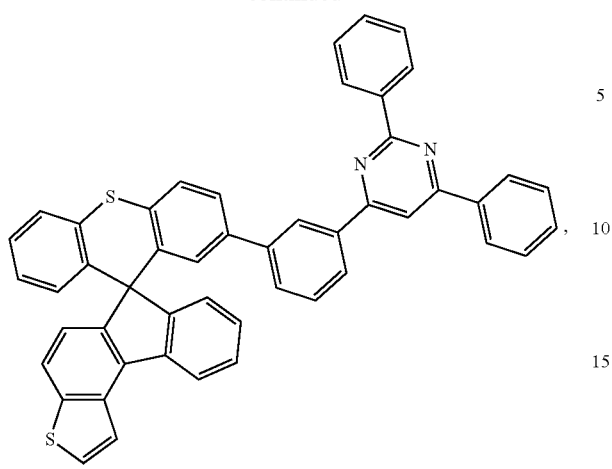
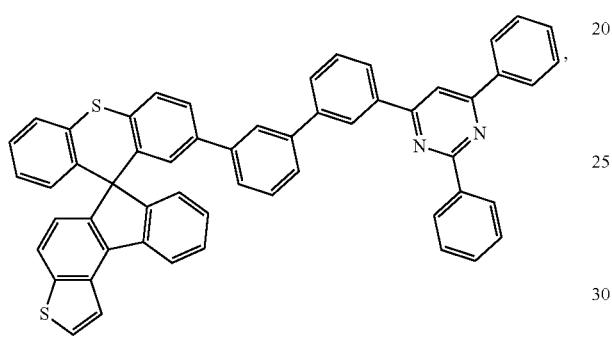
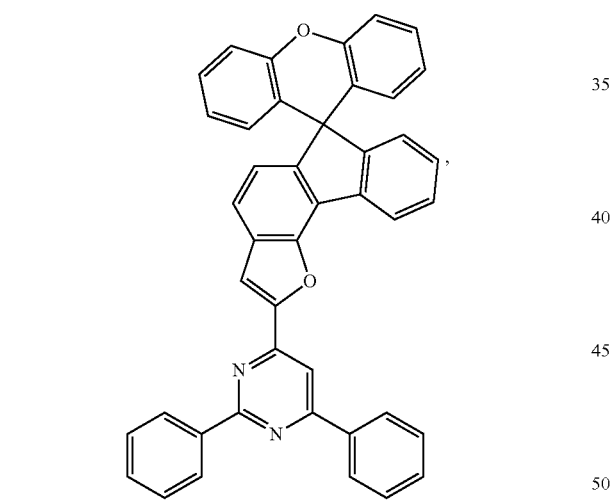
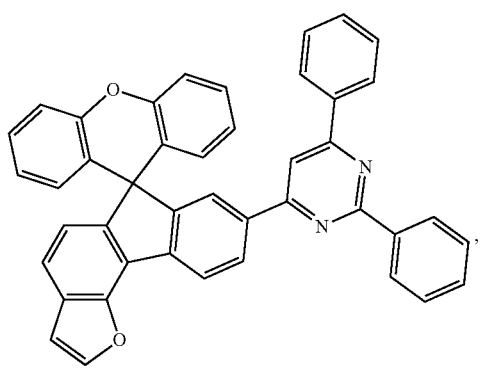
218
-continued
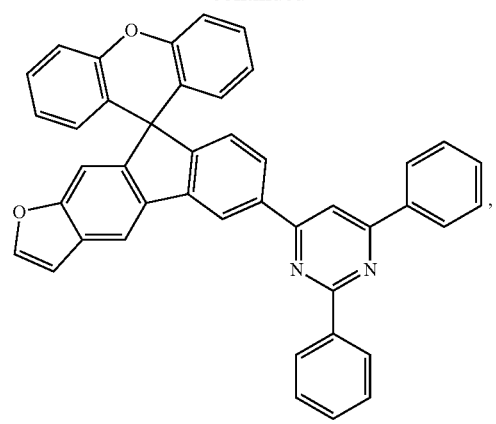
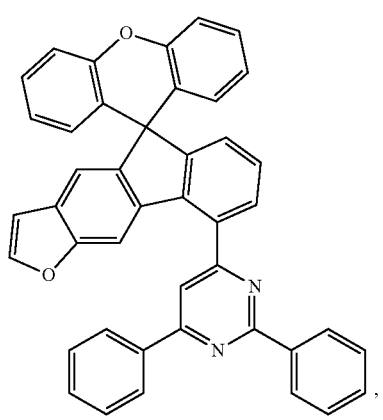
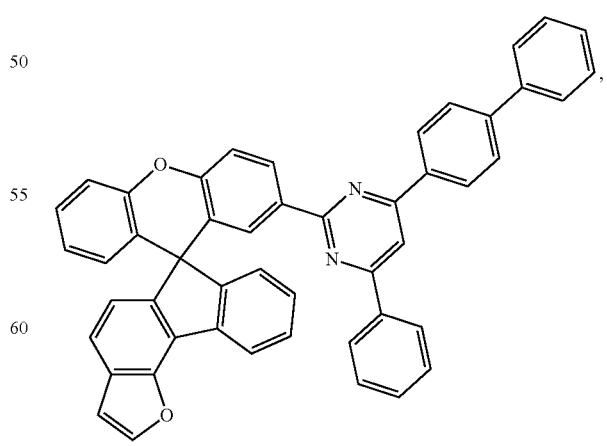

219
-continued
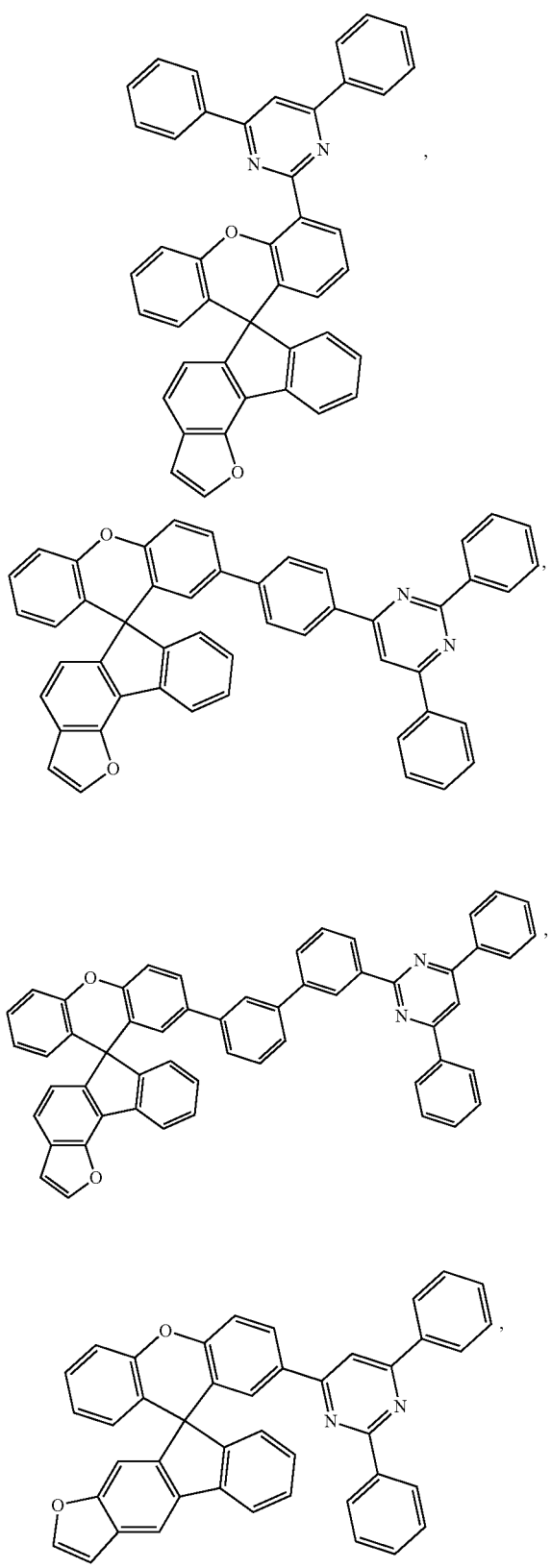
220
-continued
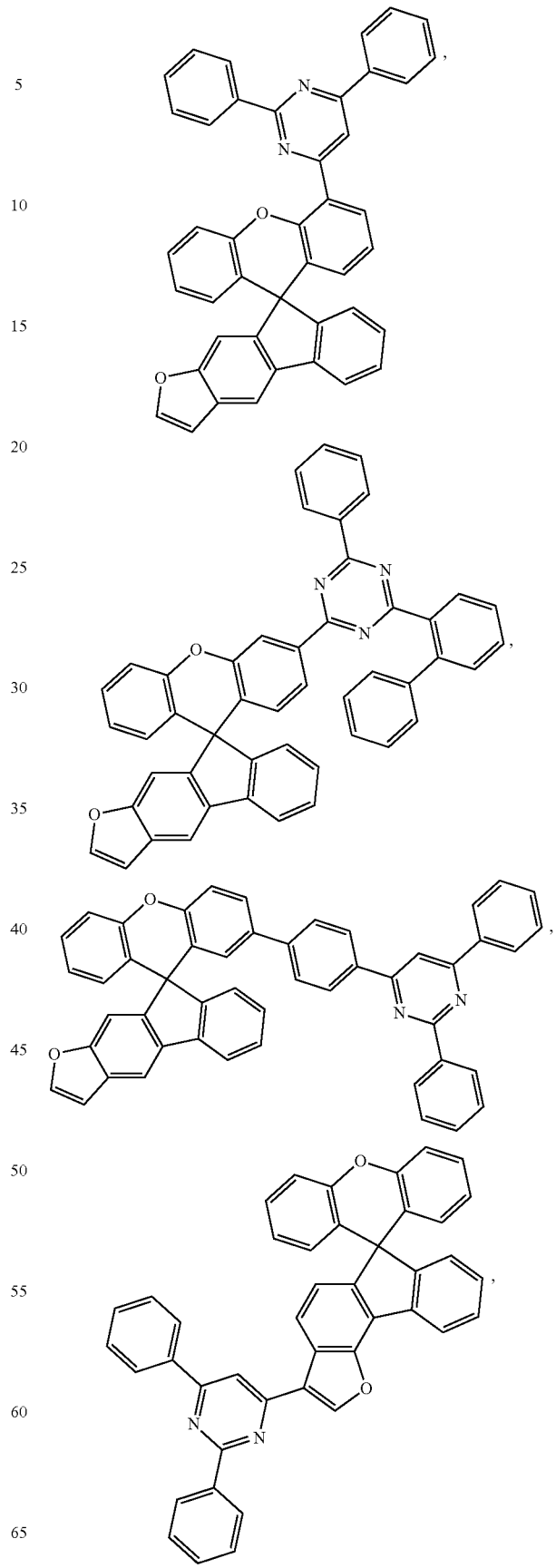

221
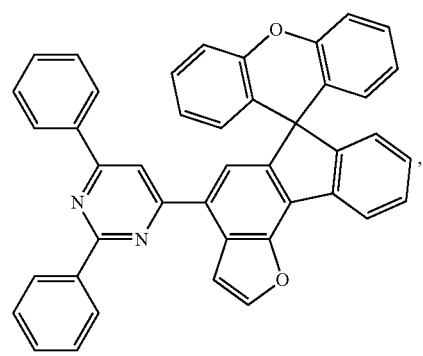
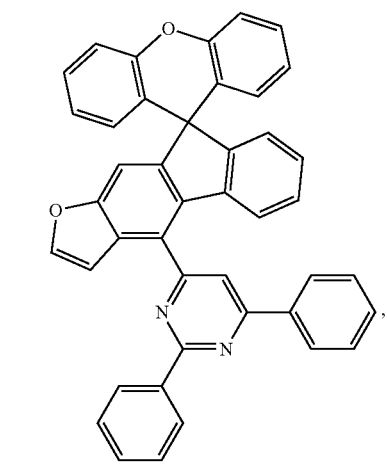
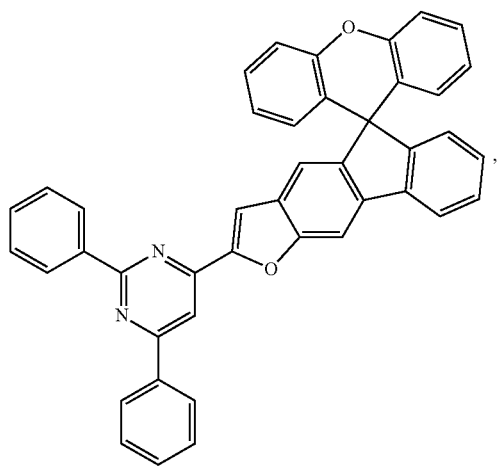
222
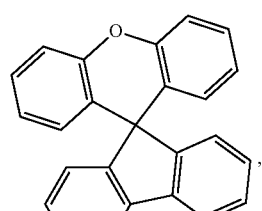
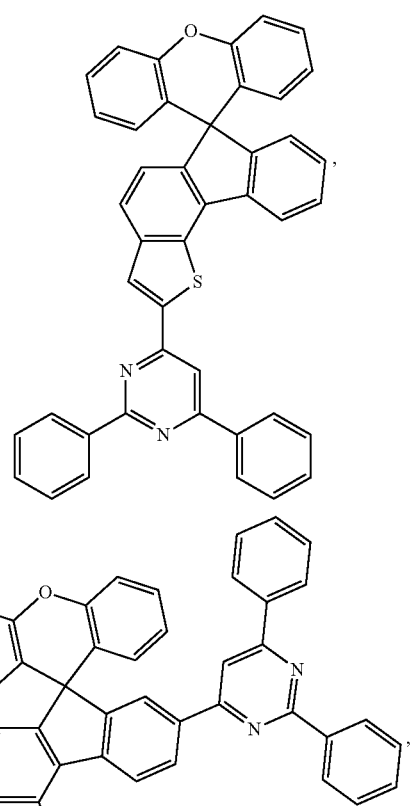
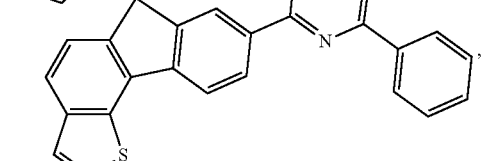
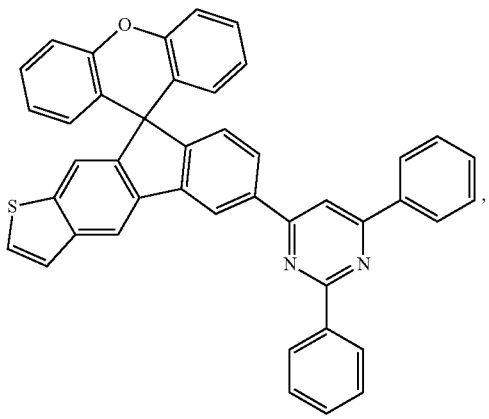

223
-continued
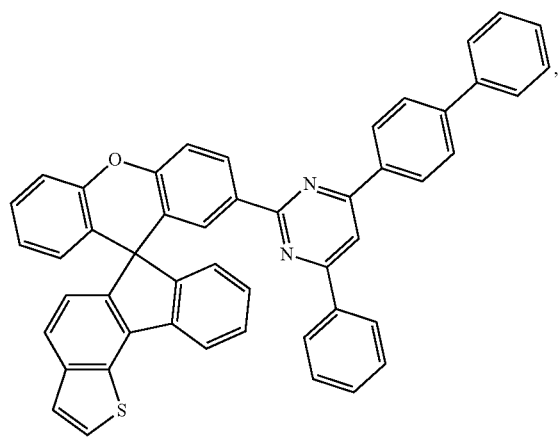
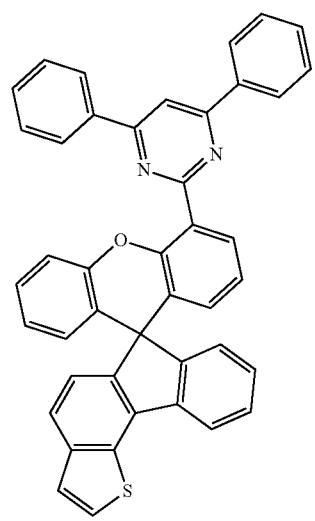
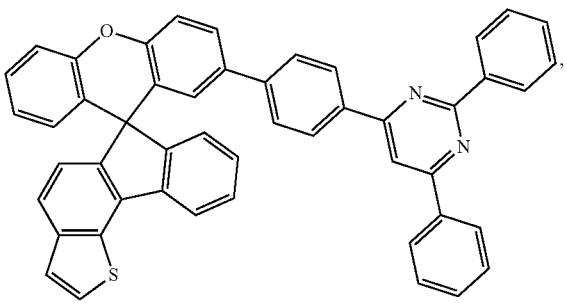
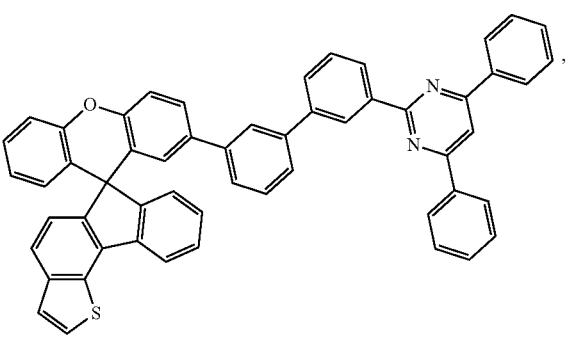
224
-continued
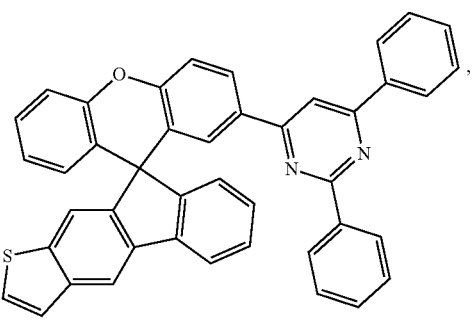
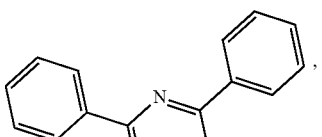
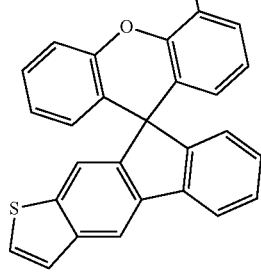
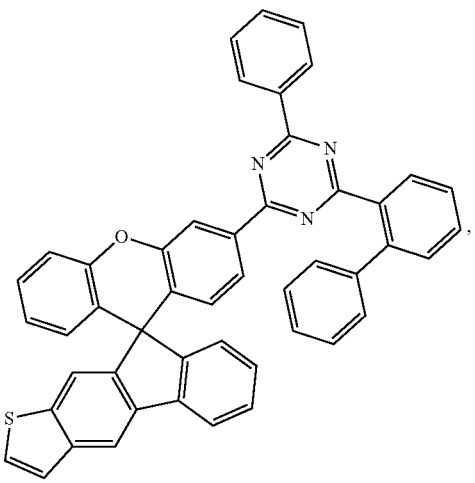
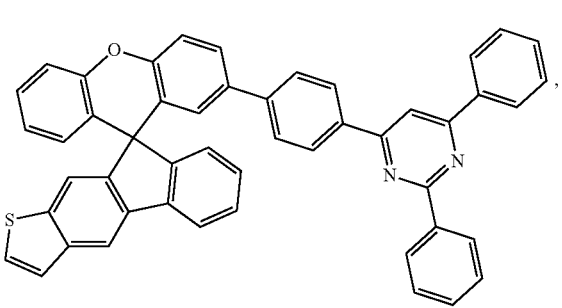

225
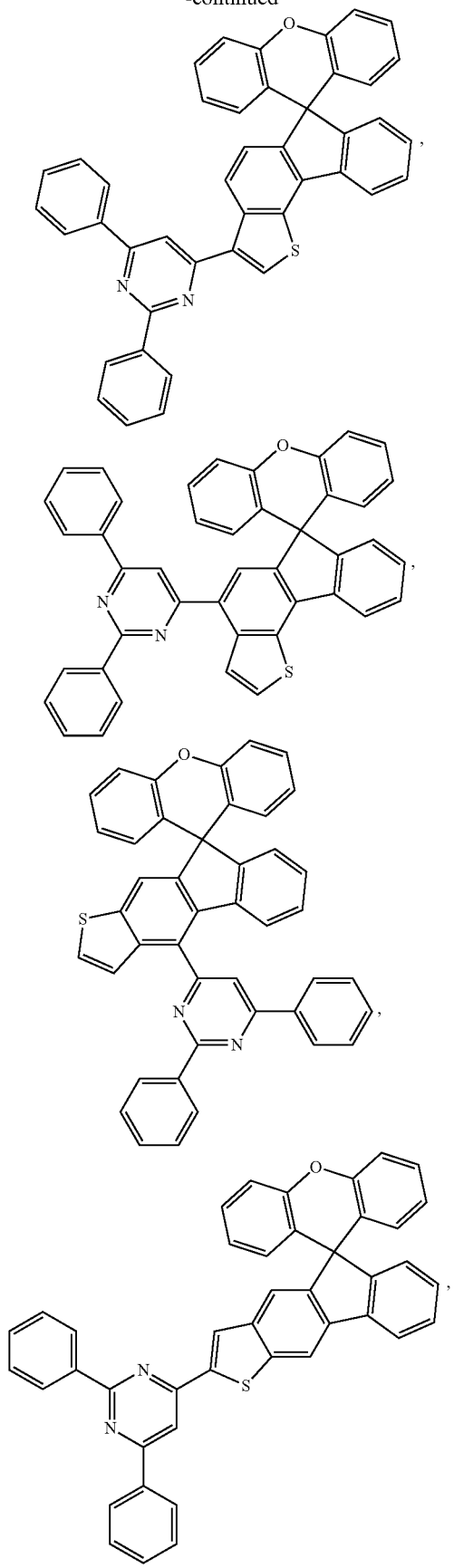
226
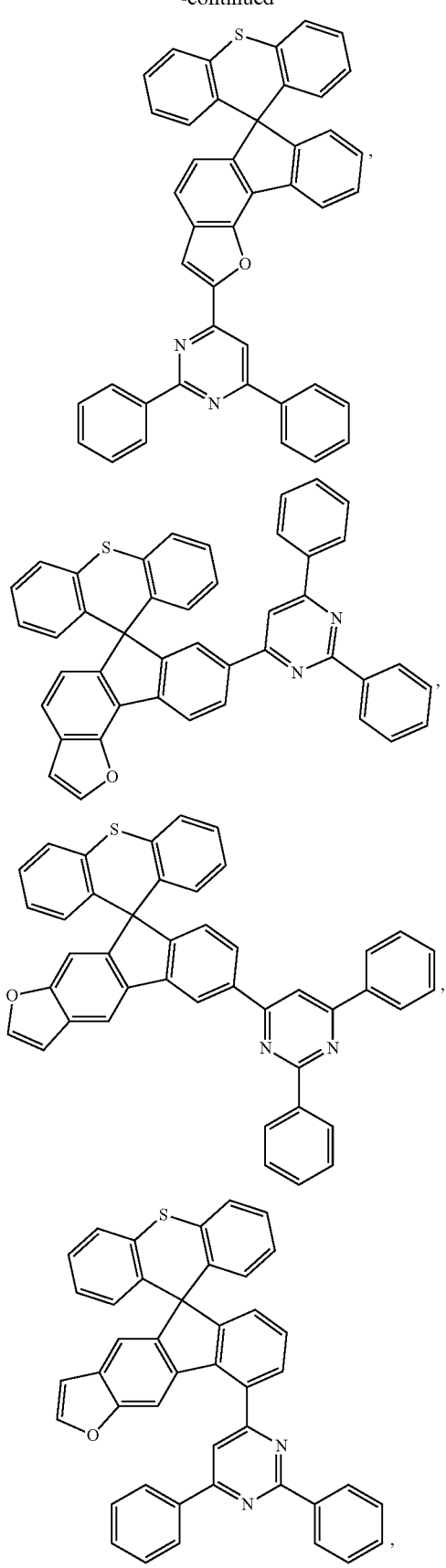

227
-continued
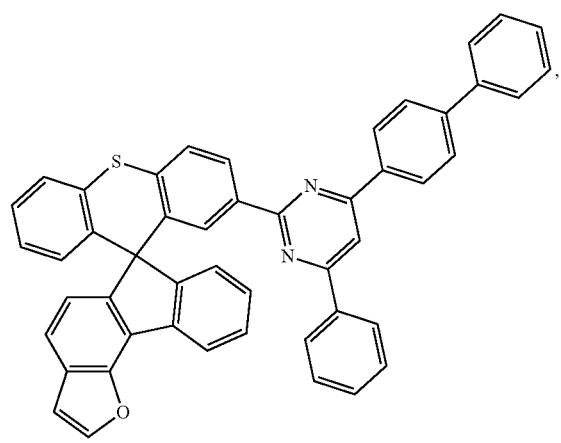
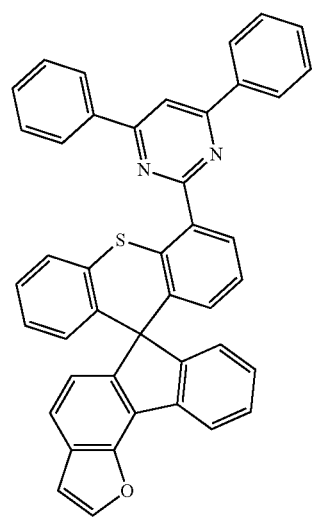
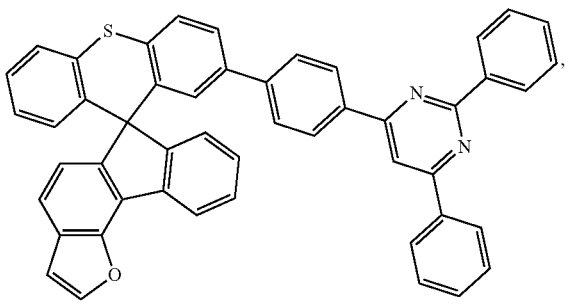
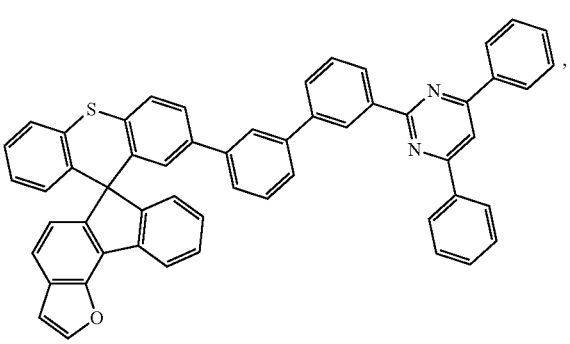
228
-continued
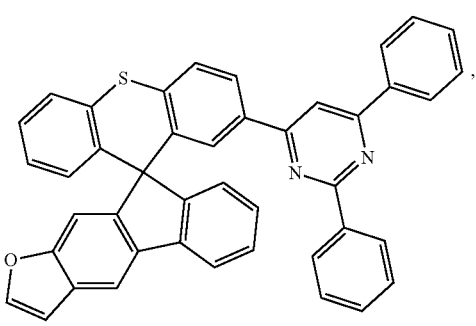
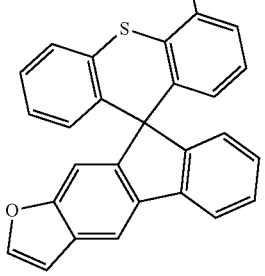
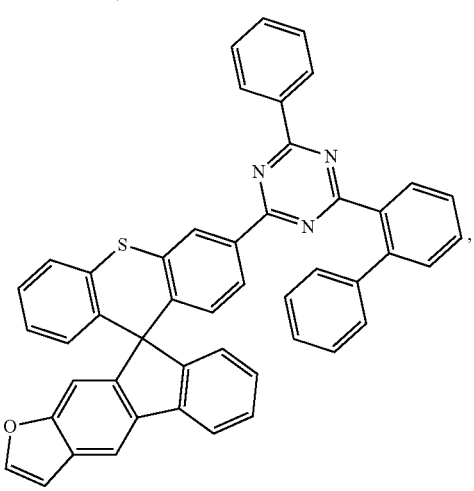
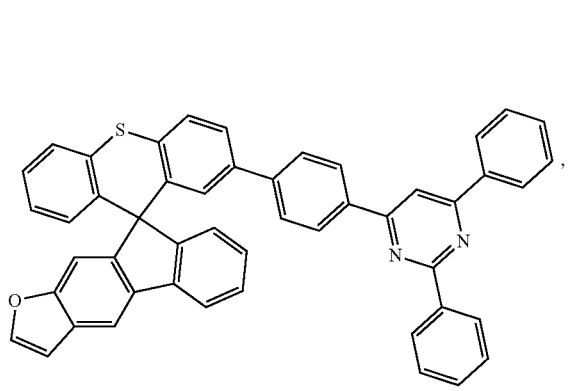

-continued
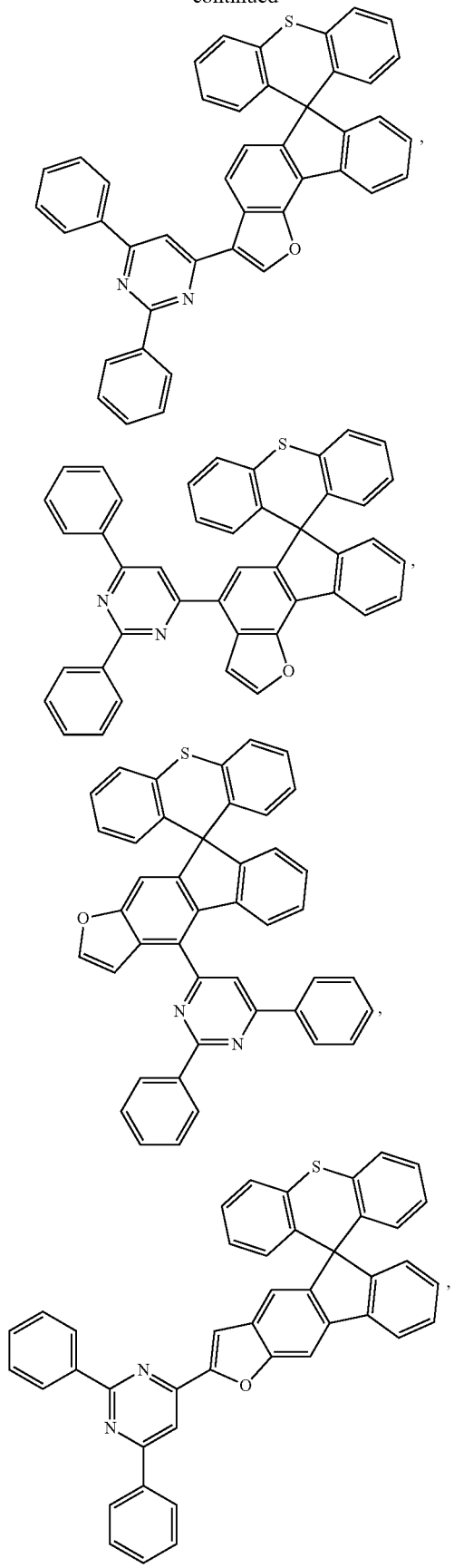
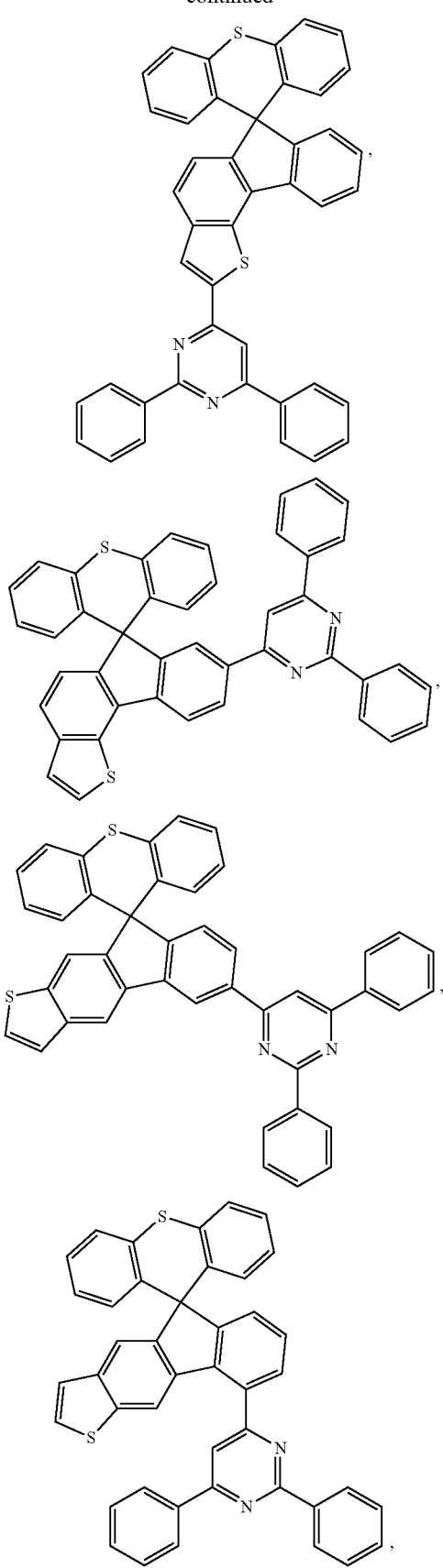

231
-continued
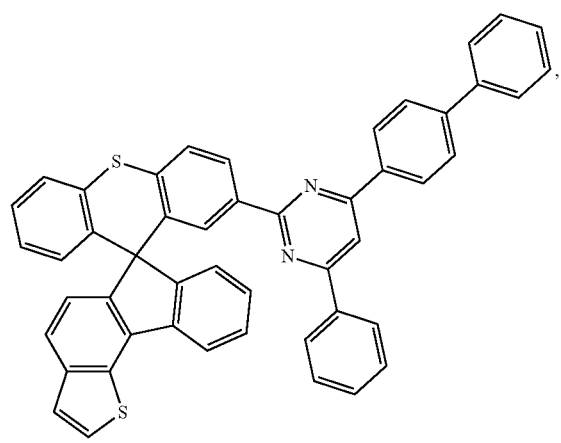
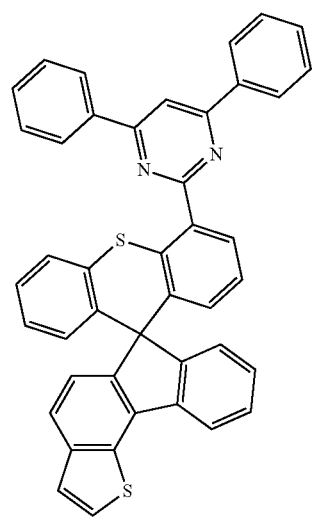
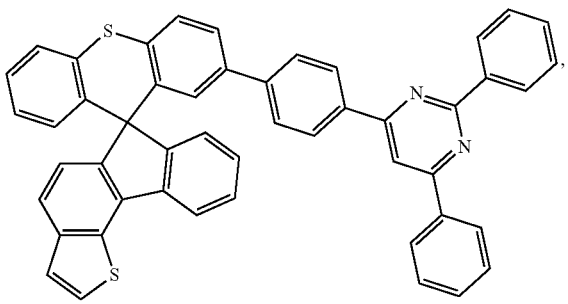
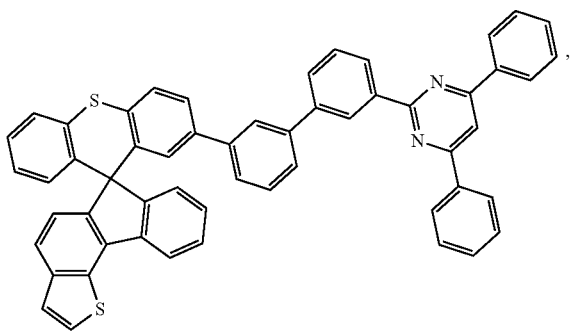
232
-continued
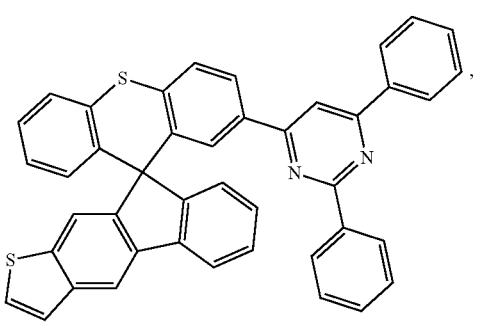
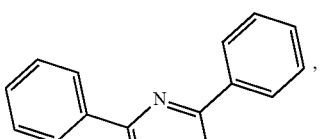
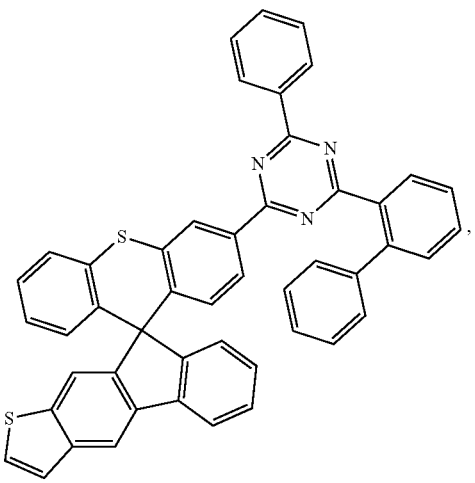
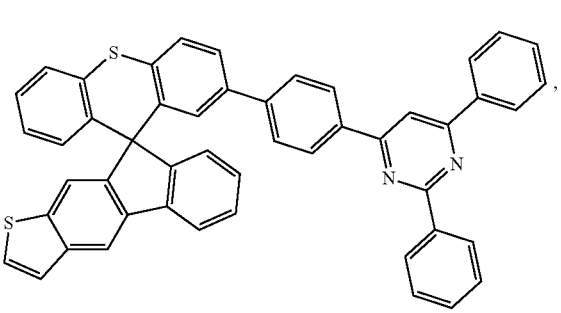

233
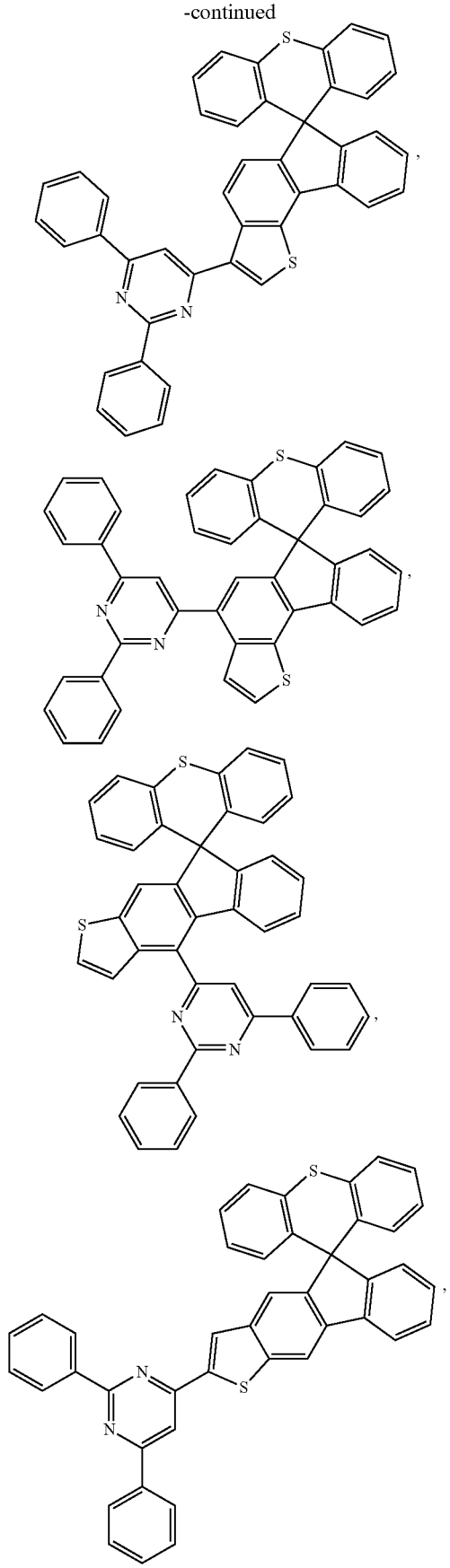
234
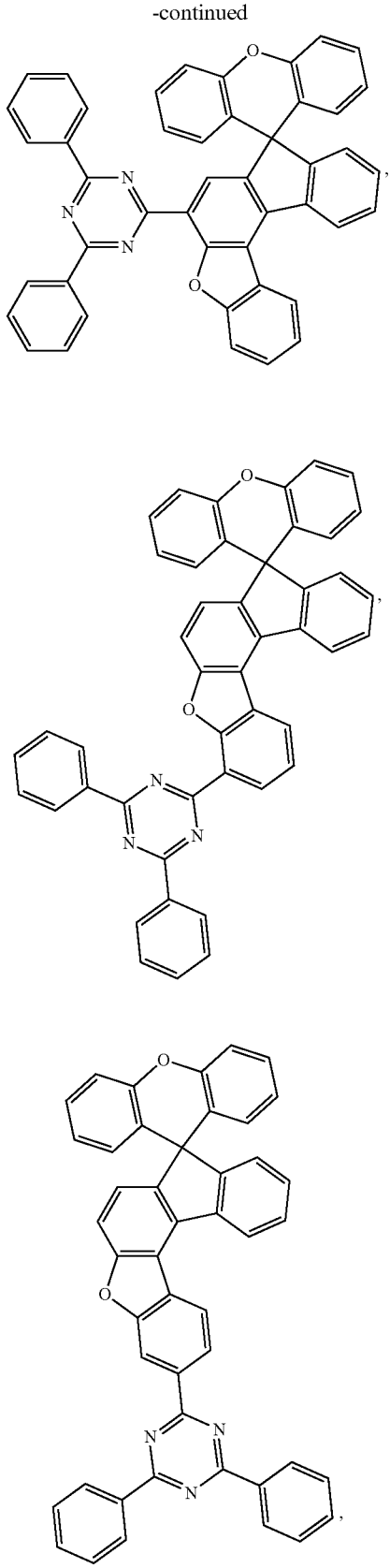

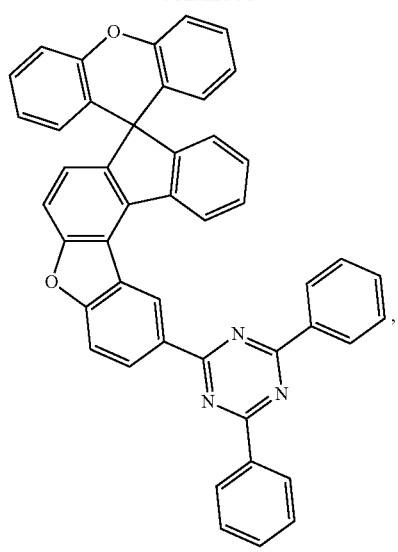
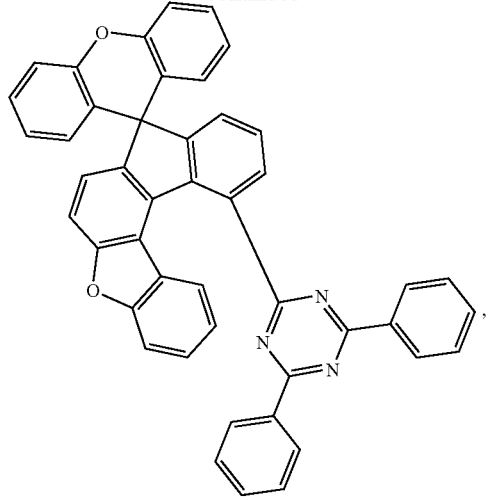
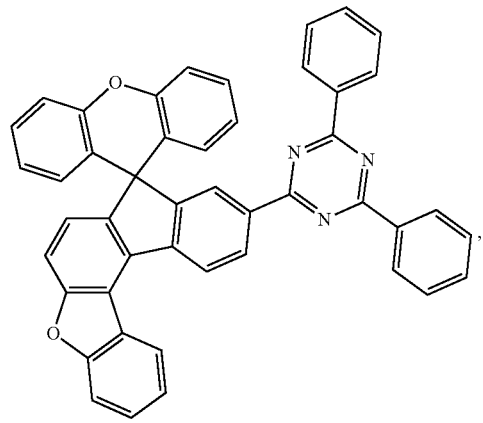
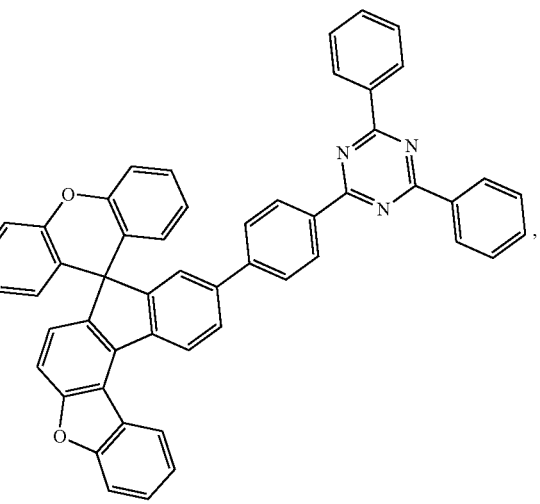
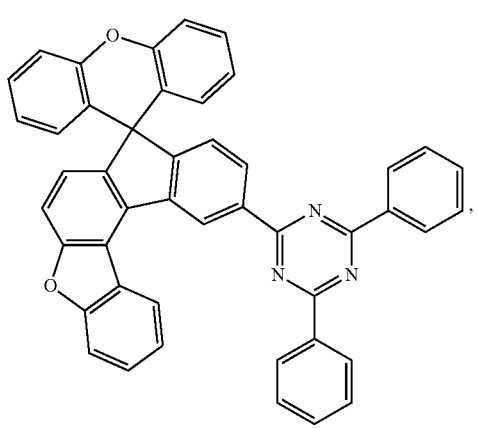
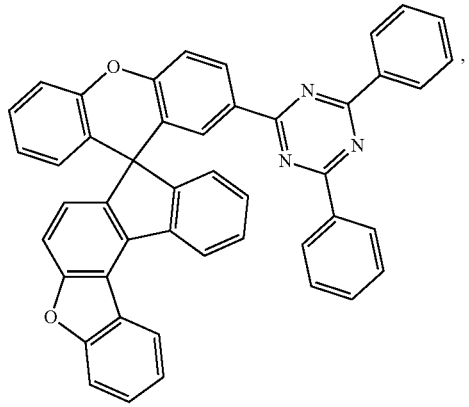

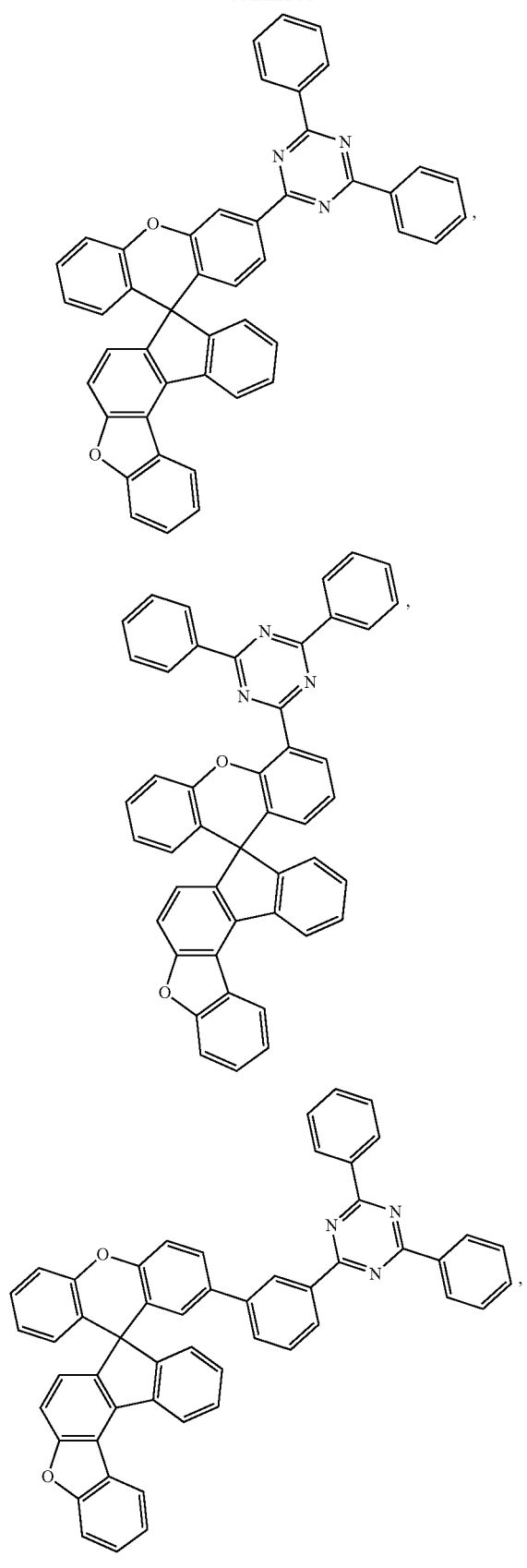
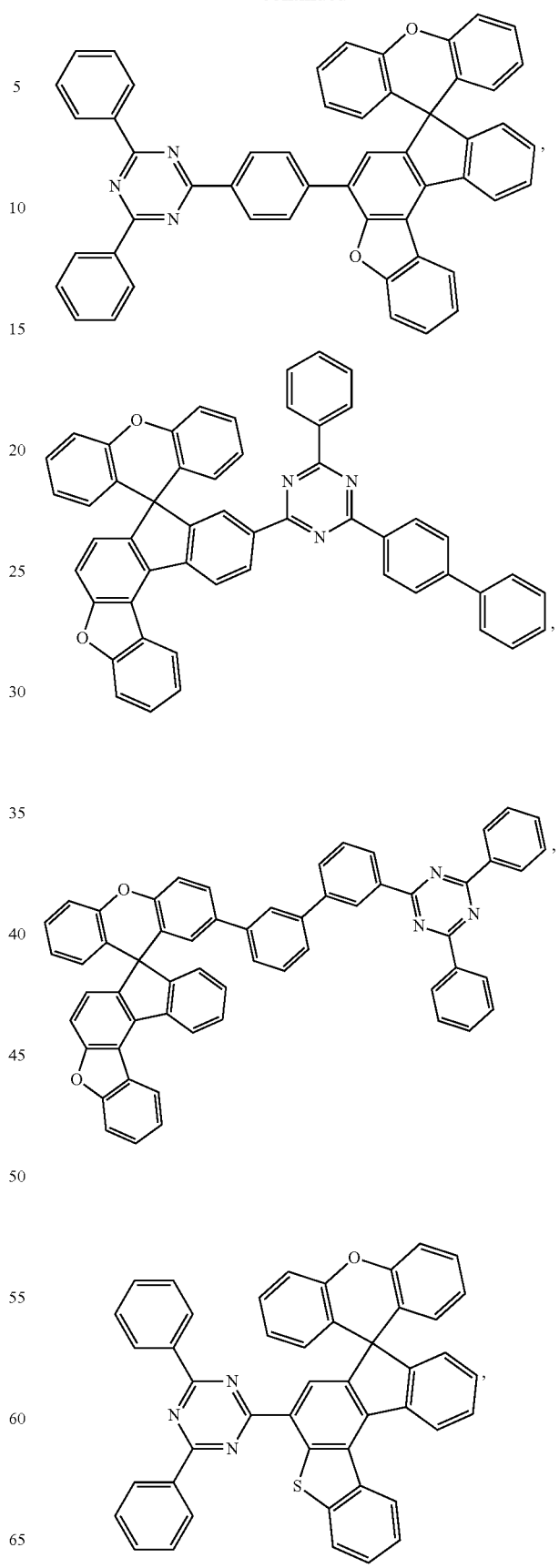

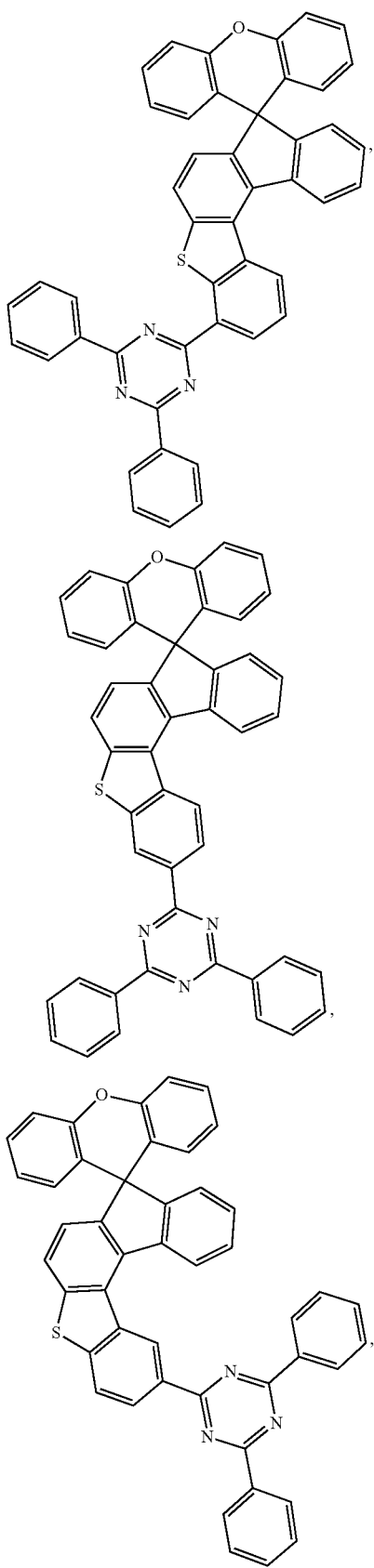
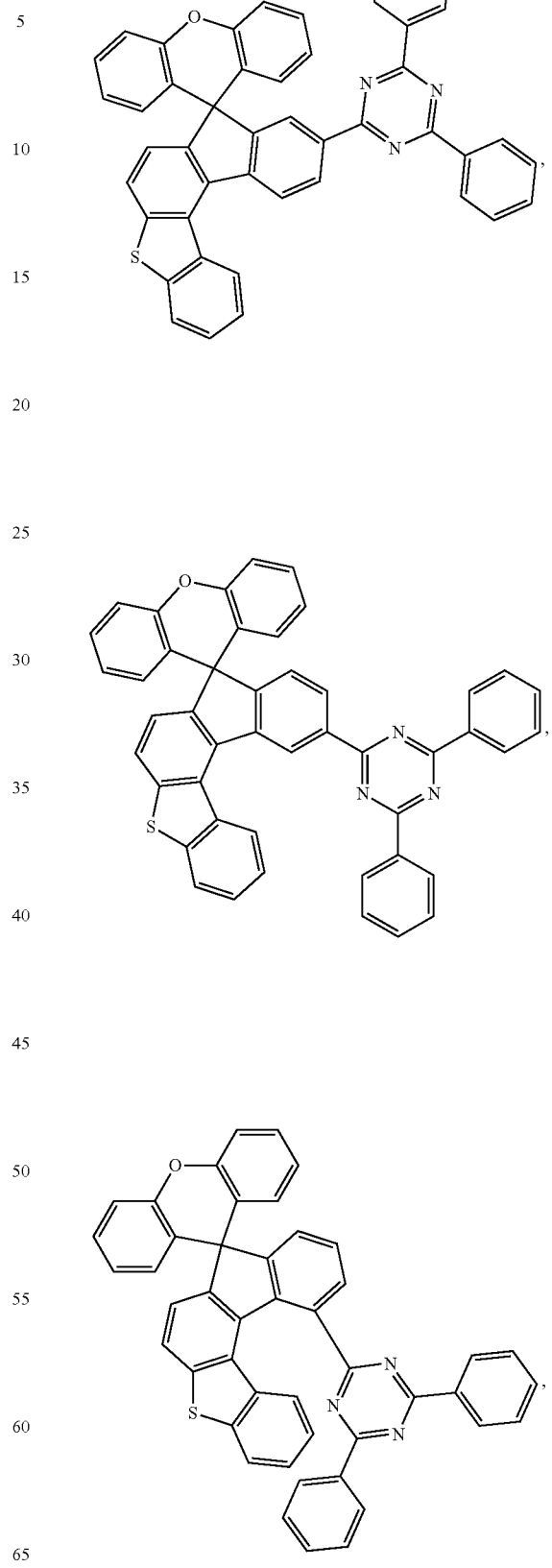

241
-continued
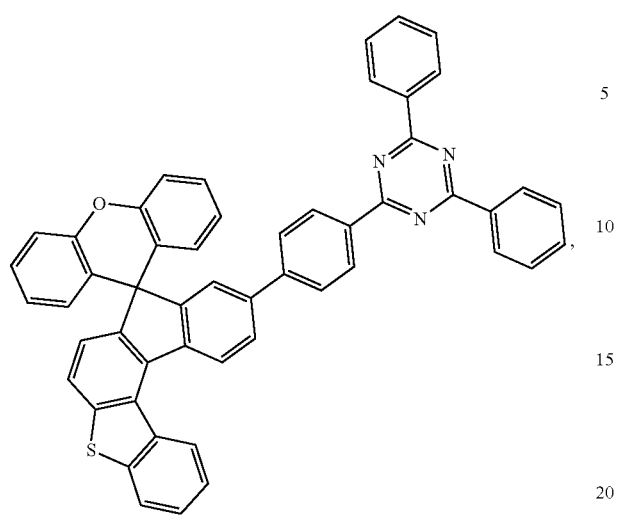
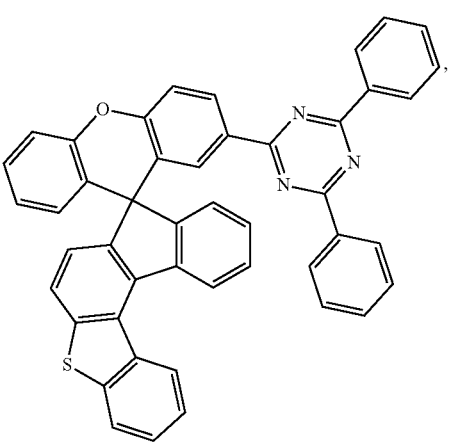
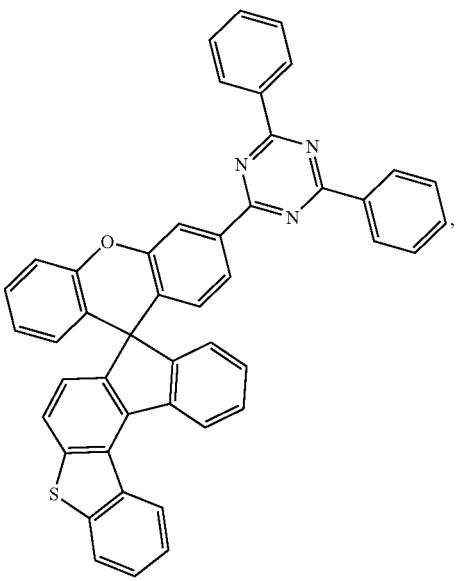
242
-continued
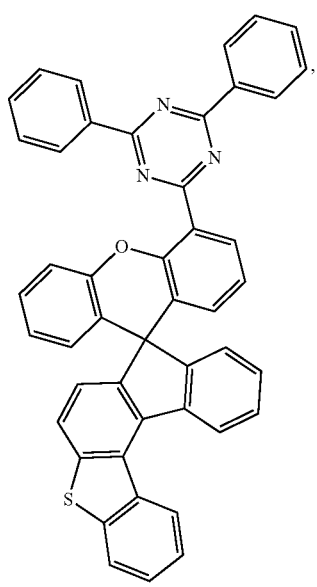
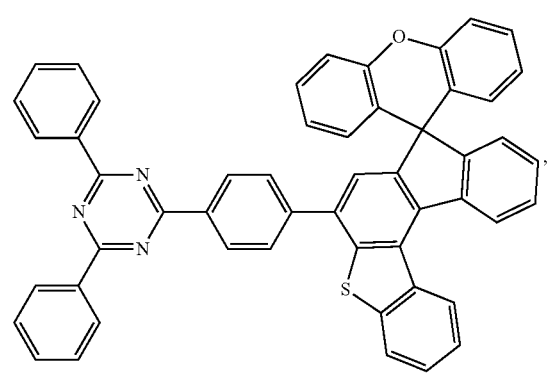

243
-continued
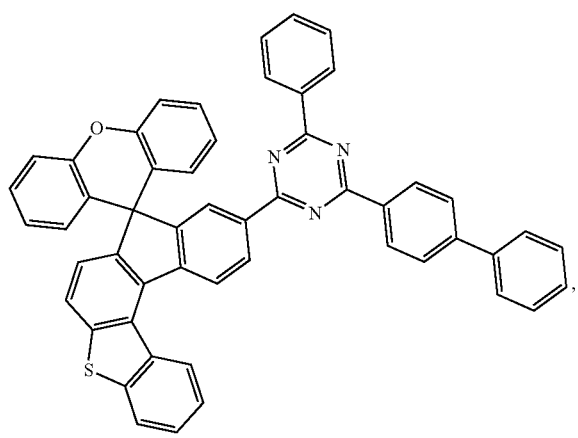
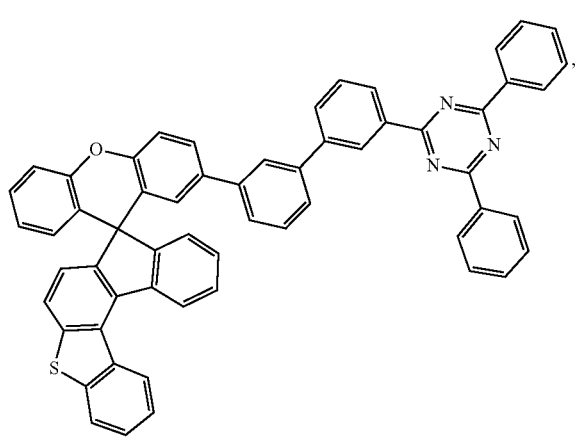
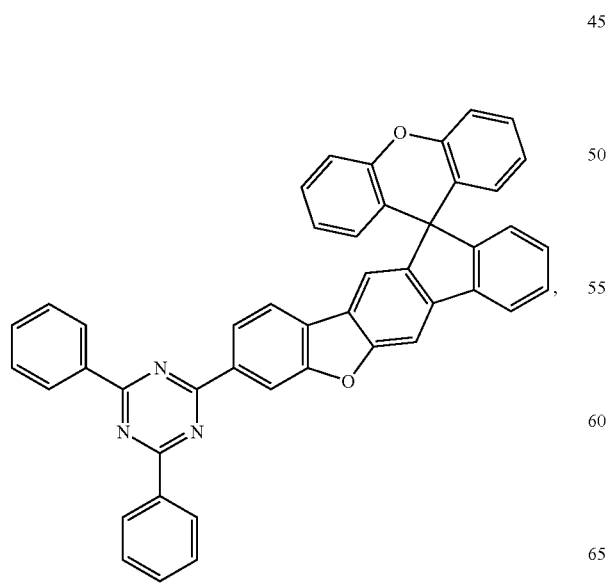
244
-continued
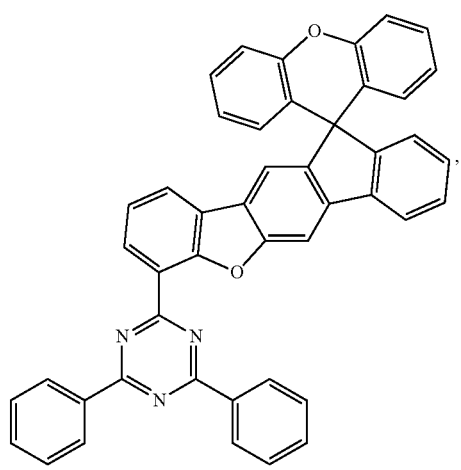
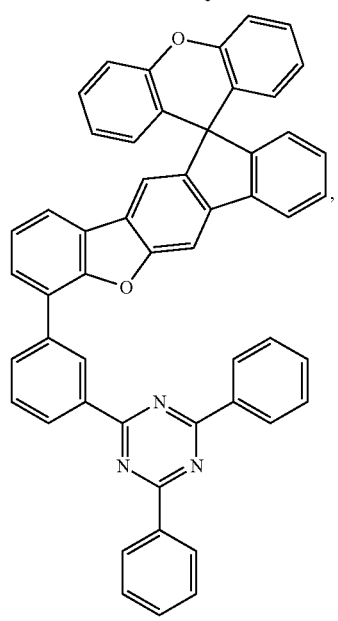
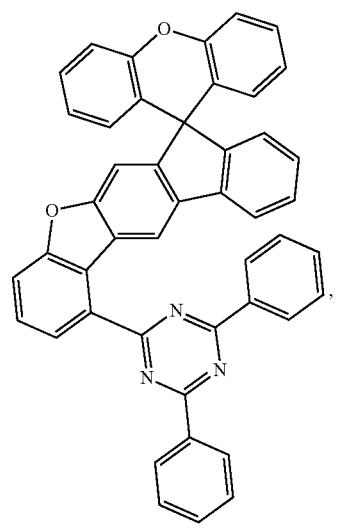

245
-continued
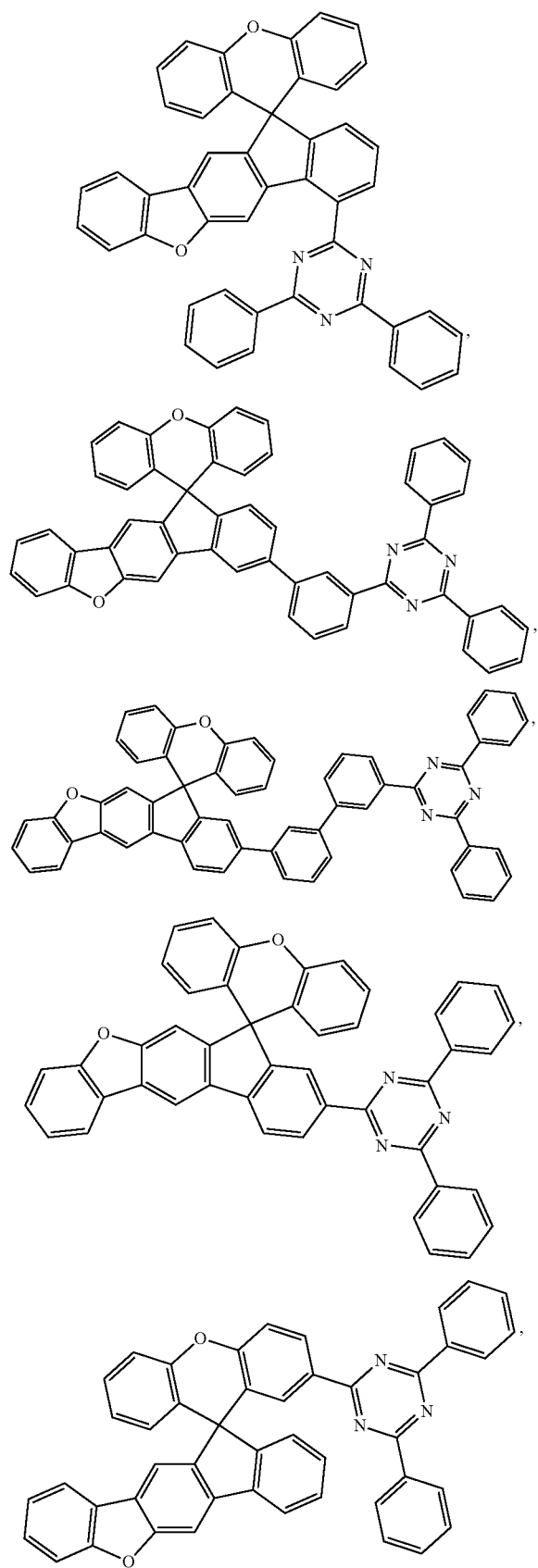
246
-continued
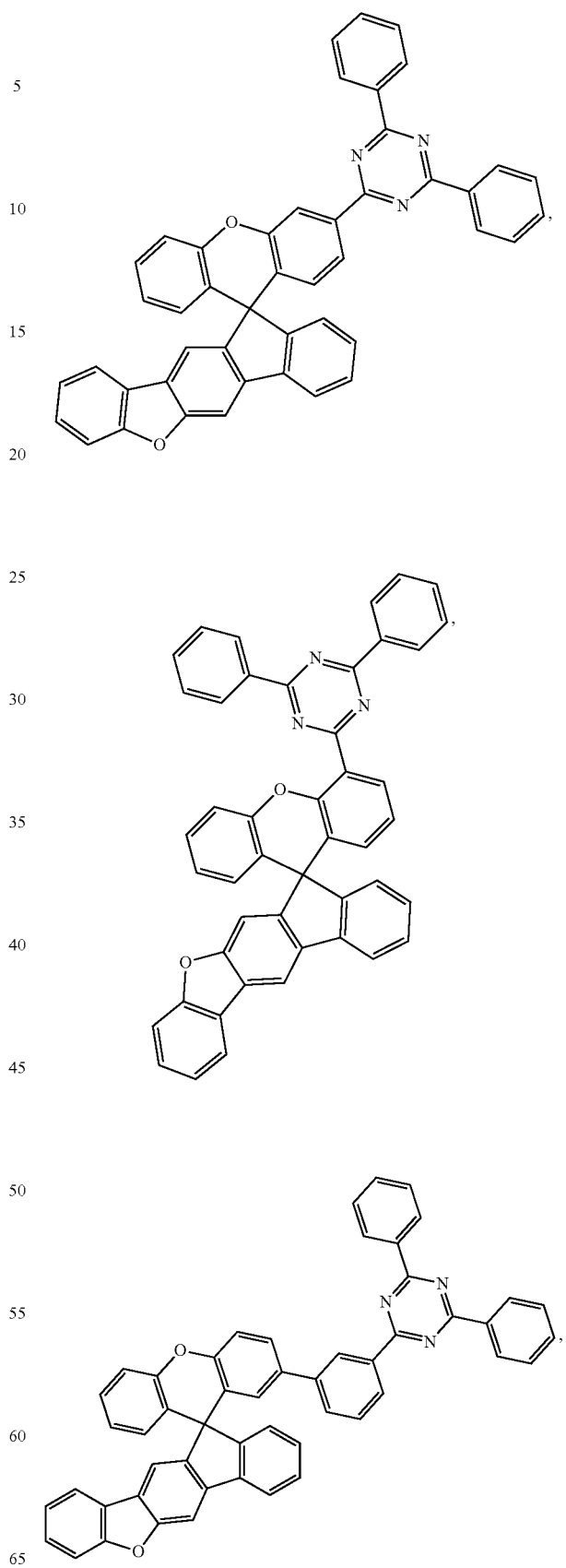

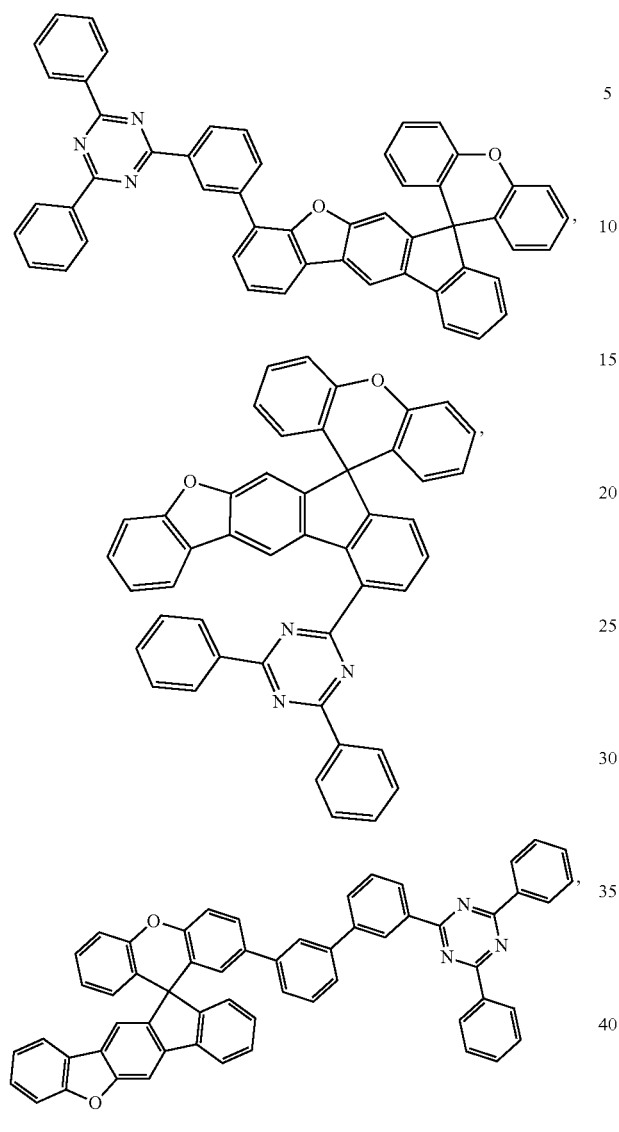
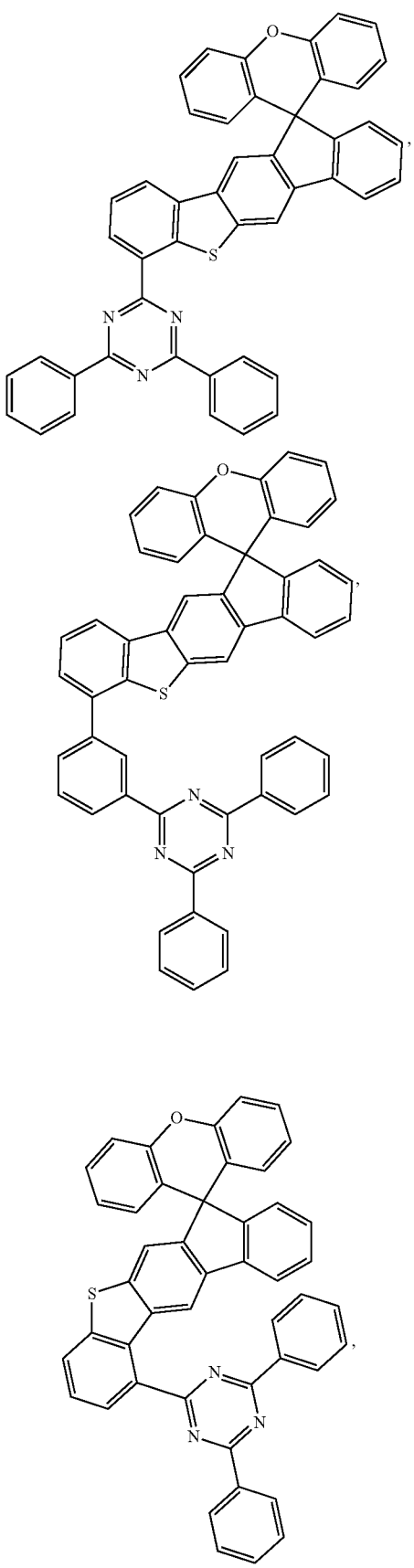

249
-continued
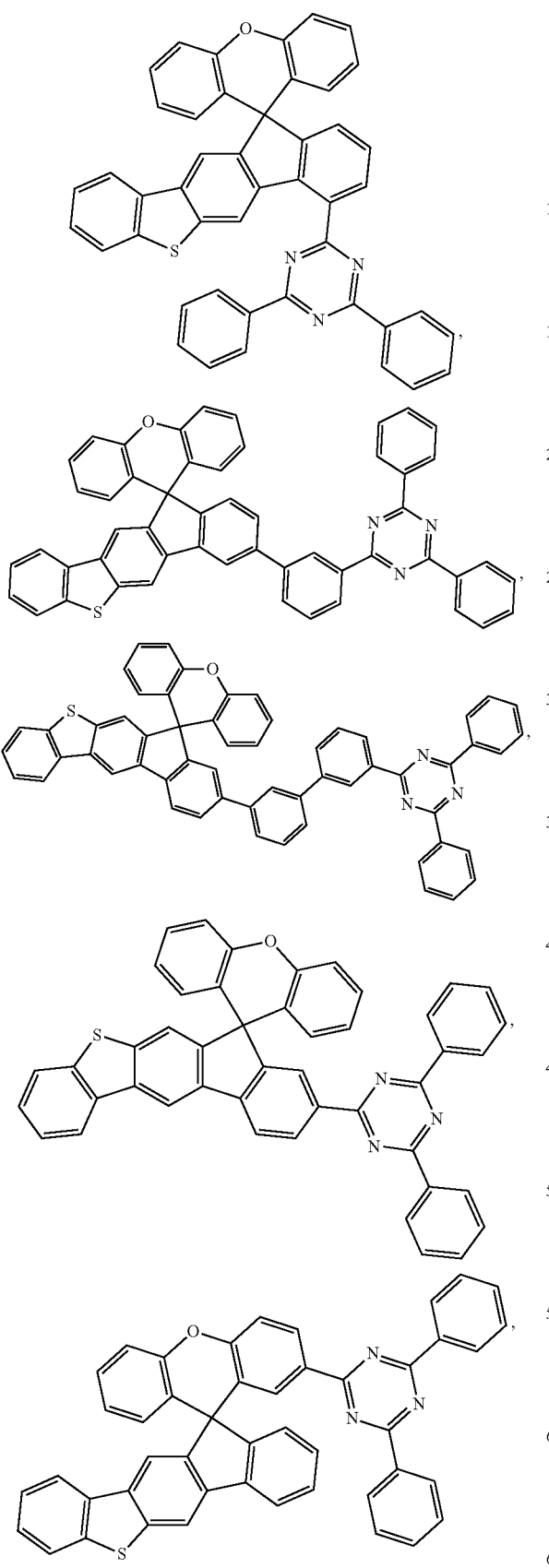
250
-continued
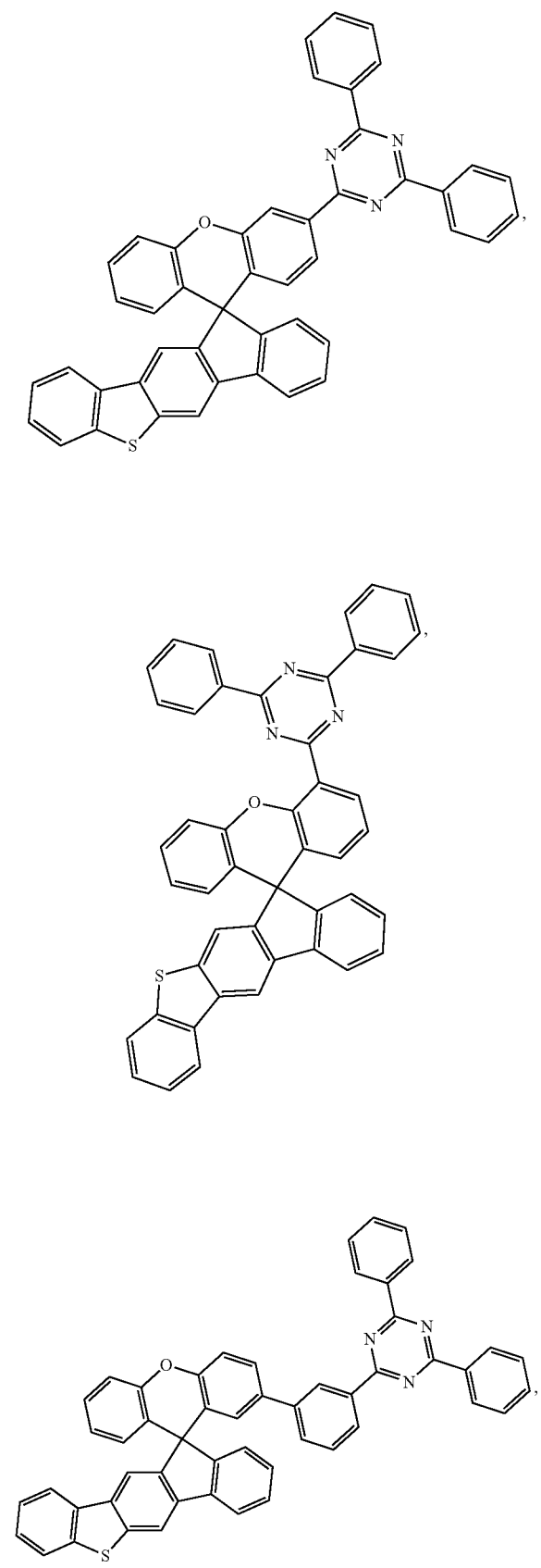

251
-continued
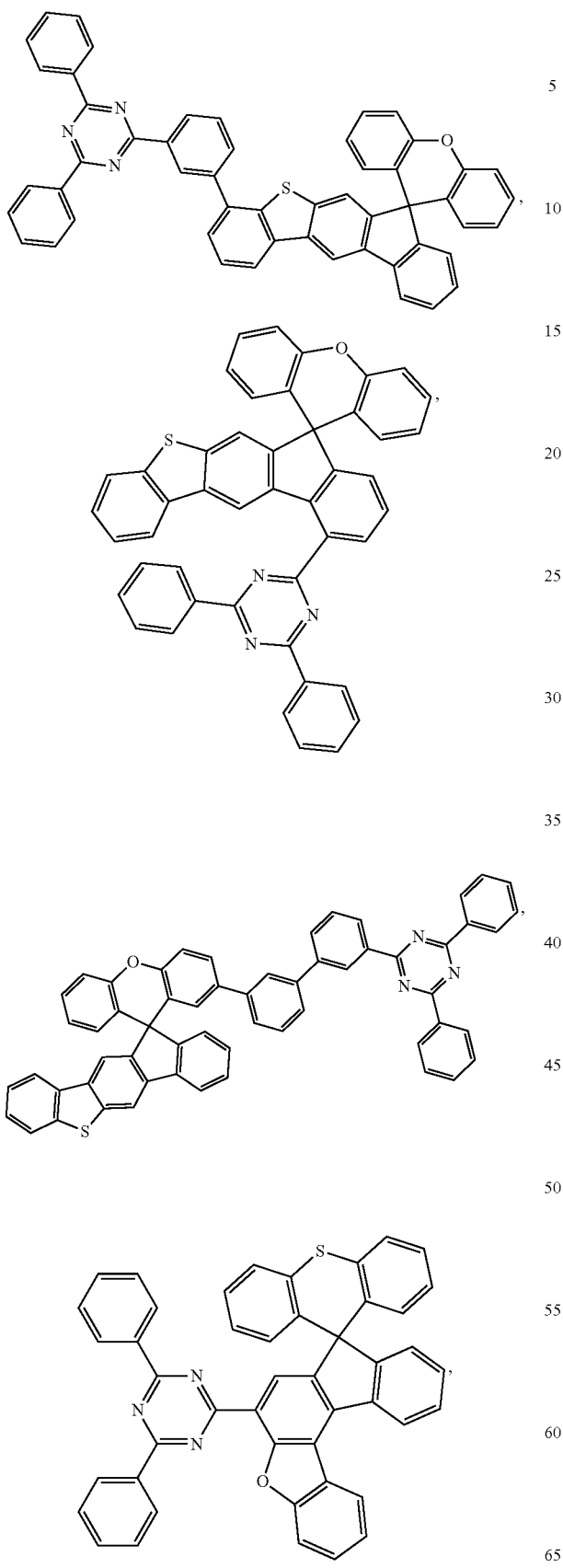
252
-continued
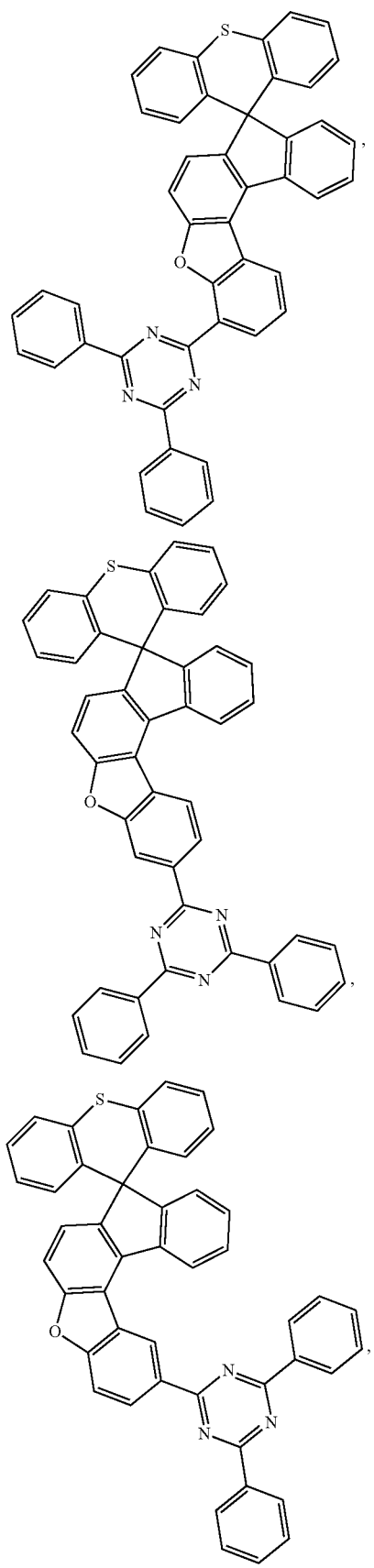

253
-continued
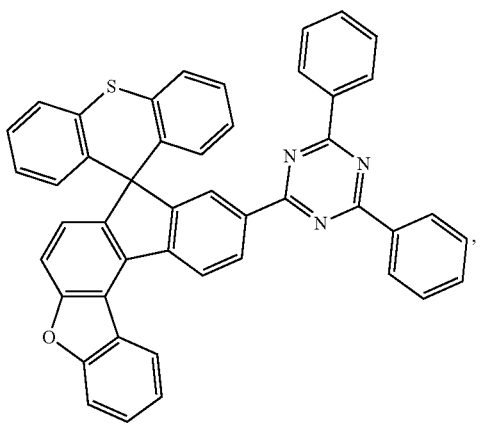
254
-continued
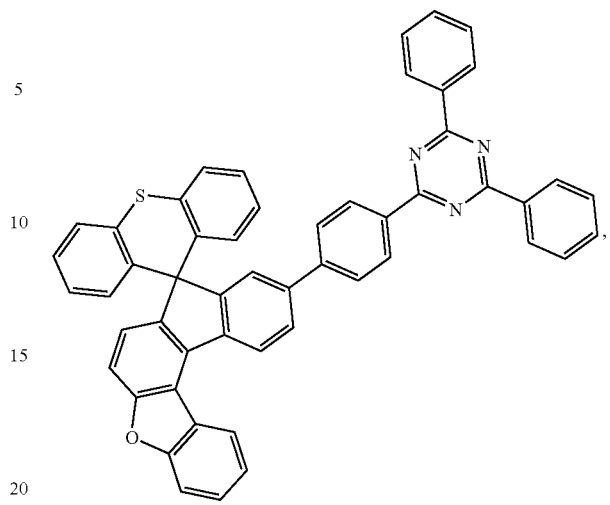
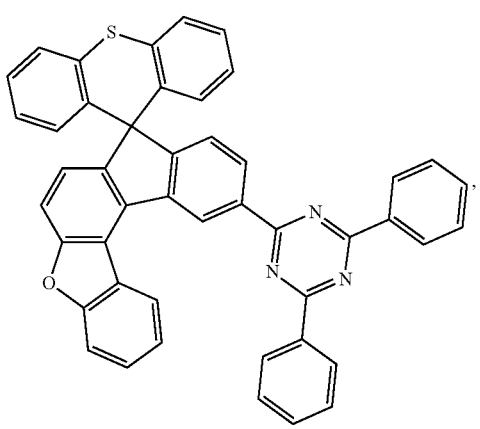
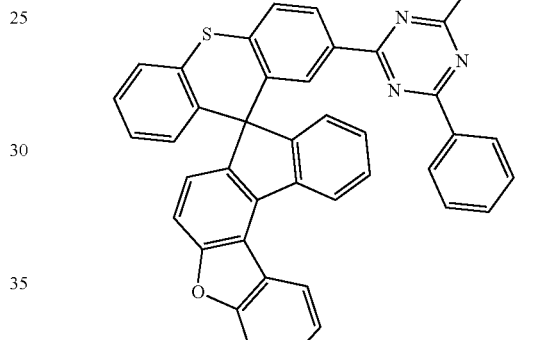
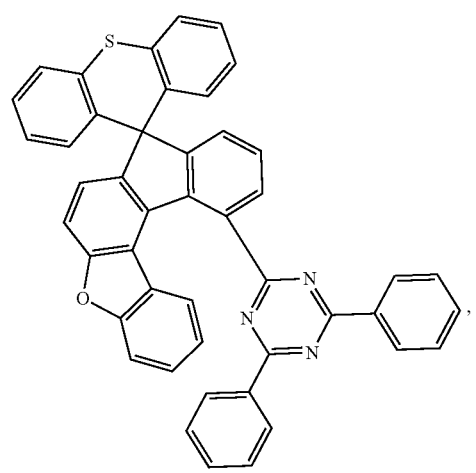
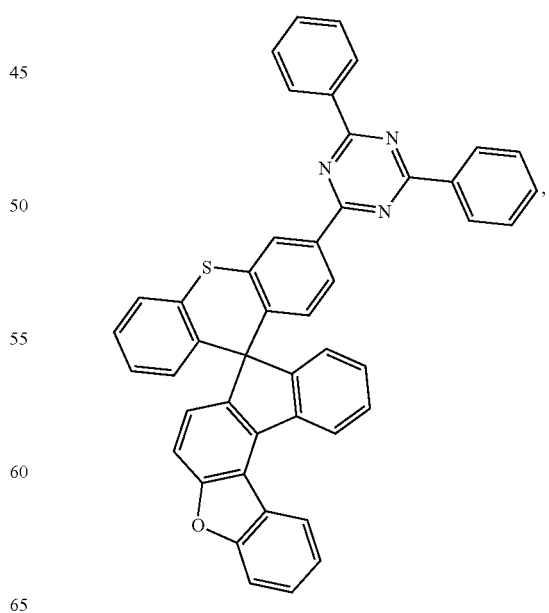

255
-continued
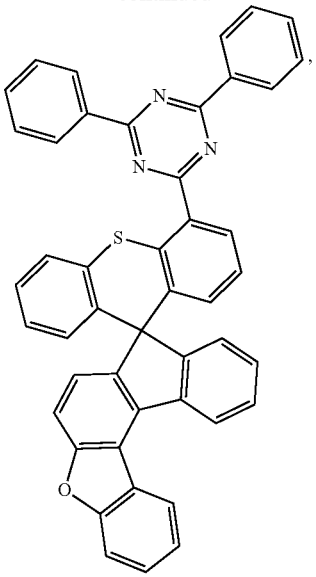
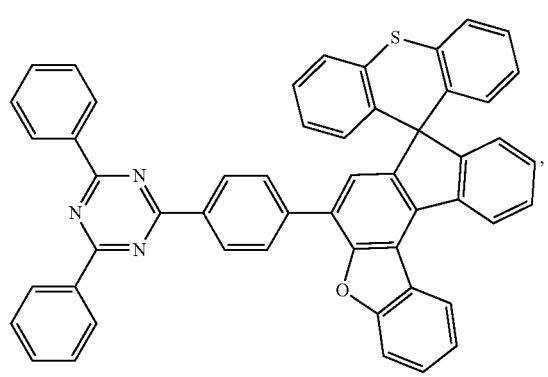
256
-continued
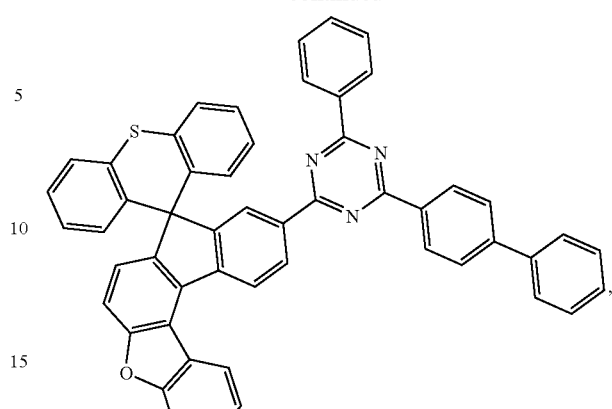
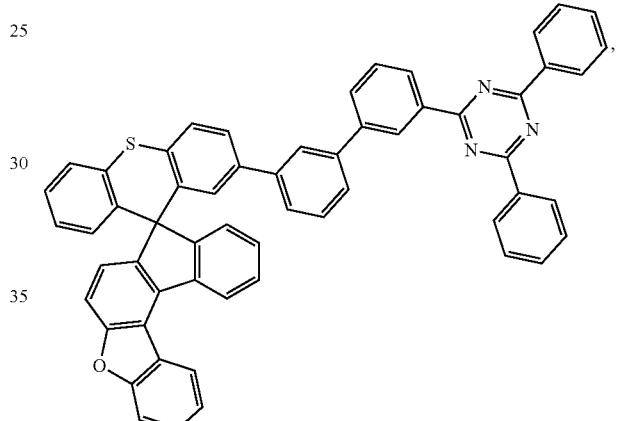
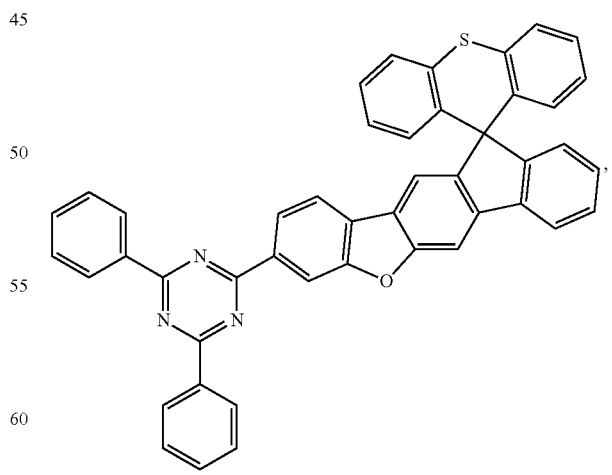

257
-continued
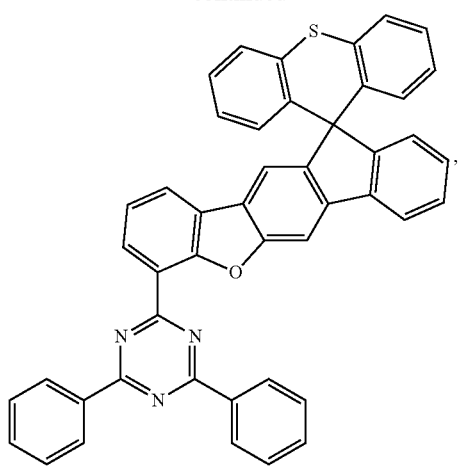
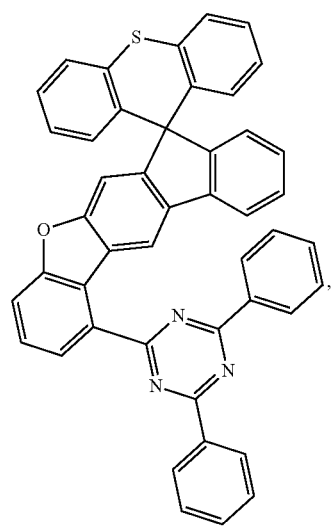
258
-continued
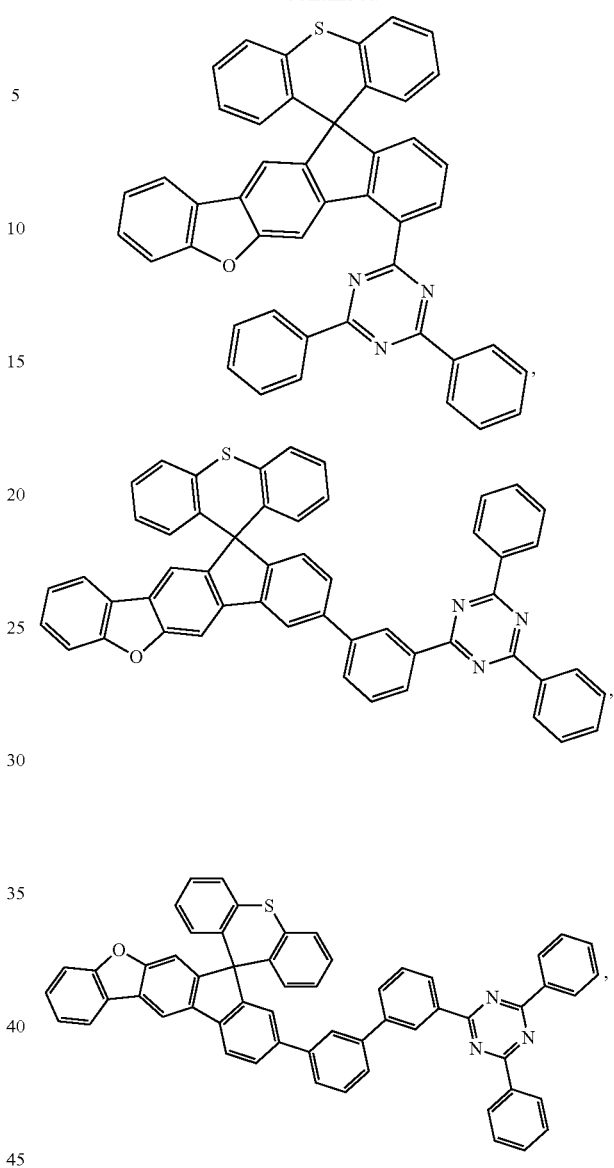

259
-continued
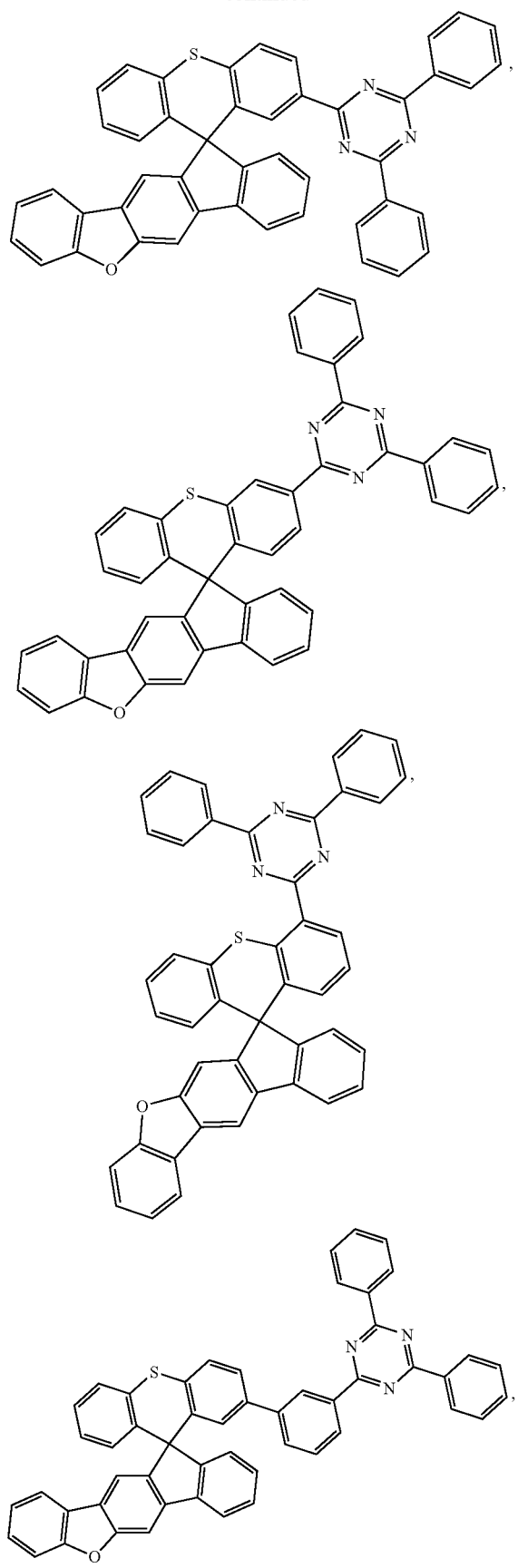
260
-continued
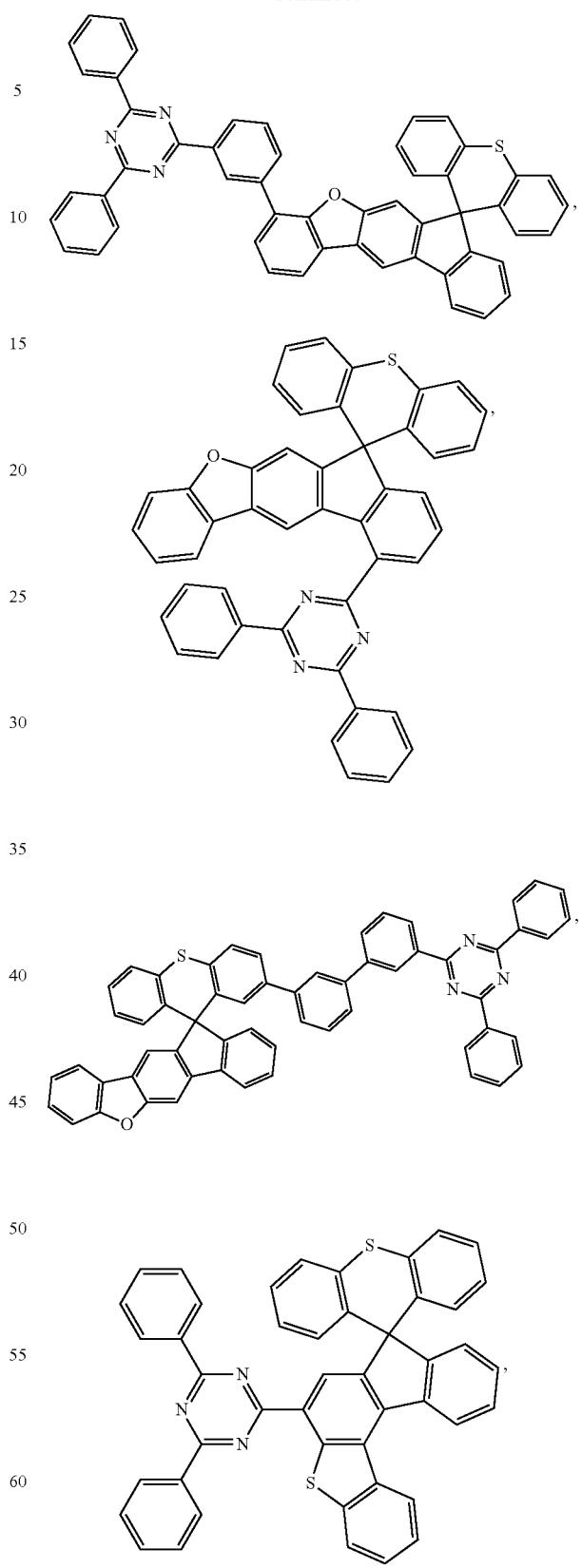

261
-continued
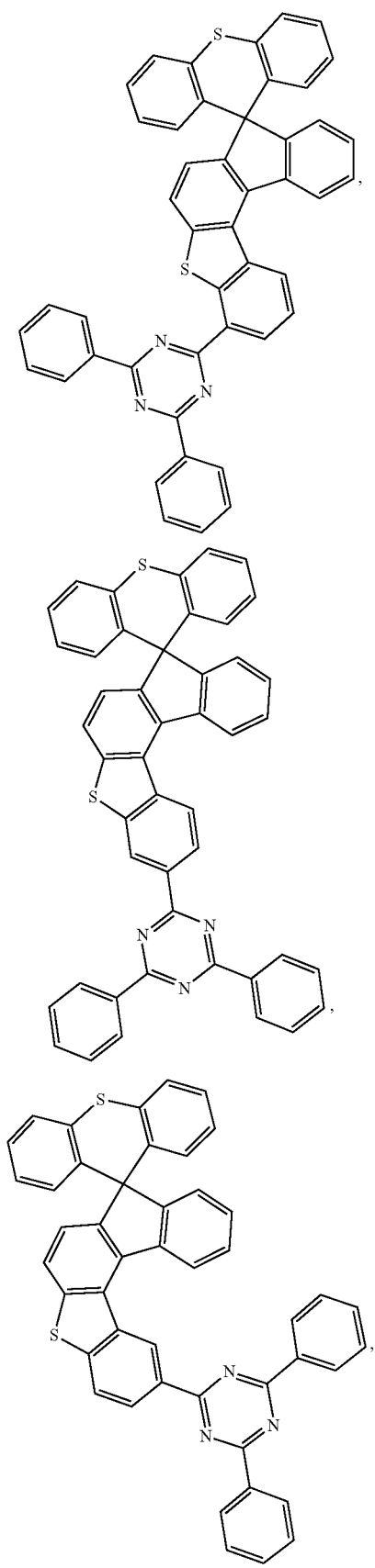
262
-continued
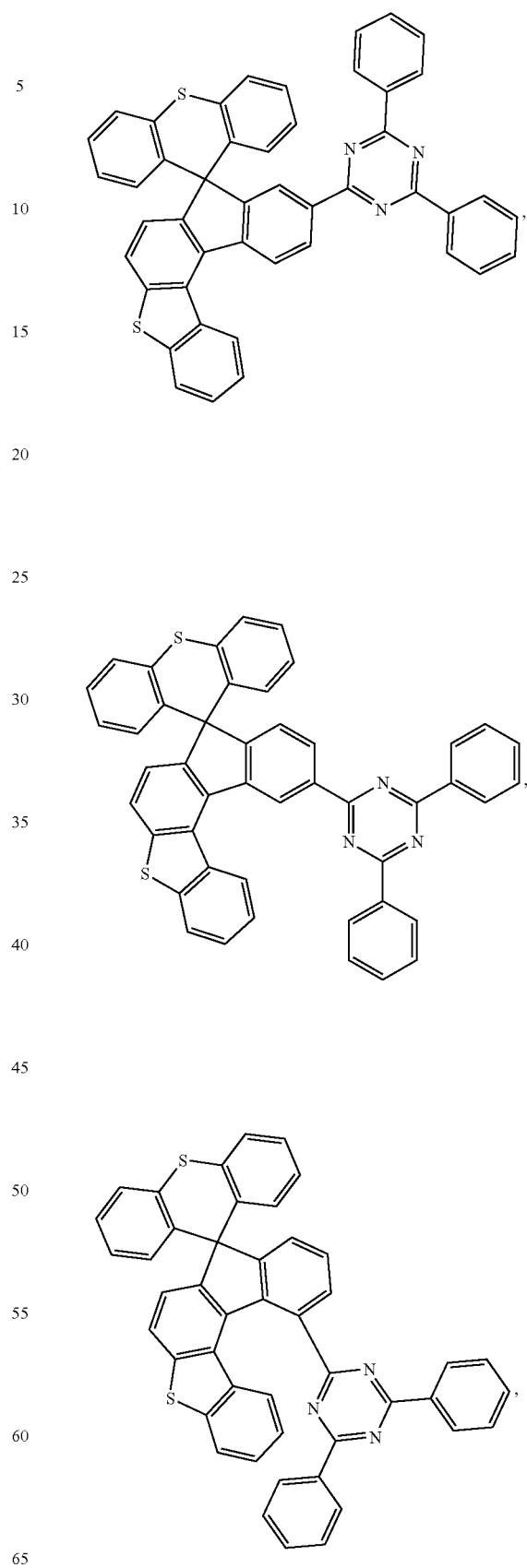

263
-continued
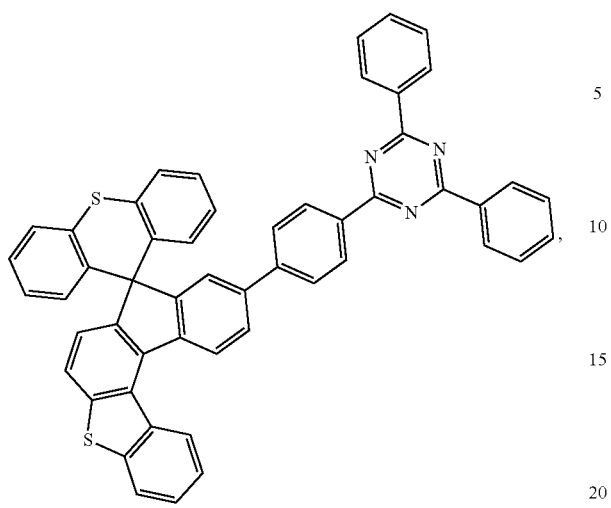
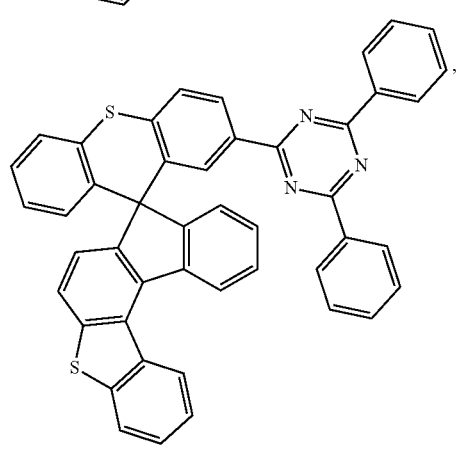
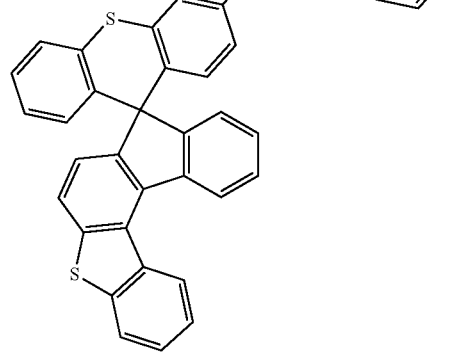
264
-continued
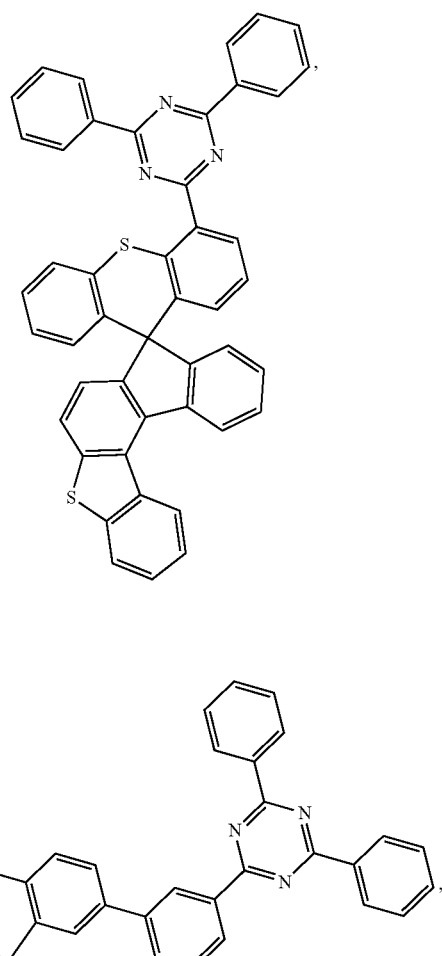
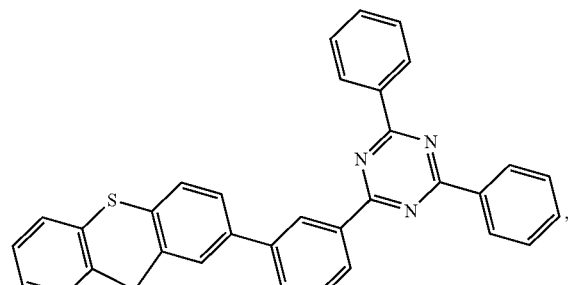
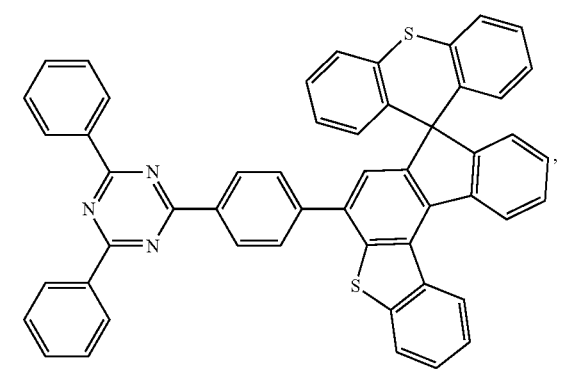

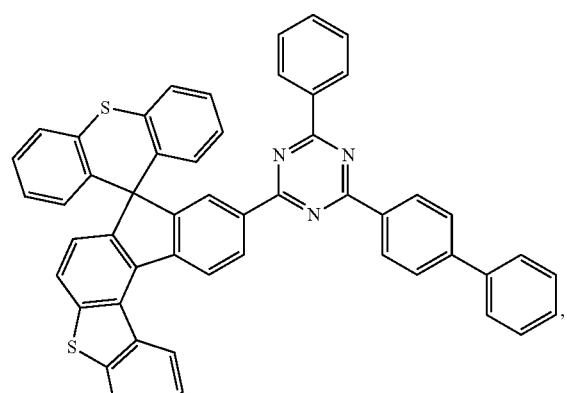
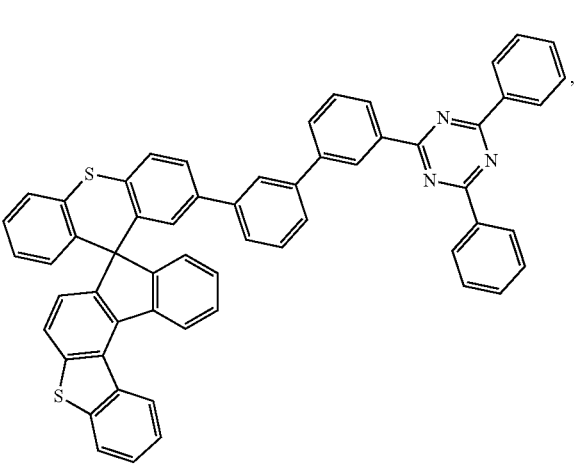
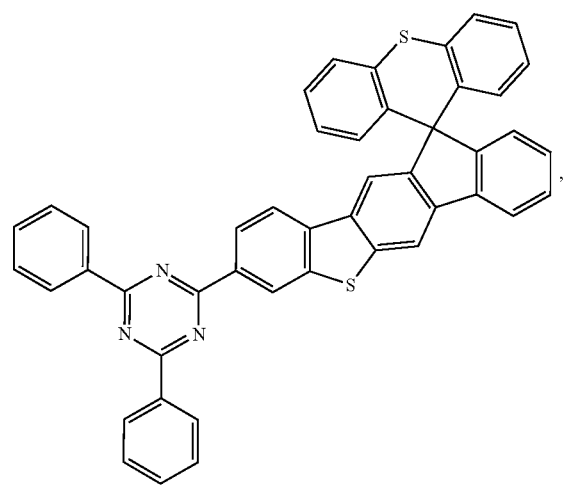
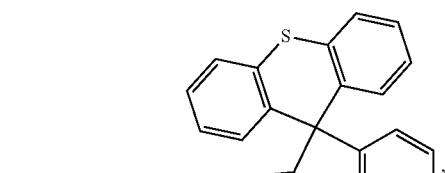
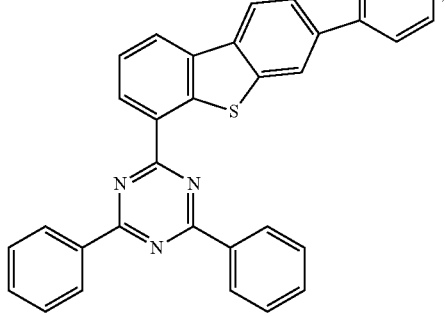
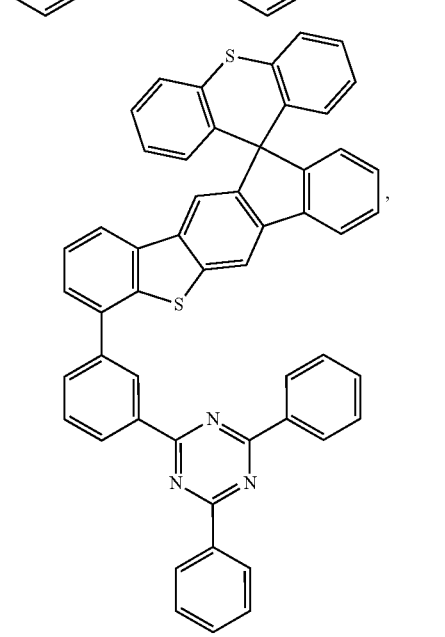
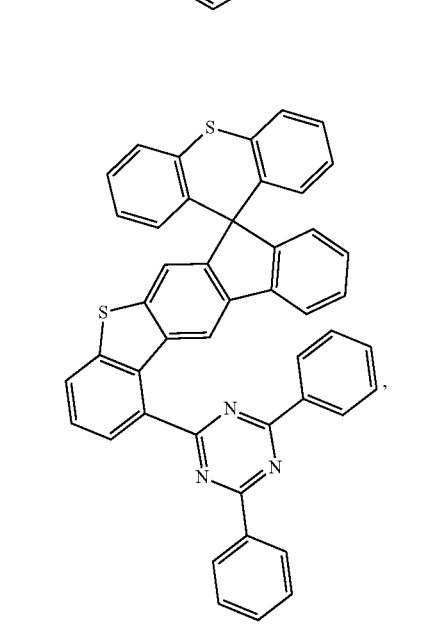

267
-continued
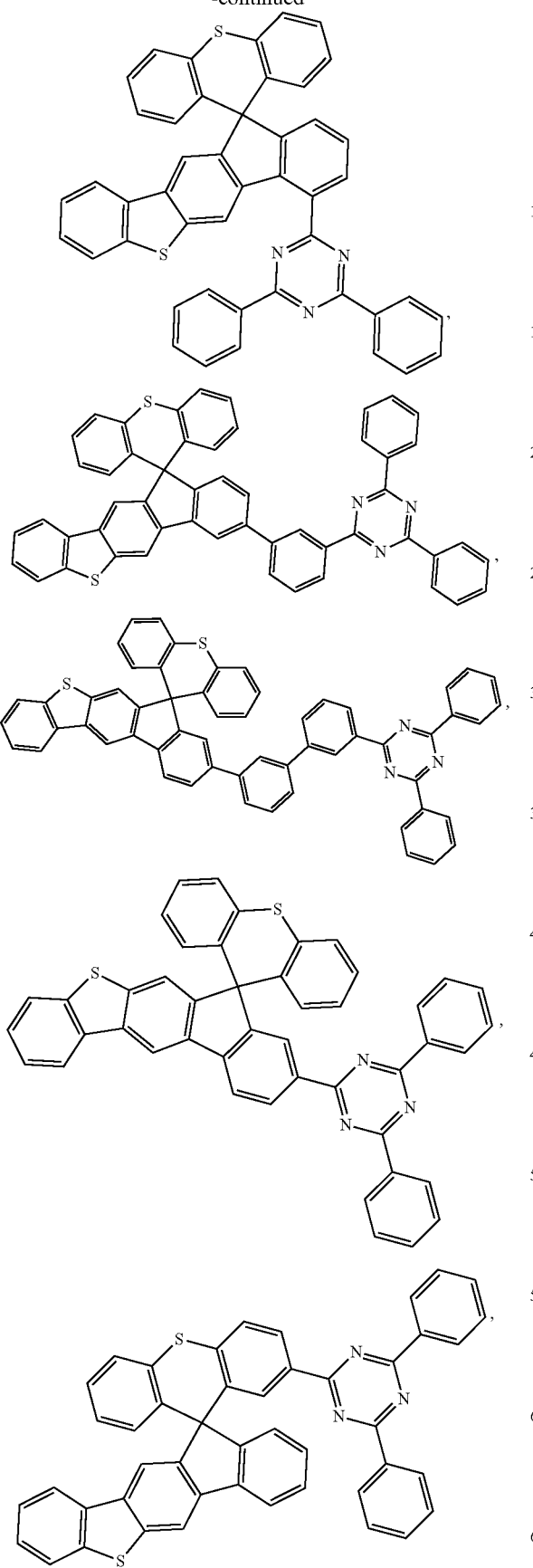
268
-continued
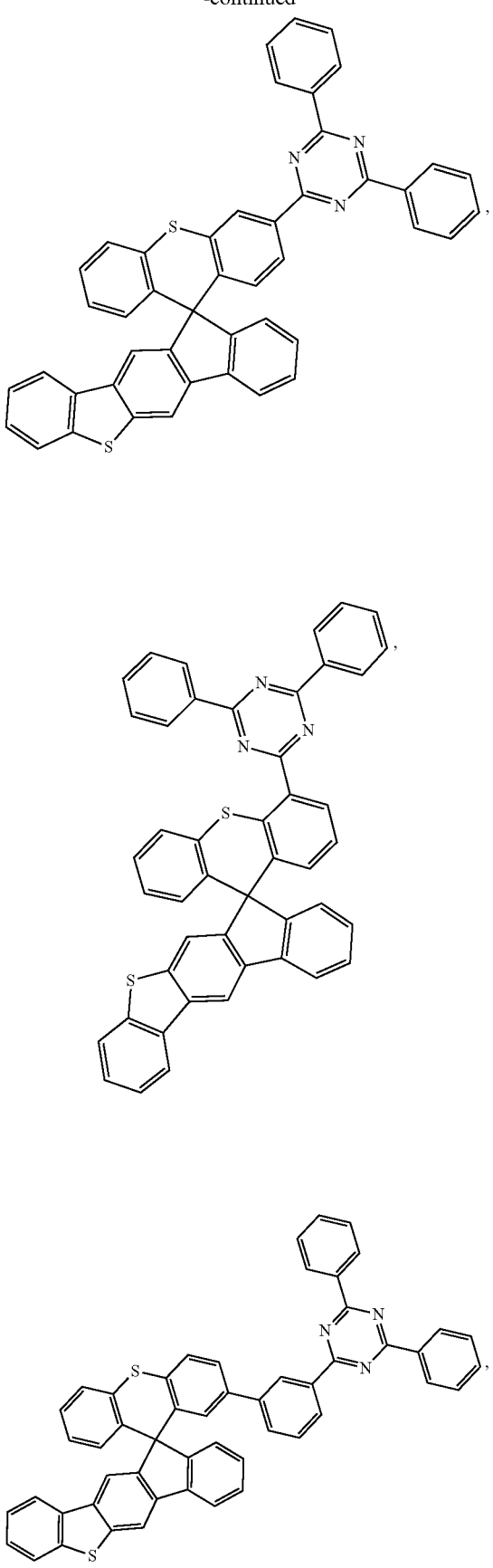

269
-continued
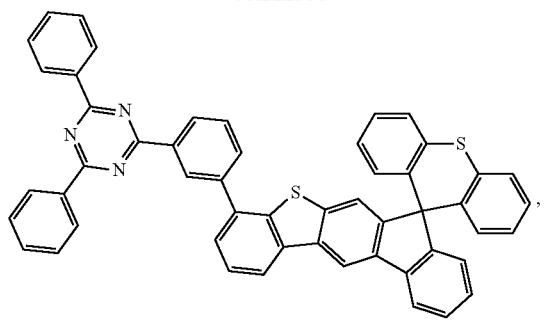
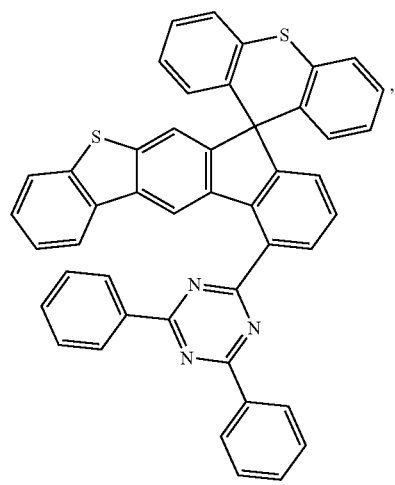
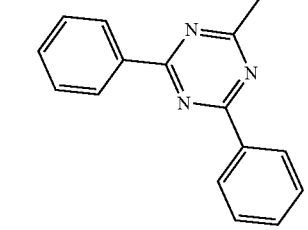
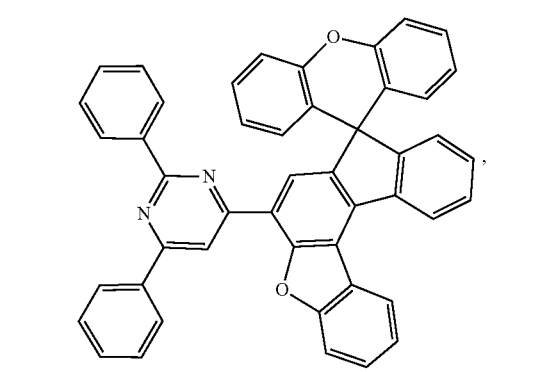
270
-continued
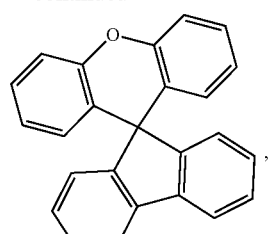
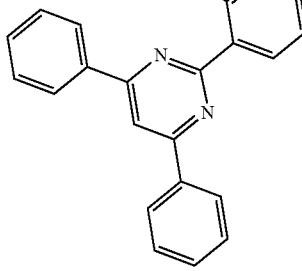
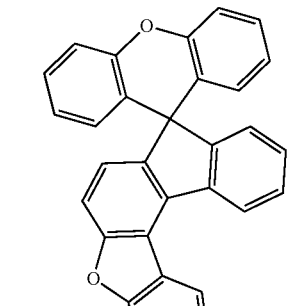
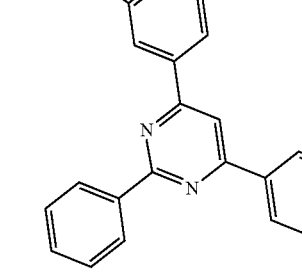
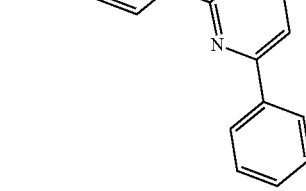

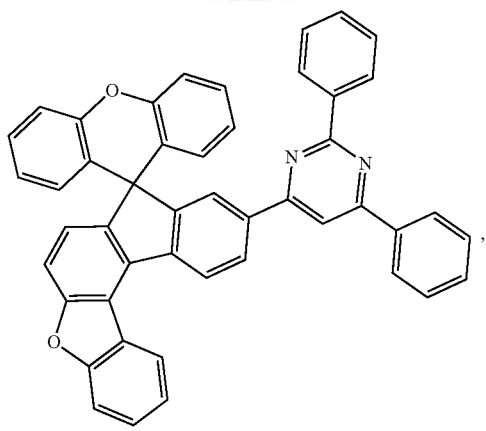
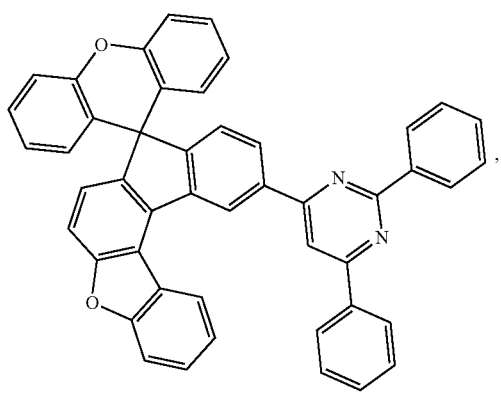
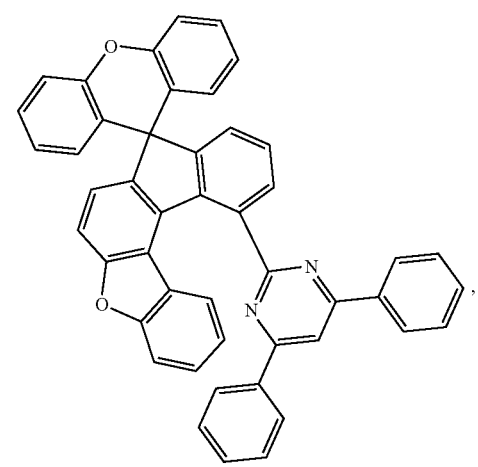
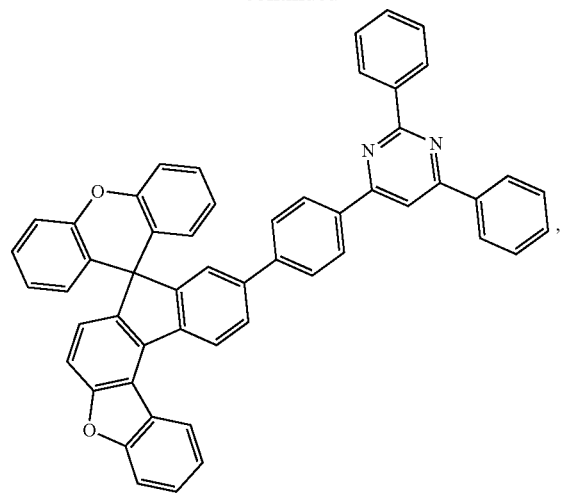
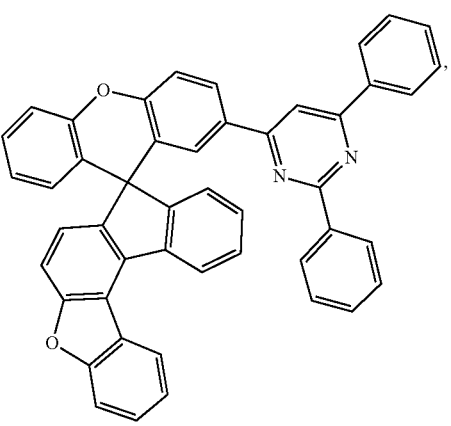
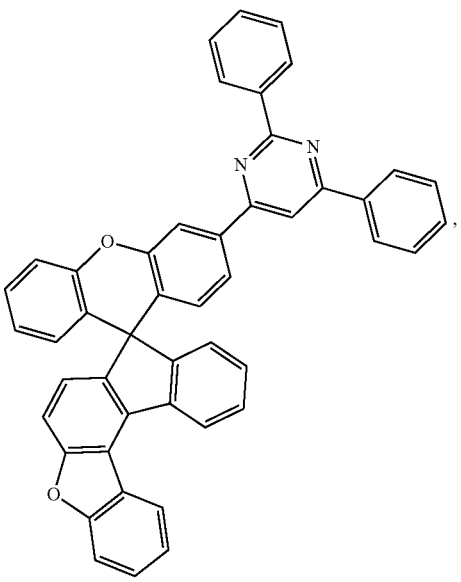

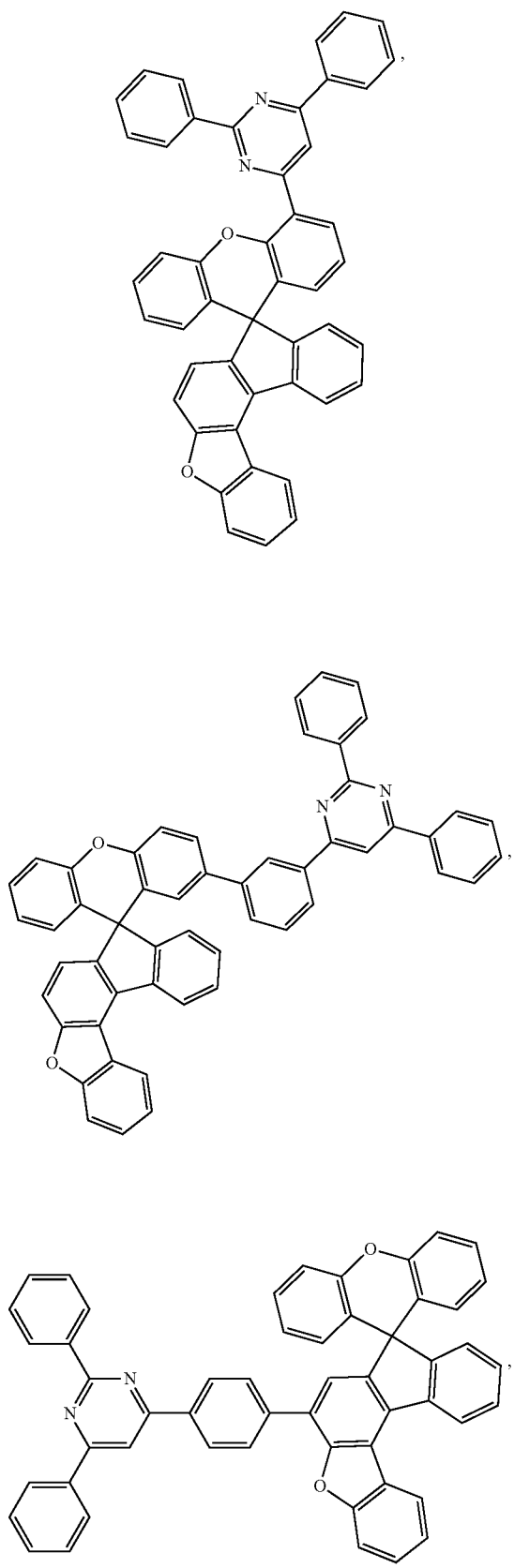
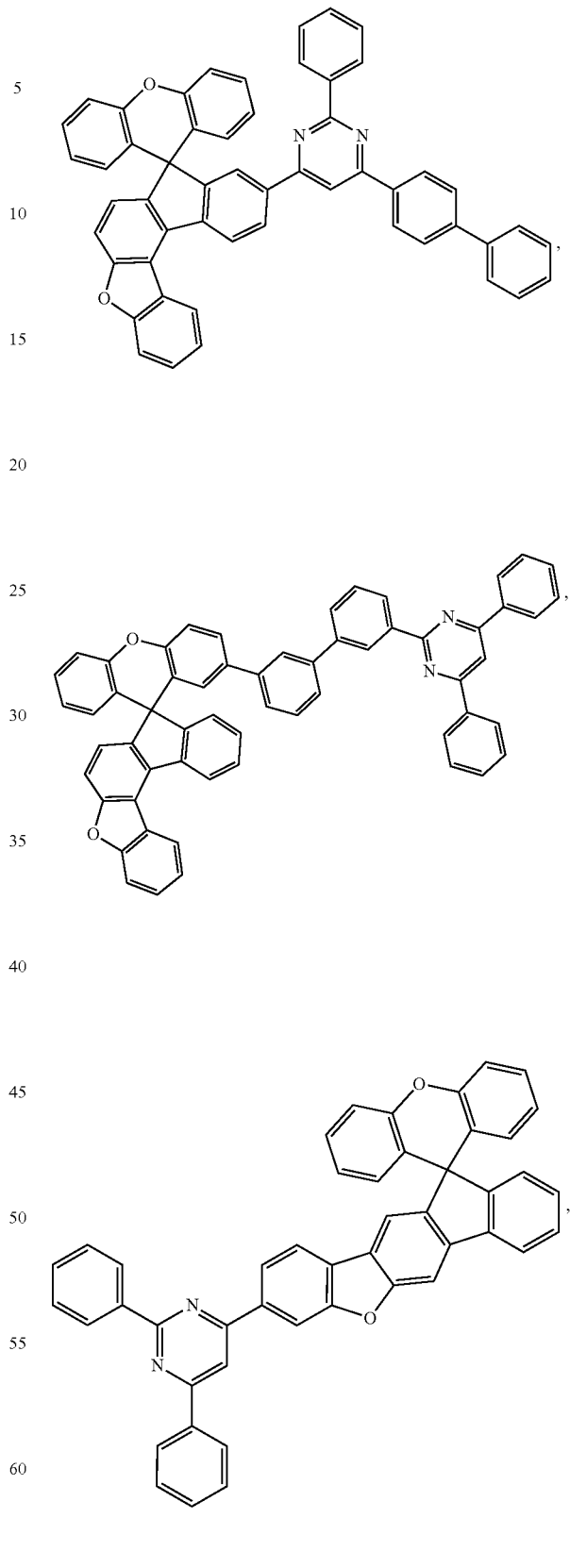

275
-continued
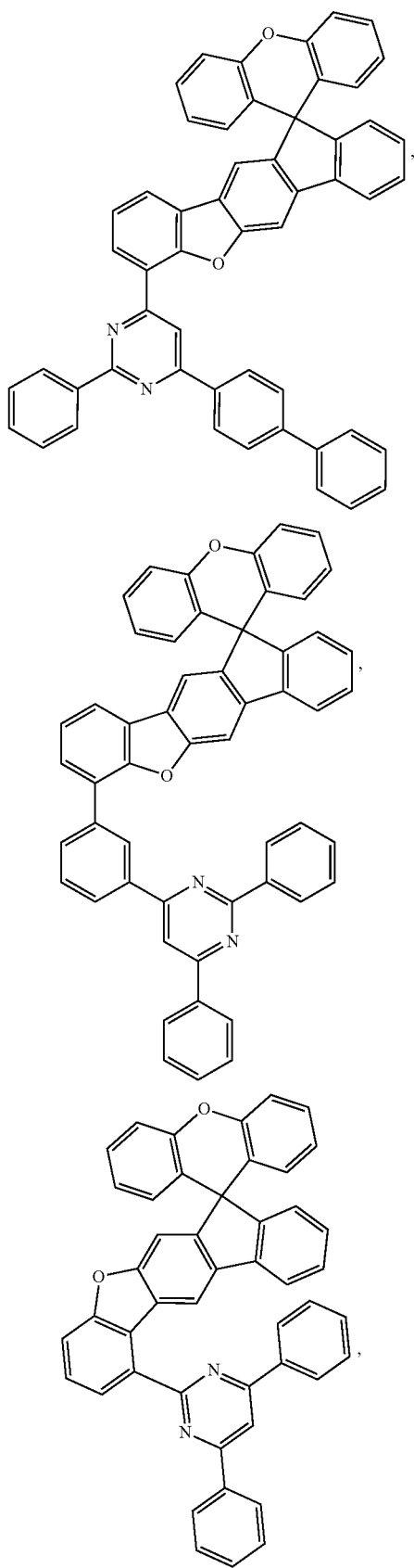
276
-continued
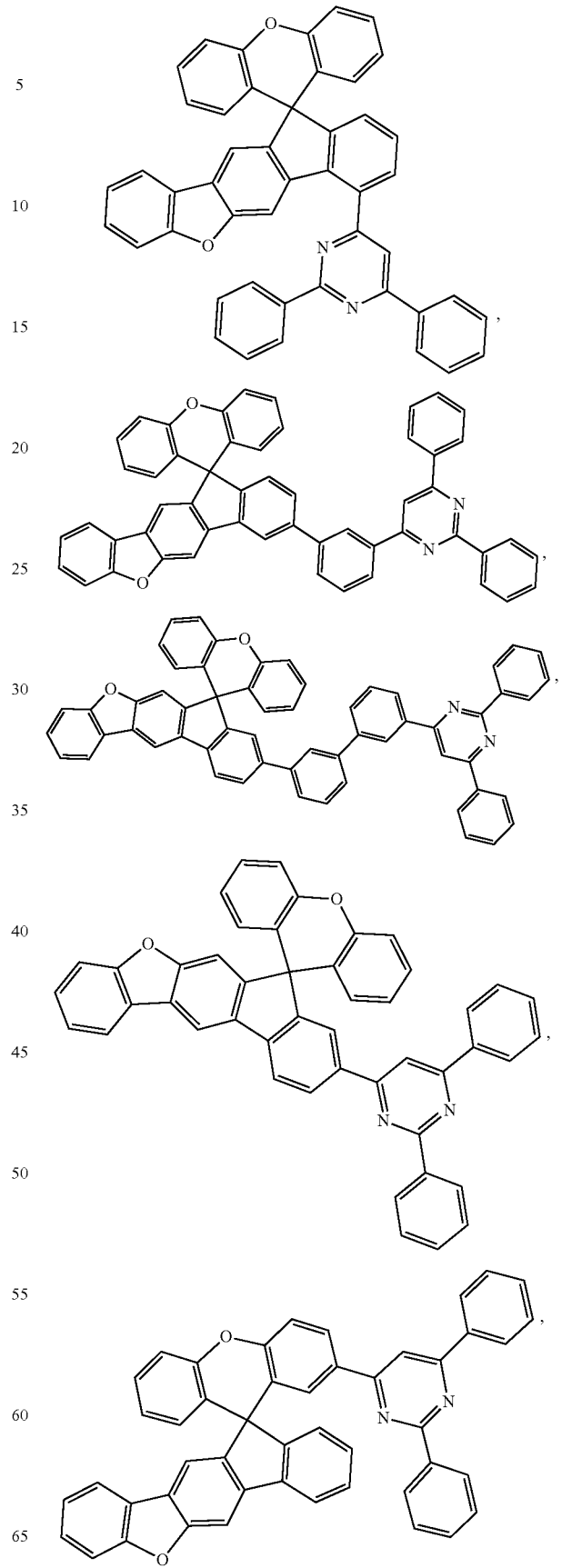

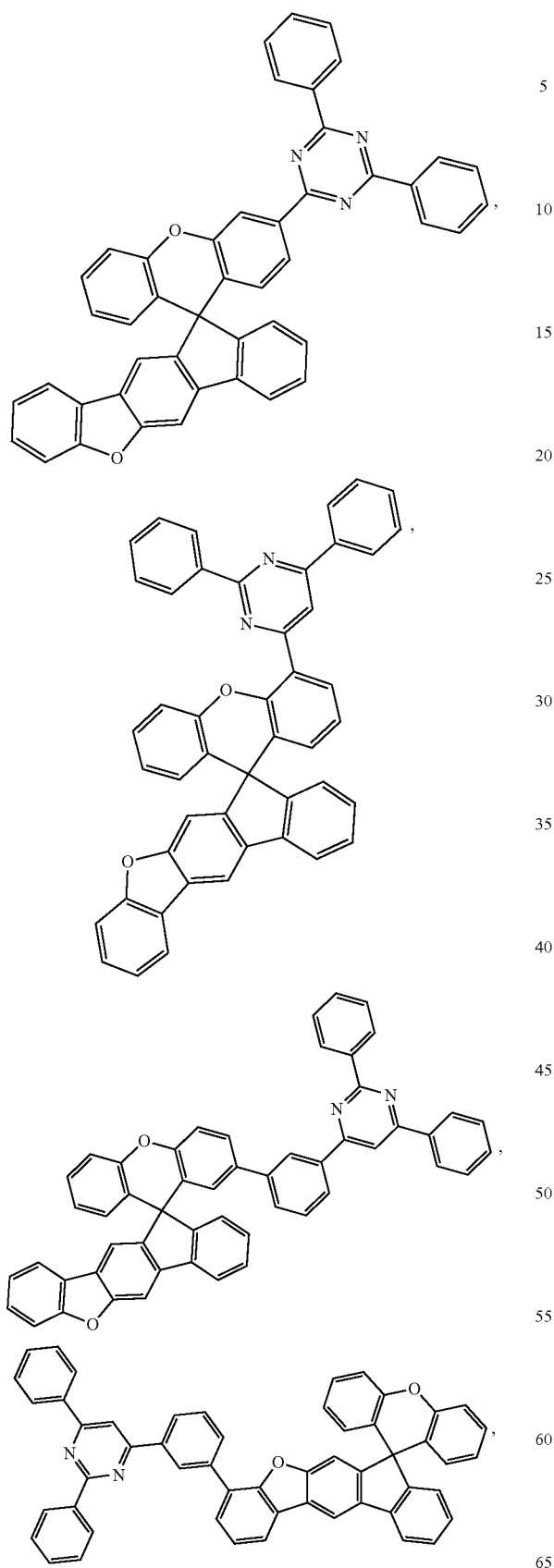
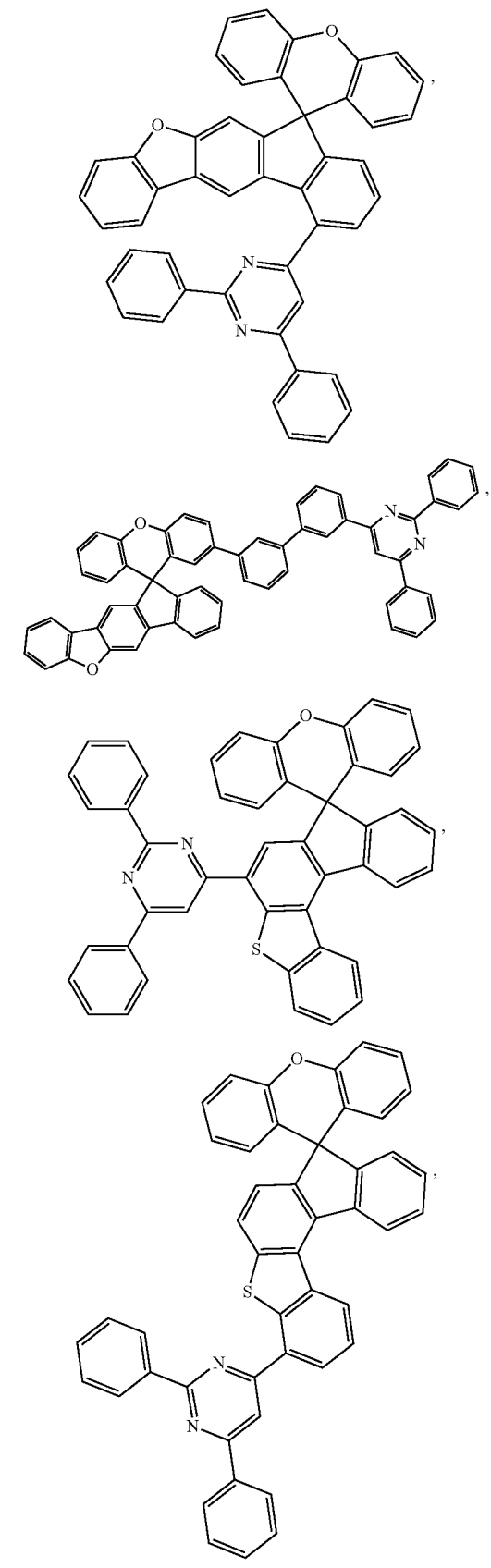

279
-continued
280
-continued
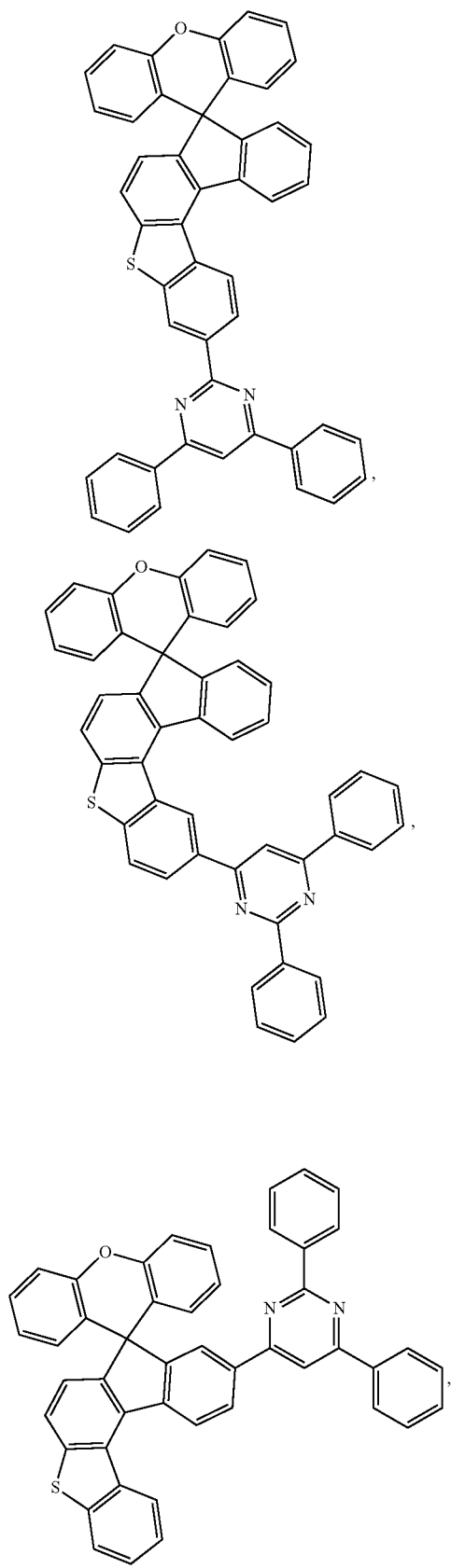
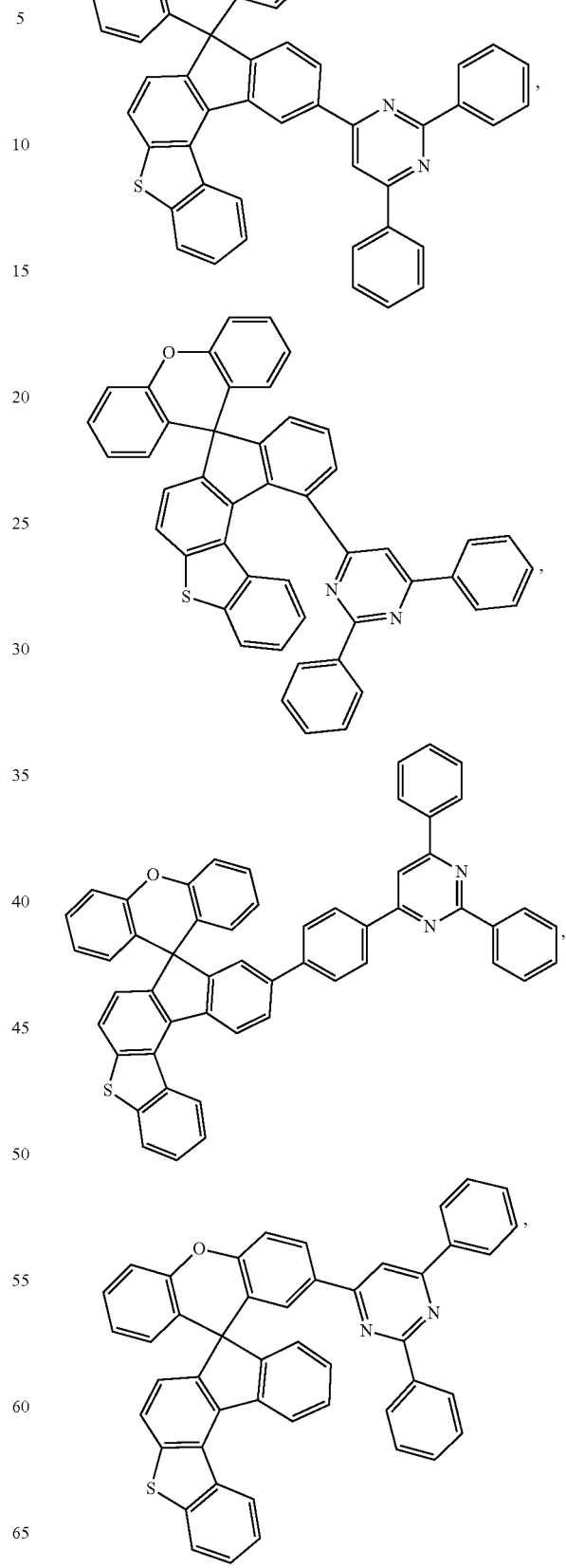

281
-continued
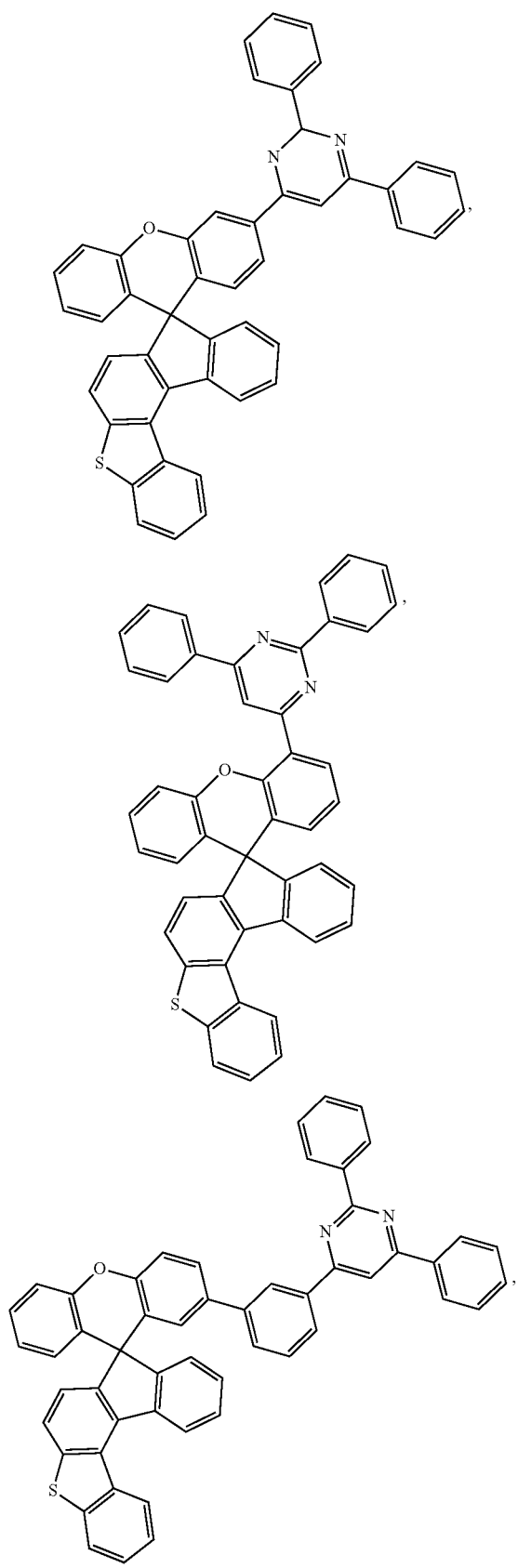
282
-continued
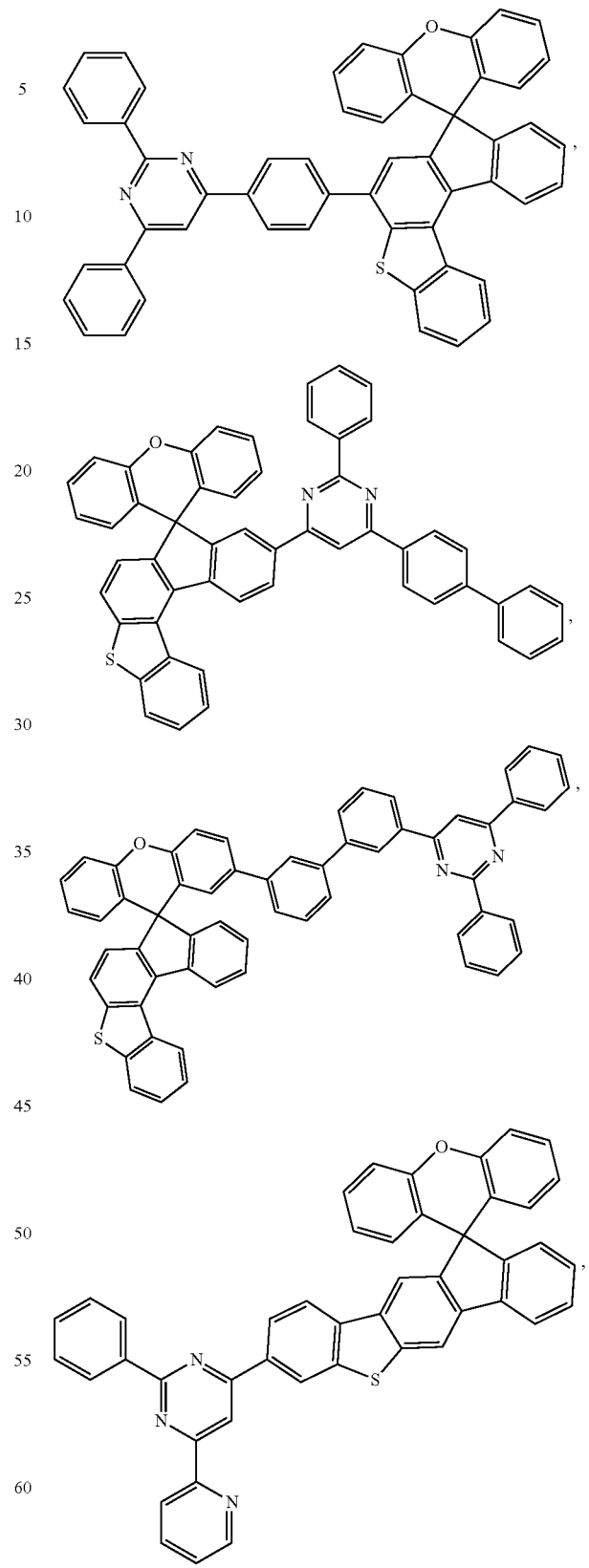

283
-continued
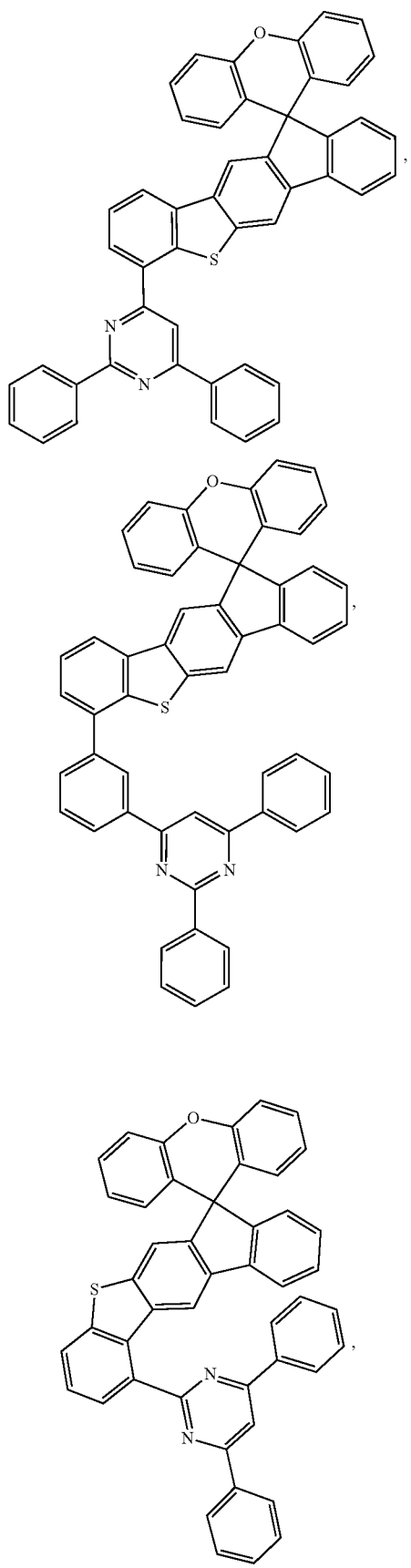
284
-continued
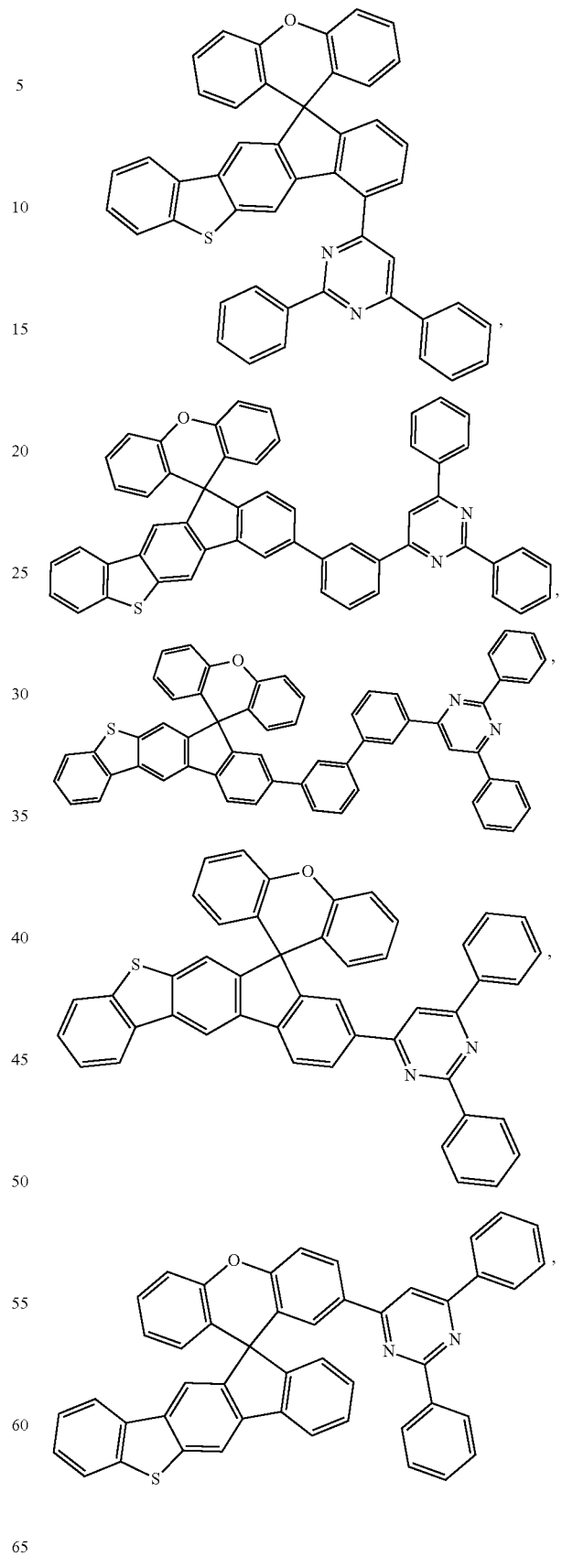

-continued
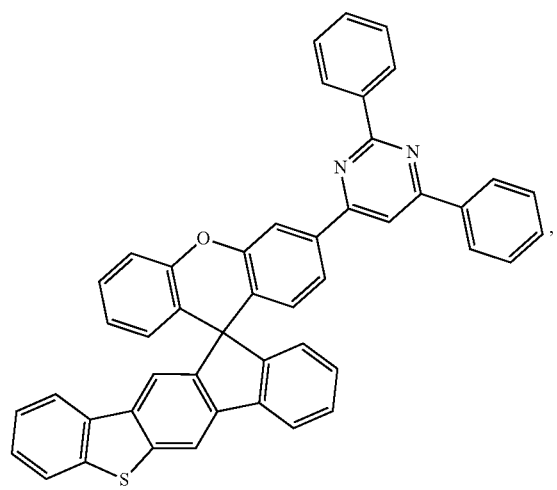
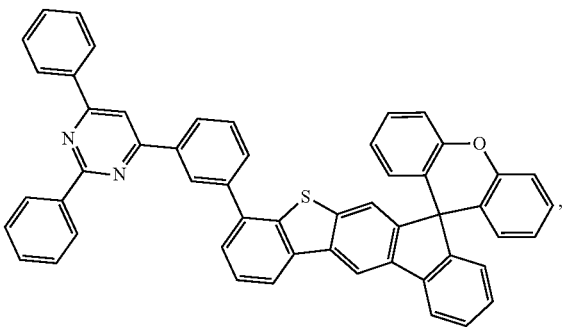
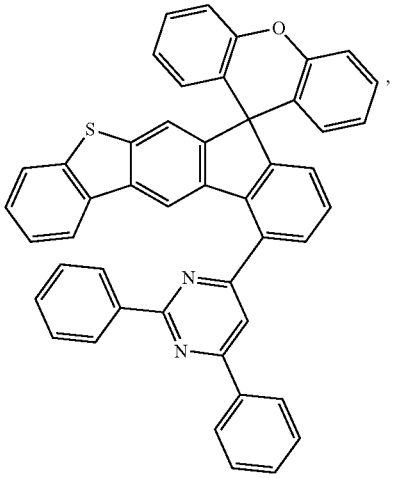
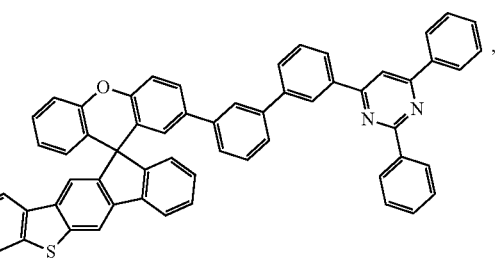
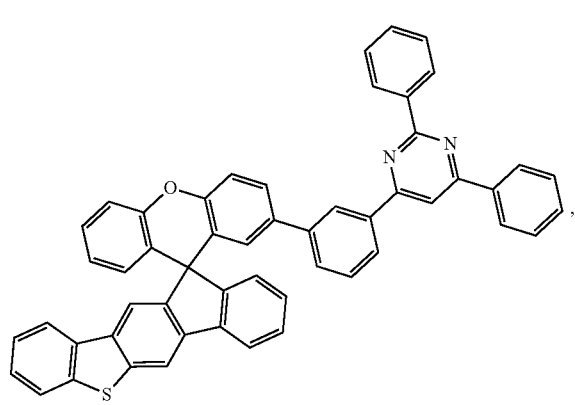
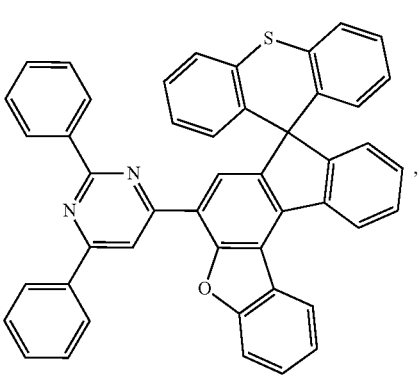

287
-continued
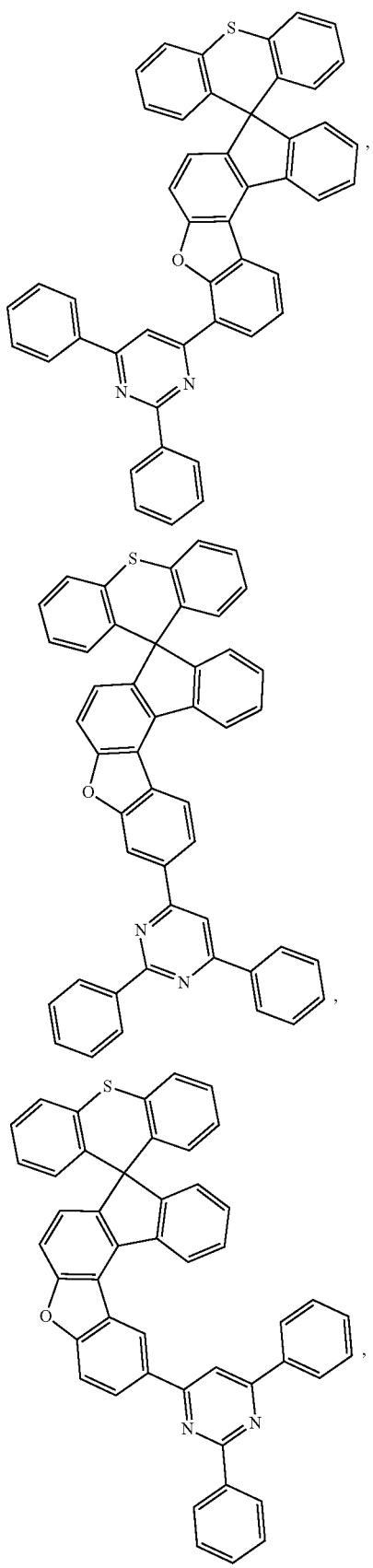
288
-continued
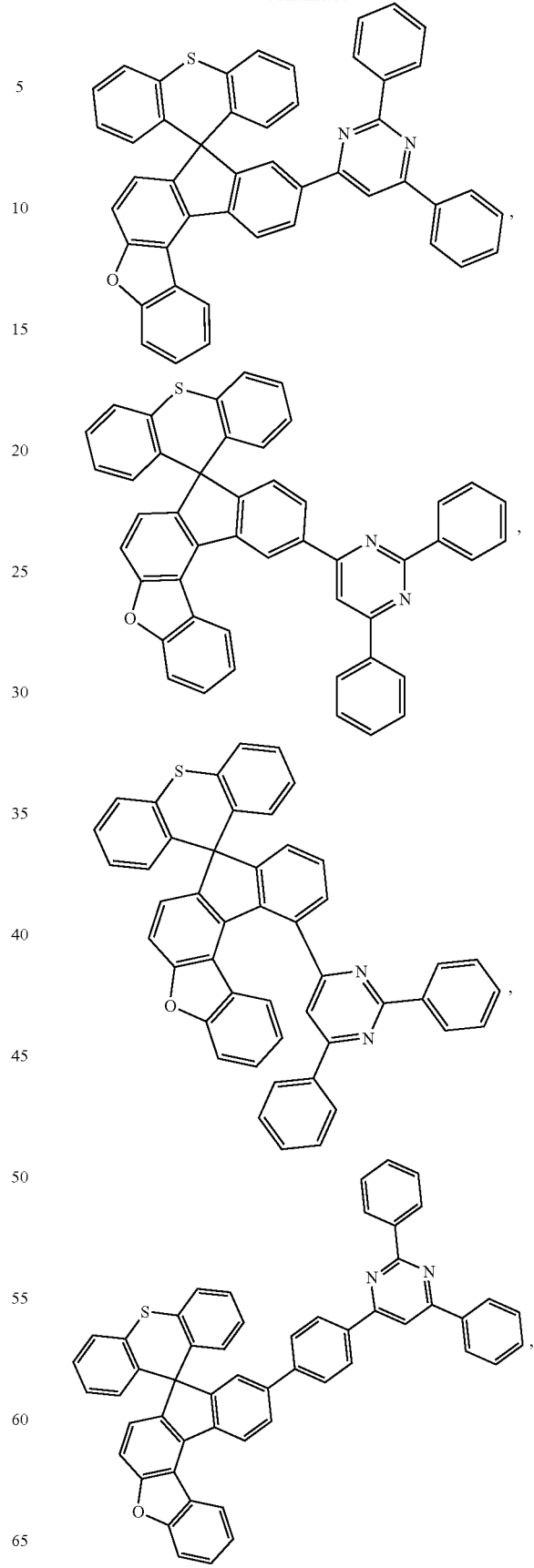

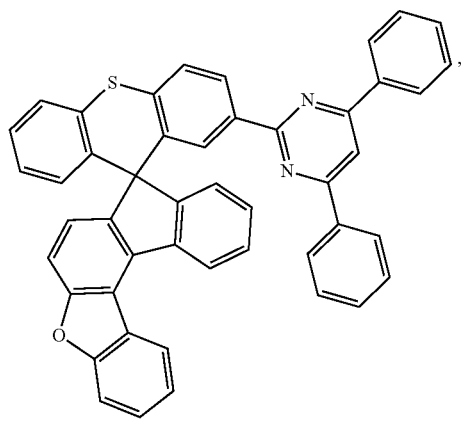
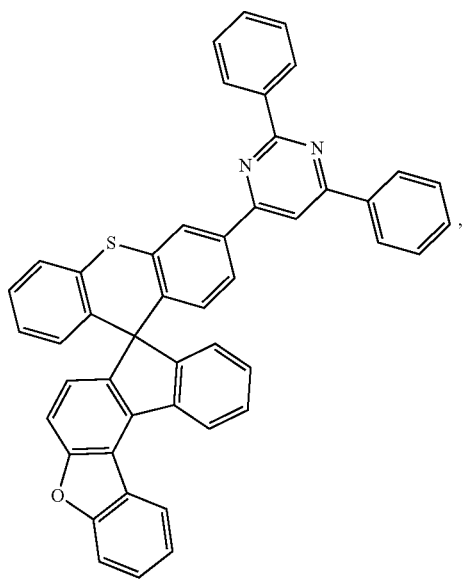
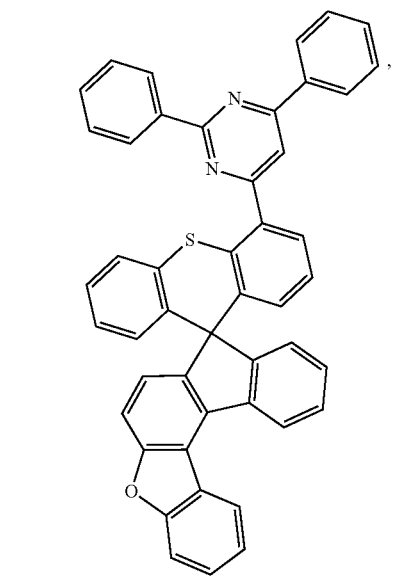
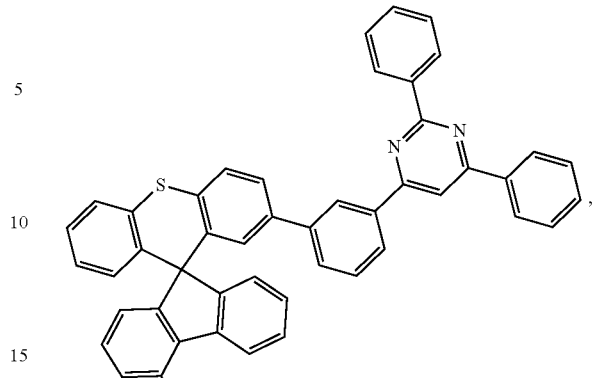
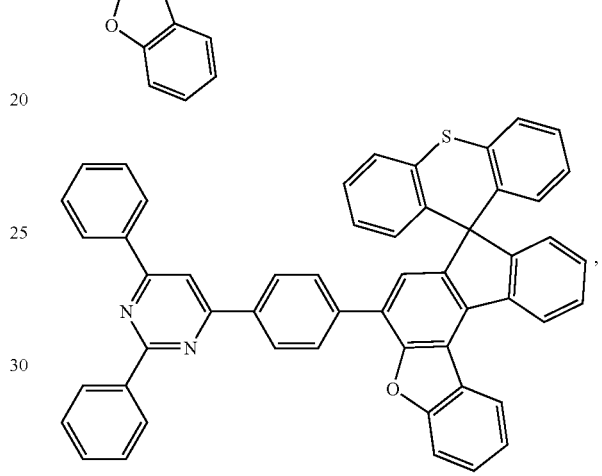
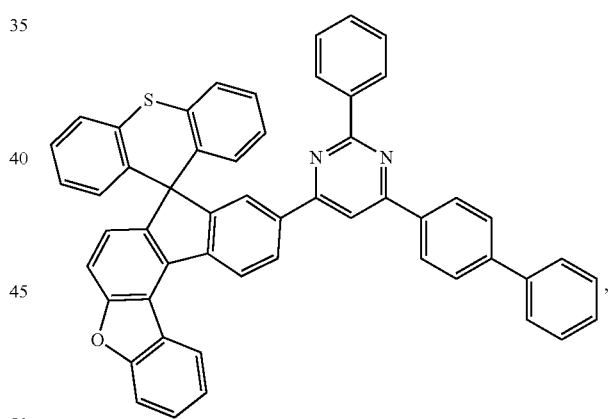
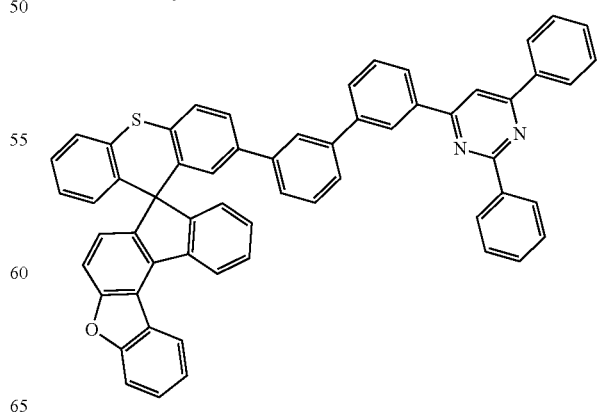

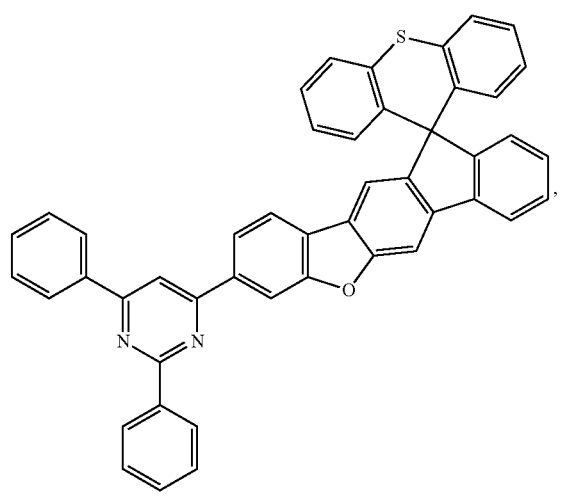
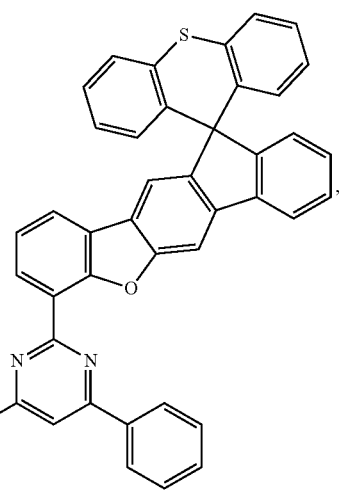
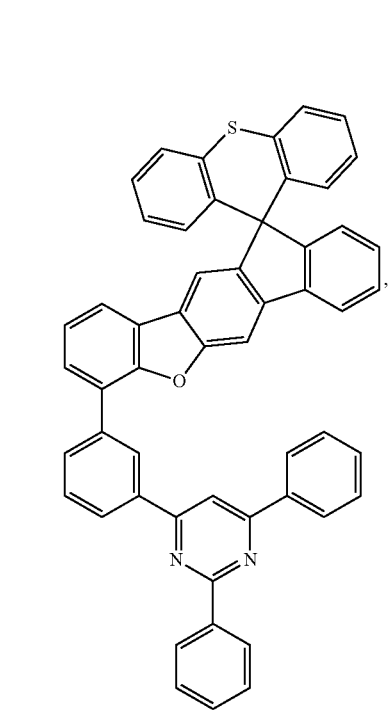
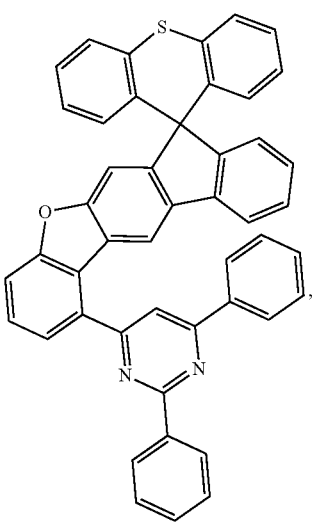
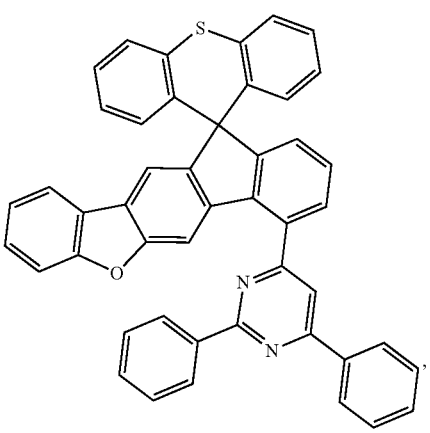
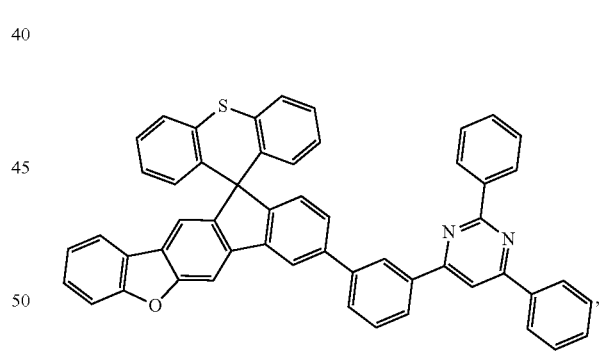
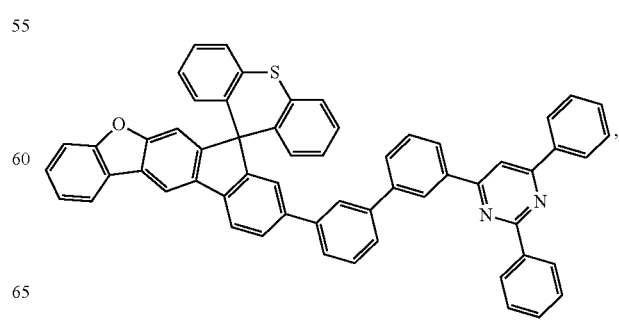

293
-continued
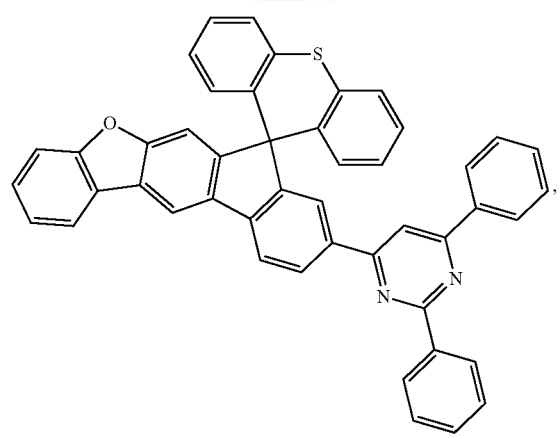
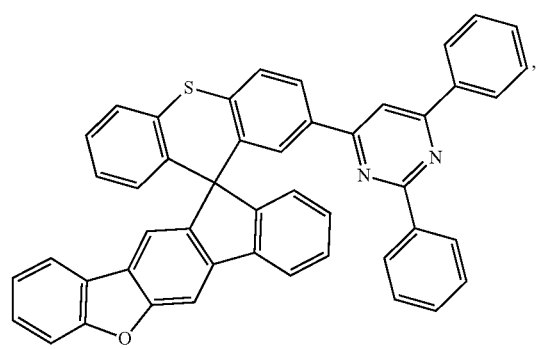
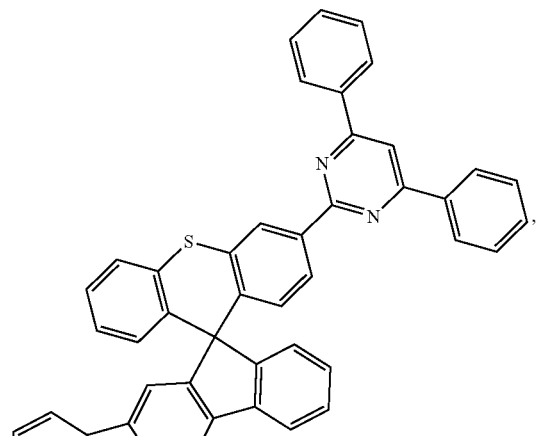
294
-continued
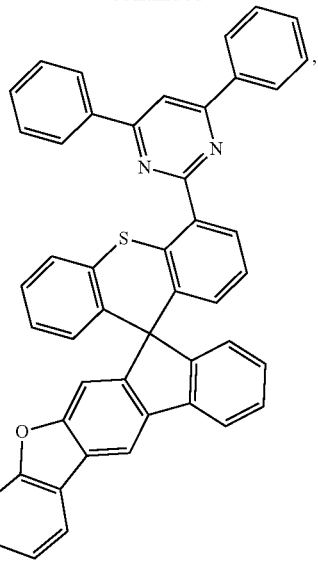
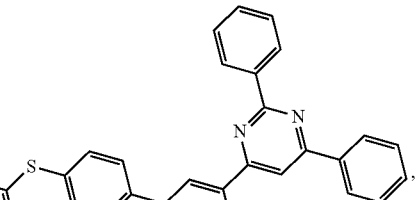
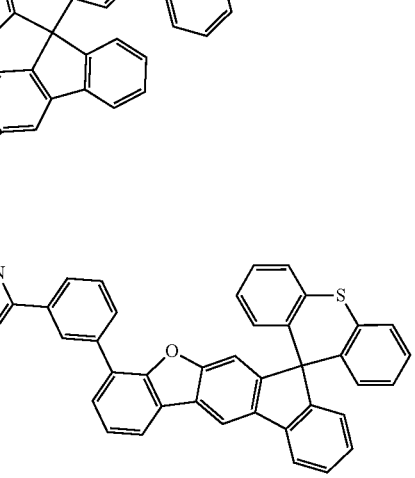
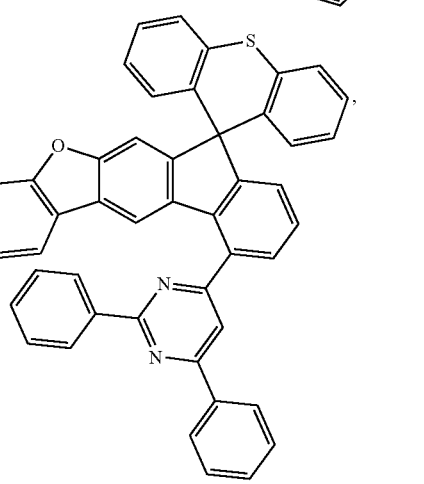

295
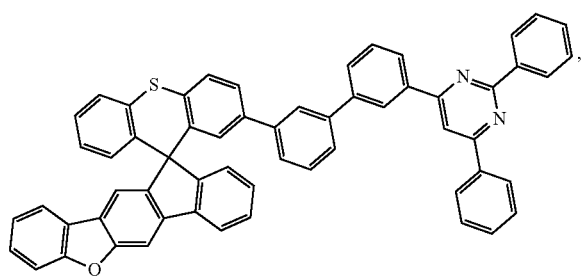
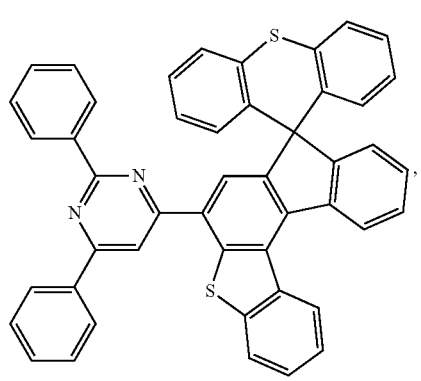
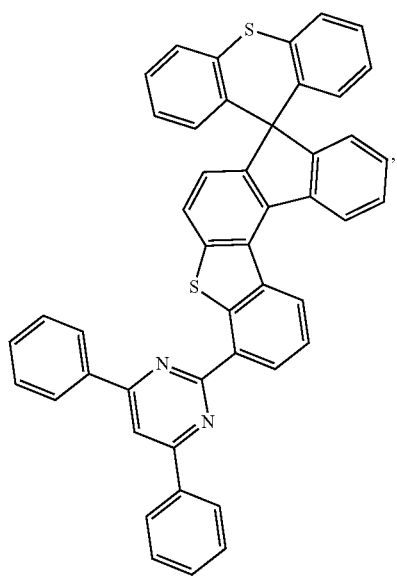
296
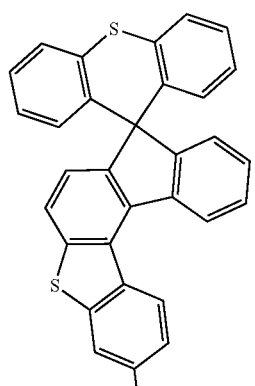
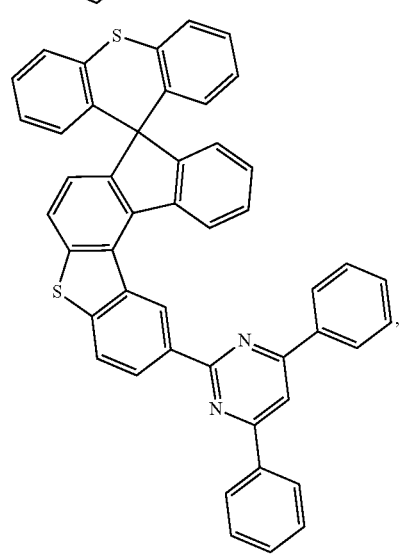
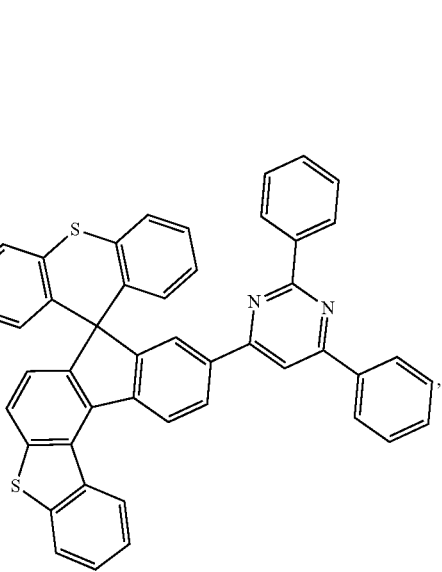

297
-continued
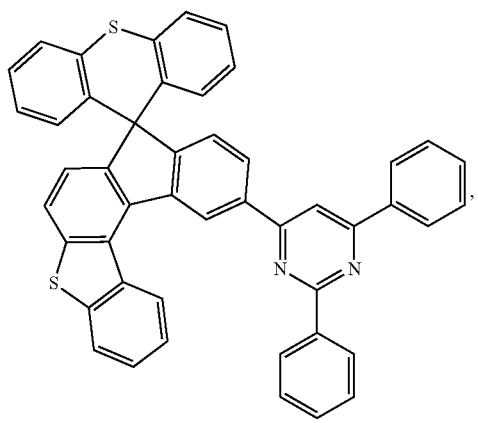
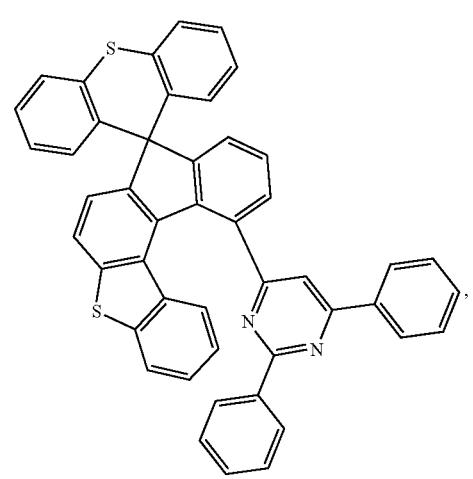
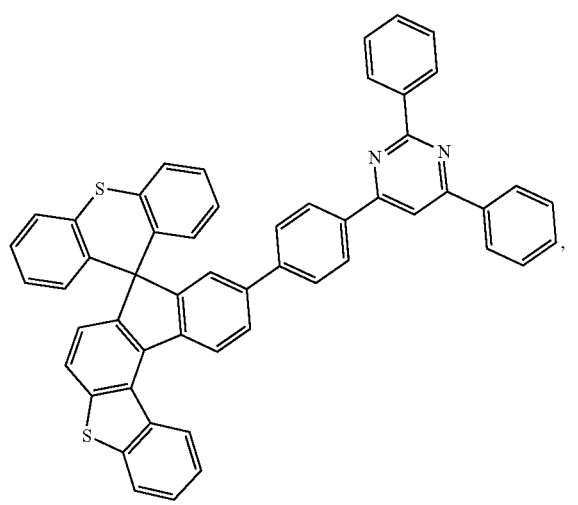
298
-continued
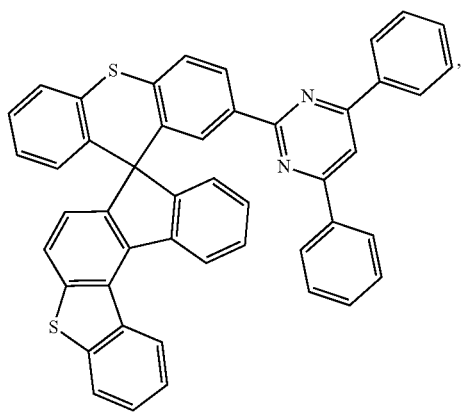
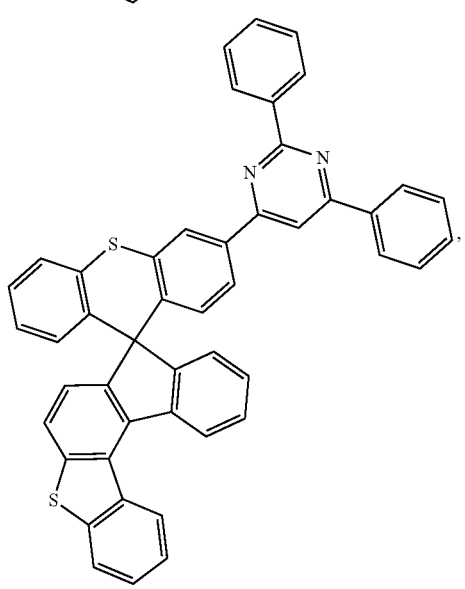
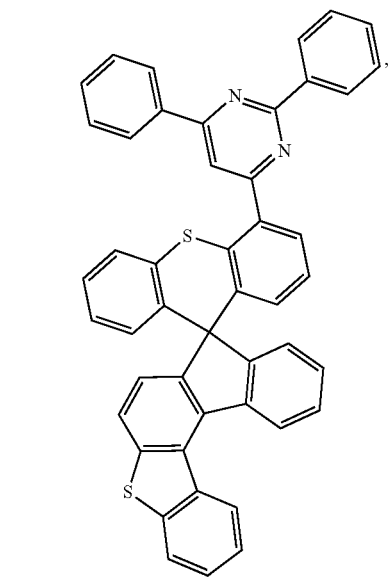

299
-continued
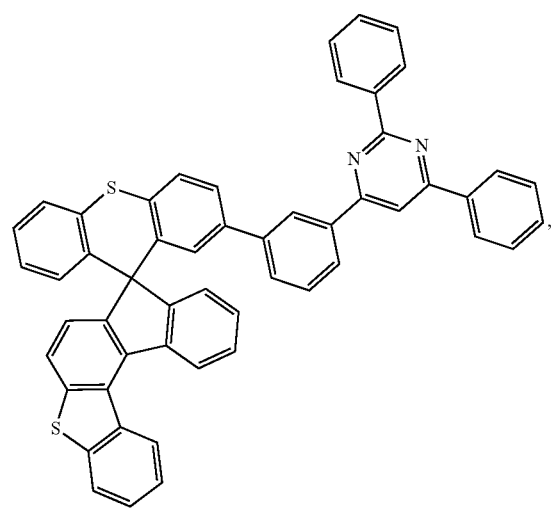,
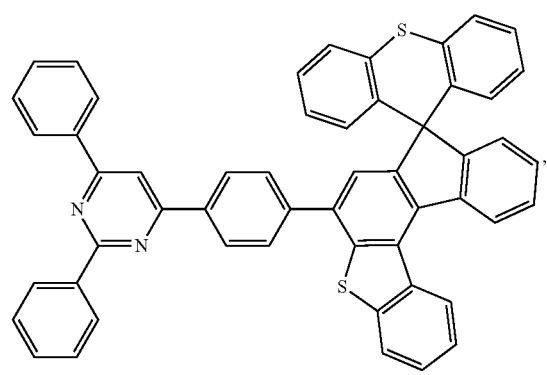,
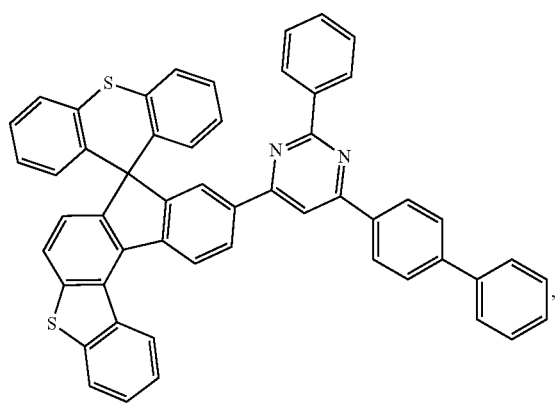,
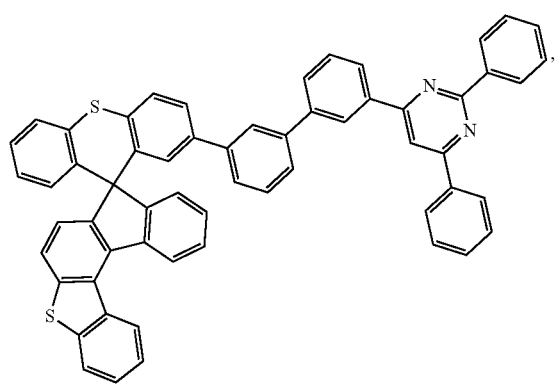,
300
-continued
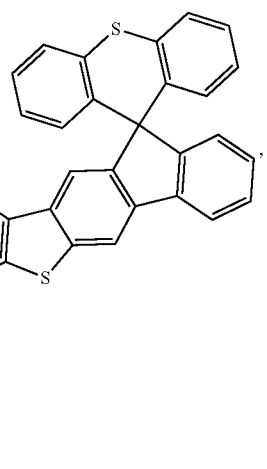,
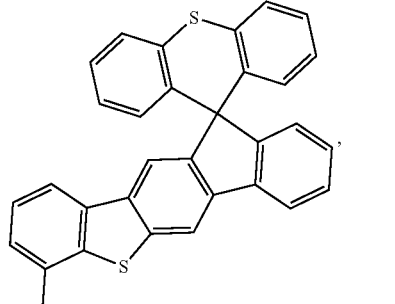,
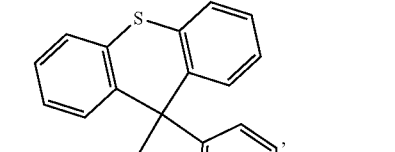,

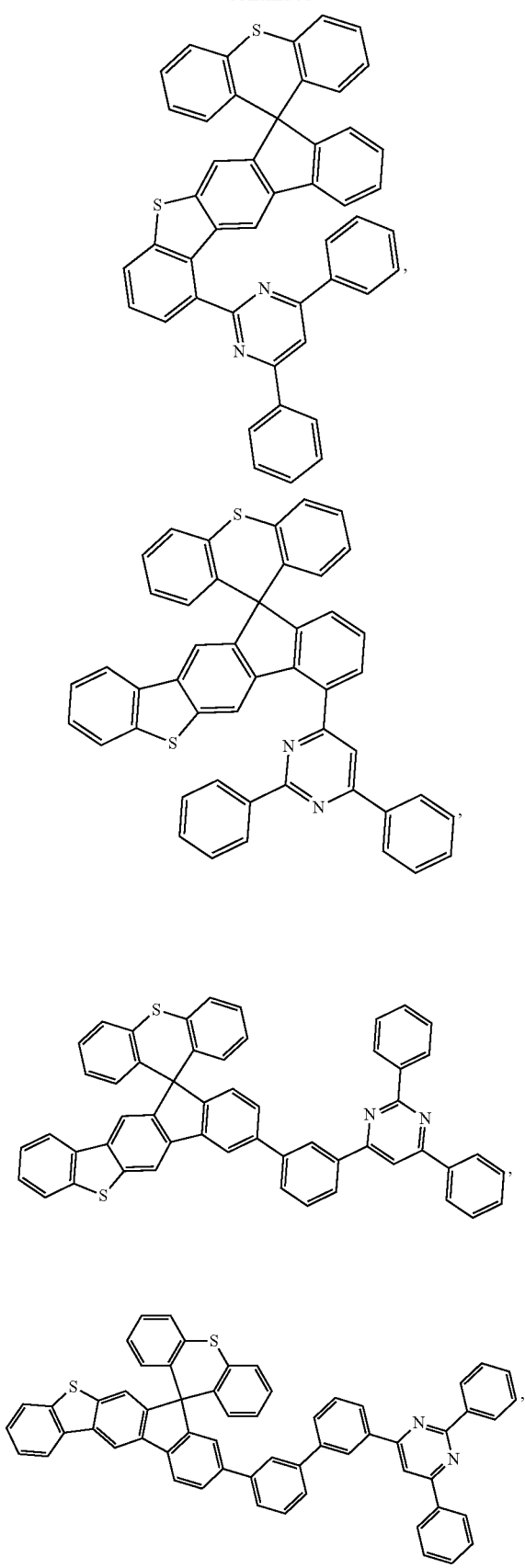

303
-continued
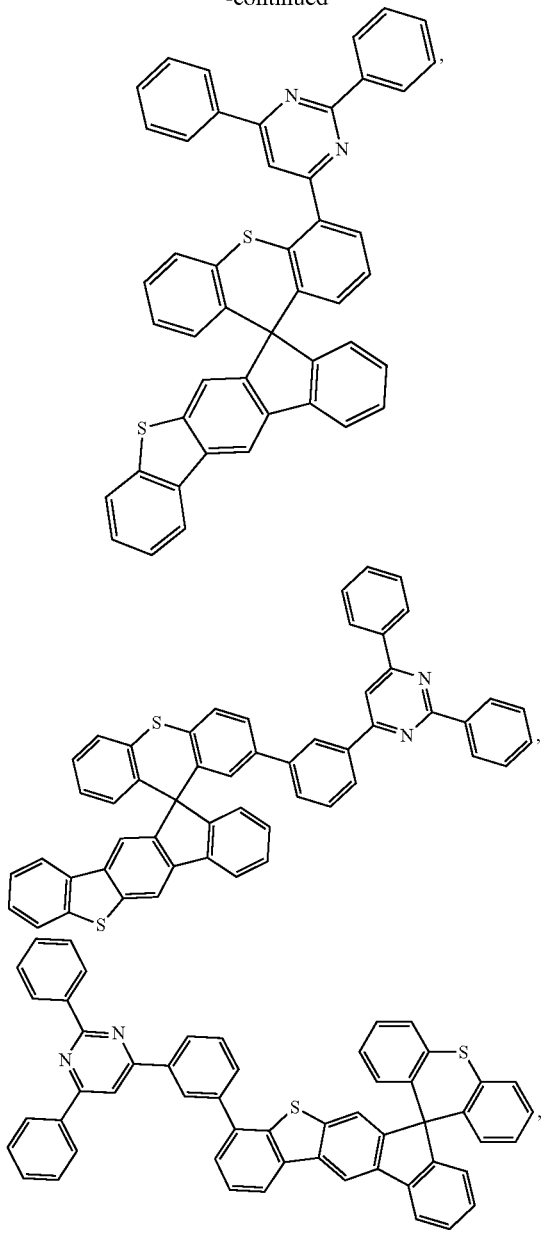
304
-continued
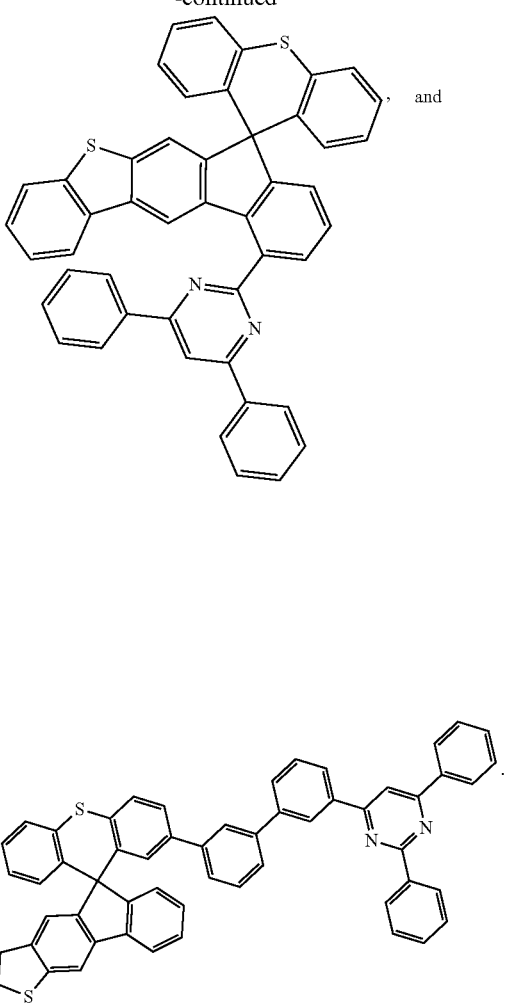
8. An organic light emitting device comprising a first electrode; a second electrode that is disposed to face the first electrode; and one or more organic material layers that are disposed between the first electrode and the second electrode, wherein one or more layers of the organic material layers include the compound according to claim 1.
* * * * *